US012637440B2

(12) United States Patent
Yoon et al.

(10) Patent No.: US 12,637,440 B2
(45) Date of Patent: May 26, 2026

(54) AMIDE DERIVATIVE USEFUL AS DIACYLGLYCEROL ACYLTRANSFERASE 2 INHIBITOR, AND USE THEREOF

(71) Applicant: LG CHEM, LTD., Seoul (KR)

(72) Inventors: Seung Hyun Yoon, Seoul (KR); Hyun Woo Joo, Seoul (KR); Bo Kyung Seo, Seoul (KR); Eun Jin Lee, Seoul (KR); Jin Young Jung, Seoul (KR); Su Young Yoon, Seoul (KR); Young Shin Kwak, Seoul (KR); Woo Young Cho, Seoul (KR); Min Mi Jo, Seoul (KR)

(73) Assignee: LG CHEM, LTD., Seoul (KR)

( * ) Notice: Subject to any disclaimer, the term of this patent is extended or adjusted under 35 U.S.C. 154(b) by 1008 days.

(21) Appl. No.: 17/788,393

(22) PCT Filed: Dec. 22, 2020

(86) PCT No.: PCT/KR2020/018933
§ 371 (c)(1),
(2) Date: Jun. 23, 2022

(87) PCT Pub. No.: WO2021/133038
PCT Pub. Date: Jul. 1, 2021

(65) Prior Publication Data

US 2023/0101389 A1 Mar. 30, 2023

(30) Foreign Application Priority Data

Dec. 23, 2019 (KR) ........................ 10-2019-0173456

(51) Int. Cl.
*C07D 401/04* (2006.01)
*C07D 401/14* (2006.01)

(52) U.S. Cl.
CPC ......... *C07D 401/04* (2013.01); *C07D 401/14* (2013.01)

(58) Field of Classification Search
CPC .................................................... C07D 401/14
See application file for complete search history.

(56) References Cited

U.S. PATENT DOCUMENTS

2012/0172369 A1 7/2012 Ting et al.
2015/0259323 A1* 9/2015 Cabral ...................... A61P 9/10 544/122
2018/0051012 A1 2/2018 Boehm et al.
2023/0078941 A1 3/2023 Yoon et al.

FOREIGN PATENT DOCUMENTS

| | | | |
|---|---|---|---|
| CN | 106103425 | A | 11/2016 |
| JP | 2017-507979 | A | 3/2017 |
| JP | 2019-524831 | A | 9/2019 |
| KR | 10-2016-0115997 | A | 10/2016 |
| KR | 10-2019-0035897 | A | 4/2019 |
| KR | 10-2021-0081286 | A | 7/2021 |
| WO | 2010-022055 | A2 | 2/2010 |
| WO | 2011-031628 | A1 | 3/2011 |
| WO | 2012-024179 | A1 | 2/2012 |
| WO | 2018-033832 | A1 | 2/2018 |
| WO | 2022050749 | A1 | 3/2022 |

OTHER PUBLICATIONS

Supplementary European Search Report issued for European Patent Application No. 20607919.3 on Dec. 13, 2022, 8 pages.
Xian, "Yaowu Huaxue Ketang Biji," People's Military Medical Press, 2011, pp. 10-11.
Office Action issued for Chinese Patent Application No. 202080089274.6 on Aug. 17, 2023, 12 pages.
Notice of Reasons for Refusal issued for Japanese Patent Application No. 2022-539022 on Aug. 21, 2023, 8 pages.
Written Decision on Registration issued for Korean Patent Application No. 10-2020-0181228 on Jul. 10, 2023, 6 pages.
International Search Report issued for International Application No. PCT/KR2020/018933 on Mar. 30, 2021, 8 pages.

* cited by examiner

*Primary Examiner* — Jeffrey S Lundgren
*Assistant Examiner* — Eric Tran
(74) *Attorney, Agent, or Firm* — ROTHWELL, FIGG, ERNST & MANBECK, P.C.

(57) ABSTRACT

The present invention relates to an amide derivative compound, which exhibits the activity of a diacylglycerol acyltransferase (DGAT) 2 inhibitor and is represented by chemical formula (1), a pharmaceutical composition comprising same as an active ingredient, and a use thereof.

6 Claims, No Drawings

AMIDE DERIVATIVE USEFUL AS DIACYLGLYCEROL ACYLTRANSFERASE 2 INHIBITOR, AND USE THEREOF

CROSS REFERENCE TO RELATED APPLICATION(S)

This application is a 35 U.S.C. 371 National Phase Entry Application from PCT/KR2020/018933 filed on Dec. 22, 2020, which claims priority to and the benefits of Korean Patent Application No. 10-2019-0173456, filed with the Korean Intellectual Property Office on Dec. 23, 2019, the entire contents of which are incorporated herein by reference.

TECHNICAL FIELD

The present invention relates to an amide derivative compound represented by Formula (1) showing inhibitory activity against diacylglycerol acyltransferase 2 (DGAT2), a pharmaceutical composition comprising the same as an active ingredient, and use thereof.

BACKGROUND ART

The improvement of living standards according to economic development, frequent consumption of instant foods, and changes to meat-based dietary habits caused excessive accumulation of caloric energy in the body. These changes in the dietary life of modern people have also led to a reduction in caloric energy consumption due to lack of exercise, leading to a serious prevalence of metabolic diseases such as obesity, hyperlipidemia, diabetes, cardiovascular disease and coronary artery disease. Specifically, obesity is one of the rapidly increasing diseases and is reported to be the cause of metabolic diseases such as diabetes. The development of therapeutic agents for metabolic diseases by controlling the functions of enzymes involved in the biosynthetic pathway of triglycerides—which is the main cause of obesity—is drawing attention.

Neutral fats, such as triglycerides (TG), play a very important role in the storage function as an energy source in the body. However, when neutral fats are excessively accumulated in organs or tissues, they cause obesity, hypertriglyceridemia, fatty liver, etc., thereby causing serious diseases such as diabetes, arteriosclerosis, metabolic abnormalities and hypofunction of organs. Diacylglycerol acyltransferase—which is a crucial enzyme in the biosynthesis of triglycerides—is found in various tissues of mammals, and is an enzyme that synthesizes TG by binding fatty acyl-CoA to the hydroxyl group of diacylglycerol in the final step of the glycerol phosphate pathway which is the main pathway for triglyceride synthesis. At present, two isoforms—DGAT1 and DGAT2—are known. Although their biochemical functions are similar, there is a difference in that DGAT1 is mainly expressed in the small intestine and adipose tissue, and DGAT2 is mainly expressed in the liver and adipose tissue. In addition, with respect to the gene family, DGAT1 belongs to the ACAT family, and DGAT2 belongs to the MGAT family. As such, it is expected that their role in TG biosynthesis is also different.

Several studies, including animal studies, have shown that DGAT2 primarily contributes to the biosynthesis of TG in vivo. Unlike DGAT2 knockout mice-which hardly synthesize TG and die shortly after birth due to an abnormal skin layer, DGAT1 knockout mice showed a slight decrease in TG levels and no problems with the survival of the mice (Stone S J et al., 2000. Nat. Genet. 25: 87-90). In addition, as a result of reducing the expression level of DGAT1 or DGAT2 by using antisense oligonucleotide (ASO) in an animal model of fatty liver, fatty liver symptoms were alleviated and the rate of glucose production in the liver was significantly reduced only when the amount of DGAT2 was reduced (Choi C S et al., 2007. Hepatology. 45: 1366-74).

The underlying molecular mechanisms have not been fully elucidated, but it has been thought that the inhibition of DGAT2 results in down-regulation of the expression of multiple genes encoding proteins involved in lipid production, such as sterol regulatory element-binding proteins 1c (SREBP1c) and stearoyl CoA-desaturase 1 (SCD1). At the same time, it has been thought that the oxidative pathway was induced by an increase in genes such as carnitine palmitoyltransferase 1 (CPT1). This change in turn leads to a decrease in hepatic DAG and TAG lipid levels, and thus improved insulin responsiveness in the liver. In addition, the inhibition of DGAT2 inhibited hepatic VLDL TAG secretion and reduced circulating cholesterol levels. Finally, plasma apolipoprotein B (APOB) levels were suppressed, which was thought to be due to the reduced supply of TAG in the lipidation of the newly synthesized APOB protein. That is, when DGAT2 is inhibited, beneficial effects on both glycemic control and plasma cholesterol profile showed, which means that the inhibition of DGAT2 can be applied to the treatment of metabolic disorders.

DISCLOSURE OF INVENTION

Technical Problem

An object of the present invention is to provide a novel amide derivative compound represented by Formula (1) showing inhibitory activity against diacylglycerol acyltransferase 2 (DGAT2).

Another object of the present invention is to provide a method of preparing the amide derivative compound.

Still another object of the present invention is to provide a pharmaceutical composition for the treatment of metabolic diseases associated with DGAT2 comprising the amide derivative compound as an active ingredient, and a method for preparing thereof.

Still another object of the present invention is to provide a method for treating metabolic diseases associated with DGAT2 in a subject in which efficacy in animal models of diseases is improved as well as efficacy and convenience in taking in the subject are improved by using the amide derivative compound as an active ingredient having improve physical and chemical properties compared to conventional compounds.

Solution to Problem

In order to achieve the above object, the present invention provides a compound of the following Formula (1), or a pharmaceutically acceptable salt or isomer:

[Formula (1)]

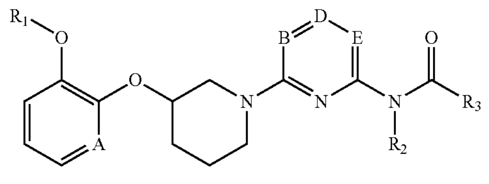

wherein

A, B and E are each independently CH or N;

D is N, CH or C-haloalkyl;

$R_1$ is alkyl, cycloalkyl or haloalkyl;

$R_2$ is hydrogen or alkyl;

$R_3$ is -G-J-L;

wherein G is —NH— or a direct bond;

J is alkylene, alkenylene, alkylene-arylene, alkylene-amino-arylene, alkylene-aryloxylene-alkylene, alkylene-cycloalkyl, alkenylene-cycloalkyl, alkoxylene-arylene, arylene, cycloalkyl, aryl, aryl-alkyl, heterocycloalkylene, heterocycloalkylene-arylene, heterocycloalkylene-heteroarylene or heterocycloalkyl;

L is hydrogen, halo, amino, nitro, carboxy (—COOH), aminocarbonylalkyl, carboxyalkyl, carboxyalkoxy, carboxyalkyl-aryl, cycloalkyl, aryl, aryloxy, heterocycloalkyl or heteroaryl; or $R_2$ and $R_3$ together with nitrogen atom to which they are attached may form heterocycloalkyl;

wherein the alkyl, alkylene, alkylene-arylene, alkenyl, alkenylene, cycloalkyl, carboxyalkyl, carboxyalkoxy, alkoxyalkyl, aminocarbonyl, aryl, aryl-alkyl, arylene, aryloxy, heterocycloalkyl or heteroaryl is optionally substituted with one or more substituents selected from hydroxy, halo, oxo, nitro, —COOH, —$CH_2$COOH, alkyl, alkenyl, alkoxy, haloalkyl, alkylsulfonyl, alkylcarbonyl, alkoxycarbonyl and heteroaryl-alkyl; and the heterocycloalkylene, heterocycloalkyl, heteroarylene or heteroaryl includes one or more heteroatoms selected from N, O and S.

The compound of Formula (1) according to the present invention may form a pharmaceutically acceptable salt. A pharmaceutically acceptable salt may include an acid-addition salt which is formed from an inorganic acid such as hydrochloric acid, sulfuric acid, nitric acid, phosphoric acid, hydrobromic acid and hydroiodic acid; an organic acid such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acid such as methanesulfonic acid, ethanesulfonic acid, benzenesulfonic acid and p-toluenesulfonic acid, which form non-toxic acid-addition salt including pharmaceutically acceptable anion. In addition, a pharmaceutically acceptable carboxylic acid salt includes the salt with alkali metal or alkali earth metal such as lithium, sodium, potassium, calcium and magnesium; salts with amino acid such as lysine, arginine and guanidine; an organic salt such as dicyclohexylamine, N-methyl-D-glucamine, tris(hydroxymethyl)methylamine, diethanolamine, choline and triethylamine. The compound of Formula (1) according to the present invention may be converted into their salts by conventional methods.

Meanwhile, since the compound of Formula (1) according to the present invention can have an asymmetric carbon center and asymmetric axis or plane, they can exist as E- or Z-isomer, R- or S-isomer, racemic mixtures or diastereoisomer mixtures and each diastereoisomer, all of which are within the scope of the present invention.

Herein, unless indicated otherwise, the term "the compound of Formula (1)" is used to mean all the compounds of Formula (1), including the pharmaceutically acceptable salts and isomers thereof.

Herein, the following concepts defined to the substituents are used to define the compound of Formula (1).

The term "halogen" or "halo" means fluoride (F), chlorine (Cl), bromine (Br) or iodine (I).

The term "alkyl" or "alkylene" means straight or branched hydrocarbons, may include a single bond, a double bond or a triple bond, and is preferably $C_1$-$C_{10}$ alkyl or $C_1$-$C_{10}$ alkylene, or $C_1$-$C_7$ alkyl or $C_1$-$C_7$ alkylene. Examples of alkyl include, but are not limited to, methyl, ethyl, n-propyl, i-propyl, n-butyl, i-butyl, tert-butyl, acetylene, vinyl, trifluoromethyl and the like.

The term "alkenyl" or "alkenylene" means straight or branched hydrocarbons having at least one carbon-carbon double bond, and is preferably $C_2$-$C_{10}$ alkenyl or $C_2$-$C_{10}$ alkenylene, or $C_2$-$C_7$ alkenyl or $C_2$-$C_7$ alkenylene. Examples of alkenyl include, but are not limited to, vinyl, allyl, butenyl, isopropenyl, isobutenyl and the like.

The term "cycloalkyl" means partially or fully saturated single or fused ring hydrocarbons, and is preferably $C_3$-$C_{10}$-cycloalkyl. Examples of cycloalkyl include, but are not limited to, cyclopropyl, cyclobutyl, cyclopentyl, cyclohexyl, cycloheptyl and the like.

Unless otherwise defined, the term "alkoxy" means alkyloxy having 1 to 10 carbon atoms.

Unless otherwise defined, the term "cycloalkoxy" means cycloalkyloxy having 3 to 10 carbon atoms.

The term "aryl" or "arylene" means aromatic hydrocarbons, preferably $C_5$-$C_{12}$ aryl or $C_5$-$C_{12}$ arylene, more preferably $C_6$-$C_{10}$ aryl or $C_6$-$C_{10}$ arylene, and includes, but is not limited to, phenyl, naphthyl and the like.

The term "heteroaryl" or "heteroarylene" means 3- to 12-membered, more preferably 5- to 12-membered aromatic hydrocarbons which form a single or fused ring-which may be fused with benzo or $C_3$-$C_8$ cycloalkyl-including one or more heteroatoms selected from N, O and S as a ring member. Examples of heteroaryl include, but are not limited to, pyridinyl, pyrimidinyl, pyridazinyl, pyrazinyl, oxadiazolyl, isoxadiazolyl, tetrazolyl, triazolyl, indolyl, indazolyl, isoxazolyl, oxazolyl, thiazolyl, isothiazolyl, furanyl, benzofuranyl, imidazolyl, thiophenyl, benzthiazole, benzimidazole, quinolinyl, indolinyl, 1,2,3,4-tetrahydroisoquinolyl, 3,4-dihydroisoquinolinyl, thiazolopyridyl, 2,3-dihydrobenzofuran, 2,3-dihydrothiophene, 2,3-dihydroindole, benzo[1,3]dioxin, chroman, thiochroman, 1,2,3,4-tetrahydroquinoline, 4H-benzo[1,3]dioxin, 2,3-dihydrobenzo[1,4]-dioxin, 6,7-dihydro-5H-cyclopenta[d]pyrimidine and the like.

The term "heterocycloalkyl" means partially or fully saturated hydrocarbons which form a single or fused ring including one or more heteroatoms selected from N, O and S, and is preferably 3- to 12-membered heterocycloalkyl or 5- to 12-membered heterocycloalkyl. Examples of heterocycloalkyl include, but are not limited to, pyrrolidinyl, piperidinyl, morpholinyl, imidazolinyl, piperazinyl, tetrahydrofuran, tetrahydrothiofuran and the like.

Aryl-alkyl, alkyl-aryl and heteroaryl-alkyl mean groups which are formed by the combination of the above-mentioned aryl and alkyl, or heteroaryl and alkyl. Examples include, but are not limited to, benzyl, thiophenemethyl, pyrimidinemethyl and the like.

According to one embodiment of the present invention, in the above Formula (1)

A, B and E are each independently CH or N;

D is N, CH or C-halo-$C_1$-$C_7$ alkyl;

$R_1$ is $C_1$-$C_7$ alkyl, $C_3$-$C_{10}$ cycloalkyl or halo-$C_1$-$C_7$ alkyl;

$R_2$ is hydrogen or $C_1$-$C_7$ alkyl;

$R_3$ is -G-J-L;

wherein G is —NH— or a direct bond;

J is $C_1$-$C_7$ alkylene, $C_2$-$C_7$ alkenylene, $C_1$-$C_7$ alkylene-$C_6$-$C_{10}$ arylene, $C_1$-$C_7$ alkylene-amino-$C_6$-$C_{10}$ arylene, $C_1$-$C_7$ alkylene-$C_6$-$C_{10}$ aryloxylene-$C_1$-$C_7$ alkylene, $C_1$-$C_7$ alkylene-$C_3$-$C_{10}$ cycloalkyl, $C_2$-$C_7$ alkenylene- $C_3$-$C_{10}$ cycloalkyl, $C_1$-$C_7$ alkoxylene-$C_6$-$C_{10}$ arylene, $C_6$-$C_{10}$ arylene, $C_3$-$C_{10}$ cycloalkyl, $C_6$-$C_{10}$ aryl, $C_6$-$C_{10}$ aryl-$C_1$-$C_7$ alkyl, 5- to 12-membered heterocycloalkylene, 5- to 12-membered heterocycloalkylene-$C_6$-$C_{10}$ arylene, 5- to 12-membered heterocycloalkylene-5- to 12-membered heteroarylene or 5- to 12-membered heterocycloalkyl;

L is hydrogen, halo, amino, nitro, carboxy (—COOH), aminocarbonyl-$C_1$-$C_7$ alkyl, carboxy-$C_1$-$C_7$ alkyl, carboxy-$C_1$-$C_7$ alkoxy, carboxy-$C_1$-$C_7$ alkyl-$C_6$-$C_{10}$ aryl, $C_3$-$C_{10}$ cycloalkyl, $C_6$-$C_{10}$ aryl, $C_6$-$C_{10}$ aryloxy, 5- to 12-membered heterocycloalkyl or 5- to 12-membered heteroaryl; or $R_2$ and $R_3$ together with nitrogen atom to which they are attached may form 5- to 12-membered heterocycloalkyl;

wherein the alkyl, alkylene, alkylene-arylene, alkenyl, alkenylene, cycloalkyl, carboxyalkyl, carboxyalkoxy, alkoxyalkyl, aminocarbonyl, aryl, aryl-alkyl, arylene, aryloxy, heterocycloalkyl or heteroaryl is optionally substituted with 1 to 4 substituents selected from hydroxy, halo, oxo, nitro, —COOH, —$CH_2$COOH, $C_1$-$C_7$ alkyl, $C_2$-$C_7$ alkenyl, $C_1$-$C_7$ alkoxy, halo-$C_1$-$C_7$ alkyl, $C_1$-$C_7$ alkylsulfonyl, $C_1$-$C_7$ alkylcarbonyl, $C_1$-$C_7$ alkoxycarbonyl and 5- to 12-membered heteroaryl-$C_1$-$C_7$ alkyl; and the heterocycloalkylene, heterocycloalkyl, heteroarylene or heteroaryl includes 1 to 5 heteroatoms selected from N, O and S.

Representative compounds of Formula (1) according to the present invention include, but are not limited to, the following compounds:

(R)-1-(3,5-bis(trifluoromethyl)phenyl)-3-(6-(3-(2-ethoxyphenoxy)piperidin-1-yl)pyrazin-2-yl)urea;

((6-((R)-3-(2-ethoxyphenoxy)piperidin-1-yl)pyrazin-2-yl)carbamoyl)-L-phenylalanine;

(R)—N-(6-(3-(2-ethoxyphenoxy)piperidin-1-yl)pyrazin-2-yl)morpholine-4-carboxamide;

(R)—N-(6-(3-(2-ethoxyphenoxy)piperidin-1-yl)pyrazin-2-yl)pyrrolidine-1-carboxamide;

1-((6-((R)-3-(2-ethoxyphenoxy)piperidin-1-yl)pyrazin-2-yl)carbamoyl)pyrrolidine-3-carboxylic acid;

(R)—N-(6-(3-(2-ethoxyphenoxy)piperidin-1-yl)pyrazin-2-yl)benzamide;

(R)-4-chloro-N-(6-(3-(2-ethoxyphenoxy)piperidin-1-yl)pyrazin-2-yl)benzamide;

(R)—N-(6-(3-(2-ethoxyphenoxy)piperidin-1-yl)pyrazin-2-yl)-3-methoxybenzamide;

(R)—N-(6-(3-(2-ethoxyphenoxy)piperidin-1-yl)pyrazin-2-yl)-4-methoxybenzamide;

(R)—N-(6-(3-(2-ethoxyphenoxy)piperidin-1-yl)pyrazin-2-yl)-4-nitrobenzamide;

(R)-2-((6-(3-(2-ethoxyphenoxy)piperidin-1-yl)pyrazin-2-yl)carbamoyl)benzoic acid;

(R)-2-(4-((6-(3-(2-ethoxyphenoxy)piperidin-1-yl)pyrazin-2-yl)carbamoyl)phenyl)acetic acid;

(R)-2-(4-((6-(3-(2-ethoxyphenoxy)piperidin-1-yl)pyrazin-2-yl)carbamoyl)phenyl)-2-methylpropanoic acid;

(R)-2-(4-((6-(3-(2-ethoxyphenoxy)piperidin-1-yl)pyrazin-2-yl)carbamoyl)phenoxy)-2-methylpropanoic acid;

(R)—N-(6-(3-(2-ethoxyphenoxy)piperidin-1-yl)pyrazin-2-yl)-1-(methylsulfonyl)piperidine)-4-carboxamide;

(R)-1-acetyl-N-(6-(3-(2-ethoxyphenoxy)piperidin-1-yl)pyrazin-2-yl)piperidine)-4-carboxamide;

(R)—N-(6-(3-(2-ethoxyphenoxy)piperidin-1-yl)pyrazin-2-yl)-1-(isopropylsulfonyl)piperidine-4-carboxamide;

(R)—N-(6-(3-(2-ethoxyphenoxy)piperidin-1-yl)pyrazin-2-yl)-1-(5-ethylpyrimidin-2-yl)piperidine-4-carboxamide;

(R)-4-((6-(3-(2-ethoxyphenoxy)piperidin-1-yl)pyrazin-2-yl)amino)-4-oxobutanoic acid;

(1R)-2-((6-((R)-3-(2-ethoxyphenoxy)piperidin-1-yl)pyrazin-2-yl)carbamoyl)cyclopentane-1-carboxylic acid;

(R)-4-((6-(3-(2-ethoxyphenoxy)piperidin-1-yl)pyrazin-2-yl)carbamoyl)bicyclo[2.2.2]octane-1-carboxylic acid;

(R)-4-((6-(3-(2-ethoxyphenoxy)piperidin-1-yl)pyrazin-2-yl)amino)-2,2-dimethyl-4-oxobutanoic acid;

(R)-1-(6-(3-(2-ethoxyphenoxy)piperidin-1-yl)pyrazin-2-yl)-3,3-dimethylpyrrolidine-2,5-dione;

(R)-5-((6-(3-(2-ethoxyphenoxy)piperidin-1-yl)pyrazin-2-yl)amino)-2,2-dimethyl-5-oxopentanoic acid;

(R)-5-((6-(3-(2-ethoxyphenoxy)piperidin-1-yl)pyrazin-2-yl)amino)-3,3-dimethyl-5-oxopentanoic acid;

(R)—N-(6-(3-(2-ethoxyphenoxy)piperidin-1-yl)pyrazin-2-yl)-2-(3-trifluoromethyl)phenyl)acetamide;

(R)-2-(3,5-bis(trifluoromethyl)phenyl)-N-(6-(3-(2-ethoxyphenoxy)piperidin-1-yl)pyrazin-2-yl)acetamide;

(R)—N-(6-(3-(2-ethoxyphenoxy)piperidin-1-yl)pyrazin-2-yl)-2-phenylacetamide;

(R)—N-(6-(3-(2-ethoxyphenoxy)piperidin-1-yl)pyrazin-2-yl)-3-phenylpropanamide;

(R)-2-(3-chlorophenyl)-N-(6-(3-(2-ethoxyphenoxy)piperidin-1-yl)pyrazin-2-yl)acetamide;

(R)—N-(6-(3-(2-ethoxyphenoxy)piperidin-1-yl)pyrazin-2-yl)-2-methyl-2-phenylpropanamide;

(R)-4-(2-((6-(3-(2-ethoxyphenoxy)piperidin-1-yl)pyrazin-2-yl)amino)-2-oxoethyl)benzoic acid;

(R)-3-(2-((6-(3-(2-ethoxyphenoxy)piperidin-1-yl)pyrazin-2-yl)amino)-2-oxoethyl)benzoic acid;

(R)-2-(4-(2-((6-(3-(2-ethoxyphenoxy)piperidin-1-yl)pyrazin-2-yl)amino)-2-oxoethyl)phenyl)acetic acid;

(R)-2-(4-(2-amino-2-oxoethyl)phenyl-N-(6-(3-(2-ethoxyphenoxy)piperidin-1-yl)pyrazin-2-yl)acetamide;

(R)—N-(6-(3-(2-ethoxyphenoxy)piperidin-1-yl)pyrazin-2-yl)-2-(4-hydroxyphenyl)acetamide;

(R)-4-(4-(2-((6-(3-(2-ethoxyphenoxy)piperidin-1-yl)pyrazin-2-yl)amino)-2-oxoethyl)phenoxy)butanoic acid;

(R)-2-(4-(2-((6-(3-(2-ethoxyphenoxy)piperidin-1-yl)pyrazin-2-yl)amino-2-oxoethyl)phenoxy)-2-methylpropanoic acid;

(R)-2-(4-(1-((6-(3-(2-ethoxyphenoxy)piperidin-1-yl)pyrazin-2-yl)amino)-2-methyl-1-oxopropan-2-yl)phenyl)-2-methylpropanoic acid;

(R)-4-(3-((6-(3-(2-ethoxyphenoxy)piperidin-1-yl)pyrazin-2-yl)amino)-3-oxopropyl)benzoic acid;

(R,E)-4-(3-((6-(3-(2-ethoxyphenoxy)piperidin-1-yl)pyrazin-2-yl)amino)-3-oxoprop-1-en-1-yl)benzoic acid;

(R,E)-4-(3-((6-(3-(2-ethoxyphenoxy)piperidin-1-yl)pyrazin-2-yl)amino)-2-methyl-3-oxoprop-1-en-1-yl)benzoic acid;

4-(3-((6-((R)-3-(2-ethoxyphenoxy)piperidin-1-yl)pyrazin-2-yl)amino)-2-methyl-3-oxopropyl)benzoic acid;

(R)-4-(3-((6-(3-(2-ethoxyphenoxy)piperidin-1-yl)pyrazin-2-yl)amino)-3-oxopropyl)-2-fluorobenzoic acid;

(R)-4-(3-((6-(3-(2-ethoxyphenoxy)piperidin-1-yl)pyrazin-2-yl)amino)-3-oxopropyl)-2-methylbenzoic acid;

(R)-4-(3-((6-(3-(2-ethoxyphenoxy)piperidin-1-yl)pyrazin-2-yl)amino)-3-oxopropyl)-2-methoxybenzoic acid;

(R)-2-chloro-4-(3-((6-(3-(2-ethoxyphenoxy)piperidin-1-yl)pyrazin-2-yl)amino)-3-oxopropyl)benzoic acid;

(R)-3-(3-((6-(3-(2-ethoxyphenoxy)piperidin-1-yl)pyrazin-2-yl)amino)-3-oxopropyl)benzoic acid;

(R)-2-(4-(3-((6-(3-(2-ethoxyphenoxy)piperidin-1-yl)pyrazin-2-yl)amino)-3-oxopropyl)phenyl)acetic acid;

(R)-3-(4-(2-amino-2-oxoethyl)phenyl-N-(6-(3-(2-ethoxyphenoxy)piperidin-1-yl)pyrazin-2-yl)propenamide;
(R)-2-(4-(3-((6-(3-(2-ethoxyphenoxy)piperidin-1-yl)pyrazin-2-yl)amino)-3-oxopropyl)phenyl)-2-methylpropanoic acid;
(R)-1-(4-(3-((6-(3-(2-ethoxyphenoxy)piperidin-1-yl)pyrazin-2-yl)amino)-3-oxopropyl)phenyl)cyclopropane-1-carboxylic acid;
(R)-4-(3-((6-(3-(2-ethoxyphenoxy)piperidin-1-yl)pyrazin-2-yl)amino)-3-oxopropyl)-2,6-difluorobenzoic acid;
(R)-2,6-dichloro-4-(3-((6-(3-(2-ethoxyphenoxy)piperidin-1-yl)pyrazin-2-yl)amino)-3-oxopropyl)benzoic acid;
(R)-4-(3-((6-(3-(2-ethoxyphenoxy)piperidin-1-yl)pyrazin-2-yl)amino)-3-oxopropyl)-2,6-dimethylbenzoic acid;
(R)-1-(4-(3-((6-(3-(2-ethoxyphenoxy)piperidin-1-yl)pyrazin-2-yl)amino)-3-oxopropyl)phenyl)piperidine-4-carboxylic acid;
(R)-1-(4-((6-(3-(2-ethoxyphenoxy)piperidin-1-yl)pyrazin-2-yl)carbamoyl-2,6-difluorophenyl)piperidine-4-carboxylic acid;
(R)-2-(1-(4-((6-(3-(2-ethoxyphenoxy)piperidin-1-yl)pyrazin-2-yl)carbamoyl-2,6-difluorophenyl)piperidin-4-yl)acetic acid;
(R)-4-(4-((6-(3-(2-ethoxyphenoxy)piperidin-1-yl)pyrazin-2-yl)carbamoyl)piperidin-1-yl)benzoic acid;
(R)-2-(4-(3-((6-(3-(2-ethoxyphenoxy)piperidin-1-yl)pyrazin-2-yl)amino)-3-oxopropyl)phenoxy)-2-methylpropanoic acid;
(R)-3-(4-(3-((6-(3-(2-ethoxyphenoxy)piperidin-1-yl)pyrazin-2-yl)amino)-3-oxopropyl)phenyl)propanoic acid;
(R)-4-(4-((6-(3-(2-ethoxyphenoxy)piperidin-1-yl)pyrazin-2-yl)carbamoyl)phenoxy)benzoic acid;
(R)-3-(4-(3-((6-(R)-3-(2-ethoxyphenoxy)piperidin-1-yl)pyrazin-2-yl)amino)-2-oxoethyl)phenyl)-2-methylpropanoic acid;
(S)-3-(4-(3-((6-(R)-3-(2-ethoxyphenoxy)piperidin-1-yl)pyrazin-2-yl)amino)-2-oxoethyl)phenyl)-2-methylpropanoic acid;
(R)-3-(4-(2-((6-(3-(2-ethoxyphenoxy)piperidin-1-yl)pyrazin-2-yl)amino)-2-oxoethyl)phenyl)-2,2-dimethylpropanoic acid;
(R)-2-(4-(2-((6-(3-(2-ethoxyphenoxy)piperidin-1-yl)pyridin-2-yl)amino)-2-oxoethyl)phenyl)acetic acid;
(R)-2-(4-(3-(6-(3-(2-ethoxyphenoxy)piperidin-1-yl)pyrazin-2-yl)ureido)phenyl)acetic acid;
(R)-2-(4-(2-((6-(3-(2-ethoxyphenoxy)piperidin-1-yl)pyridin-2-yl)amino)-2-oxoethyl)phenyl)-2-methylpropanoic acid;
(R)-2-(4-(2-((6-(3-(2-ethoxyphenoxy)piperidin-1-yl)pyrazin-2-yl)amino)-2-oxoethyl)phenyl)-2-methylpropanoic acid;
(R)-2-(4-(3-((6-(3-(2-ethoxyphenoxy)piperidin-1-yl)pyridin-2-yl)amino)-3-oxopropyl)phenyl)-2-methylpropanoic acid;
(R)-3-(4-(2-((6-(3-(2-ethoxyphenoxy)piperidin-1-yl)pyridin-2-yl)amino-2-oxoethyl)phenyl)-2,2-dimethylpropanoic acid;
(R)-3-(4-(2-((4-(3-(2-ethoxyphenoxy)piperidin-1-yl)-6-(trifluoromethyl)pyrimidin-2-yl)amino-2-oxoethyl)phenyl)-2,2-dimethylpropanoic acid;
(R)-3-(4-(1-((6-(3-(2-ethoxyphenoxy)piperidin-1-yl)pyrazin-2-yl)amino)-2-methyl-1-oxopropan-2-yl)phenyl)propanoic acid;
(R)-3-(4-((2-((6-(3-(2-ethoxyphenoxy)piperidin-1-yl)pyrazin-2-yl)carbamoyl)allyl)amino)phenyl)propanoic acid;
(R)-2-(4-((6-(3-(2-ethoxyphenoxy)piperidin-1-yl)pyrazin-2-yl)carbamoyl)piperidin-1-yl)pyrimidine-5-carboxylic acid;
3-(3-((R)-3-((6-((R)-3-((3-ethoxypyridin-2-yl)oxy)piperidin-1-yl)pyrazin-2-yl)carbamoyl)piperidin-1-yl)phenyl-2,2-dimethylpropanoic acid;
(R)-3-(4-(1-((4-(3-(2-ethoxyphenoxy)piperidin-1-yl)pyrimidin-2-yl)amino)-2-methyl-1-oxopropan-2-yl)phenyl)-2,2-dimethylpropanoic acid;
(R)-3-(4-(1-((4-(3-((3-ethoxypyridin-2-yl)oxy)piperidin-1-yl)pyrimidin-2-yl)amino)-2-methyl-1-oxopropan-2-yl)phenyl)-2,2-dimethylpropanoic acid;
(R)-2-(4-(4-((6-(3-(2-ethoxyphenoxy)piperidin-1-yl)pyrazin-2-yl)carbamoyl)piperidin-1-yl)phenyl)acetic acid;
(R)-2-(4-(4-((6-(3-(2-ethoxyphenoxy)piperidin-1-yl)pyrazin-2-yl)carbamoyl)piperidin-1-yl)phenyl)-2-methylpropanoic acid;
(R)-2-(6-(4-((6-(3-(2-ethoxyphenoxy)piperidin-1-yl)pyrazin-2-yl)carbamoyl)piperidin-1-yl)pyridin-3-yl)-2-methylpropanoic acid;
(R)-2-(5-(4-((6-(3-(2-ethoxyphenoxy)piperidin-1-yl)pyrazin-2-yl)carbamoyl)piperidin-1-yl)-2H-tetrazol-2-yl)acetic acid;
(R)-4-(4-((6-(3-(2-ethoxyphenoxy)piperidin-1-yl)pyrazin-2-yl)carbamoyl)piperidin-1-yl)-4-oxobutanoic acid;
(R)-2-(4-((6-(3-(2-ethoxyphenoxy)piperidin-1-yl)pyrazin-2-yl)carbamoyl)piperidin-1-yl)acetic acid;
3-(3-((R)-3-((6-((R)-3-(2-ethoxyphenoxy)piperidin-1-yl)pyrazin-2-yl) carbamoyl)piperidin-1-yl)phenyl)-2,2-dimethylpropanoic acid;
(R)-1-(4-(1-((6-(3-(2-ethoxyphenoxy)piperidin-1-yl)pyrazin-2-yl)amino)-2-methyl-1-oxopropan-2-yl)phenyl)piperidine-4-carboxylic acid;
6-(3-((6-((R)-3-(2-ethoxyphenoxy)piperidin-1-yl)pyrazin-2-yl)carbamoyl)pyrrolidin-1-yl)nicotinic acid;
N-(6-((R)-3-(2-ethoxyphenoxy)piperidin-1-yl)pyrazin-2-yl)-3-methylpyrrolidine-3-carboxamide;
6-(3-((6-((R)-3-(2-ethoxyphenoxy)piperidin-1-yl)pyrazin-2-yl)carbamoyl)-3-methylpyrrolidin-1-yl)nicotinic acid;
(R)-2-(4-(2-((6-(3-(2-isopropoxyphenoxy)piperidin-1-yl)pyrazin-2-yl)amino)-2-oxoethyl)phenyl)acetic acid;
(R)-2-(4-(3-((6-(3-(2-methoxyphenoxy)piperidin-1-yl)pyrazin-2-yl)amino)-3-oxopropyl)phenyl)-2-methylpropanoic acid;
(R)-2-methyl-2-(4-(3-oxo-3-((6-(3-(2-(trifluoromethoxy)phenoxy)piperidin-1-yl)pyrazin-2-yl)amino)propyl)phenyl)propanoic acid;
(R)-2-(4-(3-((6-(3-(2-(2-fluoroethoxy)phenoxy)piperidin-1-yl)pyrazin-2-yl)amino)-3-oxopropyl)phenyl)-2-methylpropanoic acid;
(R)-3-(4-(2-((6-(3-(2-(2-fluoroethoxy)phenoxy)piperidin-1-yl)pyrazin-2-yl)amino)-2-oxoethyl)phenyl)-2,2-dimethylpropanoic acid;
(R)-3-(4-(2-((6-(3-(2-cyclopropoxyphenoxy)piperidin-1-yl)pyrazin-2-yl)amino)-2-oxoethyl)phenyl)-2,2-dimethylpropanoic acid;
(R)-3-(4-(2-((6-(3-(2-cyclobutoxyphenoxy)piperidin-1-yl)pyrazin-2-yl)amino)-2-oxoethyl)phenyl)-2,2-dimethylpropanoic acid;
(R)-2-(4-(3-((6-(3-(2-cyclopropoxyphenoxy)piperidin-1-yl)pyrazin-2-yl)amino)-3-oxopropyl)phenyl)-2-methylpropanoic acid;
(R)-2-(4-(3-((6-(3-(2-cyclobutoxyphenoxy)piperidin-1-yl)pyrazin-2-yl)amino)-3-oxopropyl)phenyl)-2-methylpropanoic acid;

(R)-2-(4-(2-((6-(3-(2-ethoxyphenoxy)piperidin-1-yl)pyrazin-2-yl)amino-2-oxoethyl)phenoxy)acetic acid;
(R)-2-(4-(2-((6-(3-(2-ethoxyphenoxy)piperidin-1-yl)pyrazin-2-yl)amino)-2-oxoethoxy)phenyl)acetic acid;
2-(4-(2-((6-((R)-3-(2-ethoxyphenoxy)piperidin-1-yl)pyrazin-2-yl)amino)-2-oxoethoxy)phenyl)propanoic acid;
(R)-3-(4-(2-((6-(3-(2-ethoxyphenoxy)piperidin-1-yl)pyrazin-2-yl)amino)-2-oxoethyl)phenoxy-2,2-dimethyl-propanoic acid;
(R)-2-(4-(2-((6-((R)-3-(2-ethoxyphenoxy)piperidin-1-yl)pyrazin-2-yl)amino)-2-oxoethyl)phenoxy)propanoic acid;
(S)-2-(4-(2-((6-((R)-3-(2-ethoxyphenoxy)piperidin-1-yl)pyrazin-2-yl)amino)-2-oxoethyl)phenoxy)propanoic acid;
(R)-2-(4-(2-((6-(3-((3-ethoxypyridin-2-yl)oxy)piperidin-1-yl)pyrazin-2-yl)amino)-2-oxoethyl)phenoxy)-2-methyl-propanoic acid;
(R)-2-(4-(2-((2-(3-(2-ethoxyphenoxy)piperidin-1-yl)pyrimidin-4-yl)amino)-2-oxoethyl)phenoxy)-2-methylpropanoic acid;
(R)-2-(4-((4-(2-((6-(3-(2-ethoxyphenoxy)piperidin-1-yl)pyrazin-2-yl)amino)-2-oxoethyl)phenoxy)methyl)phenyl)-2-methylpropanoic acid;
(R)-2-(4-(3-((6-(3-((3-ethoxypyridin-2-yl)oxy)piperidin-1-yl)pyrazin-2-yl)amino)-3-oxopropyl)phenoxy)-2-methyl-propanoic acid;
(R)-2-(4-(3-((2-(3-(2-ethoxyphenoxy)piperidin-1-yl)pyrimidin-4-yl)amino)-3-oxopropyl)phenoxy)-2-methyl-propanoic acid;
(R)-3-(4-(1-((6-(3-(2-ethoxyphenoxy)piperidin-1-yl)pyrazin-2-yl)amino)-2-methyl-1-oxopropan-2-yl)phenyl)-2,2-dimethylpropanoic acid;
(R)-2-(4-(3-((6-(3-(2-ethoxyphenoxy)piperidin-1-yl)pyrazin-2-yl)amino)-2,2-dimethyl-3-oxopropyl)phenyl)-2-methylpropanoic acid;
(R)-3-(4-(2-((2-(3-(2-ethoxyphenoxy)piperidin-1-yl)pyrimidin-4-yl)amino)-2-oxoethyl)phenyl)-2,2-dimethyl-propanoic acid;
(R)-3-(4-(2-((4-(3-(2-ethoxyphenoxy)piperidin-1-yl)pyrimidin-2-yl)amino)-2-oxoethyl)phenyl)-2,2-dimethyl-propanoic acid;
(R)-3-(4-(2-((4-(3-((3-ethoxypyridin-2-yl)oxy)piperidin-1-yl)pyrimidin-2-yl)amino)-2-oxoethyl)phenyl)-2,2-dimethylpropanoic acid;
(R)-3-(4-(2-((2-(3-((3-ethoxypyridin-2-yl)oxy)piperidin-1-yl)pyrimidin-4-yl)amino)-2-oxoethyl)phenyl)-2,2-dimethylpropanoic acid;
(R)-3-(4-(2-((6-(3-((3-ethoxypyridin-2-yl)oxy)piperidin-1-yl)pyrazin-2-yl)amino)-2-oxoethyl)phenyl)-2,2-dimethylpropanoic acid;
(R)-4-(3-((6-(3-(2-ethoxyphenoxy)piperidin-1-yl)pyrazin-2-yl)amino)-3-oxopropyl)bicyclo[2.2.2]octane-1-carboxylic acid;
(R)-4-(2-((6-(3-(2-ethoxyphenoxy)piperidin-1-yl)pyrazin-2-yl)amino)-2-oxoethyl)bicyclo[2.2.2]octane-1-carboxylic acid;
(R)-4-(3-((2-(3-(2-ethoxyphenoxy)piperidin-1-yl)pyrimidin-4-yl)amino)-3-oxopropyl)bicyclo[2.2.2]octane-1-carboxylic acid;
(R)-4-(3-((6-(3-((3-ethoxypyridin-2-yl)oxy)piperidin-1-yl)pyrazin-2-yl)amino)-3-oxopropyl)bicyclo[2.2.2]octane-1-carboxylic acid;
(R,E)-4-(3-((6-(3-(2-ethoxyphenoxy)piperidin-1-yl)pyrazin-2-yl)amino)-3-oxoprop-1-en-1-yl)bicyclo[2.2.2]octane-1-carboxylic acid;
(R)-2-(4-(3-((2-(3-(2-ethoxyphenoxy)piperidin-1-yl)pyrimidin-4-yl)amino)-3-oxopropyl)phenyl)-2-methylpropanoic acid
(R)-2-(4-(3-((6-(3-((3-ethoxypyridin-2-yl)oxy)piperidin-1-yl)pyrazin-2-yl)amino)-3-oxopropyl)phenyl)-2-methyl-propanoic acid;
(R)-3-(4-(1-((2-(3-(2-ethoxyphenoxy)piperidin-1-yl)pyrimidin-4-yl)amino)-2-methyl-1-oxopropan-2-yl)phenyl)-2,2-dimethylpropanoic acid;
(R)-3-(4-(1-((6-(3-((3-ethoxypyridin-2-yl)oxy)piperidin-1-yl)pyrazin-2-yl)amino)-2-methyl-1-oxopropan-2-yl)phenyl)-2,2-dimethylpropanoic acid;
(R)-3-(4-(1-((6-(3-(2-cyclobutoxyphenoxy)piperidin-1-yl)pyrazin-2-yl)amino)-2-methyl-1-oxopropan-2-yl)phenyl)-2,2-dimethylpropanoic acid;
(R)-3-(3-(3-((6-(3-(2-ethoxyphenoxy)piperidin-1-yl)pyrazin-2-yl)amino)-3-oxopropyl)phenyl)-2,2-dimethyl-propanoic acid;
(R)-3-(3-(3-((6-(3-((3-ethoxypyridin-2-yl)oxy)piperidin-1-yl)pyrazin-2-yl)amino)-3-oxopropyl)phenyl)-2,2-dimethylpropanoic acid;
(R)-3-(3'-((6-(3-(2-ethoxyphenoxy)piperidin-1-yl)pyrazin-2-yl)carbamoyl)-[1,1'-biphenyl]-3-yl)-2,2-dimethylpropanoic acid; and
(R)-3-(3'-((6-(3-(2-ethoxyphenoxy)piperidin-1-yl)pyrazin-2-yl)carbamoyl)-[1,1'-biphenyl]-4-yl)-2,2-dimethylpropanoic acid.

The terms and abbreviations used herein retain their original meanings unless indicated otherwise.

The present invention also provides a method for preparing the compound of Formula (1). Hereinafter, the method for preparing the compound of Formula (1) is explained based on exemplary reactions in order to illustrate the present invention. However, a person skilled in the art could prepare the compound of Formula (1) by various methods based on the structure of Formula (1), and such methods should be interpreted as being within the scope of the present invention. That is, the compound of Formula (1) may be prepared by the methods described herein or by combining various methods disclosed in the prior art, which should be interpreted as being within the scope of the present invention. Accordingly, a method for preparing the compound of Formula (1) is not limited to the following methods.

The compound of Formula (1) of the present invention may be prepared by directly introducing a substituted amide group such as a compound of Formula (4) into compound (2), or by introducing a protected amine into compound (2), removing the protecting group, and then performing an amidation reaction on the prepared compound (3), according to the method of Reaction Scheme 1 below.

[Reaction Scheme 1]

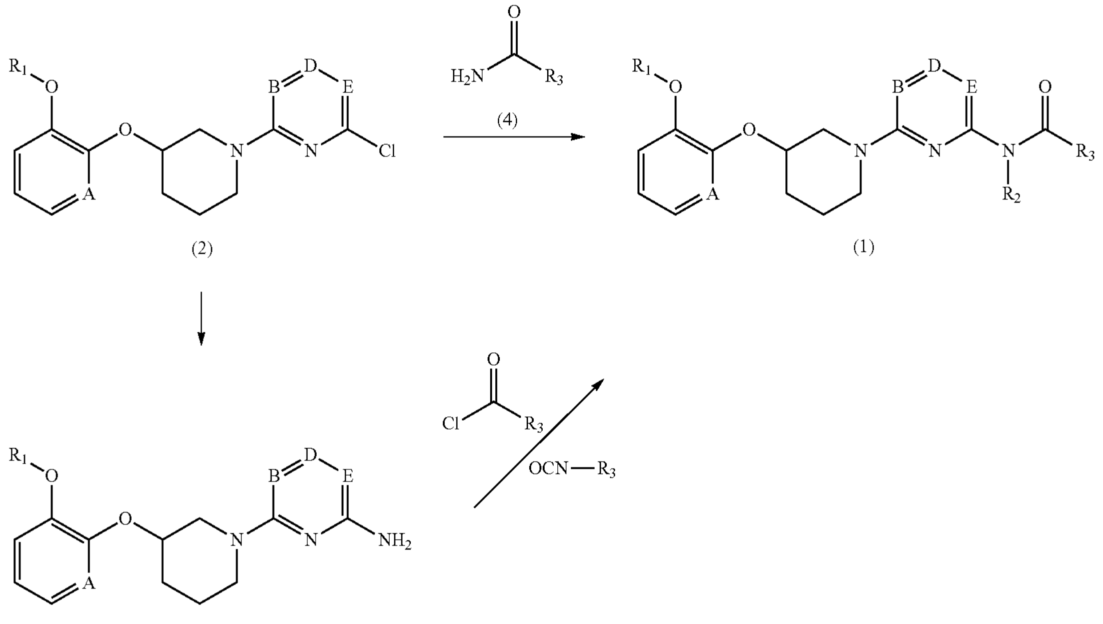

(2) (1) (3)

Compound (2) may be prepared from tert-butyl-3-hydroxypiperidine-1-carboxylate as a starting material according to the method of following Reaction Scheme 2.

[Reaction Scheme 2]

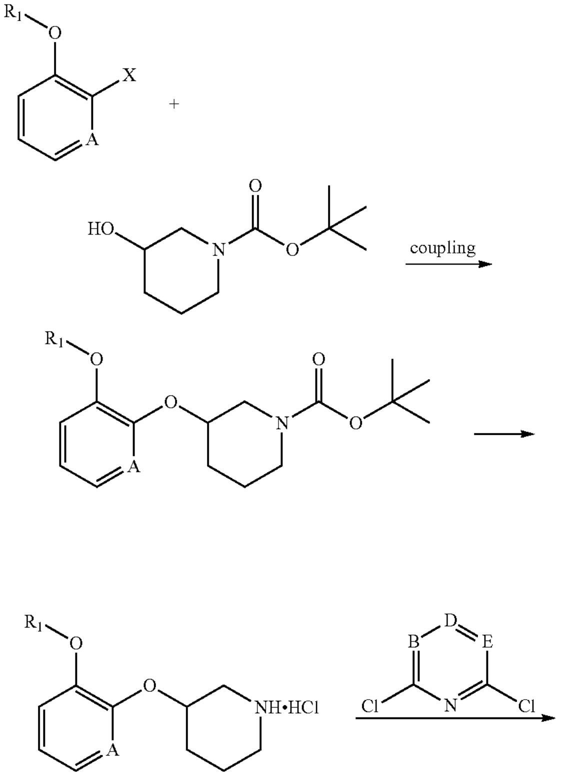

-continued

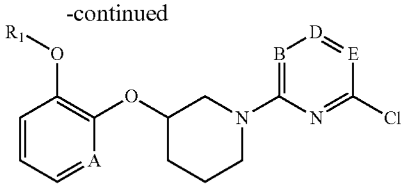

(2)

X = OH or Cl

In addition, compound (3) may be prepared according to the method of following Reaction Scheme 3.

[Reaction Scheme 3]

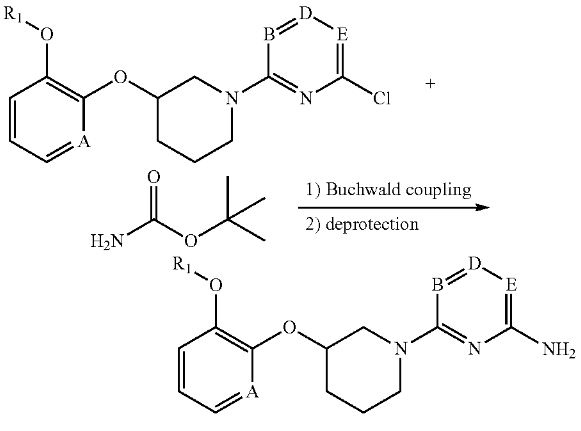

(3)

Amide derivatives in the compound of Formula (4) in Scheme 1 can be obtained by treatment with thionyl chloride or oxalyl chloride from a suitable acid and then treatment with ammonia water. For example, methyl 4-(3-amino-3-oxopropyl)benzoate can be prepared according to the method of Reaction Scheme 4 below.

[Reaction Scheme 4]

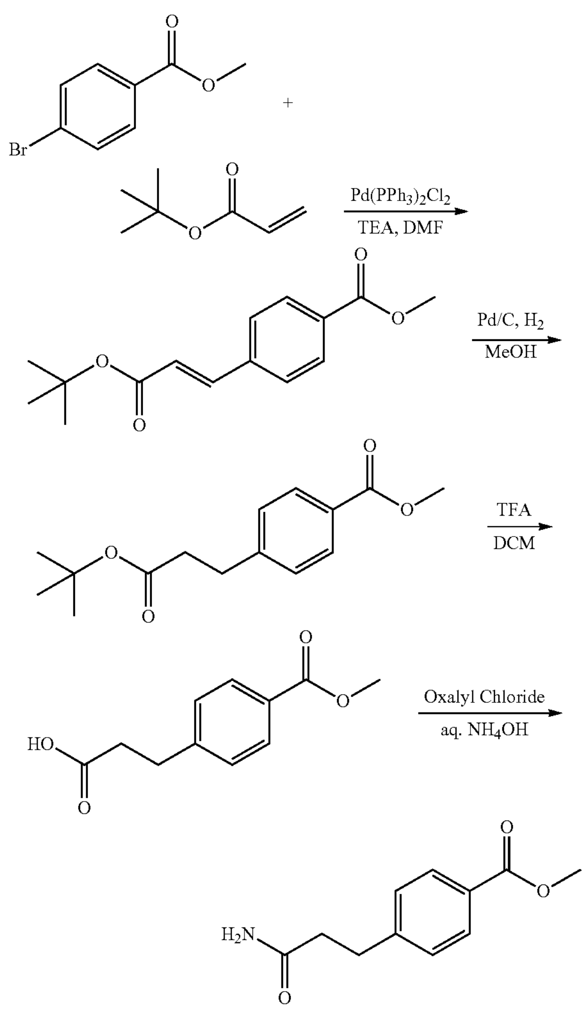

A compound not specifically described in the preparation method of the present specification is a known compound or a compound that can be easily synthesized from a known compound by a known synthesis method or a similar method.

The compound of Formula (1) obtained by the above methods can be separated or purified from the reaction products by conventional methods such as recrystallization, ionospheresis, silica gel column chromatography or ion-exchange chromatography.

As explained above, the compounds according to the present invention, starting materials or intermediates for the preparation thereof can be prepared by a variety of methods, which should be interpreted as being within the scope of the present invention in respect to the preparation of the compound of Formula (1).

The compound of Formula (1) according to the present invention exhibits inhibitory activity against diacylglycerol acyltransferase 2 (DGAT2). Accordingly, the present invention provides a pharmaceutical composition for the treatment of diseases associated with DGAT2 comprising the compound of Formula (1), or a pharmaceutically acceptable salt or isomer thereof, together with a pharmaceutically acceptable carrier. Various kinds of prodrugs, which are converted into the compound of Formula (1) in vivo, are also within the scope of the present invention.

Exemplary diseases associated with DGAT2 which can be treated by the pharmaceutical composition according to the present invention include, but are not limited to, that selected from the group consisting of fatty liver, nonalcoholic steatohepatitis (NASH), nonalcoholic fatty liver disease (NAFLD), diabetes, obesity, hyperlipidemia, atherosclerosis and hypercholesterolemia.

In the present invention, a "pharmaceutical composition" may include other components such as carriers, diluents, excipients, etc., in addition to the active ingredient of the present invention. Accordingly, the pharmaceutical composition may include pharmaceutically acceptable carriers, diluents, excipients or combinations thereof, if necessary. The pharmaceutical composition facilitates the administration of compounds into the body. Various methods for administering the compounds include, but are not limited to, oral, injection, aerosol, parenteral and local administration.

Herein, a "carrier" means a compound that facilitates the addition of compounds into the cell or tissue. For example, dimethylsulfoxide (DMSO) is a conventional carrier facilitating the administration of many organic compounds into living cells or tissues.

Herein, a "diluent" means a compound that not only stabilizes a biologically active form but is diluted in solvent dissolving the compounds. A dissolved salt in buffer is used as a diluent in this field. A conventionally used buffer is a phosphate buffer saline mimicking salt form in body fluid. Since a buffer solution can control the pH of the solution at low concentration, a buffer diluent hardly modifies the biological activity of compounds.

Herein, "pharmaceutically acceptable" means such property that does not impair the biological activity and physical property of compounds.

The compounds according to the present invention can be formulated as various pharmaceutically administered dosage forms. In the preparation of the pharmaceutical composition of the present invention, an active component—specifically, the compound of Formula (1) or a pharmaceutically acceptable salt or isomer thereof—is mixed with selected pharmaceutically acceptable carriers considering the dosage form to be prepared. For example, the pharmaceutical composition of the present invention can be formulated as injections, oral preparations and the like, as needed.

The compound of the present invention can be formulated by conventional methods using known pharmaceutical carriers and excipients, and inserted into a unit or multi-unit containers. The formulations may be solution, suspension or emulsion in oil or aqueous solvent and include conventional dispersing agents, suspending agents or stabilizing agents. In addition, the compound may be, for example, dry powder form which is dissolved in sterilized pyrogen-free water before use. The compound of the present invention can be formulated into suppositories by using a conventional suppository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the compounds of the present invention with at least one carrier selected from inert diluents such as sucrose, lactose or starch, lubricants such as magnesium stearate, disintegrating agents, binders and the like.

The compound or a pharmaceutical composition comprising the same according to the present invention can be administered in combination with other drugs—for example, other metabolic disorder therapeutic agents—as required.

The dose of the compound of Formula (1) according to the present invention is determined by a physician's prescription considering the patient's body weight, age and disease condition. A typical dose for adults is in the range of about 0.3 to 500 mg per day according to the frequency and intensity of administration. A typical daily dose of intramuscular or intravenous administration for adults is in the range of about 1 to 300 mg per day which can be administered in divided unit dosages. Some patients need a higher daily dose.

Herein, the term "treatment" is used to mean deterring, delaying or ameliorating the progress of diseases in a subject exhibiting symptoms of diseases.

Advantageous Effects of Invention

The novel amide derivative compound of Formula (1) according to the present invention exhibits excellent inhibitory activity against diacylglycerol acyltransferase 2 (DGAT2), and thus can be usefully used in the prevention, alleviation or treatment of metabolic disorders associated with DGAT2. In addition, the novel amide derivative compound of Formula (1) according to the present invention exhibits increased lipophilicity and liver selectivity, thereby improving efficacy through increased exposure to the liver, as well as expecting the advantages of convenience in taking because the half-life is relatively long in disease animal models and clinical practice.

MODE FOR THE INVENTION

Hereinafter, the present invention will be described in more detail through preparation examples and examples. However, these examples are only illustrative, and the scope of the present invention is not limited thereto.

In the following examples, M refers to molar concentration, and N refers to normal concentration. In addition, the descriptions of abbreviations and terms used in the Reaction Scheme, Preparation Examples and Examples are as follows:

DCM: dichloromethane
DIPEA: diisopropylethylamine
DMF: N,N-dimethylformamide
EA: ethyl acetate
HCl: hydrochloric acid
TBAF: tetrabutylammonium fluoride
TEA: triethylamine
TFA: trifluoroacetic acid
THF: tetrahydrofuran

Preparation Example 1: (R)-2-chloro-6-(3-(2-ethoxyphenoxy)piperidin-1-yl)pyrazine

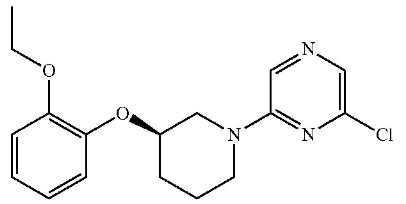 [SMILES: CCOc1ccccc1O[C@@H]1CCCN(c2cncc(Cl)n2)C1]

Step 1: Tert-butyl-(R)-3-(2-ethoxyphenoxy)piperidine-1-carboxylate (S)-tert-butyl-3-hydroxypiperidine-1-carboxylate (30.0 g, 149 mmol), 2-ethoxyphenol (20.6 g, 149 mmol) and triphenylphosphine (43.8 g, 167 mmol) were dissolved in 500 mL of toluene and stirred at room temperature. To the reaction mixture, diethylazodicarboxylate (30.4 mL) was diluted in 50 ml of toluene and slowly added dropwise. After stirring at room temperature for 15 hours, the reaction mixture was filtered, washed with 300 mL of diethyl ether and washed with 100 mL of 3 N sodium hydroxide solution. The organic solvent was dried over magnesium sulfate and removed under reduced pressure. The purification was carried out by silica gel column (ethyl acetate:hexane=1:6) to obtain the desired product. (Yield: 47%)

m/z $(M+NH_4)^+$ calculated for $C_{18}H_{27}NO_4$: 344, found 344.2.

$^1$H NMR (300 MHz, CHLOROFORM-D): δ 6.89-6.95 (m, 4H), 4.07 (m, 3H), 3.9 (bs, 1H), 3.66 (bs, 1H), 3.16 (m, 2H), 2.07 (bs, 1H), 1.76-1.83 (m, 2H), 1.45 (m+s, 3H)

Step 2: (R)-3-(2-ethoxyphenoxy)piperidine hydrochloride

Tert-butyl-(R)-3-(2-ethoxyphenoxy)piperidine-1-carboxylate (10.0 g, 31.1 mmol) obtained in Step 1 was dissolved in 100 mL of dichloromethane, and 4 M hydrochloric acid solution was added dropwise thereto at room temperature. After stirring at room temperature for 4 hours, the termination of the reaction was confirmed by TLC experiment, and the organic solvent was removed under reduced pressure. After dilution with ethyl acetate, the mixture was washed with an aqueous sodium hydrogen carbonate solution, and the organic solvent was dried over magnesium sulfate. The compound obtained through distillation under reduced pressure was used in the next reaction without further purification.

m/z $(M+H)^+$ calculated for $C_{13}H_{19}NO_2$: 221.3, found 222.1.

Step 3: (R)-2-chloro-6-(3-(2-ethoxyphenoxy)piperidin-1-yl)pyrazine (R)-3-(2-ethoxyphenoxy)piperidine hydrochloride obtained in Step 2, 2,6-dichloropyrazine (5.10 g, 34.2 mmol) and triethylamine (13 mL, 93 mmol) were mixed with 100 mL of ethanol and stirred at room temperature. After stirring at room temperature for 24 hours, the termination of the reaction was confirmed through TLC experiment. After removing the organic solvent under reduced pressure, the mixture was dissolved in ethyl acetate and washed with brine. The organic solvent was dried over magnesium sulfate and removed under reduced pressure. The purification was carried out by silica gel column (ethyl acetate:hexane=1:3) to obtain the desired product. (Yield: 91%)

m/z $(M+Na)^+$ calculated for $C_{17}H_{20}ClN_3O_2$:Na 356.8, found 356.1.

$^1$H-NMR (500 MHz, CHLOROFORM-D) δ 7.93 (s, 1H), 7.74 (s, 1H), 7.04-6.93 (m, 2H), 6.92-6.80 (m, 2H), 4.35-4.24 (m, 1H), 4.07-3.89 (m, 3H), 3.82-3.68 (m, 1H), 3.67-3.46 (m, 2H), 2.09 (q, J=4.3 Hz, 1H), 2.02-1.97 (m, 1H), 1.93 (q, J=4.3 Hz, 1H), 1.68-1.58 (m, 1H), 1.38 (t, J=7.0 Hz, 3H)

Preparation Example 2: (R)-6-(3-(2-ethoxyphenoxy)piperidin-1-yl)pyrazin-2-amine

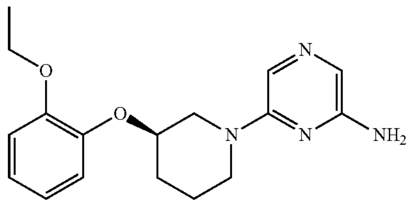 [SMILES: CCOc1ccccc1O[C@@H]1CCCN(c2cncc(N)n2)C1]

Step 1: Tert-butyl (R)-(6-(3-(2-ethoxyphenoxy)piperidin-1-yl)pyrazin-2-yl)carbamate (R)-2-chloro-6-(3-(2-ethoxyphenoxy)piperidin-1-yl) pyrazine (1.41 g, 4.22 mmol) obtained in Preparation Example 1, tert-butyl carbamate (0.55) g, 4.65 mmol), cesium carbonate (3.44 g, 10.56 mmol), 4,5-bis(diphenylphosphino)-9,9-dimethylxanthine (220 mg, 0.38 mmol) and tris(dibenzylideneacetone)dipalladium(0) (232 mg, 0.25 mmol) were dissolved in 50 mL of 1,4-dioxane, dissolved oxygen was removed through nitrogen bubbling under stirring, and then the inflow of external air was blocked in an airtight container. The reaction mixture was stirred at 110° C. for 5 hours and then cooled to room temperature. After filtering through a Celite pad and removing the organic solvent under reduced pressure, the mixture was dissolved in ethyl acetate and washed with brine. The organic solvent was dried over magnesium sulfate and removed under reduced pressure. The purification was carried out by silica gel column (ethyl acetate:hexane=3:1) to obtain the desired product. (Yield: 89%)

m/z $(M+H)^+$ calculated for $C_{22}H_{30}N_4O_4$: 415.5, found 415.0.

$^1$H-NMR (500 MHz, CHLOROFORM-D) δ 8.40 (s, 1H), 7.78 (s, 1H), 6.96 (t, J=7.0 Hz, 2H), 6.91-6.77 (m, 2H), 6.66 (s, 1H), 4.48-4.15 (m, 1H), 4.14-3.85 (m, 3H), 3.84-3.69 (m, 1H), 3.52-3.41 (1H), 3.40-3.23 (m, 1H), 2.11 (t, J=6.1 Hz, 1H), 2.01-1.92 (m, 1H), 1.88 (q, J=4.3 Hz, 1H), 1.57 (dt, J=13.4, 4.0 Hz, 1H), 1.52 (s, 9H), 1.37 (t, J=7.0 Hz, 3H)

Step 2: (R)-6-(3-(2-ethoxyphenoxy)piperidin-1-yl) pyrazin-2-amine

Tert-butyl (R)-(6-(3-(2-ethoxyphenoxy)piperidin-1-yl) pyrazin-2-yl)carbamate obtained in Step 1 was dissolved in 10 mL of dichloromethane, and 2 mL of trifluoroacetic acid was added dropwise thereto while stirring. After confirming that the reaction was completed by TLC, the organic solvent was removed under reduced pressure. The reaction mixture was diluted with ethyl acetate and washed with an aqueous sodium hydrogen carbonate solution. The organic solvent was dried with magnesium sulfate and removed under reduced pressure to obtain a crude product, and the next reaction was carried out without further purification.

m/z $(M+H)^+$ calculated for $C_{17}H_{22}N_4O_2$: 315.3, found 315.0.

$^1$H NMR (300 MHz, CHLOROFORM-D): δ 7.49 (s, 1H), 7.28 (s, 1H), 7.27 (d, 1H), 6.90-7.05 (m, 3H), 3.80-4.25 (m, 7H), 3.25 (m, 2H), 2.18 (m, 1H), 1.75-1.98 (m, 2H), 1.91 (m, 1H), 1.43 (t, 3H), 1.27 (m, 1H)

Preparation Example 3: Methyl 2-(4-carbamoylphenyl)acetate

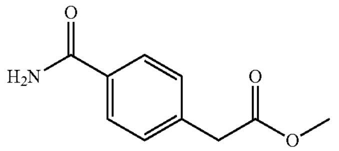

Step 1: 4-(2-Methoxy-2-oxoethyl)benzoic acid 0.34 mL of thionyl chloride was slowly added dropwise to 150 mL of methanol at 0° C. Then, 4-(carboxymethyl) benzoic acid (17.0 g, 94 mmol) was dissolved and stirred at room temperature for 5.5 hours. After confirming that the reaction was completed by TLC, the organic solvent was removed under reduced pressure. The reaction mixture was diluted with 200 mL of diethyl ether, washed with an aqueous sodium hydrogen carbonate solution (2×50 mL) and water (30 mL), and the obtained aqueous solution layer was acidified at 0° C. with concentrated hydrochloric acid. The obtained solid was filtered, washed with water and dried to obtain the desired product. (Yield: 71%)

Step 2: Methyl 2-(4-carbamoylphenyl)acetate 4-(2-Methoxy-2-oxoethyl)benzoic acid (1.0 g, 5.15 mmol) obtained in Step 1 was dissolved in 30 ml of dichloromethane, and thionyl chloride (0.8 ml, 10.3 mmol) was slowly added dropwise at room temperature. After stirring at room temperature for 4 hours, the organic solvent was removed under reduced pressure. The mixture was dissolved in 5 mL of THF, and then slowly added dropwise to 25% aqueous ammonia solution at 0° C. After stirring for 1 hour, the resulting solid was filtered to obtain the desired product.

Preparation Example 4: Methyl 2-(4-carbamoylphenyl)-2-methylpropanoate

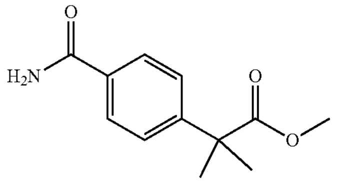 [SMILES: COC(=O)C(C)(C)c1ccc(C(N)=O)cc1]

Step 1: 2-(Trimethylsilyl)ethyl 4-(2-methoxy-2-oxoethyl)benzoate 4-(2-Methoxy-2-oxoethyl)benzoic acid (7.1 g, 36.6 mmol) obtained in Step 1 of Preparation Example 3 was dissolved in 12 mL of THF in the presence of nitrogen, and 2-(trimethylsilyl)ethan-1-ol (6.5 g, 54.8 mmol) and triphenylphosphine (24 g, 91 mmol) were sequentially added. Diisopropyl azodicarboxylate (16.35 mL) was dissolved in 30 mL of THF and slowly added dropwise thereto. The mixture was stirred at room temperature for 15 hours. After confirming that the starting materials disappeared by TLC, the mixture was filtered and washed with 100 mL of diethyl ether. After washing the organic layer with 3 N sodium hydroxide solution, the organic solvent was dried over magnesium sulfate and removed under reduced pressure. The purification was carried out by silica gel column (ethyl acetate:hexane=1:10) to obtain the desired product. (Yield: 35%)

Step 2: 2-(Trimethylsilyl)ethyl 4-(1-methoxy-2-methyl-1-oxoprop-2-yl)benzoate 2-(Trimethylsilyl)ethyl 4-(2-methoxy-2-oxoethyl)benzoate (3.81 g, 12.9 mmol) obtained in Step 1 was dissolved in 50 mL of dimethylformamide, and sodium hydride (60%, 1.04 g, 25.9 mmol) was slowly added dropwise at 0° C. After stirring for 15 minutes, iodomethane (1.62 mL, 25.9 mmol) was slowly added dropwise and stirred at room temperature for 12 hours. The reaction was terminated with 1 N aqueous hydrochloric acid solution, and the reaction mixture was extracted with ethyl acetate (2×30 mL) and washed with brine (20 mL). The organic solvent was dried over magnesium sulfate and removed under reduced pressure. The purification was carried out by silica gel column (ethyl acetate:hexane=1:9) to obtain the desired product. (Yield: 76%)

Step 3: 4-(1-Methoxy-2-methyl-1-oxoprop-2-yl)benzoic acid 2-(Trimethylsilyl)ethyl 4-(1-methoxy-2-methyl-1-oxoprop-2-yl)benzoate (1.0 g, 3.10 mmol) obtained in Step 2 was dissolved in 10 mL of THF in the presence of nitrogen, and 1.0 M TBAF (4.65 mL, 4.65 mmol) was added at 0° C. and stirred at room temperature for 12 hours. After confirming that the starting materials disappeared by TLC, THF was concentrated under reduced pressure, adjusted to pH 2 with 1 N hydrochloric acid solution together with $H_2O$ (3 mL), and the resulting solid was obtained by filtration.

Step 4: Methyl 2-(4-carbamoylphenyl)-2-methylpropanoate 4-(1-Methoxy-2-methyl-1-oxoprop-2-yl)benzoic acid obtained in Step 3 was used in a similar manner to Step 2 of Preparation Example 3 to obtain the desired product.

Preparation Example 5: Ethyl 2-(4-carbamoylphenoxy)-2-methylpropanoate

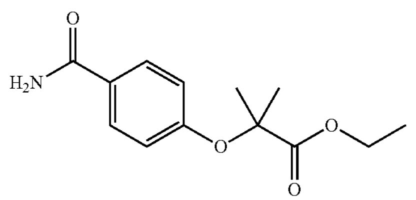 [SMILES: CCOC(=O)C(C)(C)Oc1ccc(C(N)=O)cc1]

Using benzyl 4-hydroxybenzoate (0.73 g, 3.20 mmol) and ethyl 2-bromo-2-methylpropanoate (0.563 ml, 3.84 mmol), the methods of Preparation Example 7, Step 2 of Preparation Example 10 and Step 3 of Preparation Example 6 were performed sequentially to obtain the desired product. (Yield: 46%)

$^1$H-NMR (500 MHz, CHLOROFORM-D): δ 7.72 (d, 2H), 6.85 (d, 2H), 5.97 (s, 1H), 5.75 (s, 1H), 4.23 (m, 2H), 1.63 (s, 6H), 1.23 (t, 3H)

Preparation Example 6: Methyl 2-(4-(2-amino-2-oxoethyl)phenyl)acetate

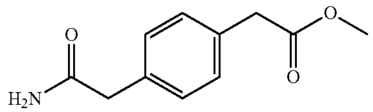

Step 1: Dimethyl 2,2'-(1,4-phenylene)diacetate

Acetyl chloride (2.9 mL, 40.8 mmol) was slowly added dropwise to methanol (20 mL) at 0° C. Then, 1,4-phenylenediacetic acid (4.0 g, 20.6 mmol) was dissolved, and the mixture was stirred under reflux for 5 hours. After confirming that the reaction was completed by TLC, the mixture was cooled to room temperature, and the organic solvent was removed under reduced pressure. The reaction product was diluted with 100 mL of ethyl acetate, washed with an aqueous sodium hydrogen carbonate solution and brine, and the organic solvent was dried over magnesium sulfate and removed under reduced pressure to obtain the desired product.

$^1$H-NMR (500 MHz, CHLOROFORM-D) δ 7.24 (s, 2H), 3.68 (s, 3H), 3.61 (s, 2H)

Step 2: 2-(4-(2-Methoxy-2-oxoethyl)phenyl)acetic acid

Dimethyl 2,2'-(1,4-phenylene)diacetate (4.58 g, 20.6 mmol) obtained in Step 1 was dissolved in THF (30 mL) and methanol (10 mL), and 10 mL of 2 N sodium hydroxide was slowly added dropwise and stirred at room temperature for 3 hours. The organic solvent was removed under reduced pressure, and the reaction mixture was diluted with water and acidified with 2 N hydrochloric acid solution. After extraction with ethyl acetate, the organic solvent was dried over magnesium sulfate and removed under reduced pressure. The desired product was obtained through recrystallization. (Yield: 30%)

$^1$H-NMR (500 MHz, CHLOROFORM-D) δ 7.25 (d, J=4.9 Hz, 4H), 3.68 (s, 3H), 3.66-3.62 (2H), 3.61 (s, 2H)

Step 3: Methyl 2-(4-carbamoylphenoxy)-2-methylpropanoate 2-(4-(2-Methoxy-2-oxoethyl)phenyl)acetic acid (1.0 g, 4.8 mmol) obtained in Step 2 was dissolved in 30 mL of dichloromethane, and thionyl chloride (0.7 mL, 9.6 mmol) was slowly added dropwise at room temperature. After stirring at room temperature for 4 hours, the organic solvent was removed under reduced pressure, and the reaction mixture was dissolved in 5 m of THF, and then slowly added dropwise to 25% aqueous ammonia solution at 0° C. After stirring for 1 hour, the resulting solid was filtered to obtain the desired product. (Yield: 74%)

$^1$H-NMR (500 MHz, DMSO-D6) δ 7.42 (s, 1H), 7.15 (dd, J=12.2, 7.9 Hz, 4H), 6.83 (s, 1H), 3.60 (s, 2H), 3.57 (d, J=4.3 Hz, 3H), 3.30 (s, 2H)

Preparation Example 7: Ethyl 4-(4-(2-amino-2-oxoethyl)phenoxy)butanoate

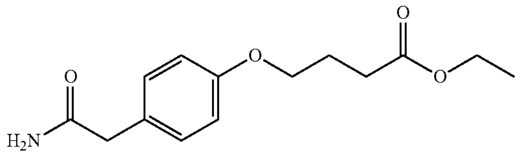 [SMILES: CCOC(=O)CCCOc1ccc(CC(N)=O)cc1]

2-(4-Hydroxyphenyl)acetamide (1.00 g, 6.62 mmol), ethyl 4-bromobutanoate (1.041 ml, 7.28 mmol) and cesium carbonate (4.31 g, 13.23 mmol) were dissolved in DMF (22.05 mL). The reaction mixture was stirred at room temperature for 48 hours. When the reaction was completed, water was added to the reaction solution, followed by extraction with ethyl acetate. The organic layer was concentrated under reduced pressure and purified by silica gel column (ethyl acetate:hexane=2:1) to obtain the desired product. (Yield: 66%)

$^1$H-NMR (500 MHz, CHLOROFORM-D): δ 7.16 (d, 2H), 6.85 (d, 2H), 5.89 (s, 1H), 5.45 (s, 1H), 4.13 (m, 2H), 3.97 (t, 2H), 3.48 (s, 2H), 2.51 (m, 2H), 2.10 (m, 2H), 1.25 (t, 3H)

Preparation Example 8: Ethyl 2-(4-(2-amino-2-oxoethyl)phenoxy)-2-methylpropanoate

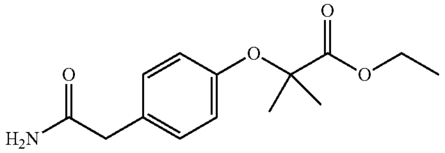 [SMILES: CCOC(=O)C(C)(C)Oc1ccc(CC(N)=O)cc1]

2-(4-Hydroxyphenyl)acetamide (2.0 g, 13.23 mmol) and ethyl 2-bromo-2-methylpropanoate (3.88 mL, 26.5 mmol) were used in a similar manner to Preparation Example 7 to obtain the desired product. (Yield: 26%)

$^1$H-NMR (500 MHz, CHLOROFORM-D): δ 7.11 (d, 2H), 6.79 (d, 2H), 6.03 (s, 1H), 5.54 (s, 1H), 4.22 (m, 2H), 3.46 (s, 2H), 1.56 (s, 6H), 1.24 (t, 3H)

Preparation Example 9: Methyl 2-(4-(1-amino-2-methyl-1-oxopropan-2-yl)phenyl)-2-methylpropanoate

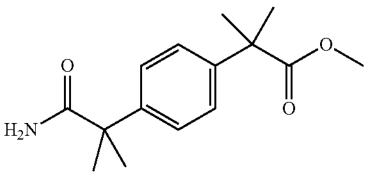 [SMILES: COC(=O)C(C)(C)c1ccc(C(C)(C)C(N)=O)cc1]

Step 1: Dimethyl 2,2'-(1,4-phenylene)bis(2-methylpropanoate)

Dimethyl 2,2'-(1,4-phenylene)diacetate (3.0 g, 13.5 mmol) obtained in Step 1 of Preparation Example 6 was dissolved in 50 mL of dimethylformamide, and sodium hydride (60%, 2.16 g, 54 mmol) was slowly added dropwise. After stirring for 15 minutes, iodomethane (3.71 mL, 59.4 mmol) was slowly added dropwise and stirred at room temperature for 12 hours. The reaction was terminated with a 1 N aqueous hydrochloric acid solution, the resulting product was extracted with ethyl acetate and washed with brine, and the organic solvent was dried with magnesium sulfate and removed under reduced pressure. The purification was carried out by silica gel column (ethyl acetate: hexane=1:9) to obtain the desired product. (Yield: 76%)

$^1$H-NMR (400 MHz, CHLOROFORM-D) δ 7.28 (s, 4H), 3.66 (s, 6H), 1.57 (s, 12H)

Step 2: Methyl 2-(4-(1-amino-2-methyl-1-oxopropan-2-yl)phenyl)-2-methylpropanoate Using dimethyl 2,2'-(1,4-phenylene)bis(2-methylpropanoate) obtained in Step 1, the methods of Steps 2 and 3 of Preparation Example 6 were sequentially performed to obtain the title compound. (Yield: 26%)

$^1$H-NMR (400 MHz, CHLOROFORM-D) δ 7.25-7.29 (m, 4H), 5.31-5.38 (brs, 2H), 3.66 (s, 3H), 1.56 (s, 12H)

Preparation Example 10: Methyl 4-(3-amino-3-oxopropyl)benzoate

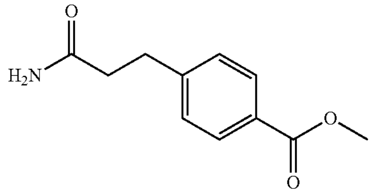

Step 1: Methyl (E)-4-(3-tert-butoxy)-3-oxoprop-1-en-1-yl)benzoate

Methyl 4-bromobenzoate (16.4 g, 0.07 mol), tert-butyl acrylate (18 g, 0.14 mol) and triethylamine (50 mL, 0.35 mol) were dissolved in 200 mL of dimethylformamide, and the dissolved oxygen was removed by bubbling with nitrogen, and bis(triphenylphosphine) palladium dichloride (2.5 g, 3.58 mmol) was added and stirred at 75° C. for 12 hours. The organic solvent was removed under reduced pressure, and the reaction mixture was diluted with ethyl acetate, washed with brine and dried with magnesium sulfate. The organic solvent was removed under reduced pressure. The purification was carried out by silica gel column (ethyl acetate:hexane=1:3) to obtain the desired product. (Yield: 79%)

$^1$H-NMR (500 MHz, CHLOROFORM-D) δ 7.56 (d, J=15.9 Hz, 1H), 7.46 (d, J=8.7 Hz, 2H), 7.28 (d, J=7.9 Hz, 2H), 6.34 (d, J=15.9 Hz, 1H), 3.70 (s, 3H), 3.64 (s, 2H), 1.53 (s, 9H)

Step 2: Methyl 4-(3-(tert-butoxy)-3-oxopropyl)benzoate

Methyl (E)-4-(3-tert-butoxy)-3-oxoprop-1-en-1-yl)benzoate (5.0 g, 18 mmol) obtained in Step 1 was dissolved in 50 mL of methanol, palladium charcoal (0.5 g) was added dropwise, and a reduction reaction was performed using a hydrogen balloon. After confirming that the reaction was complete, the resulting product was filtered through a Celite pad, and the organic solvent was removed under reduced pressure to obtain the desired product. (Yield: 93%)

$^1$H-NMR (500 MHz, CHLOROFORM-D) δ 7.17 (dd, J=18.3, 7.9 Hz, 4H), 3.68 (s, 3H), 3.59 (s, 2H), 2.88 (t, J=7.9 Hz, 2H), 2.52 (t, J=7.6 Hz, 2H), 1.41 (s, 9H)

Step 3: 3-(4-(Methoxycarbonyl)phenyl)propanoic acid

Methyl 4-(3-(tert-butoxy)-3-oxopropyl)benzoate (4.67 g, 16.8 mmol) obtained in Step 2 was dissolved in 100 mL of 20% trifluoroacetic acid/dichloromethane solution and stirred at room temperature for 2 hours. After confirming that the reaction was completed, the organic solvent was removed under reduced pressure, and the desired product was obtained through recrystallization. (Yield: 100%)

$^1$H-NMR (500 MHz, CHLOROFORM-D) δ 9.58 (s, 2H), 7.18 (dd, J=19.0, 7.9 Hz, 4H), 3.70 (s, 3H), 3.61 (s, 2H), 2.95 (t, J=7.6 Hz, 2H), 2.69 (t, J=7.9 Hz, 2H)

Step 4: Methyl 4-(3-amino-3-oxopropyl)benzoate

Using 3-(4-(methoxycarbonyl)phenyl)propanoic acid (2.08 g, 9.98 mmol) obtained in Step 3, the desired product was obtained through an amidation reaction in a similar manner to Step 3 of Preparation Example 6. (Yield: 65%)

$^1$H-NMR (500 MHz, CHLOROFORM-D) δ 7.18 (q, J=7.7 Hz, 4H), 5.41 (s, 2H), 3.66 (d, J=15.9 Hz, 3H), 3.59 (s, 2H), 3.02-2.87 (2H), 2.51 (t, J=7.6 Hz, 2H)

Preparation Example 11: Methyl (E)-4-(3-amino-3-oxoprop-1-en-1-yl)benzoate

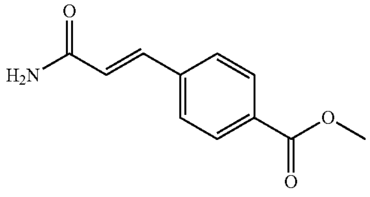

Using methyl (E)-4-(3-tert-butoxy)-3-oxoprop-1-en-1-yl) benzoate (0.09 g, 0.44 mmol) obtained in Step 1 of Preparation Example 10, the desired product was obtained through a hydrolysis reaction (yield: 100%) and amidation reaction (yield: 76%) in a similar manner to Steps 3 and 4 of Preparation Example 10.

$^1$H-NMR (400 MHz, CHLOROFORM-D) δ 8.05 (d, J=8.4 Hz, 2H), 7.68 (d, J=15.6 Hz, 1H), 7.58 (d, J=8.4 Hz, H), 6.53 (d, J=15.6 Hz, 1H), 5.5 (brds, 2H), 3.93 (s, 3H)

Preparation Example 12: Methyl (E)-4-(3-amino-2-methyl-3-oxoprop-1-en-1-yl)benzoate

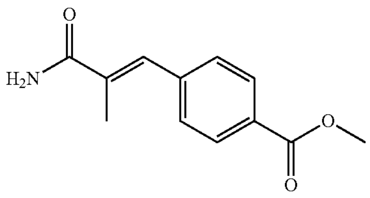 [SMILES: COC(=O)c1ccc(/C=C(\C)C(N)=O)cc1]

Step 1: Methyl (E)-4-(3-(tert-butoxy)-2-methyl-3-oxoprop-1-en-1yl)benzoate

Tert-butyl methacrylate (3.97 g, 27.9 mmol) and methyl 4-bromobenzoate (3.0 g, 13.95 mmol) were used in a similar manner to Step 1 of Preparation Example 10 to obtain the desired product. (Yield: 48%)

$^1$H-NMR (500 MHz, METHANOL-D3) δ 8.04 (d, J=6.7 Hz, 2H), 7.95 (d, J=7.3 Hz, 2H), 7.58 (s, 1H), 7.42 (dd, J=20.5, 13.1 Hz, 2H), 7.25 (dd, J=4.0, 2.8 Hz, 6H), 3.99-3.85 (m, 7H), 3.63 (s, 2H), 2.11-2.01 (m, 3H), 1.47-1.36 (9H)

Step 2: (E)-3-(4-(methoxycarbonyl)phenyl)-2-methylacrylic acid

Methyl (E)-4-(3-(tert-butoxy)-2-methyl-3-oxoprop-1-en-1yl)benzoate (0.72 g, 2.59 mmol) obtained in Step 1 was used in a similar manner to Step 3 of Preparation Example 10 to obtain the desired product. (Yield: 100%)

$^1$H-NMR (500 MHz, CHLOROFORM-D) δ 8.07 (d, J=7.9 Hz, 2H), 7.97 (d, J=7.9 Hz, 2H), 7.80 (s, 1H), 7.47 (d, J=7.9 Hz, 2H), 7.28 (d, J=7.9 Hz, 2H), 7.25 (s, 5H), 7.23 (s, 1H), 6.41 (s, 1H), 5.62 (s, 1H), 3.93 (s, 3H), 3.89 (d, J=13.4 Hz, 3H), 3.69 (s, 2H), 2.17-2.07 (m, 3H)

Step 3: Methyl (E)-4-(3-amino-2-methyl-3-oxoprop-1-en-1-yl)benzoate

Using (E)-3-(4-(methoxycarbonyl)phenyl)-2-methylacrylic acid (0.57 g, 2.59 mmol) obtained in Step 2, the desired product was obtained through an amidation reaction in a similar manner to Step 4 of Preparation Example 10. (Yield: 92%)

$^1$H-NMR (500 MHz, CHLOROFORM-D) δ 8.10-8.02 (2H), 7.98 (d, J=7.9 Hz, 2H), 7.45 (d, J=10.4 Hz, 1H), 7.42-7.34 (m, 2H), 7.29 (d, J=7.9 Hz, 2H), 5.81 (s, 1H), 5.38-5.28 (m, 1H), 3.93 (s, 3H), 3.90 (s, 3H), 3.72 (s, 2H), 2.17 (s, 2H), 2.12 (d, J=1.2 Hz, 3H), 2.03 (d, J=10.4 Hz, 0H), 1.26 (t, J=7.0 Hz, 2H), 0.88 (t, J=7.0 Hz, 1H)

Preparation Example 13: Methyl 4-(3-amino-2-methyl-3-oxopropyl)benzoate

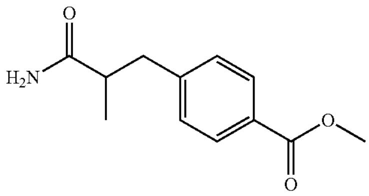 [SMILES: COC(=O)c1ccc(CC(C)C(N)=O)cc1]

Step 1: Methyl 4-(3-(tert-butoxy)-2-methyl-3-oxopropyl)benzoate

Using methyl (E)-4-(3-(tert-butoxy)-2-methyl-3-oxoprop-1-en-1yl)benzoate (1.12 g, 4.05 mmol) obtained in Step 1 of Preparation Example 12, the desired product was obtained through a reduction reaction in a similar manner to Step 2 of Preparation Example 10. (Yield: 96%)

$^1$H-NMR (500 MHz, CHLOROFORM-D) δ 7.98-7.91 (m, 2H), 7.28-7.25 (m, 2H), 7.24 (s, 1H), 3.91 (d, J=10.4 Hz,

3H), 3.05-2.95 (m, 1H), 2.72-2.59 (m, 2H), 1.58 (s, 0H), 1.43-1.32 (m, 10H), 1.17 (s, 0H), 1.17-1.10 (3H)

Step 2: 3-(4-(Methoxycarbonyl)phenyl)-2-methylpropanoic acid

Methyl 4-(3-(tert-butoxy)-2-methyl-3-oxopropyl)benzoate (1.08 g, 3.90 mmol) obtained in Step 1 was used in a similar manner to Step 3 of Preparation Example 10 to obtain the desired product. (Yield: 100%)

$^1$H-NMR (500 MHz, CHLOROFORM-D) δ 7.95 (q, J=7.7 Hz, 2H), 7.35-7.22 (m, 2H), 3.99-3.85 (m, 3H), 3.11 (q, J=6.5 Hz, 1H), 2.87-2.69 (m, 2H), 2.34 (d, J=15.3 Hz, 1H), 1.32-1.13 (m, 3H)

Step 3: Methyl 4-(3-amino-2-methyl-3-oxopropyl)benzoate

Using 3-(4-(methoxycarbonyl)phenyl)-2-methylpropanoic acid (0.87 g, 3.90 mmol) obtained in Step 2, the desired product was obtained through an amidation reaction in a similar manner to Step 4 of Preparation Example 10. (Yield: 92%)

$^1$H-NMR (500 MHz, CHLOROFORM-D) δ 8.10-8.02 (2H), 7.98 (d, J=7.9 Hz, 2H), 7.45 (d, J=10.4 Hz, 1H), 7.42-7.34 (m, 2H), 7.29 (d, J=7.9 Hz, 2H), 5.81 (s, 1H), 5.38-5.28 (m, 1H), 3.93 (s, 3H), 3.90 (s, 3H), 3.72 (s, 2H), 2.17 (s, 2H), 2.12 (d, J=1.2 Hz, 3H), 2.03 (d, J=10.4 Hz, 0H), 1.26 (t, J=7.0 Hz, 2H), 0.88 (t, J=7.0 Hz, 1H)

Preparation Example 14: Methyl 4-(3-amino-3-oxopropyl)-2-fluorobenzoate

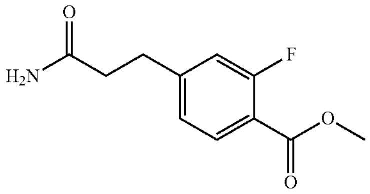 [SMILES: COC(=O)c1ccc(CCC(N)=O)cc1F]

Step 1: Methyl (E)-4-(3-(tert-butoxy)-3-oxoprop-1-en-1yl)-2-fluorobenzoate

Methyl 4-bromo-2-fluorobenzoic acid (0.34 g, 1.46 mmol) and tert-butyl acrylate (0.37 g, 2.92 mmol) were used in a similar manner to Step 1 of Preparation Example 10 to obtain the desired product. (Yield: 56%)

$^1$H-NMR (500 MHz, CHLOROFORM-D) δ 7.94 (s, 1H), 7.51 (d, J=15.9 Hz, 1H), 7.32 (d, J=7.9 Hz, 1H), 7.26 (t, J=5.8 Hz, 1H), 6.43 (d, J=15.9 Hz, 1H), 3.93 (s, 3H), 1.53 (s, 9H)

Step 2: Methyl 4-(3-(tert-butoxy)-3-oxopropyl)-2-fluorobenzoate

Using methyl (E)-4-(3-(tert-butoxy)-3-oxoprop-1-en-1yl)-2-fluorobenzoate (0.23 g, 0.82 mmol) obtained in Step 1, the desired product was obtained through a reduction reaction in a similar manner to Step 2 of Preparation Example 10. (Yield: 99%)

$^1$H-NMR (500 MHz, CHLOROFORM-D): δ 7.85 (t, J=7.9 Hz, 1H), 7.04 (dd, J=7.9, 1.2 Hz, 1H), 6.98 (dd, J=11.6, 1.2 Hz, 1H), 3.91 (s, 3H), 2.93 (t, J=7.6 Hz, 2H), 2.55 (t, J=7.3 Hz, 2H), 1.41 (s, 9H)

Step 3: 3-(3-Fluoro-4-(methoxycarbonyl)phenyl)propanoic acid

Methyl 4-(3-(tert-butoxy)-3-oxopropyl)-2-fluorobenzoate (0.23 g, 0.82 mmol) obtained in Step 2 was used in a similar manner to Step 3 of Preparation Example 10 to obtain the desired product. (Yield: 98%)

$^1$H-NMR (500 MHz, CHLOROFORM-D): δ 10.05 (s, 1H), 7.87 (t, J=7.9 Hz, 1H), 7.12-7.04 (m, 1H), 7.00 (d, J=11.6 Hz, 1H), 3.92 (s, 3H), 2.99 (t, J=7.6 Hz, 2H), 2.72 (t, J=7.6 Hz, 2H)

Step 4: Methyl 4-(3-amino-3-oxopropyl)-2-fluorobenzoate 3-(3-Fluoro-4-(methoxycarbonyl)phenyl)propanoic acid (0.18 g, 0.8 mmol) obtained in Step 3 was used in a similar manner to Step 4 of Preparation Example 10 to obtain the desired product. (Yield: 95%)

Preparation Example 15: Methyl 4-(3-amino-3-oxopropyl)-2-methylbenzoate

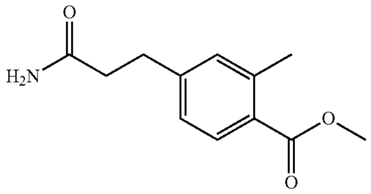 [SMILES: COC(=O)c1ccc(CCC(N)=O)cc1C]

Step 1: Methyl (E)-4-(3-(tert-butoxy)-3-oxoprop-1-en-1yl)-2-methylbenzoate

Methyl 4-bromo-2-methylbenzoate (1.0 g, 4.54 mmol) and tert-butyl acrylate (1.15 g, 9.08 mmol) were used in a similar manner to Step 1 of Preparation Example 10 to obtain the desired product. (Yield: 100%)

$^1$H-NMR (500 MHz, CHLOROFORM-D): δ 7.90 (d, J=7.9 Hz, 1H), 7.54 (d, J=15.9 Hz, 1H), 7.42-7.31 (2H), 6.42 (d, J=15.9 Hz, 1H), 3.89 (s, 3H), 2.60 (s, 3H), 1.53 (s, 9H)

Step 2: Methyl 4-(3-(tert-butoxy)-3-oxopropyl)-2-methylbenzoate

Using methyl (E)-4-(3-(tert-butoxy)-3-oxoprop-1-en-1yl)-2-methylbenzoate (1.2 g, 4.34 mmol) obtained in Step 1, the desired product was obtained through a reduction reaction in a similar manner to Step 2 of Preparation Example 10. (Yield: 96%)

$^1$H-NMR (500 MHz, CHLOROFORM-D): δ 7.89-7.78 (m, 1H), 7.06 (d, J=6.1 Hz, 2H), 3.86 (s, 3H), 2.89 (t, J=7.6 Hz, 2H), 2.57 (s, 3H), 2.52 (d, J=7.9 Hz, 2H), 1.41 (s, 9H)

Step 3: 3-(4-Methoxycarbonyl)-3-methylphenyl)propanoic acid

Methyl 4-(3-(tert-butoxy)-3-oxopropyl)-2-methylbenzoate (1.16 g, 4.17 mmol) obtained in Step 2 was used in a similar manner to Step 3 of Preparation Example 10 to obtain the desired product. (Yield: 92%)

$^1$H-NMR (500 MHz, CHLOROFORM-D): δ 10.96 (s, 1H), 7.85 (d, J=8.6 Hz, 1H), 7.08 (s, 2H), 3.88 (s, 3H), 2.95 (t, J=7.6 Hz, 2H), 2.70 (t, J=7.6 Hz, 2H), 2.57 (s, 3H)

Step 4: Methyl 4-(3-amino-3-oxopropyl)-2-methylbenzoate

Using 3-(4-methoxycarbonyl)-3-methylphenyl)propanoic acid (0.9 g, 4.04 mmol) obtained in Step 3, the desired product was obtained through an amidation reaction in a similar manner to Step 4 of Preparation Example 10. (Yield: 90%)

$^1$H-NMR (500 MHz, CHLOROFORM-D): δ 7.84 (t, J=4.3 Hz, 1H), 7.08 (d, J=5.5 Hz, 2H), 5.37 (d, J=22.0 Hz, 2H), 3.86 (s, 3H), 2.96 (t, J=7.6 Hz, 2H), 2.56 (s, 3H), 2.52 (t, J=7.6 Hz, 2H)

Preparation Example 16: Methyl 4-(3-amino-3-oxopropyl)-2-methoxybenzoate

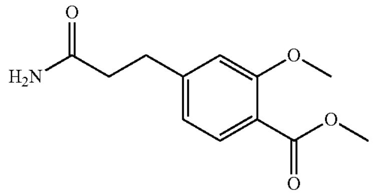 [SMILES: COC(=O)c1ccc(CCC(N)=O)cc1OC]

Methyl 4-bromo-2-methoxybenzoate (0.98 g, 4.00 mmol) was used in a similar manner to Preparation Example 10 to obtain the desired product. (Yield: 39%)

Preparation Example 17: Methyl 4-(3-amino-3-oxopropyl)-2-chlorobenzoate

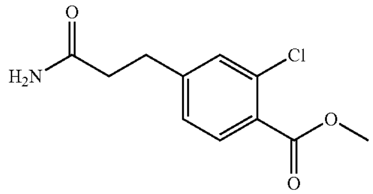 [SMILES: COC(=O)c1ccc(CCC(N)=O)cc1Cl]

Step 1: Methyl (E)-4-(3-(tert-butoxy)-3-oxoprop-1-en-1yl)-2-chlorobenzoate

Methyl 4-bromo-2-chlorobenzoate (2.0 g, 8.73 mmol) and tert-butyl acrylate (2.24 g, 17.5 mmol) were used in a similar manner to Step 1 of Preparation Example 10 to obtain the desired product. (Yield: 85%)

$^1$H-NMR (400 MHz, CHLOROFORM-D) δ 7.84 (d, J=8 Hz, 1H), 7.58 (d, J=1.2 Hz, 1H), 7.54 (d, J=13.6 Hz, 1H), 7.42 (d, J=8 Hz, 1H), 6.43 (d, J=16 Hz, 1H), 3.94 (s, 3H), 1.54 (s, 9H)

Step 2: Methyl 4-(3-(tert-butoxy)-3-oxopropyl)-2-chlorobenzoate

Using methyl (E)-4-(3-(tert-butoxy)-3-oxoprop-1-en-1yl)-2-chlorobenzoate (0.28 g, 0.93 mmol) obtained in Step 1, the desired product was obtained through a reduction reaction in a similar manner to Step 2 of Preparation Example 10. (Yield: 89%)

$^1$H-NMR (400 MHz, CHLOROFORM-D) δ 7.78 (d, J=8H, 1H), 7.30 (s, 1H), 7.15 (d, J=8 Hz, 1H), 3.92 (s, 3H), 2.92 (t, J=8 Hz, 2H), 2.55 (t, J=8 Hz, 2H), 1.42 (s, 9H)

Step 3: 3-(3-Chloro-4-(methoxycarbonyl)phenyl)propanoic acid

Methyl 4-(3-(tert-butoxy)-3-oxopropyl)-2-chlorobenzoate (0.25 g, 0.83 mmol) obtained in Step 2 was used in a similar manner to Step 3 of Preparation Example 10 to obtain the desired product. (Yield: 100%)

$^1$H-NMR (400 MHz, CHLOROFORM-D) δ 7.79 (s, J=8 Hz, 1H), 7.32 (d, J=4 Hz, 1H), 7.17 (dd, J=8 Hz, 4 Hz, 1H), 3.92 (s, 3H), 2.97 (t, J=8 Hz, 2H), 2.70 (t, J=8 Hz, 2H)

Step 4: Methyl 4-(3-amino-3-oxopropyl)-2-chlorobenzoate

Using 3-(3-chloro-4-(methoxycarbonyl)phenyl)propanoic acid (0.20 g, 0.83 mmol) obtained in Step 3, the desired product was obtained through an amidation reaction in a similar manner to Step 4 of Preparation Example 10. (Yield: 89%)

$^1$H-NMR (400 MHz, CHLOROFORM-D) δ 7.78 (d, J=8 Hz, 1H), 7.32 (s, 1H), 7.17 (d, J=8 Hz, 1H), 3.92 (s, 3H), 2.99 (t, J=8 Hz, 2H), 2.53 (t, J=8 Hz, 2H)

Preparation Example 18: Methyl 3-(3-amino-3-oxopropyl)benzoate

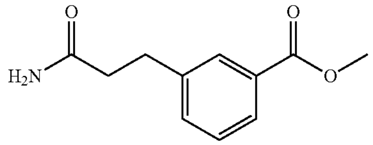

Step 1: Methyl (E)-3-(3-(tert-butoxy)-3-oxoprop-1-en-1-yl)benzoate

Methyl 3-formylbenzoate (0.60 g, 3.65 mmol) and (tert-butoxycarbonylmethylene)triphenylphosphorane (2.06 g, 5.48 mmol) were dissolved in dichloromethane (18.27 mL) and stirred at room temperature for 16 hours. The reaction solution was concentrated under reduced pressure and purified by silica gel column (ethyl acetate:hexane=1:4) to obtain the desired product. (Yield: 94%)

Step 2: Methyl 3-(3-(tert-butoxy)-3-oxopropyl)benzoate

Methyl (E)-3-(3-(tert-butoxy)-3-oxoprop-1-en-1-yl)benzoate (0.90 g, 3.43 mmol) obtained in Step 1 was used in a similar manner to Step 2 of Preparation Example 10 to obtain the desired product. (Yield: 99%)

Step 3: Methyl 3-(3-amino-3-oxopropyl)benzoate

Using methyl 3-(3-(tert-butoxy)-3-oxopropyl)benzoate (0.90 g, 3.40 mmol) obtained in Step 2, the methods of Steps 3 and 4 of Preparation Example 10 were sequentially performed to obtain the desired product. (Yield: 78%)

Preparation Example 19: Methyl 2-(4-(3-amino-3-oxopropyl)phenyl)acetate

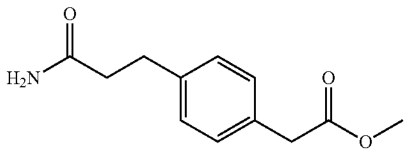 [SMILES: COC(=O)Cc1ccc(CCC(N)=O)cc1]

Step 1: Methyl (E)-4-(3-tert-butoxy)-3-oxoprop-1-en-1-yl)benzoate

Methyl 2-(4-bromophenyl)acetate (16.4 g, 70.0 mmol) and tert-butyl acrylate (18.0 g, 140.0 mmol) were used in a similar manner to Step 1 of Preparation Example 10 to obtain the desired product. (Yield: 79%)

$^1$H-NMR (500 MHz, CHLOROFORM-D) δ 7.56 (d, J=15.9 Hz, 1H), 7.46 (d, J=8.7 Hz, 2H), 7.28 (d, J=7.9 Hz, 2H), 6.34 (d, J=15.9 Hz, 1H), 3.70 (s, 3H), 3.64 (s, 2H), 1.53 (s, 9H)

Step 2: Methyl 4-(3-(tert-butoxy)-3-oxopropyl)benzoate

Using methyl (E)-4-(3-tert-butoxy)-3-oxoprop-1-en-1-yl) benzoate (5.0 g, 18.0 mmol) obtained in Step 1, the desired product was obtained through a reduction reaction in a similar manner to Step 2 of Preparation Example 10. (Yield: 93%)

$^1$H-NMR (500 MHz, CHLOROFORM-D) δ 7.17 (dd, J=18.3, 7.9 Hz, 4H), 3.68 (s, 3H), 3.59 (s, 2H), 2.88 (t, J=7.9 Hz, 2H), 2.52 (t, J=7.6 Hz, 2H), 1.41 (s, 9H)

Step 3: 3-(4-(2-Methoxy-2-oxoethyl)phenyl)propanoic acid

Methyl 4-(3-(tert-butoxy)-3-oxopropyl)benzoate (4.67 g, 16.8 mmol) obtained in Step 2 was used in a similar manner to Step 3 of Preparation Example 10 to obtain the desired product. (Yield: 100%)

$^1$H-NMR (500 MHz, CHLOROFORM-D) δ 9.58 (s, 2H), 7.18 (dd, J=19.0, 7.9 Hz, 4H), 3.70 (s, 3H), 3.61 (s, 2H), 2.95 (t, J=7.6 Hz, 2H), 2.69 (t, J=7.9 Hz, 2H)

Step 4: Methyl 2-(4-(3-amino-3-oxopropyl)phenyl)acetate

Using 3-(4-(2-methoxy-2-oxoethyl)phenyl)propanoic acid (3.73 g, 16.8 mmol) obtained in Step 3, the desired product was obtained through an amidation reaction in a similar manner to Step 4 of Preparation Example 10. (Yield: 65%)

$^1$H-NMR (500 MHz, CHLOROFORM-D) δ 7.18 (q, J=7.7 Hz, 4H), 5.41 (s, 2H), 3.66 (d, J=15.9 Hz, 3H), 3.59 (s, 2H), 3.02-2.87 (2H), 2.51 (t, J=7.6 Hz, 2H)

Preparation Example 20: Methyl 2-(4-(3-amino-3-oxopropyl)phenyl-2-methylpropanoate

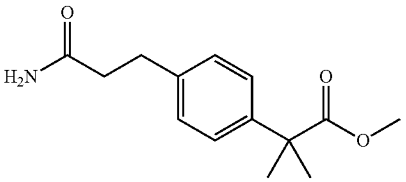 [SMILES: COC(=O)C(C)(C)c1ccc(CCC(N)=O)cc1]

Step 1: Tert-butyl (E)-3-(4-(1-methoxy-2-methyl-1-oxopropan-2-yl)phenyl)acrylate Methyl 2-(4-bromophenyl)-2-methylpropanoate (1.0 g, 3.89 mmol) and tert-butyl acrylate (0.98 g, 7.8 mmol) were used in a similar manner to Step 1 of Preparation Example 10 to obtain the desired product. (Yield: 79%)

$^1$H-NMR (500 MHz, CHLOROFORM-D): δ 7.56 (dd, J=15.9, 4.3 Hz, 1H), 7.51-7.42 (2H), 7.41-7.31 (m, 2H), 6.34 (dd, J=15.9, 4.9 Hz, 1H), 3.66 (d, J=4.9 Hz, 3H), 1.58 (d, J=4.9 Hz, 6H), 1.53 (d, J=4.9 Hz, 9H)

Step 2: Methyl 2-(4-(3-(tert-butoxy)-3-oxopropyl) phenyl)-2-methylpropanoate

Using tert-butyl (E)-3-(4-(1-methoxy-2-methyl-1-oxo-propan-2-yl)phenyl)acrylate (0.93 g, 3.06 mmol) obtained in Step 1, the desired product was obtained through a reduction reaction in a similar manner to Step 2 of Preparation Example 10. (Yield: 96%)

$^1$H-NMR (500 MHz, CHLOROFORM-D): δ 7.23 (s, 2H), 7.15 (d, J=7.9 Hz, 2H), 3.63 (s, 3H), 2.87 (t, J=7.9 Hz, 2H), 2.52 (t, J=7.9 Hz, 2H), 1.55 (s, 6H), 1.40 (s, 9H)

Step 3: 3-(4-(1-Methoxy-2-methyl-1-oxopropan-2-yl)phenyl)propanoic acid

Methyl 2-(4-(3-(tert-butoxy)-3-oxopropyl)phenyl)-2-methylpropanoate (0.90 g, 2.92 mmol) obtained in Step 2 was used in a similar manner to Step 3 of Preparation 10 to obtain the desired product. (Yield: 96%)

$^1$H-NMR (500 MHz, CHLOROFORM-D): δ 7.26 (d, J=7.3 Hz, 2H), 7.16 (d, J=7.9 Hz, 2H), 3.66 (s, 3H), 3.03-2.84 (2H), 2.82-2.55 (2H), 1.56 (s, 6H)

Step 4: Methyl 2-(4-(3-amino-3-oxopropyl)phenyl)-2-methylpropanoate

Using 3-(4-(1-methoxy-2-methyl-1-oxopropan-2-yl)phenyl)propanoic acid (0.7 g, 2.8 mmol) obtained in Step 3, the desired product was obtained through an amidation reaction in a similar manner to Step 4 of Preparation Example 10. (Yield: 99%)

$^1$H-NMR (500 MHz, CHLOROFORM-D): δ 7.25 (dd, J=6.4, 2.1 Hz, 2H), 7.17 (d, J=7.9 Hz, 2H), 5.36 (s, 2H), 3.64 (s, 3H), 3.00-2.90 (2H), 2.52 (t, J=7.6 Hz, 2H), 1.56 (d, J=4.3 Hz, 6H)

Preparation Example 21: Methyl 1-(4-(3-amino-3-oxopropyl)phenyl)cyclopropane-1-carboxylate

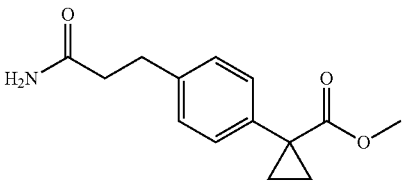 [SMILES: COC(=O)C1(c2ccc(CCC(N)=O)cc2)CC1]

Step 1: Methyl (E)-1-(4-(3-(tert-butoxy)-3-oxoprop-1-en-1-yl)phenyl)cyclopropane-1-carboxylate Methyl 1-(4-bromophenyl)cyclopropane-1-carboxylate (1.0 g, 3.92 mmol) and tert-butyl acrylate (0.99 g, 7.84 mmol) were used in a similar manner to Step 1 of Preparation Example 10 to obtain the desired product. (Yield: 78%)

$^1$H-NMR (500 MHz, CHLOROFORM-D): δ 7.56 (d, J=15.9 Hz, 1H), 7.44 (d, J=7.9 Hz, 2H), 7.33 (d, J=7.9 Hz, 2H), 6.34 (d, J=15.9 Hz, 1H), 3.62 (s, 3H), 1.62 (t, J=3.4 Hz, 2H), 1.52 (s, 9H), 1.19 (t, J=3.4 Hz, 2H)

Step 2: Methyl 1-(4-(3-(tert-butoxy)-3-oxopropyl)phenyl)cyclopropane-1-carboxylate Using methyl (E)-1-(4-(3-(tert-butoxy)-3-oxoprop-1-en-1-yl)phenyl)cyclopropane-1-carboxylate (0.93 g, 3.08 mmol) obtained in Step 1, the desired product was obtained through a reduction reaction in a similar manner to Step 2 of Preparation Example 10. (Yield: 96%)

$^1$H-NMR (500 MHz, CHLOROFORM-D): δ 7.24 (d, J=8.6 Hz, 2H), 7.13 (d, J=7.9 Hz, 2H), 3.61 (s, 3H), 2.89 (t, J=7.9 Hz, 2H), 2.53 (t, J=7.9 Hz, 2H), 1.57 (q, J=3.7 Hz, 2H), 1.40 (d, J=4.9 Hz, 9H), 1.16 (q, J=3.7 Hz, 2H)

Step 3: 3-(4-(1-(Methoxycarbonyl)cyclopropyl)phenyl)propanoic acid

Methyl 1-(4-(3-(tert-butoxy)-3-oxopropyl)phenyl)cyclopropane-1-carboxylate (0.90 g, 2.96 mmol) obtained in Step 2 was used in a similar manner to Step 3 of Preparation Example 10 to obtain the desired product. (Yield: 97%)

$^1$H-NMR (500 MHz, CHLOROFORM-D): δ 8.61 (s, 1H), 7.26 (d, J=8.6 Hz, 2H), 7.15 (d, J=7.9 Hz, 2H), 3.64 (s, 3H), 2.95 (t, J=7.3 Hz, 2H), 2.74 (s, 2H), 1.61 (q, J=3.5 Hz, 2H), 1.20 (q, J=3.5 Hz, 2H)

Step 4: Methyl 1-(4-(3-amino-3-oxopropyl)phenyl)cyclopropane-1-carboxylate

Using 3-(4-(1-(methoxycarbonyl)cyclopropyl)phenyl)propanoic acid (0.7 g, 2.82 mmol) obtained in Step 3, the desired product was obtained through an amidation reaction in a similar manner to Step 4 of Preparation Example 10. (Yield: 95%)

$^1$H-NMR (500 MHz, CHLOROFORM-D): δ 7.28-7.24 (m, 2H), 7.15 (d, J=8.6 Hz, 2H), 5.41 (s, 2H), 3.61 (t, J=2.4 Hz, 3H), 2.95 (t, J=7.6 Hz, 2H), 2.52 (t, J=7.6 Hz, 2H), 1.58 (q, J=3.7 Hz, 2H), 1.16 (q, J=3.5 Hz, 2H)

Preparation Example 22: Methyl 4-(3-amino-3-oxopropyl)-2,6-difluorobenzoate

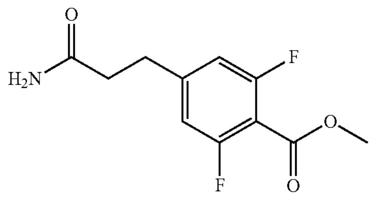 [SMILES: COC(=O)c1c(F)cc(CCC(N)=O)cc1F]

Methyl 4-bromo-2,6-difluorobenzoate (1.0 g, 3.98 mmol) was used in a similar manner to Preparation 10 to obtain the desired product. (Yield: 39%)

$^1$H-NMR (400 MHz, CHLOROFORM-D): δ 6.81 (d, J=9.1 Hz, 2H), 5.35 (s, 2H), 3.92 (s, 3H), 3.02-2.92 (t, 2H), 2.51 (t, J=7.5 Hz, 2H)

Preparation Example 23: 2-(trimethylsilyl)ethyl 4-(3-amino-3-oxopropyl)2,6-dichlorobenzoate

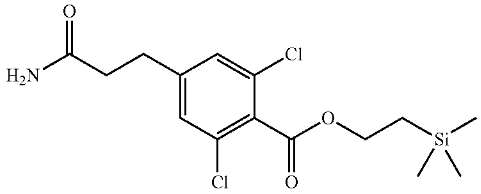 [SMILES: C[Si](C)(C)CCOC(=O)c1c(Cl)cc(CCC(N)=O)cc1Cl]

Step 1: 2-(Trimethylsilyl)ethyl 4-bromo-2,6-dichlorobenzoate

After dissolving 4-bromo-2,6-dichlorobenzoic acid (300 mg, 1.112 mmol) in 8 mL of THF in the presence of nitrogen, 2-(trimethylsilyl)ethan-1-ol (0.250 mL, 1.667 mmol), diisopropyl azodicarboxylate (0.530 mL, 2.56 mmol) and triphenylphosphine (729 mg, 2.78 mmol) were sequentially added at 0° C. and stirred at room temperature for 2 hours. After confirming that the starting materials disappeared by TLC, the reaction was terminated with water, followed by extraction with ethyl acetate (30 mL×3). The extracted solvent was dried over magnesium sulfate, and the organic solvent was removed under reduced pressure. The purification was carried out by silica gel column (ethyl acetate:hexane=1:10) to obtain the desired product. (Yield: 47%)

$^1$H NMR (300 MHz, CHLOROFORM-D): δ 7.52 (s, 2H), 4.52-4.46 (m, 2H), 1.20-1.14 (m, 2H), 0.10 (s, 9H)

Step 2: 2-(Trimethylsilyl)ethyl (E)-4-(3-(tert-butoxy)-3-oxoprop-1-en-1-yl)-2,6-dichlorobenzoate 2-(Trimethylsilyl)ethyl 4-bromo-2,6-dichlorobenzoate (205 mg, 0.554 mmol) obtained in Step 1 was used in a similar manner to Step 1 of Preparation Example 10 to obtain the desired product.

$^1$H NMR (300 MHz, CHLOROFORM-D): δ 7.45 (s, 2H), 7.44 (d, J=15.9 Hz, 1H), 6.41 (d, J=15.9 Hz, 1H), 4.53-4.47 (m, 2H), 1.55 (s, 9H) 1.21-1.15 (m, 2H), 0.10 (s, 9H)

Step 3: 2-(Trimethylsilyl)ethyl 4-(3-(tert-butoxy)-3-oxopropyl)-2,6-dichlorobenzoate Using 2-(trimethylsilyl)ethyl (E)-4-(3-(tert-butoxy)-3-oxoprop-1-en-1-yl)-2,6-dichlorobenzoate (150 mg, 0.453 mmol) obtained in Step 2, the desired product was obtained through a reduction reaction in a similar manner to Step 2 of Preparation Example 10.

$^1$H NMR (300 MHz, CHLOROFORM-D): δ 7.19 (s, 2H), 3.98 (s, 3H), 2.87 (t, J=7.5 Hz, 2H), 2.54 (t, J=7.5 Hz, 2H), 1.44 (s, 9H)

Step 4: 3-(3,5-Dichloro-4-((2-(trimethylsilyl)ethyl) carbonyl)phenyl)propanoic acid 2-(Trimethylsilyl)ethyl 4-(3-(tert-butoxy)-3-oxopropyl)-2,6-dichlorobenzoate (141 mg, 0.423 mmol) obtained in Step 3 was used in a similar manner to Step 3 of Preparation Example 10 to obtain the desired product.

Step 5: 2-(Trimethylsilyl)ethyl 4-(3-amino-3-oxopropyl)2,6-dichlorobenzoate

Using 3-(3,5-dichloro-4-((2-(trimethylsilyl)ethyl)carbonyl)phenyl)propanoic acid obtained in Step 4, the desired product was obtained through an amidation reaction in a similar manner to Step 4 of Preparation Example 10.

Preparation Example 24: 2-(trimethylsilyl)ethyl 4-(3-amino-3-oxopropyl)-2,6-dimethylbenzoate

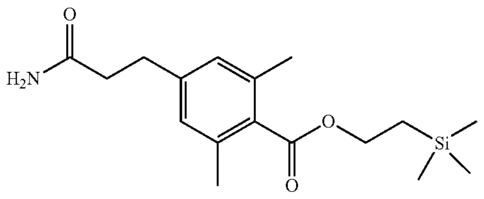 [SMILES: Cc1cc(CCC(N)=O)cc(C)c1C(=O)OCC[Si](C)(C)C]

Step 1: 2-(Trimethylsilyl)ethyl 4-bromo-2,6-dimethylbenzoate

4-Bromo-2,6-dimethylbenzoic acid (2.0 g, 8.73 mmol) was used in a similar manner to Step 1 of Preparation Example 23 to obtain the desired product. (Yield: 69%)

$^1$H-NMR (500 MHz, CHLOROFORM-D): δ 7.19 (s, 2H), 4.40 (t, J=8.9 Hz, 2H), 2.29 (s, 6H), 1.11 (t, J=8.9 Hz, 2H), 0.07 (d, J=3.1 Hz, 9H)

Step 2: 2-(Trimethylsilyl)ethyl (E)-4-(3-(tert-butoxy)-3-oxoprop-1-en-1-yl)-2,6-dimethylbenzoate 2-(Trimethylsilyl)ethyl 4-bromo-2,6-dimethylbenzoate (1.99 g, 6.04 mmol) obtained in Step 1 was used in a similar manner to Step 1 of Preparation Example 10 to obtain the desired product. (Yield: 50%)

$^1$H-NMR (500 MHz, CHLOROFORM-D): δ 7.49 (d, J=15.9 Hz, 1H), 7.17-7.10 (2H), 6.35 (d, J=15.9 Hz, 1H), 4.41 (t, J=8.9 Hz, 2H), 2.30 (s, 6H), 1.52 (s, 9H), 1.16-1.07 (m, 2H), 0.07 (d, J=2.4 Hz, 9H)

Step 3: 2-(Trimethylsilyl)ethyl 4-(3-(tert-butoxy)-3-oxopropyl)-2,6-dimethylbenzoate Using 2-(trimethylsilyl)ethyl (E)-4-(3-(tert-butoxy)-3-oxoprop-1-en-1-yl)-2,6-dimethylbenzoate (1.13 g, 3.0 mmol) obtained in Step 2, the desired product was obtained through a reduction reaction in a similar manner to Step 2 of Preparation Example 10. (Yield: 69%)

$^1$H-NMR (500 MHz, CHLOROFORM-D): δ 6.85 (s, 2H), 4.39 (t, J=8.9 Hz, 2H), 2.81 (d, J=7.9 Hz, 2H), 2.49 (t, J=7.9 Hz, 2H), 2.29 (s, 6H), 1.45-1.39 (9H), 1.16-1.07 (m, 2H), 0.06 (s, 9H)

Step 4: 3-(3,5-Dimethyl-4-((2-(trimethylsilyl)ethyl) carbonyl)phenyl)propanoic acid 2-(Trimethylsilyl)ethyl 4-(3-(tert-butoxy)-3-oxopropyl)-2,6-dimethylbenzoate (0.78 g, 2.06 mmol) obtained in Step 3 was used in a similar manner to Step 3 of Preparation Example 10 to obtain the desired product. (Yield: 60%)

Step 5: 2-(Trimethylsilyl)ethyl 4-(3-amino-3-oxopropyl)-2,6-dimethylbenzoate

Using 3-(3,5-dimethyl-4-((2-(trimethylsilyl)ethyl)carbonyl)phenyl)propanoic acid obtained in Step 4, the desired product was obtained through an amidation reaction in a similar manner to Step 4 of Preparation Example 10. (Yield: 88%)

Preparation Example 25: Ethyl 1-(4-(3-amino-3-oxopropyl)phenyl)piperidine-4-carboxylate

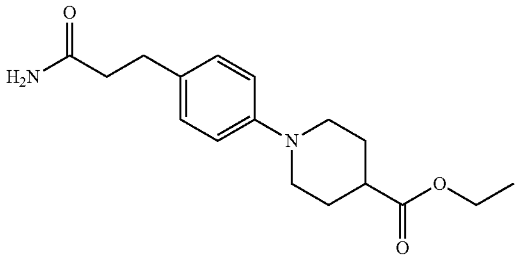 [SMILES: CCOC(=O)C1CCN(c2ccc(CCC(N)=O)cc2)CC1]

Step 1: Ethyl 1-(4-formylphenyl)piperidine-4-carboxylate

4-Fluorobenzaldehyde (0.864 mL 8.06 mmol), ethyl piperidine-4-carboxylate (1.490 mL, 9.67 mmol) and potassium carbonate (5.57 g, 40.3 mmol) were dissolved in DMF (16.11 mL). The temperature was raised to 100° C. and stirred for 16 hours. When the reaction was completed, water was added to the reaction solution, followed by extraction with ethyl acetate. The organic layer was concentrated under reduced pressure and purified by silica gel column (ethyl acetate:hexane=1:4) to obtain the desired product. (Yield: 81%)

$^1$H-NMR (500 MHz, CHLOROFORM-D): δ δ 9.72 (d, J=3.1 Hz, 1H), 7.70 (m, 2H), 6.97-6.78 (m, 2H), 4.12 (m, 2H), 3.91-3.72 (m, 2H), 3.10-2.88 (m, 2H), 2.61-2.43 (m, 1H), 2.08-1.89 (m, 2H), 1.87-1.69 (m, 2H), 1.23 (m, 3H)

Step 2: Ethyl (E)-1-(4-(3-(tert-butoxy)-3-oxoprop-1-en-1-yl)phenyl)piperidine-4-carboxylate Ethyl 1-(4-formylphenyl)piperidine-4-carboxylate (0.52 g, 1.990 mmol) obtained in Step 1 and (tert-butoxycarbonylmethylene)triphenylphosphorane (0.974 g, 2.59 mmol) were dissolved in dichloromethane (9.95 mL) and stirred at room temperature for 16 hours. The reaction solution was concentrated under reduced pressure and purified by silica gel column (ethyl acetate:hexane=1:4) to obtain the desired product. (Yield: 84%)

$^1$H-NMR (500 MHz, CHLOROFORM-D): δ 7.50 (d, J=15.9 Hz, 1H), 7.39 (d, J=8.6 Hz, 2H), 6.86 (d, J=8.6 Hz, 2H), 6.19 (d, J=15.9 Hz, 1H), 4.15 (q, J=7.1 Hz, 2H), 3.74 (m, 2H), 2.98-2.80 (m, 2H), 2.55-2.37 (m, 1H), 2.11-1.94 (m, 2H), 1.94-1.74 (m, 2H), 1.51 (s, 9H), 1.26 (t, J=7.0 Hz, 3H)

Step 3: Ethyl 1-(4-(3-(tert-butoxy)-3-oxopropyl)phenyl)piperidine-4-carboxylate Using ethyl (E)-1-(4-(3-(tert-butoxy)-3-oxoprop-1-en-1-yl)phenyl)piperidine-4-carboxylate (0.60 g, 1.669 mmol) obtained in Step 2, the desired product was obtained through a reduction reaction in a similar manner to Step 2 of Preparation Example 10. (Yield: 99%)

Step 4: Ethyl 1-(4-(3-amino-3-oxopropyl)phenyl)piperidine-4-carboxylate

Using ethyl 1-(4-(3-(tert-butoxy)-3-oxopropyl)phenyl)piperidine-4-carboxylate (0.60 g, 1.660 mmol) obtained in Step 3, the methods of Steps 3 and 4 of Preparation Example 10 were sequentially performed to obtain the desired product. (Yield: 69%)

Preparation Example 26: Ethyl 1-(4-carbamoyl-2,6-difluorophenyl)piperidine-4-carboxylate

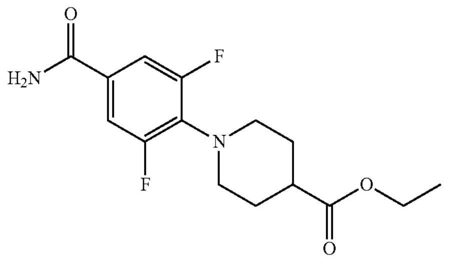 [SMILES: CCOC(=O)C1CCN(c2c(F)cc(C(N)=O)cc2F)CC1]

Using tert-butyl 3,4,5-trifluorobenzoate (0.50 g, 2.15 mmol) and ethyl piperidine-4-carboxylate (0.398 ml, 2.58 mmol), the methods of Step 1 of Preparation Example 25, and Steps 3 and 4 of Preparation Example 10 were sequentially performed to obtain the desired product. (Yield: 58%)

$^1$H-NMR (400 MHz, CHLOROFORM-D): δ 7.33 (m, 2H), 5.78 (s, 2H), 4.19 (m, 2H), 3.42 (d, 2H), 3.17 (t, 2H), 2.50 (m, 1H), 2.00-1.82 (m, 4H), 1.29 (t, 3H)

Preparation Example 27: Ethyl 2-(1-(4-carbamoyl-2,6-difluorophenyl)piperidin-4-yl)acetate

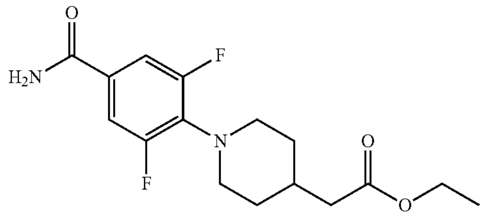 [SMILES: CCOC(=O)CC1CCN(c2c(F)cc(C(N)=O)cc2F)CC1]

Tert-butyl 3,4,5-trifluorobenzoate (0.50 g, 2.15 mmol) and ethyl 2-(piperidin-4-yl) acetate (0.44 g, 2.58 mmol) were used in a similar manner to Preparation Example 26 to obtain the desired product. (Yield: 59%)

$^1$H-NMR (400 MHz, CHLOROFORM-D): δ 7.27 (m, 2H), 5.67 (s, 2H), 4.18 (m, 2H), 3.38 (d, 2H), 3.17 (t, 2H), 2.30 (d, 2H), 1.97 (m, 1H), 1.79 (d, 2H), 1.45 (m, 2H), 1.29 (t, 3H)

Preparation Example 28: Ethyl 2-(4-(3-amino-3-oxopropyl)phenoxy)-2-methylpropanoate

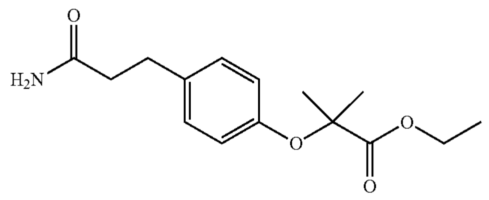 [SMILES: CCOC(=O)C(C)(C)Oc1ccc(CCC(N)=O)cc1]

4-Hydroxybenzaldehyde (1.0 g, 8.19 mmol) and ethyl 2-bromo-2-methylpropanoate (2.404 ml, 16.38 mmol) were used in a similar manner to Preparation Example 25 to obtain the desired product. (Yield: 29%)

$^1$H-NMR (500 MHz, CHLOROFORM-D): δ 7.07 (d, 2H), 6.77 (d, 2H), 5.29 (s, 2H), 4.25 (m, 2H), 2.91 (t, 2H), 2.50 (t, 2H), 1.59 (s, 6H), 1.26 (t, 3H)

Preparation Example 29: Ethyl 3-(4-(3-amino-3-oxopropyl)phenyl)propanoate

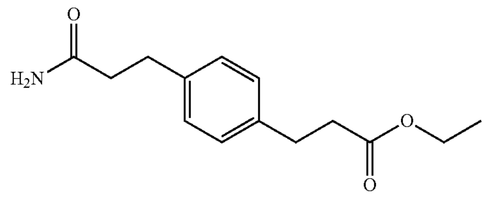 [SMILES: CCOC(=O)CCc1ccc(CCC(N)=O)cc1]

Using 4-bromobenzaldehyde (0.5 g, 2.70 mmol) and (carbethoxymethylene) triphenylphosphorane (1.224 g, 3.51 mmol), the methods of Step 1 of Preparation Example 18 and Preparation Example 10 were sequentially performed to obtain the desired product. (Yield: 66%)

$^1$H-NMR (500 MHz, CHLOROFORM-D): δ 7.14 (m, 4H), 5.36 (s, 2H), 4.12 (m, 2H), 2.93 (m, 4H), 2.60 (t, 2H), 2.52 (t, 2H), 1.25 (t, 3H)

Preparation Example 30: Ethyl 4-(4-carbamoylphenoxy)benzoate

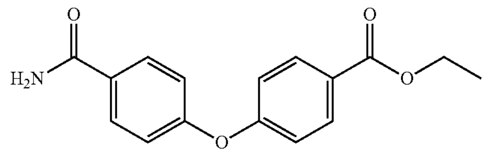 [SMILES: CCOC(=O)c1ccc(Oc2ccc(C(N)=O)cc2)cc1]

Using benzyl 4-fluorobenzoate (0.5 g, 2.172 mmol) and ethyl 4-hydroxybenzoate (0.361 g, 2.172 mmol), the methods of Step 1 of Preparation Example 25, Step 2 of Preparation Example 10 and Step 3 of Preparation Example 6 were sequentially performed to obtain the desired product. (Yield: 11%)

$^1$H-NMR (500 MHz, CHLOROFORM-D): δ 8.06 (d, 2H), 7.84 (d, 2H), 7.08 (m, 4H), 6.03 (s, 1H), 5.63 (s, 1H), 4.38 (m, 2H), 1.40 (t, 3H)

Preparation Example 31: Methyl (R)-3-(4-(2-amino-2-oxoethyl)phenyl)-2-methylpropanoate

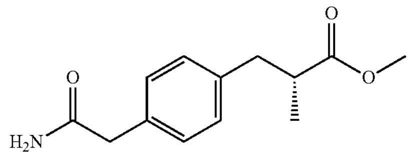 [SMILES: COC(=O)[C@H](C)Cc1ccc(CC(N)=O)cc1]

Step 1: Tert-butyl 2-(4-((R)-3-((S)-4-benzyl-2-oxooxazolidin-3-yl)-2-methyl-3-oxopropyl)phenyl)acetate (S)-4-benzyl-3-propionyloxazolidin-2-one (1.363 g, 5.84 mmol) was dissolved in anhydrous tetrahydrofuran, the temperature was lowered to −78° C., and the mixture was stirred for 15 minutes. Sodium bis(trimethylsilyl)amide (3.38 ml, 6.43 mmol, 1.0 M in THF) was slowly added dropwise. After the reaction solution was stirred at the same temperature for 1 hour, tert-butyl 2-(4-(bromomethyl)phenyl)acetate (2 g, 7.01 mmol) was added dropwise. After stirring at the same temperature for 6 hours, the temperature was raised to room temperature. A saturated aqueous ammonium chloride solution was added to terminate the reaction, and the mixture was extracted with ethyl acetate. The organic layer was concentrated under reduced pressure and purified by silica gel column (ethyl acetate:hexane=1:2) to obtain the desired product. (Yield: 94%)

$^1$H-NMR (500 MHz, CHLOROFORM-D): δ 7.17 (d, J=7.9 Hz, 2H), 7.10 (d, J=7.9 Hz, 2H), 3.63 (s, 3H), 3.48 (s, 2H), 3.00 (q, J=6.7 Hz, 1H), 2.77-2.67 (m, 1H), 2.66-2.58 (m, 1H), 1.42 (s, 9H), 1.13 (d, J=7.3 Hz, 3H)

Step 2: Methyl (R)-3-(4-(2-(tert-butoxy)-2-oxoethyl)phenyl)-2-methylpropanoate

Tert-butyl 2-(4-((R)-3-((S)-4-benzyl-2-oxooxazolidin-3-yl)-2-methyl-3-oxopropyl)phenyl)acetate (2.4 g, 5.49 mmol) obtained in Step 1 was dissolved in tetrahydrofuran (21 mL) and water (7 mL), and hydrogen peroxide (3.36 mL, 54.9 mmol) and lithium hydroxide (0.921 g, 21.94 mmol) were added sequentially at room temperature. The reaction solution was stirred at room temperature for 3 hours, and the reaction was terminated with 1 N hydrochloric acid. The resulting product was extracted with ethyl acetate and concentrated under reduced pressure. The crude compound was dissolved in diethyl ether (28 mL), and the temperature was lowered to 0° C. Diazomethane (0.5 M in diethyl ether) was added dropwise until the color of the solution turned yellow. The reaction solution was concentrated under reduced pressure and purified by silica gel column (ethyl acetate: hexane=1:4) to obtain the desired product. (Yield: 31%)

Step 3: Methyl (R)-3-(4-(2-amino-2-oxoethyl)phenyl)-2-methylpropanoate

Using methyl (R)-3-(4-(2-(tert-butoxy)-2-oxoethyl)phenyl)-2-methylpropanoate (0.5 g, 1.71 mmol) obtained in Step 2, the methods of Steps 3 and 4 of Preparation Example 10 were sequentially performed to obtain the desired product. (Yield: 87%)

$^1$H-NMR (400 MHz, CHLOROFORM-D): δ 7.16 (m, 4H), 5.35 (s, 2H), 3.62 (s, 3H), 3.54 (s, 2H), 3.00 (m, 1H), 2.68 (m, 2H), 1.14 (d, J=6.9 Hz, 3H)

Preparation Example 32: Methyl (S)-3-(4-(2-amino-2-oxoethyl)phenyl)-2-methylpropanoate

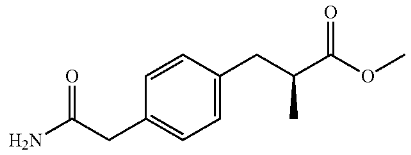 [SMILES: COC(=O)[C@@H](C)Cc1ccc(CC(N)=O)cc1]

(R)-4-benzyl-3-propionyloxazolidin-2-one (0.744 g, 3.19 mmol) and tert-butyl 2-(4-(bromomethyl)phenyl)acetate (1.00 g, 3.51 mmol) were used in a similar manner to Preparation Example 31 to obtain the desired product. (Yield: 25%)

$^1$H-NMR (400 MHz, CHLOROFORM-D): δ 7.16 (m, 4H), 5.38 (s, 2H), 3.62 (s, 3H), 3.54 (s, 2H), 3.00 (m, 1H), 2.68 (m, 2H), 1.13 (t, J=7.5 Hz, 3H)

Preparation Example 33: Methyl 3-(4-(2-amino-2-oxoethyl)phenyl)-2,2-dimethylpropanoate

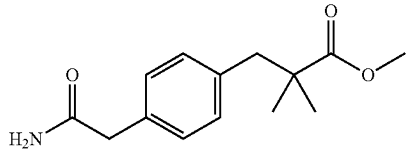 [SMILES: COC(=O)C(C)(C)Cc1ccc(CC(N)=O)cc1]

Step 1: 2-(4-(3-Methoxy-2,2-dimethyl-3-oxopropyl)phenyl)acetic acid Diisopropylamine (1.867 mL, 13.10 mmol) was added to anhydrous tetrahydrofuran (20 mL), and 2.5 M n-butyllithium (5.24 mL, 13.10 mmol) was slowly added dropwise at −78° C. The reaction solution was stirred at the same temperature for 20 minutes. After raising the temperature to room temperature and stirring for 10 minutes, the temperature was lowered to −78° C. again and stirred for 10 minutes. The reaction solution was added dropwise to methyl isobutyrate (1.501 mL, 13.10 mmol) dissolved in anhydrous tetrahydrofuran (20 mL). The reaction solution was stirred at −78° C. for 1 hour and slowly added dropwise to 2-(4-(bromomethyl)phenyl)acetic acid (1 g, 4.37 mmol) dissolved in anhydrous tetrahydrofuran (20 mL). The temperature was raised to room temperature, and the reaction solution was stirred for 20 minutes. The reaction was terminated by adding 1N aqueous hydrochloric acid (10 mL) to the reaction solution, followed by extraction with diethyl ether. The organic layer was concentrated under reduced pressure and purified by silica gel column (methanol:dichloromethane=1:9) to obtain the desired product. (Yield: 82%).

$^1$H-NMR (500 MHz, CHLOROFORM-D): δ 7.17 (d, J=7.9 Hz, 2H), 7.06 (d, J=7.9 Hz, 2H), 3.65 (s, 3H), 3.61 (s, 2H), 2.83 (s, 2H), 1.17 (s, 6H)

Step 2: Methyl 3-(4-(2-amino-2-oxoethyl)phenyl)-2,2-dimethylpropanoate 2-(4-(3-Methoxy-2,2-dimethyl-3-oxopropyl)phenyl)acetic acid (0.90 g, 3.60 mmol) obtained in Step 1 was used in a similar manner to Step 3 of Preparation Example 6 to obtain the desired product. (Yield: 87%)

$^1$H-NMR (500 MHz, CHLOROFORM-D): δ 7.17 (d, 2H), 7.09 (d, 2H), 5.36 (s, 2H), 3.66 (s, 3H), 3.55 (s, 2H), 2.84 (s, 2H), 1.17 (s, 6H)

Preparation Example 34: Ethyl 4-(4-carbamoylpiperidin-1-yl)benzoate

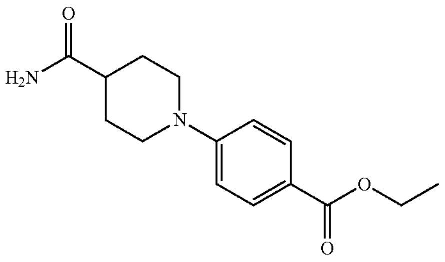 [SMILES: CCOC(=O)c1ccc(N2CCC(C(N)=O)CC2)cc1]

Using ethyl 4-fluorobenzoate (0.524 ml, 3.57 mmol) and benzyl piperidine-4-carboxylate hydrochloride (1.10 g, 4.28 mmol), the methods of Step 1 of Preparation Example 25, Step 2 of Preparation Example 10 and Step 3 of Preparation Example 6 were sequentially performed to obtain the desired product. (Yield: 26%)

$^1$H-NMR (400 MHz, CHLOROFORM-D): δ 7.97 (d, 2H), 6.92 (d, 2H), 5.51 (s, 1H), 5.41 (s, 1H), 4.40 (m, 2H), 3.96 (d, 2H), 2.98 (m, 2H), 2.46 (m, 1H), 2.05 (m, 2H), 1.94 (m, 2H), 1.43 (t, 3H)

Preparation Example 35: 1-(5-Ethylpyrimidin-2-yl)piperidine-4-carboxamide

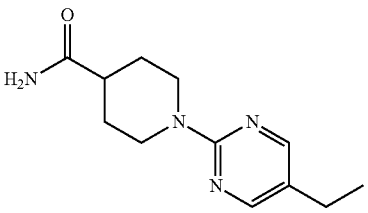 [SMILES: CCc1cnc(N2CCC(C(N)=O)CC2)nc1]

Step 1: Ethyl 1-(5-ethylpyrimidin-2-yl)piperidine-4-carboxylate

Ethyl piperidine-4-carboxylate (0.980 mL, 6.36 mmol), cesium carbonate (2.176 g, 6.68 mmol) and 2-chloro-5-ethylpyrimidine (0.796 mL, 6.55 mmol) were dissolved in DMF (6.36 mL) and stirred at 100° C. for 4 hours. When the reaction was completed, water was added to the reaction solution, followed by extraction with ethyl acetate. The organic layer was concentrated under reduced pressure and purified by silica gel column (ethyl acetate:hexane=1:4) to obtain the desired product. (Yield: 96%)

$^1$H-NMR (500 MHz, CHLOROFORM-D): δ 8.16 (s, 2H), 4.61 (m, 2H), 4.14 (q, J=7.1 Hz, 2H), 3.09-2.91 (m, 2H), 2.62-2.51 (m, 1H), 2.45 (q, J=7.5 Hz, 2H), 1.96 (m, 2H), 1.80-1.63 (m, 2H), 1.25 (t, J=7.3 Hz, 3H), 1.18 (t, J=7.6 Hz, 3H)

Step 2: 1-(5-Ethylpyrimidin-2-yl)piperidine-4-carboxamide

Using ethyl 1-(5-ethylpyrimidin-2-yl)piperidine-4-carboxylate (0.56 g, 2.127 mmol) obtained in Step 1, the methods of Steps 2 and 3 of Preparation Example 6 were sequentially performed to obtain the desired product. (Yield: 14%)

$^1$H-NMR (500 MHz, CHLOROFORM-D): δ 8.16 (s, 2H), 5.49 (s, 2H), 4.76 (m, 2H), 2.94 (m, 2H), 2.48 (m, 3H), 1.96 (m, 2H), 1.70 (m, 2H), 1.19 (t, 3H)

Preparation Example 36: Methyl 2-(4-(2-amino-2-oxoethyl)phenyl)2-methylpropanoate

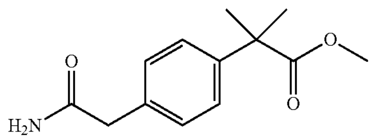 [SMILES: COC(=O)C(C)(C)c1ccc(CC(N)=O)cc1]

Step 1: Methyl 2-(4-(bromomethyl)phenyl)-2-methylpropanoate

Methyl 2-methyl-2-(p-tolyl)propanoate was dissolved in DCE (55.3 mL), and N-bromosuccinimide (4.63 g, 26.0 mmol) and azobisisobutyronitrile (0.085 g, 0.520 mmol) were added. The reaction mixture was stirred at 80° C. for 2 hours and 30 minutes. The solvent was removed under reduced pressure, diluted with EA, washed with brine, and the organic solvent was dried over magnesium sulfate. The purification was carried out by silica gel column to obtain the desired product. (Yield: 56.7%)

$^1$H-NMR (400 MHz, CHLOROFORM-D) δ 7.37-7.27 (m, 4H), 4.47 (s, 2H), 3.65 (d, J=4.6 Hz, 3H), 1.56 (d, J=3.2 Hz, 6H)

Step 2: Methyl 2-(4-cyanomethyl)phenyl)-2-methylpropanoate

Methyl 2-(4-(bromomethyl)phenyl)-2-methylpropanoate (100 mg, 0.369 mmol) obtained in Step 1 was dissolved in DMF (5 mL), and potassium cyanide (36.0 mg, 0.553 mmol) was added and stirred at room temperature for 16 hours. After the reaction was terminated by adding water, the resulting product was diluted with diethyl ether, washed with brine, and the organic solvent was dried with magnesium sulfate. The purification was carried out by silica gel column to obtain the desired product. (Yield: 52.4%)

$^1$H-NMR (400 MHz, CHLOROFORM-D) δ 7.34 (d, J=8.7 Hz, 2H), 7.28 (d, J=8.2 Hz, 2H), 3.71 (s, 2H), 3.64 (s, 3H), 1.54 (d, J=15.6 Hz, 6H)

Step 3: Methyl 2-(4-(2-methoxy-2-oxoethyl)phenyl)-2-methylpropanoate

Methyl 2-(4-cyanomethyl)phenyl)-2-methylpropanoate (1.46 g, 6.72 mmol) obtained in Step 2 was dissolved in methanol (8.4 mL), and 4 N HCl solution (8.40 mL, 33.6 mmol) was added thereto. The reaction mixture was stirred at 100° C. for 16 hours. After removing the solvent under reduced pressure, the resulting product was diluted with ethyl acetate and washed with brine, and the organic solvent was dried over magnesium sulfate. The desired product was obtained by silica gel column. (Yield: 32.1%)

$^1$H-NMR (400 MHz, CHLOROFORM-D) δ 7.28 (d, J=8.2 Hz, 2H), 7.23 (d, J=8.2 Hz, 2H), 3.68 (s, 3H), 3.64 (s, 3H), 3.59 (s, 2H), 1.57 (s, 6H)

Step 4: 2-(4-(1-Methoxy-2-methyl-1-oxopropane-2-yl)phenyl)acetic acid

Methyl 2-(4-(2-methoxy-2-oxoethyl)phenyl)-2-methylpropanoate (27 mg, 0.108 mmol) obtained in Step 3 was dissolved in THF (1 mL) and methanol (1 mL), and lithium hydroxide (2.58 mg, 0.108 mmol) dissolved in water (0.5 mL) was added thereto. The reaction mixture was stirred at room temperature for 3 hours. After removing the solvent under reduced pressure, the resulting product was diluted with EA and washed with brine, and the organic solvent was dried over magnesium sulfate. The purification was carried out by silica gel column to obtain the desired product. (Yield: 100%)

$^1$H-NMR (400 MHz, CHLOROFORM-D) δ 7.36-7.19 (m, 7H), 3.75-3.57 (m, 6H), 1.69-1.50 (m, 6H)

Step 5: Methyl 2-(4-(2-amino-2-oxoethyl)phenyl)-2-methylpropanoate 2-(4-(1-Methoxy-2-methyl-1-oxopropane-2-yl)phenyl) acetic acid (26 mg, 0.110 mmol) obtained in Step 4 was used in a similar manner to Step 3 of Preparation Example 6 to obtain the desired product. (Yield: 77%)

$^1$H-NMR (400 MHz, CHLOROFORM-D) δ 7.31 (d, J=8.2 Hz, 2H), 7.22 (d, J=8.2 Hz, 2H), 5.47 (d, J=59.9 Hz, 1H), 3.64 (s, 3H), 3.55 (s, 2H), 1.56 (t, J=14.6 Hz, 6H)

Preparation Example 37: Methyl 3-(4-(1-amino-2-methyl-1-oxopropan-2-yl)phenyl)propanoate

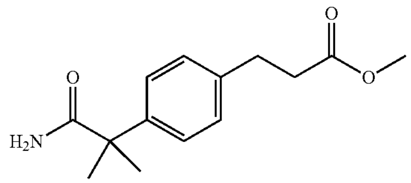 [SMILES: COC(=O)CCc1ccc(C(C)(C)C(N)=O)cc1]

2-(4-Bromophenyl)-2-methylpropanoic acid (1.00 g, 4.11 mmol) was dissolved in DCM (21 mL), oxalyl chloride (0.94 g, 7.40 mmol) was added, and 5 drops of DMF were added. The reaction mixture was stirred at room temperature for 30 minutes, and the solvent was removed under reduced pressure. The concentrate was dissolved in THF (21 mL), the temperature was lowered to 0° C., and potassium tert-butoxide (0.55 g, 4.94 mmol) was added thereto. After stirring at room temperature for 12 hours, water was added, followed by extraction with ethyl acetate. After washing with water and brine, the organic layer was dried over magnesium sulfate and concentrated under reduced pressure. Purification by column chromatography gave tert-butyl 2-(4-bromophenyl)-2-methylpropanoate. Then, the methods similar to Preparation Example 10 were sequentially performed to obtain the desired product. (Yield: 31%)

$^1$H-NMR (400 MHz, CHLOROFORM-D): δ 7.37-7.29 (m, 2H), 7.18 (d, J=8.2 Hz, 2H), 5.97 (s, 1H), 5.24 (s, 1H), 3.67 (d, J=1.4 Hz, 3H), 2.94 (t, J=7.5 Hz, 2H), 2.63 (t, J=7.8 Hz, 2H), 1.66-1.44 (m, 6H)

Preparation Example 38: Ethyl 3-(4-(3-carbamoylazetidin-1-yl)phenyl)propanoate

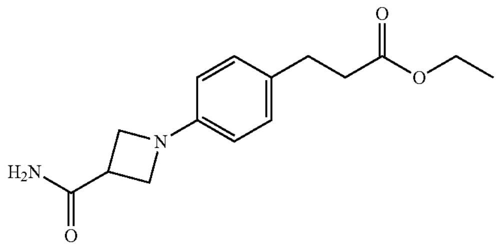 [SMILES: CCOC(=O)CCc1ccc(N2CC(C(N)=O)C2)cc1]

Step 1: Benzyl 1-(4-formylphenyl)azetidine-3-carboxylate 1-(4-Formylphenyl)azetidine-3-carboxylic acid (1.50 g, 7.31 mmol), potassium carbonate (1.11 g, 8.04 mmol) and benzyl bromide (1.25 g, 7.31 mmol) were added to DMF (7.3 mL) and stirred at room temperature for 12 hours. Water was added to the reaction mixture, followed by extraction with ethyl acetate. After washing with water and brine, the organic layer was dried over magnesium sulfate and concentrated under reduced pressure. The purification was carried out by column chromatography to obtain the desired product. (Yield: 56%)

$^1$H NMR (400 MHz, CHLOROFORM-D): δ 9.74 (s, 1H), 7.72 (d, J=8.7 Hz, 2H), 7.45-7.29 (m, 5H), 6.42 (d, J=8.7 Hz, 2H), 5.20 (s, 2H), 4.26-4.13 (m, 4H), 3.70-3.59 (m, 1H)

Step 2: 1-(4-(3-Ethoxy-3-oxopropyl)phenyl)azetidine-3-carboxylic acid

Using benzyl 1-(4-formylphenyl)azetidine-3-carboxylate (1.20 g, 4.06 mmol) obtained in Step 1, the methods of Steps 2 and 3 of Preparation Example 25 were sequentially performed to obtain the title compound. (Yield: 52%)

$^1$H NMR (400 MHz, CHLOROFORM-D): δ 7.07 (d, J=8.2 Hz, 2H), 6.43 (d, J=8.2 Hz, 2H), 4.18-3.97 (m, 6H), 3.59 (dd, J=14.4, 6.2 Hz, 1H), 2.86 (t, J=7.8 Hz, 2H), 2.56 (t, J=7.8 Hz, 2H), 1.30-1.16 (m, 3H)

Step 3: Ethyl 3-(4-(3-(chlorocarbonyl)azetin-1-yl) phenyl)propanoate

After dissolving 1-(4-(3-ethoxy-3-oxopropyl)phenyl)azetidine-3-carboxylic acid (590 mg, 2.13 mmol) obtained in Step 2 in dichloromethane, the temperature was lowered to 0° C. Oxalyl chloride (0.37 ml, 4.26 mmol) was added dropwise thereto, and the temperature was gradually raised to room temperature. After completion of the reaction, the resulting product was concentrated under reduced pressure and used in the next reaction without further purification. (Yield: 99%)

m/z $(M+H)^+$ calculated for $C_{15}H_{19}ClNO_3$: 296, found 296.

Step 4: Ethyl 3-(4-(3-carbamoylazetidin-1-yl)phenyl)propanoate

Ethyl 3-(4-(3-(chlorocarbonyl)azetin-1-yl)phenyl)propanoate (629 mg, 2.127 mmol) obtained in Step 3 was used in a similar manner to Step 3 of Preparation Example 6 to obtain the desired product. (Yield: 4%)

$^1$H-NMR (400 MHz, CHLOROFORM-D) δ 7.08-6.90 (m, 2H), 6.57 (dd, J=23.8, 15.6 Hz, 2H), 6.09 (s, NH), 5.59 (s, NH), 4.10 (q, J=7.0 Hz, 3H), 3.87-3.54 (m, 2H), 3.50-3.32 (m, 2H), 3.02-2.86 (m, 1H), 2.82 (t, J=7.8 Hz, 2H), 2.72-2.43 (m, 2H), 1.22 (t, J=7.1 Hz, 3H)

Preparation Example 39: Methyl 2-(4-carbamoylpiperidin-1-yl)pyrimidine-5-carboxylate

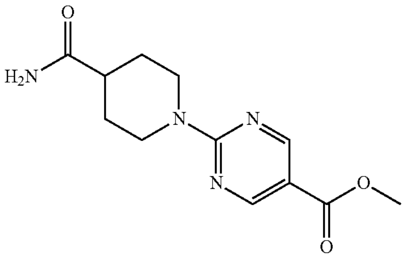 [SMILES: COC(=O)c1cnc(N2CCC(C(N)=O)CC2)nc1]

Step 1: 1-(5-(Methoxycarbonyl)pyrimidin-2-yl)piperidine-4-carboxylic acid

Piperidine-4-carboxylic acid (50 mg, 0.387 mmol) and methyl 2-chloropyrimidine-5-carboxylate (80 mg, 0.465 mmol) were dissolved in DMF, and TEA (108 μL, 0.774 mmol) was added and stirred at 80° C. After stirring for 1 hour, the termination of the reaction was confirmed by TLC. After removing DMF through the extraction process and neutralizing to obtain an organic layer, water was removed with magnesium sulfate, and the obtained material was distilled under reduced pressure and purified by column chromatography (methylene chloride:methanol=10:1) to obtain 1-(5-(methoxycarbonyl)pyrimidin-2-yl)piperidine-4-carboxylic acid (40 mg, 0.151 mmol, yield: 39%).

$^1$H-NMR (400 MHz, Methanol-D4) δ 8.77 (d, J=2.3 Hz, 2H), 4.71 (d, J=13.7 Hz, 2H), 3.83 (d, J=2.3 Hz, 3H), 3.22-3.04 (m, 2H), 2.61 (s, 1H), 2.09-1.88 (m, 2H), 1.75-1.49 (m, 2H)

Step 2: Methyl 2-(4-carbamoylpiperidin-1-yl)pyrimidine-5-carboxylate 1-(5-(Methoxycarbonyl)pyrimidin-2-yl)piperidine-4-carboxylic acid (42.8 mg, 0.151 mmol) obtained in Step 1 was used in a similar manner to Step 3 of Preparation Example 6 to obtain the desired product. (Yield: 88%)

$^1$H-NMR (400 MHz, CHLOROFORM-D) δ 8.80 (s, 2H), 8.41 (s, 1H), 4.81-4.70 (m, 2H), 4.68 (s, 1H), 3.86-3.75 (m, 3H), 3.24-3.13 (m, 1H), 2.65 (tt, J=10.7, 3.9 Hz, 1H), 2.12-1.84 (m, 5H), 1.86-1.61 (m, 3H)

Preparation Example 40: Tert-butyl 2-(4-(4-carbamoylpiperidin-1-yl)phenyl)acetate

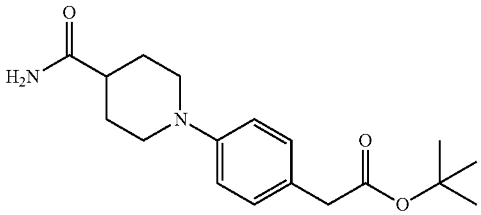 [SMILES: CC(C)(C)OC(=O)Cc1ccc(N2CCC(C(N)=O)CC2)cc1]

Using tert-butyl 2-(4-bromophenyl) acetate (0.3 g, 1.106 mmol) and ethyl piperidine-4-carboxylate (0.209 g, 1.328 mmol), the similar methods of Step 1 of Preparation Example 2, and Steps 2 and 3 of Preparation Example 6 were sequentially performed to obtain the desired product. (3 steps yield: 20.1%)

$^1$H-NMR (400 MHz, CHLOROFORM-D) δ 7.13 (d, J=8.7 Hz, 2H), 6.90-6.83 (2H), 5.60 (d, J=16.9 Hz, 2H), 3.68 (d, J=12.3 Hz, 2H), 3.42 (s, 2H), 2.70 (td, J=12.1, 2.4 Hz, 2H), 2.32-2.20 (m, 1H), 1.96 (d, J=11.0 Hz, 2H), 1.84 (qd, J=12.2, 3.7 Hz, 2H), 1.43 (d, J=10.5 Hz, 9H)

Preparation Example 41: Methyl 2-(4-(4-carbamoylpiperidin-1-yl)phenyl)-2-methylpropanoate

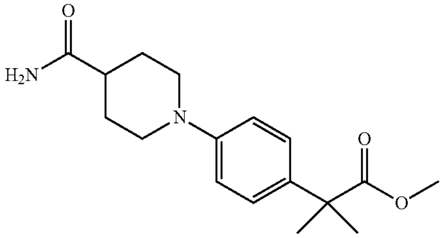 [SMILES: COC(=O)C(C)(C)c1ccc(N2CCC(C(N)=O)CC2)cc1]

Using methyl 2-(4-bromophenyl)-2-methylpropanoate (0.20 g, 0.78 mmol) and tert-butyl piperidine-4-carboxylate (0.17 g, 0.93 mmol), the methods of Preparation Example 2 and Step 3 of Preparation Example 6 were sequentially performed to obtain the desired product. (Yield: 64%)

$^1$H-NMR (400 MHz, CHLOROFORM-D): δ 7.23-7.13 (m, 2H), 6.91-6.80 (m, 2H), 5.54 (s, 2H), 3.70 (d, J=12.3 Hz, 2H), 3.63 (d, J=7.8 Hz, 3H), 2.72 (td, J=12.1, 2.3 Hz, 2H), 2.27 (qd, J=7.8, 4.0 Hz, 1H), 1.97 (d, J=10.5 Hz, 2H), 1.84 (qd, J=12.2, 3.9 Hz, 2H), 1.54 (d, J=7.3 Hz, 6H)

Preparation Example 42: Methyl 2-(6-(4-carbamoylpiperidin-1-yl)pyridin-3-yl)-2-methylpropanoate

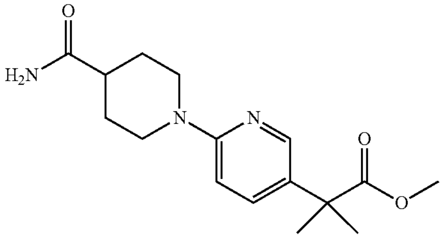 [SMILES: COC(=O)C(C)(C)c1ccc(N2CCC(C(N)=O)CC2)nc1]

Methyl 2-(6-chloropyridin-3-yl)-2-methylpropanoate (2.05 g, 9.59 mmol) and tert-butyl piperidine-4-carboxylate (2.13 g, 11.51 mmol) were used in a similar manner to Preparation Example 41 to obtain the desired product. (Yield: 12%)

$^1$H-NMR (400 MHz, CHLOROFORM-D): δ 8.15 (t, J=2.1 Hz, 1H), 7.44 (dt, J=9.0, 2.4 Hz, 1H), 6.61 (dd, J=8.9, 1.6 Hz, 1H), 5.58 (s, 2H), 4.30 (d, J=12.8 Hz, 2H), 3.62 (d, J=2.3 Hz, 3H), 2.95-2.76 (m, 2H), 2.45-2.28 (m, 1H), 2.00-1.88 (2H), 1.80-1.63 (m, 2H), 1.53 (d, J=1.8 Hz, 6H)

Preparation Example 43: Ethyl 2-(5-(4-carbamoylpiperidin-1-yl)-2H-tetrazol-2-yl)acetate

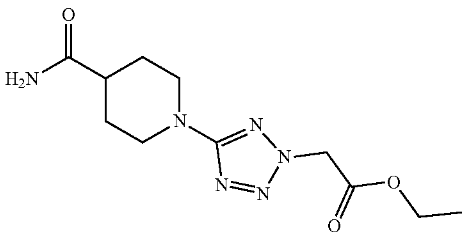 [SMILES: CCOC(=O)Cn1nnc(N2CCC(C(N)=O)CC2)n1]

Step 1: 4-Benzyl 1-(tert-butyl)-piperidine-1,4-dicarboxylate 1-(Tert-butoxycarbonyl)piperidine-4-carboxylic acid (4.37 g, 19.06 mmol) was dissolved in acetone, and benzyl bromide (2.72 mL, 22.87 mmol) and potassium carbonate (6.32 g, 45.7 mmol) were added thereto. The reflux cooler was connected, and the reaction mixture was heated for 2 hours. After completion of the reaction, the resulting product was cooled to room temperature, and water was added. The organic layer was separated and dried over magnesium sulfate. The material obtained through distillation under reduced pressure was purified by column chromatography (hexane:ethyl acetate) to obtain 4-benzyl 1-(tert-butyl)-piperidine-1,4-dicarboxylate (6.09 g, 19.07 mmol, yield: 99%).

$^1$H-NMR (400 MHz, CHLOROFORM-D) δ 7.45-7.27 (m, 6H), 5.12 (s, 2H), 4.07-3.91 (2H), 2.91-2.71 (2H), 2.56-2.39 (m, 1H), 1.88 (d, J=10.5 Hz, 2H), 1.71-1.56 (m, 2H), 1.44 (t, J=15.1 Hz, 9H)

Step 2: Benzyl piperidine-4-carboxylate

4-Benzyl 1-(tert-butyl)-piperidine-1,4-dicarboxylate (6.09 g, 19.07 mmol) obtained in Step 1 was used in a similar manner to Step 2 of Preparation Example 2 to obtain the desired product. (Yield: 48%)

$^1$H-NMR (400 MHz, METHANOL-D4) δ 7.40-7.20 (m, 5H), 5.09 (s, 2H), 2.98 (td, J=8.5, 4.1 Hz, 2H), 2.58 (td, J=12.1, 2.7 Hz, 2H), 2.50 (qd, J=7.5, 3.5 Hz, 1H), 1.86 (dd, J=13.7, 3.2 Hz, 2H), 1.70-1.47 (m, 2H)

Step 3: Benzyl 1-cyanopiperidine-4-carboxylate

Benzyl piperidine-4-carboxylate (1.9934 g, 9.09 mmol) obtained in Step 2 was dissolved in acetonitrile, DIPEA (4.76 mL, 27.3 mmol) and cyano bromide (0.573 mL, 10.91 mmol) were added and stirred at room temperature for 2 hours. After completion of the reaction, water was added. The organic layer was separated and dried over magnesium sulfate, and the material obtained through distillation under reduced pressure was purified by column chromatography (hexane:ethyl acetate) to obtain benzyl 1-cyanopiperidine-4-carboxylate (2.1838 g, 8.94 mmol, yield: 98%).

$^1$H-NMR (400 MHz, CHLOROFORM-D) δ 7.45-7.27 (m, 5H), 5.20-5.05 (2H), 3.41 (td, J=8.5, 4.3 Hz, 2H), 3.15-2.95 (m, 2H), 2.57-2.37 (m, 1H), 1.98 (dd, J=14.2, 3.7 Hz, 2H), 1.92-1.73 (2H)

Step 4: Benzyl 1-(2H-tetrazol-5-yl)piperidine-4-carboxylate

Benzyl 1-cyanopiperidine-4-carboxylate (2.1838 g, 8.94 mmol) obtained in Step 3 was dissolved in DMF, and ammonium chloride (0.717 g, 13.41 mmol) and sodium azide (0.872 g, 13.41 mmol) were added and reacted at 100° C. for 6 hours. After completion of the reaction, water was added. The organic layer was separated and dried over magnesium sulfate, and the material obtained through distillation under reduced pressure was purified by column chromatography (hexane:ethyl acetate) to obtain benzyl 1-(2H-tetrazol-5-yl)piperidine-4-carboxylate (2.57 g, 8.94 mmol, yield: 99%).

$^1$H-NMR (400 MHz, METHANOL-D4) δ 7.95 (s, 1H), 7.31 (dt, J=12.3, 4.3 Hz, 5H), 5.12 (s, 2H), 3.78 (dt, J=13.3, 3.9 Hz, 2H), 3.32 (s, 1H), 3.21-3.05 (m, 2H), 2.97 (s, 2H), 2.83 (s, 2H), 2.76-2.56 (m, 1H), 2.00 (dd, J=13.5, 3.4 Hz, 2H), 1.74 (ddd, J=24.6, 11.3, 4.0 Hz, 2H)

Step 5: Benzyl 1-(2-(2-ethoxy-2-oxoethyl)-2H-tetrazol-5-yl)piperidine-4-carboxylate Benzyl 1-(2H-tetrazol-5-yl)piperidine-4-carboxylate (1.465 g, 5.10 mmol) obtained in Step 4 was dissolved in DMF, and potassium carbonate (1.409 g, 10.20 mmol) and ethyl 2-bromoacetate (1.277 g, 7.65 mmol) were added and stirred at room temperature for 12 hours. After completion of the reaction, water was added. The organic layer was separated and dried over magnesium sulfate, and the material obtained through distillation under reduced pressure was purified by column chromatography (hexane:ethyl acetate) to obtain benzyl 1-(2-(2-ethoxy-2)-oxoethyl)-2H-tetrazol-5-yl)piperidine-4-carboxylate (1.8039 g, 4.83 mmol, yield: 95%).

$^1$H-NMR (400 MHz, CHLOROFORM-D) δ 7.44-7.27 (m, 5H), 5.17 (s, 2H), 5.13 (s, 2H), 4.31-4.19 (m, 2H), 4.03 (td, J=8.5, 4.6 Hz, 2H), 3.13-2.93 (m, 2H), 2.55 (tt, J=11.1, 3.8 Hz, 1H), 1.99 (d, J=1.8 Hz, 2H), 1.81 (ddd, J=24.8, 11.1, 4.2 Hz, 2H), 1.32-1.26 (m, 3H)

Step 6: 1-(2-(2-Ethoxy-2-oxoethyl)-2H-tetrazol-5-yl)piperidine-4-carboxylic acid Benzyl 1-(2-(2-ethoxy-2-oxoethyl)-2H-tetrazol-5-yl)piperidine-4-carboxylate (1.8039 g, 4.83 mmol) obtained in Step 5 was used in a similar manner to Step 2 of Preparation Example 10 to obtain the desired product. (Yield: 79%)

$^1$H-NMR (400 MHz, METHANOL-D4) δ 5.35 (s, 2H), 4.23 (q, J=7.2 Hz, 2H), 3.96 (dt, J=13.0, 3.5 Hz, 2H), 3.14-2.93 (m, 2H), 2.61-2.42 (m, 1H), 1.96 (dd, J=13.7, 3.2 Hz, 2H), 1.71 (ddd, J=24.7, 11.4, 4.1 Hz, 2H), 1.34-1.21 (m, 3H)

Step 7: Ethyl 2-(5-(4-carbamoylpiperidin-1-yl)-2H-tetrazol-2-yl)acetate 1-(2-(2-Ethoxy-2-oxoethyl)-2H-tetrazol-5-yl)piperidine-4-carboxylic acid (1.085 g, 4.83 mmol) obtained in Step 6 was used in a similar manner to Step 3 of Preparation Example 6 to obtain the desired product. (Yield: 13%)

$^1$H-NMR (400 MHz, METHANOL-D4) δ 5.35 (s, 2H), 4.32-4.16 (2H), 4.05 (d, J=12.8 Hz, 2H), 3.32 (d, J=6.9 Hz, 1H), 2.96 (td, J=12.6, 2.7 Hz, 2H), 2.50-2.34 (2H), 1.84 (d, J=12.3 Hz, 2H), 1.74 (td, J=12.1, 4.4 Hz, 2H), 1.26 (t, J=7.3 Hz, 3H)

Preparation Example 44: Ethyl 2-(4-carbamoylpiperidin-1-yl)acetate

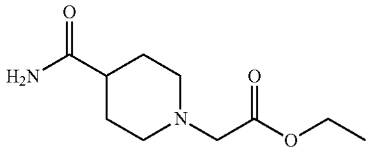

Piperidine-4-carboxamide (300 mg, 2.341 mmol) and ethyl 2-bromoacetate (311 μL, 2.81 mmol) were used in a similar manner to Step 3 of Preparation Example 43 to obtain the desired product. (Yield: 36%)

$^1$H-NMR (MeOD) δ 4.19 (q, J=7.1 Hz, 2H), 3.24 (s, 2H), 3.00 (d, J=11.3 Hz, 2H), 2.35-2.16 (m, 3H), 1.88-1.72 (m, 4H), 1.28 (t, J=7.0 Hz, 3H)

Preparation Example 45: Ethyl 1-(4-(1-amino-2-methyl-1-oxopropan-2-yl)phenyl)piperidine-4-carboxylate

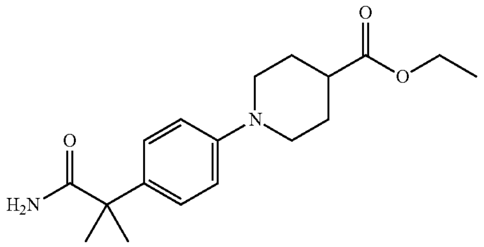 [SMILES: CCOC(=O)C1CCN(c2ccc(C(C)(C)C(N)=O)cc2)CC1]

Ethyl piperidine-4-carboxylate (0.13 g, 0.80 mmol) and tert-butyl 2-(4-bromophenyl)-2-methylpropanoate (0.2 g, 0.67 mmol) were used in a similar manner to Preparation Example 41 to obtain the desired product. (Yield: 72%)

$^1$H-NMR (400 MHz, CHLOROFORM-D): δ 7.27-7.15 (m, 2H), 6.95-6.75 (m, 2H), 5.88 (s, 1H), 5.24 (s, 1H), 4.19-4.06 (2H), 3.60 (dt, J=12.3, 3.4 Hz, 2H), 2.83-2.66 (m, 2H), 2.46-2.32 (m, 1H), 1.98 (dd, J=13.3, 2.7 Hz, 2H), 1.92-1.74 (m, 2H), 1.51 (s, 6H), 1.24 (t, J=7.1 Hz, 3H)

Preparation Example 46: Methyl 6-(3-carbamoylpyrrolidin-1-yl)nicotinate

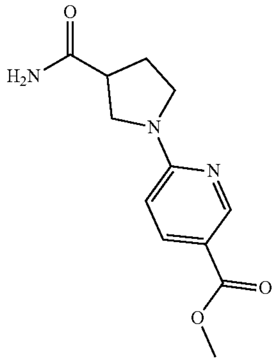 [SMILES: COC(=O)c1ccc(N2CCC(C(N)=O)C2)nc1]

Step 1: 3-Benzyl 1-(tert-butyl)pyrrolidine-1,3-dicarboxylate 1-(Tert-butoxycarbonyl)pyrrolidine-3-carboxylic acid (1.22 g, 5.67 mmol) was dissolved in DMF, and benzyl bromide (0.808 mL, 6.80 mmol) and cesium carbonate (2.216 g, 6.80 mmol) were added thereto and stirred at room temperature for 12 hours. After completion of the reaction, water was added, and the organic layer was separated and dried over magnesium sulfate. The material obtained by distillation under reduced pressure was purified by column chromatography (hexane:ethyl acetate) to obtain 3-benzyl 1-(tert-butyl)pyrrolidine-1,3-dicarboxylate (1.7 g, 5.57 mmol, yield: 98%).

$^1$H-NMR (400 MHz, CHLOROFORM-D) δ 7.34 (s, 5H), 5.12 (d, J=11.0 Hz, 2H), 3.57 (s, 2H), 3.33 (s, 1H), 3.08 (s, 1H), 2.12 (s, 2H), 1.43 (d, J=11.0 Hz, 9H)

Step 2: Benzyl pyrrolidine-3-carboxylate

3-Benzyl 1-(tert-butyl) pyrrolidine-1,3-dicarboxylate (1.7 g, 5.57 mmol) obtained in Step 1 was used in a similar manner to Step 2 of Preparation Example 2 to obtain the desired product. (Yield: 99%)

$^1$H-NMR (400 MHz, CHLOROFORM-D) δ 7.44-7.26 (m, 14H), 7.10 (dd, J=7.5, 1.6 Hz, 6H), 5.12 (s, 2H), 4.11 (q, J=7.2 Hz, 3H), 4.00 (td, J=8.5, 4.6 Hz, 2H), 3.07-2.87 (m, 2H), 2.61-2.42 (m, 1H), 1.97 (dd, J=13.5, 3.9 Hz, 2H), 1.90-1.67 (m, 2H)

Step 3: Methyl 6-(3-((benzyloxy)carbonyl)pyrrolidin-1-yl)nicotinate

Benzyl pyrrolidine-3-carboxylate (1.277 g, 6.22 mmol) obtained in Step 2 was used in a similar manner to Step 1 of Preparation Example 2 to obtain the desired product. (Yield: 46%)

$^1$H-NMR (CHLOROFORM-D) δ 8.82 (d, J=2.4 Hz, 1H), 8.02 (dd, J=9.0, 2.3 Hz, 1H), 7.44-7.30 (m, 5H), 6.35 (d, J=8.8 Hz, 1H), 5.18 (dd, J=16.0, 12.4 Hz, 2H), 3.88 (s, 3H), 3.87-3.75 (2H), 3.76-3.63 (1H), 3.63-3.48 (1H), 3.29 (t, J=7.3 Hz, 1H), 2.43-2.28 (m, 2H)

Step 4: 1-(5-(Methoxycarbonyl)pyridin-2-yl)pyrrolidine-3-carboxylic acid

Methyl 6-(3-((benzyloxy)carbonyl)pyrrolidin-1-yl)nicotinate (524 mg, 1.539 mmol) obtained in Step 3 was used in a similar manner to Step 2 of Preparation Example 10 to obtain the desired product. (Yield: 99%)

$^1$H-NMR (MeOD) δ 8.68 (d, J=2.1 Hz, 1H), 8.03 (dd, J=9.0, 2.3 Hz, 1H), 6.55 (d, J=9.2 Hz, 1H), 3.87 (s, 3H), 3.77 (t, J=5.0 Hz, 3H), 3.71-3.51 (m, 3H), 3.28 (t, J=7.2 Hz, 1H), 2.42-2.25 (m, 2H)

Step 5: Methyl 6-(3-carbamoylpyrrolidin-1-yl)nicotinate 1-(5-(Methoxycarbonyl)pyridin-2-yl)pyrrolidine-3-carboxylic acid (423 mg, 1.690 mmol) obtained in Step 4 was dissolved in DMF, the temperature was lowered to 0° C., and ammonium chloride (380 mg, 7.10 mmol), DIPEA (886 μL, 5.07 mmol) and 1-hydroxybenzotriazole (337 mg, 2.197 mmol) were added thereto. After slowly adding 1-ethyl-3-(3-dimethylaminopropyl)carbodiimide (389 mg, 2.028 mmol) to the reaction solution, the reaction temperature was raised to room temperature and stirred for 12 hours. After completion of the reaction, water was added, and the organic layer was separated and dried over magnesium sulfate. The material obtained by distillation under reduced pressure was purified by column chromatography (hexane:ethyl acetate) to obtain methyl 6-(3-carbamoylpyrrolidine-1). -yl)nicotinate (213 mg, 0.854 mmol, yield: 51%).

$^1$H-NMR (400 MHz, METHANOL-D4) δ 8.66-8.61 (1H), 8.02-7.96 (1H), 6.54-6.46 (1H), 3.85-3.80 (4H), 3.79-3.71 (1H), 3.69-3.56 (2H), 3.55-3.42 (1H), 3.23-3.06 (1H), 2.37-2.07 (3H)

Preparation Example 47: Tert-butyl 3-carbamoyl-3-methylpyrrolidine-1-carboxylate

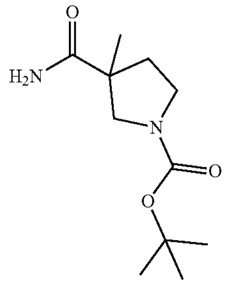 [SMILES: CC(C)(C)OC(=O)N1CCC(C)(C(N)=O)C1]

Step 1: 3-Benzyl 1-(tert-butyl) (R)-pyrrolidine-1,3-dicarboxylate (R)-1-(tert-butoxycarbonyl)pyrrolidine-3-carboxylic acid (518 mg, 2.407 mmol) was used in a similar manner to Step 1 of Preparation Example 43 to obtain the desired product. (Yield: 93%)

$^1$H-NMR (400 MHz, CHLOROFORM-D) δ 7.44-7.26 (m, 5H), 5.13 (s, 2H), 3.66-3.39 (m, 2H), 3.33 (s, 1H), 3.07 (d, J=7.3 Hz, 1H), 2.13 (t, J=7.1 Hz, 2H), 1.50-1.33 (9H)

Step 2: 3-Benzyl 1-(tert-butyl) 3-methylpyrrolidine-1,3-dicarboxylate

3-Benzyl 1-(tert-butyl) (R)-pyrrolidine-1,3-dicarboxylate (684 mg, 2.240 mmol) obtained in Step 1 was dissolved in anhydrous THF, and iodomethane (0.42 mL, 6.72 mmol) was added thereto. The reaction solution was lowered to −78° C., and then lithium bis(trimethylsilyl)amide (6.72 mL, 6.72 mmol) was slowly added dropwise. After TLC confirmation, the reaction was terminated with an aqueous ammonium hydroxide solution, and the organic layer was separated and dried over magnesium sulfate. The material obtained by distillation under reduced pressure was purified by column chromatography (hexane:ethyl acetate) to obtain 3-benzyl 1-(tert-butyl) 3-methylpyrrolidine-1,3-dicarboxylate (594 mg, 2.240 mmol, yield: 83%).

$^1$H-NMR (400 MHz, CHLOROFORM-D) δ 7.33 (dd, J=13.3, 5.5 Hz, 5H), 5.13 (s, 2H), 3.78 (dd, J=16.0, 11.0 Hz, 1H), 3.40 (td, J=13.6, 6.7 Hz, 2H), 3.19 (dd, J=33.6, 11.2 Hz, 1H), 2.32 (q, J=5.9 Hz, 1H), 1.86-1.66 (m, 1H), 1.43 (s, 9H), 1.29 (d, J=36.1 Hz, 3H)

Step 3: 1-(Tert-butoxycarbonyl)-3-methylpyrrolidine-3-carboxylic acid

3-Benzyl 1-(tert-butyl) 3-methylpyrrolidine-1,3-dicarboxylate (80 mg, 0.250 mmol) obtained in Step 2 was used in a similar manner to Step 2 of Preparation Example 10 to obtain the desired product. (Yield: 99%)

$^1$H-NMR (400 MHz, METHANOL-D4) δ 3.75 (d, J=11.0 Hz, 1H), 3.47-3.31 (m, 2H), 3.09 (d, J=11.0 Hz, 1H), 2.38-2.21 (m, 1H), 1.77 (dd, J=12.8, 5.5 Hz, 1H), 1.43 (s, 9H), 1.30 (s, 3H)

Step 4: Tert-butyl 3-carbamoyl-3-methylpyrrolidine-1-carboxylate 1-(Tert-butoxycarbonyl)-3-methylpyrrolidine-3-carboxylic acid (60 mg, 0.262 mmol) obtained in Step 3 was used in a similar manner to Step 5 of Preparation Example 46 to obtain the desired product. (Yield: 62%)

$^1$H-NMR (CHLOROFORM-D) δ 5.87-5.28 (2H), 3.81-3.61 (m, 1H), 3.50 (d, J=36.0 Hz, 2H), 3.23 (s, 1H), 2.28 (s, 1H), 1.79 (dd, J=12.5, 7.0 Hz, 1H), 1.46 (d, J=12.5 Hz, 10H), 1.36 (d, J=13.7 Hz, 3H)

Preparation Example 48: Methyl 6-(3-carbamoyl-3-methylpyrrolidin-1-yl)nicotinate

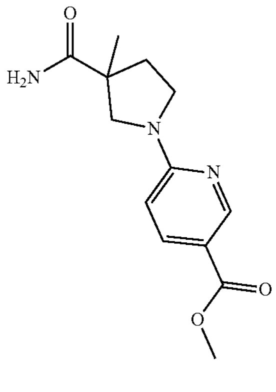 [SMILES: COC(=O)c1ccc(N2CCC(C)(C(N)=O)C2)nc1]

Step 1: Benzyl 3-methylpyrrolidine-3-carboxylate

3-Benzyl 1-(tert-butyl) 3-methylpyrrolidine-1,3-dicarboxylate (510 mg, 1.597 mmol) obtained in Step 2 of Preparation Example 47 was used in a similar manner to Step 2 of Preparation Example 2 to obtain the desired product. (Yield: 99%)

$^1$H-NMR (400 MHz, METHANOL-D4) δ 7.44-7.25 (m, 5H), 5.28-5.11 (m, 2H), 3.76 (d, J=11.9 Hz, 1H), 3.40 (ddd, J=12.6, 7.5, 4.3 Hz, 1H), 3.27-3.17 (m, 1H), 3.05 (d, J=11.9 Hz, 1H), 2.53-2.34 (m, 1H), 2.07-1.87 (m, 1H), 1.41 (s, 3H)

Step 2: Methyl 6-(3-((benzyloxy)carbonyl)-3-methylpyrrolidin-1-yl)nicotinate

Benzyl 3-methylpyrrolidine-3-carboxylate (357 mg, 1.628 mmol) obtained in Step 1 and methyl 6-chloronicotinate (307 mg, 1.791 mmol) were used in a similar manner to Step 1 of Preparation Example 2 to obtain the desired product. (Yield: 23%)

$^1$H-NMR (400 MHz, CHLOROFORM-D) δ 8.78 (d, J=2.3 Hz, 1H), 7.98 (dd, J=9.1, 2.3 Hz, 1H), 7.39-7.26 (m, 6H), 6.29 (d, J=8.7 Hz, 1H), 5.14 (d, J=1.4 Hz, 2H), 4.13-4.00 (1H), 3.85 (s, 3H), 3.58 (s, 2H), 3.48-3.30 (1H), 2.52 (t, J=6.2 Hz, 1H), 1.96 (dd, J=7.1, 5.7 Hz, 1H), 1.43 (s, 3H)

Step 3: 1-(5-(Methoxycarbonyl)pyridin-2-yl)-3-methylpyrrolidine-3-carboxylic acid Methyl 6-(3-((benzyloxy)carbonyl)-3-methylpyrrolidin-1-yl)nicotinate (130 mg, 0.367 mmol) obtained in Step 2 was used in a similar manner to Step 2 of Preparation Example 10 to obtain the desired product. (Yield: 99%)

$^1$H-NMR (MeOD) δ 8.67 (d, J=2.1 Hz, 1H), 8.01 (dd, J=9.2, 2.1 Hz, 1H), 6.52 (d, J=9.2 Hz, 1H), 4.09-3.98 (1H), 3.87 (d, J=4.6 Hz, 3H), 3.70-3.55 (m, 2H), 3.35 (s, 1H), 2.52 (t, J=6.3 Hz, 1H), 2.03-1.88 (m, 1H), 1.41 (s, 3H)

Step 4: Methyl 6-(3-carbamoyl-3-methylpyrrolidin-1-yl)nicotinate 1-(5-(Methoxycarbonyl)pyridin-2-yl)-3-methylpyrrolidine-3-carboxylic acid (97 mg, 0.367 mmol) obtained in Step 3 was used in a similar manner to Step 5 of Preparation Example 46 to obtain the desired product. (Yield: 59%)

$^1$H-NMR (MeOD) δ 8.68 (d, J=2.1 Hz, 1H), 8.03 (dd, J=9.0, 2.3 Hz, 1H), 6.53 (d, J=9.2 Hz, 1H), 3.96 (d, J=10.7 Hz, 1H), 3.88 (d, J=7.9 Hz, 3H), 3.69-3.56 (m, 2H), 2.87-2.81 (2H), 2.76 (t, J=7.5 Hz, 1H), 2.56-2.40 (m, 1H), 2.10-1.94 (1H), 1.46 (d, J=22.3 Hz, 3H)

Preparation Example 49: Tert-butyl 2-(4-(2-amino-2-oxoethyl)phenoxy)acetate

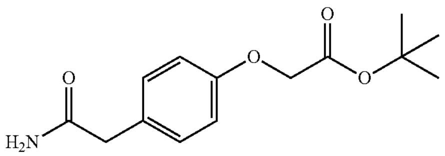 [SMILES: CC(C)(C)OC(=O)COc1ccc(CC(N)=O)cc1]

2-(4-Hydroxyphenyl)acetamide (1.00 g, 6.62 mmol) and tert-butyl 2-bromoacetate (1.36 g, 6.95 mmol) were used in a similar manner to Step 1 of Preparation Example 38 to obtain the desired product. (Yield: 85%)

$^1$H-NMR (400 MHz, CHLOROFORM-D): δ 7.22-7.14 (m, 2H), 6.87 (dt, J=9.5, 2.4 Hz, 2H), 5.34 (s, 2H), 4.50 (s, 2H), 3.52 (s, 2H), 1.48 (s, 9H)

Preparation Example 50: Methyl 2-(4-(2-amino-2-oxoethoxy)phenyl)acetate

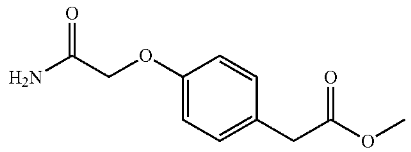 [SMILES: COC(=O)Cc1ccc(OCC(N)=O)cc1]

Using methyl 2-(4-hydroxyphenyl)acetate (1.00 g, 6.02 mmol) and tert-butyl 2-bromoacetate (1.29 g, 6.62 mmol), the methods of Step 1 of Preparation Example 38, Step 2 of Preparation Example 2 and Step 3 of Preparation Example 6 were sequentially performed to obtain the desired product. (Yield: 52%)

$^1$H-NMR (400 MHz, CHLOROFORM-D): δ 7.25-7.19 (m, 2H), 6.89 (dt, J=9.3, 2.5 Hz, 2H), 6.53 (s, 1H), 5.68 (s, 1H), 4.49 (s, 2H), 3.69 (s, 3H), 3.58 (s, 2H)

Preparation Example 51: Methyl 2-(4-(2-amino-2-oxoethoxy)phenyl)propanoate

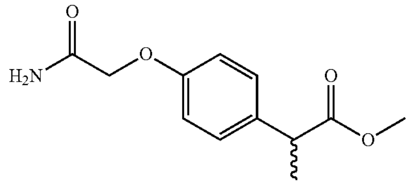 [SMILES: COC(=O)C(C)c1ccc(OCC(N)=O)cc1]

Using methyl 2-(4-(benzyloxy)phenyl)acetate (3.10 g, 12.10 mmol) and iodomethane (6.87 g, 48.4 mmol), the methods of Step 2 of Preparation Example 4, Step 2 of Preparation Example 10 and Preparation Example 50 were sequentially performed to obtain the desired product. (Yield: 63%)

$^1$H-NMR (400 MHz, CHLOROFORM-D): δ 7.22 (d, J=8.2 Hz, 2H), 6.86 (d, J=8.7 Hz, 2H), 6.52 (d, J=43.9 Hz, 2H), 4.45 (s, 2H), 3.74-3.57 (m, 4H), 1.45 (d, J=7.3 Hz, 3H)

Preparation Example 52: Methyl 3-(4-(2-amino-2-oxoethyl)phenoxy)-2,2-dimethylpropanoate

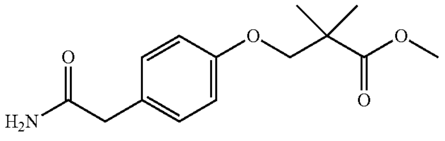 [SMILES: COC(=O)C(C)(C)COc1ccc(CC(N)=O)cc1]

Using methyl 3-hydroxy-2,2-dimethylpropanoate (0.80 g, 6.02 mmol) and methyl 2-(4-hydroxyphenyl)acetate (1.00 g, 6.02 mmol), the methods of Step 1 of Preparation Example 4, and Steps 2 and 3 of Preparation Example 6 were sequentially performed to obtain the desired product. (Yield: 34%)

$^1$H-NMR (400 MHz, CHLOROFORM-D): δ 7.13 (d, J=8.2 Hz, 2H), 6.84 (d, J=8.7 Hz, 2H), 6.02 (s, 1H), 5.52 (s, 1H), 3.91 (s, 2H), 3.66 (s, 3H), 3.46 (s, 2H), 1.28 (s, 6H)

Preparation Example 53: Ethyl (R)-2-(4-(2-amino-2-oxoethyl)phenoxy)propanoate

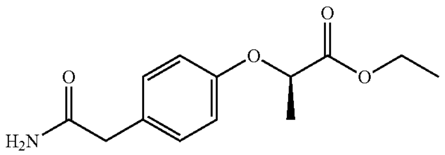 [SMILES: CCOC(=O)[C@@H](C)Oc1ccc(CC(N)=O)cc1]

Using benzyl 2-(4-hydroxyphenyl)acetate (0.80 g, 3.30 mmol) and ethyl (S)-2-hydroxypropanoate (0.43 g, 3.63 mmol), the methods of Step 1 of Preparation Example 4, and Steps 2 and 4 of Preparation Example 10 were sequentially performed to obtain the desired product. (Yield: 33%)

$^1$H-NMR (400 MHz, CHLOROFORM-D): δ 7.15 (d, J=8.2 Hz, 2H), 6.83 (d, J=8.7 Hz, 2H), 5.87 (s, 1H), 5.60 (s, 1H), 4.70 (q, J=6.9 Hz, 1H), 4.20 (q, J=7.2 Hz, 2H), 3.49 (s, 2H), 1.59 (d, J=6.9 Hz, 3H), 1.24 (t, J=7.1 Hz, 3H)

Preparation Example 54: Methyl (S)-2-(4-(2-amino-2-oxoethyl)phenoxy)propanoate

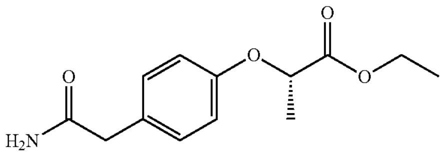 [SMILES: CCOC(=O)[C@H](C)Oc1ccc(CC(N)=O)cc1]

Using methyl (R)-2-hydroxypropanoate (1.081 ml, 11.35 mmol) and benzyl 2-(4-hydroxyphenyl)acetate (2.5 g, 10.32 mmol), the methods of Step 1 of Preparation Example 4, and Steps 2 and 4 of Preparation Example 10 were sequentially performed to obtain the desired product. (3 steps yield: 11.3%)

$^1$H-NMR (500 MHz, CHLOROFORM-D) δ 7.25-7.16 (m, 2H), 6.88 (dt, J=9.4, 2.5 Hz, 2H), 5.41 (d, J=28.4 Hz, 2H), 4.77 (q, J=6.7 Hz, 1H), 3.79 (s, 3H), 3.54 (s, 2H), 1.43-1.04 (m, 3H)

Preparation Example 55: Ethyl 2-(4-(2-amino-2-oxoethyl)phenoxy)-2-methylpropanoate

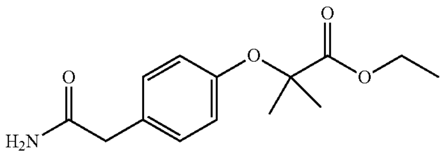 [SMILES: CCOC(=O)C(C)(C)Oc1ccc(CC(N)=O)cc1]

Using benzyl 2-(4-hydroxyphenyl) acetate (0.80 g, 3.30 mmol) and ethyl 2-bromo-2-methylpropanoate (1.29 g, 6.60 mmol), the methods of Step 1 of Preparation Example 38, and Steps 2 and 4 of Preparation Example 10 were sequentially performed to obtain the desired product. (Yield: 55%)

$^1$H-NMR (400 MHz, CHLOROFORM-D): δ 7.13 (d, J=8.2 Hz, 2H), 6.81 (d, J=8.7 Hz, 2H), 5.88-5.29 (m, 2H), 4.22 (q, J=7.2 Hz, 2H), 3.51 (s, 2H), 1.58 (s, 6H), 1.24 (t, J=7.1 Hz, 3H)

Preparation Example 56: Methyl 2-(4-((4-(2-amino-2-oxoethyl)phenoxy)methyl)phenyl)-2-methylpropanoate

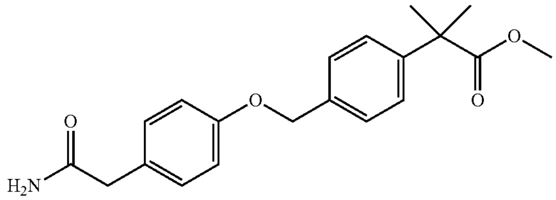 [SMILES: COC(=O)C(C)(C)c1ccc(COc2ccc(CC(N)=O)cc2)cc1]

Using methyl 2-(4-hydroxyphenyl)acetate (1.50 g, 9.03 mmol) and methyl 2-(4-(bromomethyl)phenyl)-2-methylpropanoate (2.69 g, 9.93 mmol), the methods of Step 1 of Preparation Example 38, and Steps 2 and 3 of Preparation Example 6 were sequentially performed to obtain the desired product. (Yield: 52%)

$^1$H-NMR (400 MHz, CHLOROFORM-D): δ 7.43-7.28 (m, 4H), 7.18 (dt, J=9.3, 2.5 Hz, 2H), 6.95 (dt, J=9.3, 2.5 Hz, 2H), 5.53 (s, 2H), 5.02 (s, 2H), 3.64 (s, 3H), 3.53 (s, 2H), 1.57 (s, 6H)

Preparation Example 57: (R)-2-chloro-6-(3-(2-cyclobutoxyphenoxy)piperidin-1-yl)pyrazine

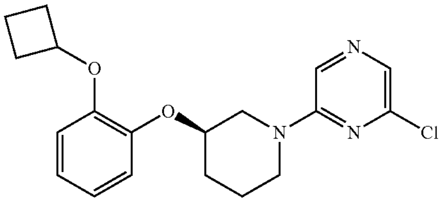 [SMILES: Clc1cncc(N2CCC[C@@H](Oc3ccccc3OC3CCC3)C2)n1]

2-(Benzyloxy)phenol (2.00 g, 9.99 mmol) and bromocyclobutane (2.70 g, 19.98 mmol) were used in a similar manner to Preparation Example 73 to obtain the desired product. (Yield: 29%)

$^1$H-NMR (400 MHz, CHLOROFORM-D): δ 7.92 (s, 1H), 7.74 (s, 1H), 7.02-6.90 (m, 2H), 6.89-6.81 (m, 1H), 6.74 (dd, J=8.0, 1.6 Hz, 1H), 4.62-4.52 (m, 1H), 4.28 (td, J=7.2, 3.5 Hz, 1H), 4.03 (dd, J=13.3, 3.2 Hz, 1H), 3.81-3.68 (m, 1H), 3.68-3.50 (m, 2H), 2.48-2.32 (m, 2H), 2.23-1.75 (m, 6H), 1.73-1.52 (m, 2H)

Preparation Example 58: Methyl 2-(4-(3-amino-2,2-dimethyl-3-oxopropyl)phenyl)-2-methylpropanoate

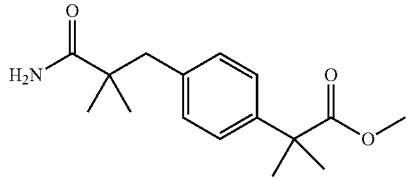 [SMILES: COC(=O)C(C)(C)c1ccc(CC(C)(C)C(N)=O)cc1]

Step 1: Tert-butyl 3-(4-(1-methoxy-2-methyl-1-oxopropan-2-yl)phenyl)-2,2-dimethylpropanoate Methyl 2-(4-(bromomethyl)phenyl)-2-methylpropanoate (5.40 g, 19.91 mmol) and tert-butyl isobutyrate (3.45 g, 23.90 mmol) were used in a similar manner to Step 1 of Preparation Example 33 to obtain the desired product. (Yield: 78%)

$^1$H-NMR (400 MHz, CHLOROFORM-D:) δ 7.20 (d, J=8.2 Hz, 2H), 7.09 (d, J=8.2 Hz, 2H), 3.63 (s, 3H), 2.78 (s, 2H), 1.54 (s, 6H), 1.41 (s, 9H), 1.11 (s, 6H)

Step 2: Methyl 2-(4-(3-amino-2,2-dimethyl-3-oxopropyl)phenyl)-2-methylpropanoate Using tert-butyl 3-(4-(1-methoxy-2-methyl-1-oxopropan-2-yl)phenyl)-2,2-dimethylpropanoate (0.50 g, 1.50 mmol) obtained in Step 1, the methods of Steps 3 and 4 of Preparation Example 10 were sequentially performed to obtain the desired product. (Yield: 72%)

$^1$H-NMR (400 MHz, CHLOROFORM-D): δ 7.19 (d, J=7.8 Hz, 2H), 7.08 (d, J=8.2 Hz, 2H), 5.81 (d, J=49.4 Hz, 2H), 3.61 (d, J=1.4 Hz, 3H), 2.79 (s, 2H), 1.52 (s, 6H), 1.15 (d, J=1.4 Hz, 6H)

Preparation Example 59: Tert-butyl 3-(4-(1-amino-2-methyl-1-oxopropan-2-yl)phenyl)-2,2-dimethylpropanoate

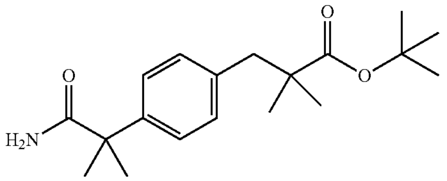 [SMILES: CC(C)(C)OC(=O)C(C)(C)Cc1ccc(C(C)(C)C(N)=O)cc1]

Using tert-butyl 3-(4-(1-methoxy-2-methyl-1-oxopropan-2-yl)phenyl)-2,2-dimethylpropanoate (0.50 g, 1.50 mmol) obtained in Step 1 of Preparation Example 58, the methods of Steps 2 and 3 of Preparation Example 6 were sequentially performed to obtain the desired product. (Yield: 76%)

$^1$H-NMR (400 MHz, CHLOROFORM-D): δ 7.25 (d, J=8.2 Hz, 2H), 7.11 (d, J=8.2 Hz, 2H), 5.85 (s, 1H), 5.31 (s, 1H), 2.78 (s, 2H), 1.53 (s, 6H), 1.41 (s, 9H), 1.10 (s, 6H)

Preparation Example 60: Benzyl (E)-4-(3-amino-3-oxoprop-1-en-1-yl)bicyclo[2.2.2]octane-1-carboxylate

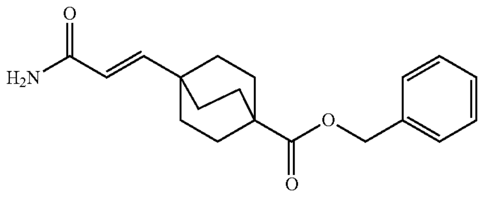 [SMILES: NC(=O)/C=C/C12CCC(C(=O)OCc3ccccc3)(CC1)CC2]

Step 1: Benzyl 4-(hydroxymethyl)bicyclo[2.2.2]octane-1-carboxylate 4-(Hydroxymethyl)bicyclo[2.2.2]octane-1-carboxylic acid (8.50 g, 46.1 mmol) and benzyl bromide (11.84 g, 69.2 mmol) were used in a similar manner to Step 1 of Preparation Example 38 to obtain the desired product. (Yield: 66%)

$^1$H-NMR (400 MHz, CHLOROFORM-D): δ 7.42-7.27 (m, 5H), 5.08 (s, 2H), 3.27 (s, 2H), 1.88-1.76 (m, 6H), 1.49-1.37 (m, 6H)

Step 2: Benzyl 4-formylbicyclo[2.2.2]octane-1-carboxylate

Oxalyl chloride (1.02 g, 8.02 mmol) was dissolved in DCM (25 mL), and the temperature was lowered to −78° C. DMSO (1.25 g, 16.04 mmol) was further added, and after 5 minutes, benzyl 4-(hydroxymethyl)bicyclo[2.2.2]octane-1-carboxylate (2.00 g, 7.29 mmol) obtained in Step 1 was dissolved in DCM (10 mL) and added. After stirring for an additional 15 minutes, triethylamine (3.69 g, 36.4 mmol) was added, and the temperature was raised to room temperature. After adding water, the reaction mixture was extracted with DCM. The organic layer was dried over magnesium sulfate, filtered, concentrated under reduced pressure, and the resulting product was used in the next reaction without further purification.

$^1$H-NMR (400 MHz, CHLOROFORM-D): δ 9.44 (s, 1H), 7.39-7.27 (m, 5H), 5.09 (s, 2H), 1.91-1.82 (m, 6H), 1.72-1.62 (m, 6H)

Step 3: Benzyl (E)-4-(3-amino-3-oxoprop-1-en-1-yl)bicyclo[2.2.2]octane-1-carboxylate Benzyl 4-formylbicyclo[2.2.2]octane-1-carboxylate (1.00 g, 3.67 mmol) obtained in Step 2 was used in a similar manner to Preparation Example 18 to obtain the desired product. (Yield: 68%)

$^1$H-NMR (400 MHz, CHLOROFORM-D): δ 7.39-7.27 (m, 5H), 6.76 (d, J=15.6 Hz, 1H), 5.65 (d, J=15.6 Hz, 1H), 5.33 (s, 2H), 5.09 (s, 2H), 1.91-1.81 (m, 6H), 1.59-1.55 (m, 6H)

Preparation Example 61: Methyl 4-(2-amino-2-oxoethyl)bicyclo[2.2.2]octane-1-carboxylate

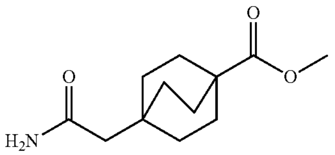 [SMILES: COC(=O)C12CCC(CC(N)=O)(CC1)CC2]

2-(4-(Methoxycarbonyl)bicyclo[2.2.2]octan-1-yl)acetic acid (0.90 g, 3.98 mmol) was used in a similar manner to Step 3 of Preparation Example 6 to obtain the desired product. (Yield: 84%)

$^1$H-NMR (400 MHz, CHLOROFORM-D): δ 5.51 (s, 2H), 3.62 (s, 3H), 2.01 (s, 2H), 1.91-1.70 (m, 6H), 1.62-1.47 (m, 6H)

Preparation Example 62: Tert-butyl 3-(3-(3-amino-3-oxopropyl)phenyl)-2,2-dimethylpropanoate

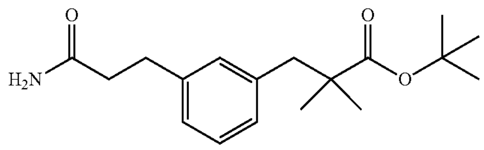 [SMILES: CC(C)(C)OC(=O)C(C)(C)Cc1cccc(CCC(N)=O)c1]

Using 1-bromo-3-(bromomethyl) benzene (5.00 g, 20.01 mmol) and tert-butyl isobutyrate (3.46 g, 24.01 mmol), the methods of Step 1 of Preparation Example 33, Step 1 of Preparation Example 10, and Steps 2 and Step 3 of Preparation Example 6 were sequentially performed to obtain the desired product. (Yield: 31%)

$^1$H-NMR (400 MHz, CHLOROFORM-D:) δ 7.17 (t, J=7.8 Hz, 1H), 7.04 (d, J=7.8 Hz, 1H), 6.99 (d, J=5.5 Hz, 2H), 5.30 (s, 2H), 2.92 (t, J=7.8 Hz, 2H), 2.78 (s, 2H), 2.50 (t, J=7.5 Hz, 2H), 1.43 (s, 9H), 1.10 (s, 6H)

Preparation Example 63: Tert-butyl 3-(4-(2-amino-2-oxoethyl)phenyl)-2,2-dimethylpropanoate

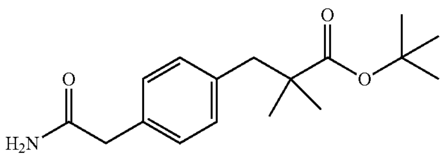 [SMILES: CC(C)(C)OC(=O)C(C)(C)Cc1ccc(CC(N)=O)cc1]

2-(4-(Bromomethyl)phenyl)acetic acid (14.0 g, 61.1 mmol) and tert-butyl isobutyrate (26.4 g, 183 mmol) were used in a similar manner to Preparation Example 33 to obtain the desired product. (Yield: 42%)

$^1$H-NMR (400 MHz, CHLOROFORM-D:) δ 7.19-7.11 (m, 4H), 5.38 (d, J=23.8 Hz, 2H), 3.54 (s, 2H), 2.80 (s, 2H), 1.46-1.37 (9H), 1.11 (s, 6H)

Preparation Example 64: Tert-butyl (R)-3-(3-(3-carbamoylpiperidin-1-yl)phenyl)-2,2-dimethylpropanoate

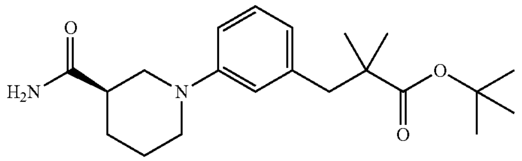 [SMILES: CC(C)(C)OC(=O)C(C)(C)Cc1cccc(N2CCC[C@@H](C(N)=O)C2)c1]

Using 1-bromo-3-(bromomethyl)benzene (5.00 g, 20.01 mmol) and tert-butyl isobutyrate (3.46 g, 24.01 mmol), the methods of Step 1 of Preparation Example 33, Step 1 of Preparation Example 2, and Steps 2 and 3 of Preparation Example 6 were sequentially performed to obtain the desired product. (Yield: 16%)

$^1$H-NMR (400 MHz, CHLOROFORM-D:) δ 7.18-7.09 (m, 1H), 6.82 (d, J=8.2 Hz, 1H), 6.79-6.66 (m, 3H), 5.80 (s, 1H), 3.30-3.23 (m, 2H), 3.16-3.08 (m, 2H), 2.77 (dd, J=16.0, 13.3 Hz, 2H), 2.59 (s, 1H), 1.92-1.77 (m, 3H), 1.77-1.64 (m, 1H), 1.45-1.35 (m, 9H), 1.15-1.06 (m, 6H)

Preparation Example 65: Benzyl (E)-2-(4-(3-amino-3-oxoprop-1-en-1-yl)phenyl)-2-methylpropanoate

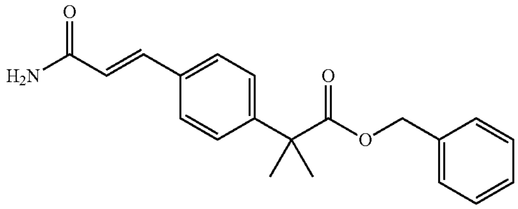 [SMILES: CC(C)(C(=O)OCc1ccccc1)c1ccc(/C=C/C(N)=O)cc1]

Using 2-(4-bromophenyl)-2-methylpropanoic acid (5.00 g, 20.57 mmol) and benzyl bromide (4.22 g, 24.68 mmol), the methods of Step 1 of Preparation Example 43, and Steps 1, 3 and 4 of Preparation Example 10 were sequentially performed to obtain the desired product. (Yield: 60%)

$^1$H-NMR (400 MHz, CHLOROFORM-D): δ 7.66-7.59 (m, 1H), 7.54-7.40 (m, 2H), 7.40-7.25 (m, 5H), 7.19-7.10 (m, 2H), 6.47-6.40 (m, 1H), 5.61 (s, 2H), 5.09 (s, 2H), 1.59 (s, 6H)

Preparation Example 66: (R)-2-chloro-4-(3-((3-ethoxypyridin-2-yl)oxy)piperidin-1-yl)pyrimidine

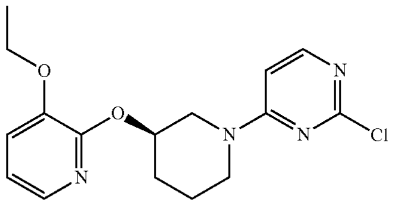 [SMILES: CCOc1cccnc1O[C@@H]1CCCN(c2ccnc(Cl)n2)C1]

(R)-3-ethoxy-2-(piperidin-3-yloxy)pyridine hydrochloride (5.90 g, 22.80 mmol) obtained in Step 3 of Preparation Example 70 and 2,4-dichloropyrimidine (3.74) g, 25.08 mmol) were used in a similar manner to Step 3 of Preparation Example 1 to obtain the desired product. (Yield: 26%)

$^1$H-NMR (400 MHz, CHLOROFORM-D): δ 7.91 (d, J=6.4 Hz, 1H), 7.70 (dd, J=4.8, 1.6 Hz, 1H), 7.03 (dd, J=7.8, 1.4 Hz, 1H), 6.82 (q, J=4.1 Hz, 1H), 6.32 (d, J=5.9 Hz, 1H), 5.19 (s, 1H), 4.05-3.59 (m, 6H), 2.25-1.90 (m, 3H), 1.76-1.57 (m, 1H), 1.31 (t, J=6.9 Hz, 3H)

Preparation Example 67: Tert-butyl 3-(4-(2-((2-chloropyrimidin-4-yl)amino)-2-oxoethyl)phenyl)-2,2-dimethylpropanoate

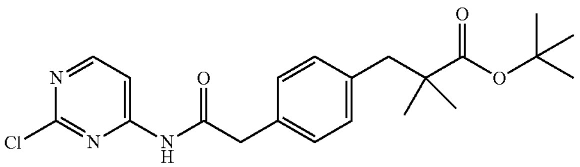 [SMILES: CC(C)(C)OC(=O)C(C)(C)Cc1ccc(CC(=O)Nc2ccnc(Cl)n2)cc1]

Tert-butyl 3-(4-(2-amino-2-oxoethyl)phenyl)-2,2-dimethylpropanoate (0.50 g, 1.50 mmol) obtained in Preparation Example 63 and 2,4-dichloropyrimidine (0.20 g, 1.34 mmol)

were used in a similar manner to Step 1 of Preparation Example 2 to obtain the desired product. (Yield: 28%)

$^1$H-NMR (400 MHz, CHLOROFORM-D): δ 8.46 (d, J=5.5 Hz, 1H), 8.11 (d, J=5.5 Hz, 1H), 8.01 (s, 1H), 7.17 (s, 4H), 3.72 (s, 2H), 3.70-3.65 (m, 1H), 2.82 (s, 2H), 1.42 (s, 9H), 1.12 (s, 6H)

Preparation Example 68: (R)-4-chloro-2-(3-(2-ethoxyphenoxy)piperidin-1-yl)pyrimidine

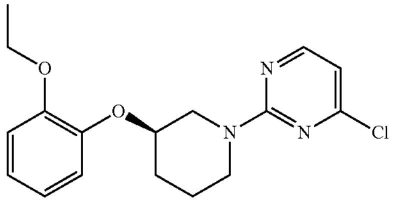 [SMILES: CCOc1ccccc1O[C@@H]1CCCN(c2nccc(Cl)n2)C1]

Tert-butyl-(R)-3-(2-ethoxyphenoxy)piperidine-1-carboxylate (15.0 g, 46.7 mmol) obtained in Step 1 of Preparation Example 1 and 2,4-dichloropyrimidine (13.9 g, 93 mmol) were used in a similar manner to Steps 2 and 3 of Preparation Example 1 to obtain the desired product. (Yield: 19%)

m/z $(M+H)^+$ calculated for $C_{17}H_{21}ClN_3O_2$: 334, found 334.

Preparation Example 69: (R)-2-chloro-4-(3-(2-ethoxyphenoxy)piperidin-1-yl)pyrimidine

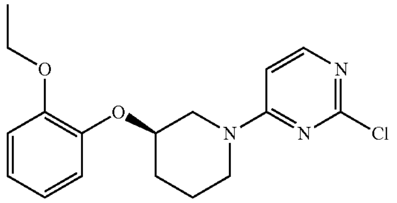 [SMILES: CCOc1ccccc1O[C@@H]1CCCN(c2ccnc(Cl)n2)C1]

Tert-butyl-(R)-3-(2-ethoxyphenoxy)piperidine-1-carboxylate (15.0 g, 46.7 mmol) obtained in Step 1 of Preparation Example 1 and 2,4-dichloropyrimidine (13.9 g, 93 mmol) were used in a similar manner to Steps 2 and 3 of Preparation Example 1 to obtain the desired product. (Yield: 72%)

m/z $(M+H)^+$ calculated for $C_{17}H_{21}ClN_3O_2$: 334, found 334.

Preparation Example 70: (R)-2-chloro-6-(3-((3-ethoxypyridin-2-yl)oxy)piperidin-1-yl)pyrazine

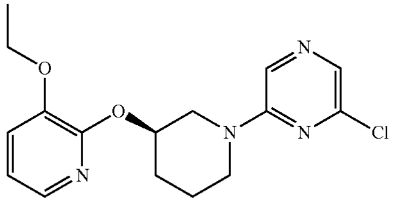 [SMILES: CCOc1cccnc1O[C@@H]1CCCN(c2cncc(Cl)n2)C1]

Step 1: 2-Chloro-3-ethoxypyridine

2-Chloro-3-hydroxypyridine (10.0 g, 77 mmol), iodoethane (14.45 g, 93 mmol) and potassium carbonate (21.34 g, 154 mmol) were added to 77 mL of DMF and stirred at room temperature for 48 hours. The reaction mixture was filtered, added with water, and then extracted with ethyl acetate. After washing with water and brine, the organic layer was dried over magnesium sulfate and concentrated under reduced pressure. The purification was carried out by column chromatography to obtain the desired product. (Yield: 99%)

$^1$H NMR (400 MHz, CHLOROFORM-D): δ 7.96 (t, J=3.0 Hz, 1H), 7.17 (d, J=3.2 Hz, 2H), 4.10 (q, J=7.0 Hz, 2H), 1.48 (t, J=7.1 Hz, 3H)

Step 2: Tert-butyl (R)-3-((3-ethoxypyridin-2-yl)oxy)piperidine-1-carboxylate

Sodium hydride (3.38 g, 84 mmol) was added to 96 mL of anhydrous DMF, and tert-butyl (R)-3-hydroxypiperidine-1-carboxylate (17.00 g, 84 mmol) was further added. The temperature was raised to 60° C., and the reaction mixture was stirred for 1 hour. 2-Chloro-3-ethoxypyridine (12.1 g, 77 mmol) obtained in Step 1 was added thereto, followed by stirring for 24 hours. Water was added to the reaction mixture, followed by extraction with ethyl acetate. After washing with water and brine, the organic layer was dried over magnesium sulfate and concentrated under reduced pressure. The purification was carried out by column chromatography to obtain the desired product. (Yield: 75%)

$^1$H NMR (400 MHz, CHLOROFORM-D): δ 7.68 (td, J=3.2, 1.7 Hz, 1H), 7.03 (dt, J=7.8, 1.4 Hz, 1H), 6.82-6.72 (m, 1H), 5.06 (s, 1H), 4.03 (q, J=7.0 Hz, 2H), 3.55 (d, J=100.2 Hz, 4H), 2.16-1.96 (m, 1H), 1.96-1.70 (m, 2H), 1.68-1.50 (m, 1H), 1.50-1.27 (m, 12H)

Step 3: (R)-3-ethoxy-2-(piperidin-3-yloxy)pyridine hydrochloride

Tert-butyl (R)-3-((3-ethoxypyridin-2-yl)oxy)piperidine-1-carboxylate (31.5 g, 98 mmol) obtained in Step 2 was used in a similar manner to Step 2 of Preparation Example 1 to obtain the title compound.

Step 4: (R)-2-chloro-6-(3-((3-ethoxypyridin-2-yl)oxy)piperidin-1-yl)pyrazine (R)-3-ethoxy-2-(piperidin-3-yloxy)pyridine hydrochloride (30 g, 116 mmol) obtained in Step 3 and 2,6-dichloropyrazine (19 g, 128 mmol) were used in a similar manner to Step 3 of Preparation Example 1 to obtain the title compound. (Yield: 80%)

$^1$H NMR (400 MHz, CHLOROFORM-D): δ 7.96 (d, J=11.0 Hz, 1H), 7.74-7.66 (m, 2H), 7.04 (dd, J=7.8, 1.4 Hz, 1H), 6.83 (dd, J=7.8, 5.0 Hz, 1H), 5.24 (td, J=7.0, 3.4 Hz, 1H), 4.05-3.83 (m, 3H), 3.83-3.70 (m, 2H), 3.67-3.53 (m, 1H), 2.22-2.09 (m, 1H), 2.07-1.93 (m, 2H), 1.75-1.60 (m, 1H), 1.35-1.27 (t, J=7.1 Hz, 3H)

Preparation Example 71: (R)-2-chloro-6-(3-(2-ethoxyphenoxy)piperidin-1-yl)pyridine

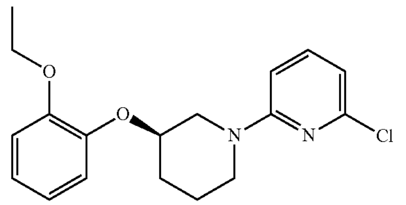 [SMILES: CCOc1ccccc1O[C@@H]1CCCN(c2cccc(Cl)n2)C1]

(R)-3-(2-ethoxyphenoxy)piperidine hydrochloride (10 g, 45.2 mmol) obtained in Step 2 of Preparation Example 1 and 2,6-dichloropyridine (11.37 g, 77 mmol) were used in a similar manner to Step 3 of Preparation Example 1 to obtain the desired product. (Yield: 41%)

$^1$H-NMR (400 MHz, CHLOROFORM-D) δ 7.44-7.29 (m, 1H), 7.17-7.05 (m, 1H), 6.94-6.86 (m, 3H), 6.73-6.49 (m, 1H), 6.49-6.32 (m, 1H), 4.30-4.17 (m, 2H), 4.04-3.96 (m, 2H), 3.95-3.78 (m, 1H), 3.35-3.18 (m, 2H), 2.22-2.07 (m, 1H), 1.97-1.75 (m, 2H), 1.64-1.52 (m, 1H), 1.40 (q, J=6.9 Hz, 3H)

Preparation Example 72: (R)-2-chloro-4-(3-(2-ethoxyphenoxy)piperidin-1-yl)-6-(trifluoromethyl)pyrimidine

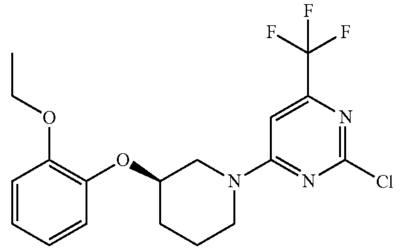 [SMILES: CCOc1ccccc1O[C@@H]1CCCN(c2cc(C(F)(F)F)nc(Cl)n2)C1]

(R)-3-(2-ethoxyphenoxy)piperidine hydrochloride (0.23 g, 0.89 mmol) obtained in Step 2 of Preparation Example 1 and 2,4-dichloro-6-(trifluoromethyl)pyrimidine (0.21 g, 0.98 mmol) were used in a similar manner to Step 3 of Preparation Example 1 to obtain the title compound. (Yield: 86%)

$^1$H NMR (400 MHz, CHLOROFORM-D): δ 7.14-6.31 (m, 5H), 4.79-3.18 (m, 7H), 2.04 (s, 3H), 1.60 (s, 1H), 1.30 (dt, J=29.7, 6.7 Hz, 3H)

Preparation Example 73: (R)-2-chloro-6-(3-(2-isopropoxyphenoxy)piperidin-1-yl)pyrazine

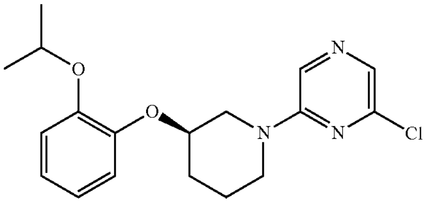 [SMILES: CC(C)Oc1ccccc1O[C@@H]1CCCN(c2cncc(Cl)n2)C1]

Step 1: 1-(Benzyloxy)-2-isopropoxybenzene 2-(Benzyloxy)phenol (1.15 g, 5.74 mmol), 2-bromopropane (1.413 g, 11.49 mmol) and potassium carbonate (3.17 g, 22.97 mmol) were dissolved in 19 mL of DMF and stirred at 45° C. for 15 hours. After confirming that the reaction was completed by TLC, the organic solvent was removed under reduced pressure. After extraction with ethyl acetate (2×30 mL), the resulting product was washed with brine (20 mL), and the organic solvent was dried over magnesium sulfate and removed under reduced pressure. The purification was carried out by silica gel column (ethyl acetate:hexane=1:30) to obtain the desired product. (Yield: 93%)

m/z $(M+H)^+$ calculated for $C_{16}H_{18}O_2$: 242, found 243.

Step 2: 2-Isopropoxyphenol 1-(Benzyloxy)-2-isopropoxybenzene (1.3 g, 5.36 mmol) obtained in Step 1 was dissolved in 40 mL of methanol, and palladium charcoal (0.143 g, 1.341 mmol) was added dropwise, followed by a deprotection reaction using a hydrogen balloon. After confirming that the reaction was complete, the resulting product was filtered with a Celite pad, and the organic solvent was removed under reduced pressure to obtain the desired product. (Yield: 99%)

$^1$H-NMR (500 MHz, CHLOROFORM-D) δ 7.02-6.75 (m, 4H), 5.69 (d, J=19.0 Hz, 1H), 4.63-4.52 (m, 1H), 1.46-1.32 (m, 6H)

Step 3: Tert-butyl (R)-3-(2-isopropoxyphenoxy)piperidine-1-carboxylate

2-Isopropoxyphenol (0.81 g, 5.32 mmol) obtained in Step 2 and (S)-tert-butyl-3-hydroxypiperidine-1-carboxylate (1.07 g, 5.32 mmol) were used in a similar manner to Step 1 of Preparation Example 1 to obtain the desired product. (Yield: 13.6%)

$^1$H-NMR (500 MHz, CHLOROFORM-D) δ 7.01-6.81 (m, 4H), 4.45 (td, J=12.2, 6.1 Hz, 1H), 4.11 (q, J=7.3 Hz, 2H), 3.62 (s, 1H), 3.27 (s, 1H), 3.16 (s, 1H), 2.03 (d, J=7.9 Hz, 2H), 1.83 (s, 1H), 1.74 (d, J=6.7 Hz, 1H), 1.42 (s, 9H), 1.32 (q, J=2.9 Hz, 6H)

Step 4: (R)-3-(2-isopropoxyphenoxy)piperidine

Tert-butyl (R)-3-(2-isopropoxyphenoxy)piperidine-1-carboxylate (0.27 g, 0.805 mmol) obtained in Step 3 was used in a similar manner to Step 2 of Preparation Example 1 to obtain the desired product.

m/z $(M+H)^+$ calculated for $C_{16}H_{18}O_2$: 235.3, found 236.2.

Step 5: (R)-2-chloro-6-(3-(2-isopropoxyphenoxy)piperidin-1-yl)pyrazine (R)-3-(2-isopropoxyphenoxy)piperidine (0.189 g, 0.803 mmol) obtained in Step 4 was used in a similar manner to Step 3 of Preparation Example 1 to obtain the desired product. (Yield: 25%)

$^1$H-NMR (500 MHz, CHLOROFORM-D) δ 7.93 (s, 1H), 7.74 (s, 1H), 7.01-6.85 (m, 4H), 4.44 (td, J=12.2, 6.1 Hz, 1H), 4.32-4.22 (m, 1H), 4.02 (dd, J=13.4, 3.1 Hz, 1H), 3.74 (qd, J=6.5, 3.8 Hz, 1H), 3.64-3.47 (m, 2H), 2.12-2.05 (m, 1H), 2.03-1.85 (m, 2H), 1.61 (qd, J=8.7, 4.3 Hz, 1H), 1.32-1.18 (m, 6H)

Preparation Example 74: (R)-2-chloro-6-(3-(2-methoxyphenoxy)piperidin-1-yl)pyrazine

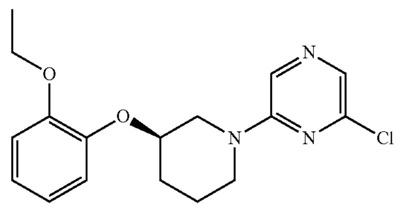 [SMILES: CCOc1ccccc1O[C@@H]1CCCN(c2cncc(Cl)n2)C1]

(S)-tert-butyl-3-hydroxypiperidine-1-carboxylate (2.00 g, 9.94 mmol) and 2-methoxyphenol (1.23 g, 9.94 mmol) were used in a similar manner to Preparation Example 1 to obtain the desired product. (3 steps yield: 32%)

$^{1}$H-NMR (400 MHz, CHLOROFORM-D) δ 7.95 (s, 1H), 7.77 (s, 1H), 7.13-6.82 (m, 4H), 4.31 (td, J=7.8, 4.1 Hz, 1H), 4.25-4.15 (m, 1H), 3.97-3.64 (m, 4H), 3.57-3.33 (m, 2H), 2.14 (d, J=5.0 Hz, 1H), 2.03-1.82 (m, 2H), 1.73-1.59 (m, 1H)

Preparation Example 75: (R)-2-chloro-6-(3-(2-(trifluoromethoxy)phenoxy)piperidin-1-yl)pyrazine

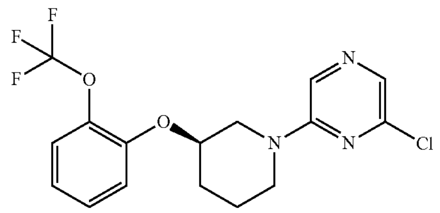 [SMILES: FC(F)(F)Oc1ccccc1O[C@@H]1CCCN(c2cncc(Cl)n2)C1]

(S)-tert-butyl-3-hydroxypiperidine-1-carboxylate (2.00 g, 9.94 mmol) and 2-(trifluoromethoxy)phenol (1.77 g, 9.94 mmol) were used in a similar manner to Preparation Example 1 to obtain the desired product. (Yield: 8%)

$^{1}$H-NMR (400 MHz, CHLOROFORM-D) δ 7.98 (s, 1H), 7.79 (s, 1H), 7.45-7.28 (1H), 7.25-7.07 (m, 2H), 6.98 (t, J=7.5 Hz, 1H), 4.39 (d, J=3.7 Hz, 1H), 4.18 (d, J=13.3 Hz, 1H), 3.93-3.70 (m, 1H), 3.67-3.39 (2H), 2.15 (d, J=18.3 Hz, 1H), 2.02-1.82 (m, 2H), 1.79-1.60 (m, 1H)

Preparation Example 76: (R)-2-chloro-6-(3-(2-(2-fluoroethoxy)phenoxy)piperidin-1-yl)pyrazine

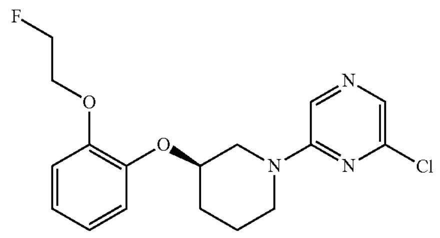 [SMILES: FCCOc1ccccc1O[C@@H]1CCCN(c2cncc(Cl)n2)C1]

Step 1: 1-(Benzyloxy)-2-(2-fluoroethoxy)benzene

2-Fluoroethan-1-ol (1.10 mL, 18.7 mmol), 2-(benzyloxy)phenol (3.26 mL, 18.7 mmol) and triphenylphosphine (5.50 g, 21.0 mmol) were dissolved in 50 mL of toluene and stirred at room temperature. To the reaction mixture, diethylazodicarboxylate (3.82 mL) diluted in 44 mL of toluene was slowly added dropwise. After stirring at room temperature for 15 hours, the mixture was filtered, washed with diethyl ether, washed with 1 N sodium hydroxide solution and dried over magnesium sulfate, and the organic solvent was removed under reduced pressure. The purification was carried out by silica gel column (ethyl acetate:hexane=1:20) to obtain the desired product. (Yield: 76%)

$^{1}$H-NMR (400 MHz, CHLOROFORM-D) δ 7.53-7.27 (m, 5H), 7.05-6.84 (m, 4H), 5.14 (s, 2H), 4.75 (dt, J=47.4, 4.2 Hz, 2H), 4.29 (dt, J=27.7, 4.3 Hz, 2H)

Step 2: 2-(2-Fluoroethoxy)phenol 1-(Benzyloxy)-2-(2-fluoroethoxy)benzene (1.50 g, 6.09 mmol) obtained in Step 1 and palladium charcoal (0.65 g, 0.61 mmol) were dissolved in 122 mL of methanol and stirred at room temperature while blowing hydrogen gas. After stirring for 15 hours, the resulting product was filtered, and the organic solvent was removed under reduced pressure. (Yield: 96%)

$^{1}$H-NMR (400 MHz, CHLOROFORM-D) δ 7.04-6.75 (m, 4H), 5.76-5.61 (1H), 4.90-4.63 (m, 2H), 4.40-4.18 (2H)

Step 3: (R)-2-chloro-6-(3-(2-(2-fluoroethoxy)phenoxy)piperidin-1-yl)pyrazine (S)-tert-butyl-3-hydroxypiperidine-1-carboxylate (1.17 g, 5.83 mmol) and 2-(2-fluoroethoxy)phenol (0.91 g, 5.8 mmol) obtained in Step 2) were used in a similar manner to Preparation Example 1 to obtain the desired product. (Yield: 24%)

$^{1}$H-NMR (400 MHz, CHLOROFORM-D) δ 7.95 (s, 1H), 7.75 (s, 1H), 7.11-6.85 (m, 4H), 4.71 (dt, J=47.6, 4.1 Hz, 2H), 4.41-4.28 (m, 1H), 4.28-4.14 (m, 2H), 4.03 (dd, J=13.5, 3.0 Hz, 1H), 3.83-3.47 (m, 3H), 2.18-2.05 (m, 1H), 2.04-1.84 (m, 2H), 1.72-1.58 (m, 1H)

Preparation Example 77: (R)-2-chloro-6-(3-(2-cyclopropoxyphenoxy)piperidin-1-yl)pyrazine

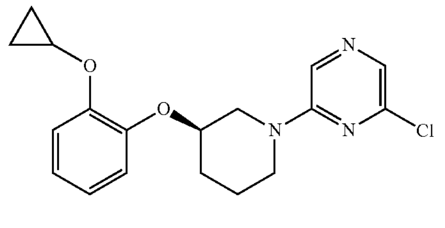 [SMILES: Clc1cncc(N2CCC[C@@H](Oc3ccccc3OC3CC3)C2)n1]

2-(Benzyloxy)phenol (2.00 g, 9.99 mmol) and cyclopropyl bromide (3.63 g, 30.0 mmol) were used in a similar manner to Preparation Example 73 to obtain the desired product. (Yield: 8.1%)

$^{1}$H-NMR (400 MHz, CHLOROFORM-D): δ 7.92 (s, 1H), 7.74 (s, 1H), 7.24-7.18 (m, 1H), 7.04-6.94 (m, 2H), 6.93-6.85 (m, 1H), 4.23 (td, J=7.5, 3.7 Hz, 1H), 4.09-4.01 (m, 1H), 3.83-3.67 (m, 2H), 3.59-3.44 (m, 2H), 2.15-2.04 (m, 1H), 2.02-1.84 (m, 2H), 1.67-1.51 (m, 1H), 0.74 (d, J=4.6 Hz, 4H)

Preparation Example 78: Tert-butyl 3-(3'-(chlorocarbonyl)-[1,1'-biphenyl]-3-yl)-2,2-dimethylpropanoate

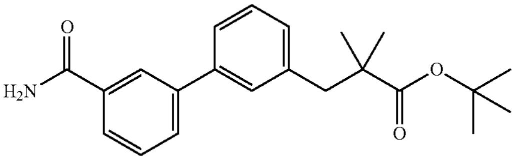 [SMILES: CC(C)(C)OC(=O)C(C)(C)Cc1cccc(-c2cccc(C(N)=O)c2)c1]

Step 1: Tert-butyl 2,2-dimethyl-3-(3-(4,4,5,5-tetramethyl-1,3,2-dioxaborolin-2-yl)phenyl)propanoate Intermediate tert-butyl 3-(3-bromophenyl)-2,2-dimethylpropanoate (0.870 g, 2.78 mmol) obtained in Preparation 64, bis(pinacolato)diboron (0.846 g, 3.33 mmol) and potassium acetate (0.818 g, 8.33 mmol) were dissolved in 1,4-dioxane (13.89 mL), and [1,1'-bis(diphenylphosphino)ferrocene]dichloropalladium-dichloromethane adduct (0.113 g, 0.139 mmol) was added. The reaction mixture was stirred under reflux at 100° C. for 16 hours. The resulting product was filtered through a Celite pad, and the organic solvent was removed under reduced pressure. The purification was carried out by silica gel column to obtain the desired product. (Yield: 32.4%)

$^1$H-NMR (400 MHz, CHLOROFORM-D): δ 7.69-7.54 (2H), 7.23 (d, J=1.4 Hz, 2H), 2.82 (s, 2H), 1.55 (d, J=1.4 Hz, 2H), 1.43 (s, 9H), 1.31 (s, 12H), 1.12 (s, 6H)

Step 2: Ethyl 3'-(3-(tert-butoxy)-2,2-dimethyl-3-oxopropyl)-[1,1'-biphenyl]-3-carboxylate Tert-butyl 2,2-dimethyl-3-(3-(4,4,5,5-tetramethyl-1,3,2-dioxaborolin-2-yl)phenyl)propanoate (0.173 g, 0.480 mmol) obtained in Step 1, ethyl 3-bromobenzoate (0.100 g, 0.437 mmol) and [1,1'-bis(diphenylphosphino)ferrocene]dichloropalladium-dichloromethane adduct (0.018 g, 0.022 mmol) were dissolved in 1,4-dioxane (4.37 mL), and 2 M sodium carbonate solution (0.655 mL, 1.310 mmol) was added dropwise, followed by stirring at 90° C. for 5 hours. After cooling to room temperature, the resulting product was filtered through a Celite pad, washed with dichloromethane and dried over magnesium sulfate, and the organic solvent was removed under reduced pressure. The purification was carried out by silica gel column to obtain the desired product. (Yield: 68.6%)

$^1$H-NMR (400 MHz, CHLOROFORM-D): δ 8.24 (t, J=1.6 Hz, 1H), 8.00 (dt, J=7.8, 1.4 Hz, 1H), 7.74 (dt, J=7.8, 1.4 Hz, 1H), 7.47 (q, J=7.5 Hz, 2H), 7.39 (s, 1H), 7.34 (t, J=7.8 Hz, 1H), 7.17 (d, J=7.8 Hz, 1H), 4.40 (q, J=7.2 Hz, 2H), 2.90 (s, 2H), 1.43-1.37 (m, 12H), 1.15 (s, 6H)

Step 3: 3'-(3-(Tert-butoxy)-2,2-dimethyl-3-oxopropyl)-[1,1'-biphenyl]-3-carboxylic acid Using ethyl 3'-(3-(tert-butoxy)-2,2-dimethyl-3-oxopropyl)-[1,1'-biphenyl]-3-carboxylate (0.1145 g, 0.299 mmol) obtained in Step 2 and 1 N sodium hydroxide, a hydrolysis reaction was performed to obtain the desired product. (Yield: 32.1%)

$^1$H-NMR (400 MHz, CHLOROFORM-D): δ 8.33 (s, 1H), 8.09 (d, J=7.8 Hz, 1H), 7.81 (d, J=7.8 Hz, 1H), 7.53 (t, J=7.8 Hz, 1H), 7.48 (d, J=7.8 Hz, 1H), 7.42 (s, 1H), 7.35 (t, J=7.8 Hz, 1H), 7.19 (d, J=7.8 Hz, 1H), 2.91 (s, 2H), 1.42 (s, 9H), 1.18 (d, J=6.4 Hz, 6H)

Step 4: Tert-butyl 3-(3'-(chlorocarbonyl)-[1,1'-biphenyl]-3-yl)-2,2-dimethylpropanoate Using 3'-(3-(tert-butoxy)-2,2-dimethyl-3-oxopropyl)-[1,1'-biphenyl]-3-carboxylic acid (0.0341 g, 0.096 mmol) obtained in Step 3, the desired product was obtained through an amidation reaction in a similar manner to Step 4 of Preparation Example 10. (Yield: 99%)

$^1$H-NMR (400 MHz, CHLOROFORM-D): δ 8.08-7.93 (m, 1H), 7.75 (dt, J=7.8, 1.4 Hz, 1H), 7.73-7.68 (m, 1H), 7.48 (t, J=7.8 Hz, 1H), 7.44 (dd, J=7.8, 1.4 Hz, 1H), 7.37 (d, J=6.4 Hz, 1H), 7.33 (t, J=7.8 Hz, 1H), 7.16 (d, J=7.8 Hz, 1H), 6.07 (d, J=135.4 Hz, 2H), 2.89 (s, 2H), 1.50-1.36 (m, 9H), 1.15 (s, 6H)

Preparation Example 79: Tert-butyl 3-(3'-(chlorocarbonyl)-[1,1'-biphenyl]-4-yl)-2,2-dimethylpropanoate

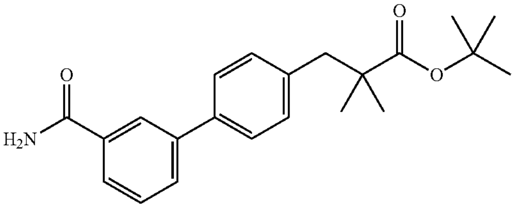 [SMILES: CC(C)(C)OC(=O)C(C)(C)Cc1ccc(-c2cccc(C(N)=O)c2)cc1]

Step 1: Tert-butyl 3-(4-bromophenyl)-2,2-dimethylpropanoate

1-Bromo-4-(bromomethyl)benzene (2.311 g, 9.25 mmol) and tert-butyl isobutyrate (2.0 g, 13.87 mmol) were used in a similar manner to Step 1 of Preparation Example 33 to obtain the desired product. (Yield: 79%)

$^1$H-NMR (400 MHz, CHLOROFORM-D): δ 7.36 (d, J=8.2 Hz, 2H), 7.02 (d, J=8.2 Hz, 2H), 2.76 (s, 2H), 1.41 (d, J=0.9 Hz, 9H), 1.10 (s, 6H)

Step 2: Tert-butyl 3-(3'-(chlorocarbonyl)-[1,1'-biphenyl]-4-yl)-2,2-dimethylpropanoate Tert-butyl 3-(4-bromophenyl)-2,2-dimethylpropanoate (2.27 g, 7.265 mmol) obtained in Step 1 was used in a similar manner to Preparation Example 78 to obtain the desired product. (Yield: 26.3%)

$^1$H-NMR (400 MHz, CHLOROFORM-D): δ 8.04 (t, J=1.6 Hz, 1H), 7.82-7.61 (2H), 7.46 (t, J=8.7 Hz, 3H), 7.21 (d, J=8.2 Hz, 2H), 6.68-6.16 (m, 2H), 2.84 (s, 2H), 1.43 (s, 9H), 1.15-1.10 (6H)

Example 1: (R)-1-(3,5-bis(trifluoromethyl)phenyl)-3-(6-(3-(2-ethoxyphenoxy)piperidin-1-yl)pyrazin-2-yl)urea

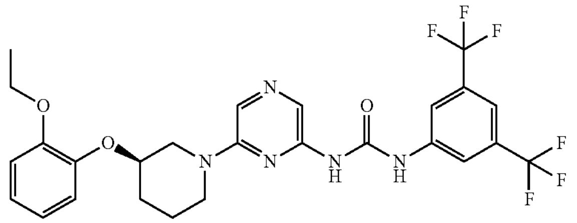 [SMILES: CCOc1ccccc1O[C@@H]1CCCN(c2cncc(NC(=O)Nc3cc(C(F)(F)F)cc(C(F)(F)F)c3)n2)C1]

(R)-6-(3-(2-ethoxyphenoxy)piperidin-1-yl)pyrazin-2-amine (0.49 g, 1.57 mmol) obtained in Preparation Example 2, 3,5-bis(trifluoromethyl)phenyl cyanate (0.44 g, 1.73 mmol) and diisopropylethylamine (0.55 ml, 3.14 mmol) were added to 30 mL of dichloromethane and stirred at room temperature for 6 hours. After confirming the completion of the reaction by TLC, the resulting product was diluted with dichloromethane and washed with an aqueous sodium hydrogen carbonate solution and brine, and the organic solvent was dried over magnesium sulfate and removed under reduced pressure. The purification was carried out by silica gel column (ethyl acetate:hexane=1:1) to obtain the desired product. (Yield: 31%)

$^1$H NMR (300 MHz, CHLOROFORM-D): δ 11.40 (s, 1H), 8.48 (s, 1H), 7.99 (s, 2H), 7.82 (s, 1H), 7.55 (s, 1H), 7.53 (s, 1H), 6.69-6.89 (m, 4H), 4.46 (m, 1H), 3.95 (m, 3H), 3.78 (m, 2H), 3.65 (m, 1H), 2.07-2.17 (m, 3H), 1.73 (m, 1H), 1.30 (t, 3H)

Example 2: ((6-((R)-3-(2-ethoxyphenoxy)piperidin-1-yl)pyrazin-2-yl)carbamoyl)-L-phenylalanine

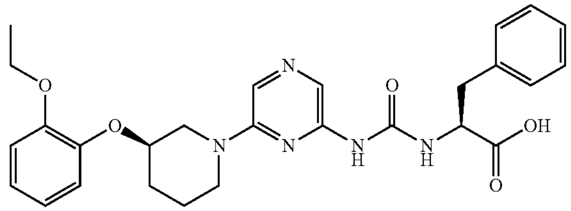 [SMILES: CCOc1ccccc1O[C@@H]1CCCN(c2cncc(NC(=O)N[C@@H](Cc3ccccc3)C(=O)O)n2)C1]

Step 1: Methyl ((6-((R)-3-(2-ethoxyphenoxy)piperidin-1-yl)pyrazin-2-yl)carbamoyl)-L-phenylalanate (S)-methyl 2-amino-3-phenylpropanate (32.5 mg, 0.1 mmol) was mixed with 1 mL of dichloromethane and stirred at 0° C. After adding 1 mL of a saturated aqueous sodium hydrogen carbonate solution to this solution, triphosgene (56.6 mg, 0.191 mmol) was added, and then (R)-6-(3-(2-ethoxyphenoxy)piperidin-1-yl)pyrazin-2-amine (50 mg, 0.159 mmol) obtained in Preparation Example 2 was added. After separating the organic layer, the solvent was converted to THF, and the reaction mixture was stirred at 70° C. for 12 hours. After removing the organic solvent under reduced pressure, the resulting product was purified by silica gel column (acetone:dichloromethane=1:3) to obtain the desired ester product. (Yield: 18%)

m/z $(M+Na)^+$ calculated for $C_{28}H_{33}N_5O_5Na$: 542.6, found 542.3.

$^1$H NMR (300 MHz, CHLOROFORM-D): δ 9.07 (d, 1H), 7.74 (s, 1H), 7.68 (s, 1H), 7.44 (s, 1H), 7.25 (m, 3H), 7.09-7.11 (2H, m), 6.87-6.96 (m, 4H), 5.04 (m, 1H), 4.26 (m, 1H), 3.98-4.03 (m, 2H), 3.73 (m, 1H), 3.71 (s, 3H), 3.45-3.50 (m, 2H), 3.17 (d, 2H), 2.98 (t, 1H), 2.07 (m, 1H), 1.80 (m, 2H), 1.58 (bs, 1H), 1.48 (m, 1H), 1.40 (t, 3H), 1.26 (m, 1H)

Step 2: ((6-((R)-3-(2-ethoxyphenoxy)piperidin-1-yl)pyrazin-2-yl)carbamoyl)-L-phenylalanine The ester compound (15 mg, 0.029 mmol) obtained in Step 1 was dissolved in 0.3 mL of THF and 0.3 mL of water. After lithium hydroxide (3 mg, 0.1 mmol) was added, the reaction mixture was stirred at 40° C. for 12 hours. After cooling to room temperature, the reaction mixture was titrated to pH 4.5 using 1 N hydrochloric acid solution and diluted with ethyl acetate. After removing the water layer, the resulting product was dried over magnesium sulfate, and the organic solvent was removed under reduced pressure to obtain the desired product.

$^1$H NMR (300 MHz, CHLOROFORM-D): δ 9.21 (s, 1H), 8.99 (s, 1H), 7.68 (s, 1H), 7.45 (s, 1H), 7.14 (m, 5H), 6.90 (m, 4H), 5.02 (m, 1H), 4.17 (m, 1H), 4.05 (m, 2H), 3.90 (d, 1H), 3.68 (m, 1H), 3.47 (m, 1H), 3.30 (m, 1H), 3.20 (m, 3H), 2.96 (m, 1H), 2.05 (m, 3H), 1.73 (m, 2H), 1.25-1.42 (m, 5H)

Example 3: (R)—N-(6-(3-(2-ethoxyphenoxy)piperidin-1-yl)pyrazin-2-yl)morpholine-4-carboxamide

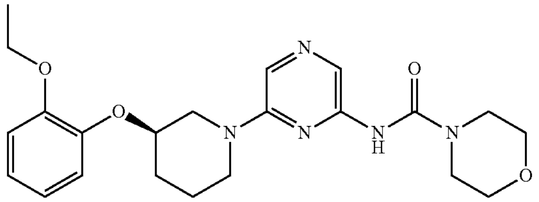 [SMILES: CCOc1ccccc1O[C@@H]1CCCN(c2cncc(NC(=O)N3CCOCC3)n2)C1]

(R)-6-(3-(2-ethoxyphenoxy)piperidin-1-yl)pyrazin-2-amine obtained in Preparation Example 2 and morpholine were used in a similar manner to Step 1 of Example 2 to obtain the desired product.

$^1$H NMR (300 MHz, CHLOROFORM-D): δ 8.54 (s, 1H), 7.82 (s, 1H), 6.86-6.99 (m, 4H), 6.57 (s, 1H), 4.31 (m, 1H), 4.00 (m, 3H), 3.75 (m, 5H), 3.57 (m, 1H), 3.50 (m, 4H), 3.39 (m, 1H), 2.13 (m, 1H), 1.93-1.96 (m, 2H), 1.60-1.63 (m, 2H), 1.39 (t, 3H), 1.26 (m, 1H)

Example 4: (R)—N-(6-(3-(2-ethoxyphenoxy)piperidin-1-yl)pyrazin-2-yl)pyrrolidine-1-carboxamide

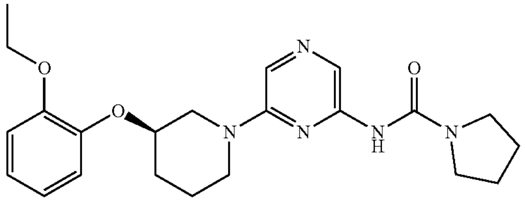 [SMILES: CCOc1ccccc1O[C@@H]1CCCN(c2cncc(NC(=O)N3CCCC3)n2)C1]

(R)-6-(3-(2-ethoxyphenoxy)piperidin-1-yl)pyrazin-2-amine obtained in Preparation Example 2 and pyrrolidine were used in a similar manner to Step 1 of Example 2 to obtain the desired product.

$^1$H NMR (300 MHz, CHLOROFORM-D): δ 8.63 (s, 1H), 7.78 (s, 1H), 6.87-6.98 (m, 4H), 6.45 (s, 1H), 4.29 (m, 1H), 3.96-4.10 (m, 3H), 3.77 (m, 1H), 3.48 (m, 5H), 3.34 (m, 1H), 2.13 (m, 1H), 1.89-1.99 (m, 7H), 1.61 (m, 1H), 1.39 (t, 3H)

Example 5: 1-((6-((R)-3-(2-ethoxyphenoxy)piperidin-1-yl)pyrazin-2-yl)carbamoyl)pyrrolidine-3-carboxylic acid

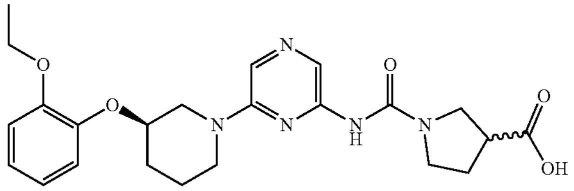 [SMILES: CCOc1ccccc1O[C@@H]1CCCN(c2cncc(NC(=O)N3CCC(C(=O)O)C3)n2)C1]

(R)-6-(3-(2-ethoxyphenoxy)piperidin-1-yl)pyrazin-2-amine obtained in Preparation Example 2 and methyl pyrrolidine-3-carboxylate were used in a similar manner to Example 2 to obtain the desired product.

$^1$H NMR (300 MHz, Methanol-D): δ 8.27 (s, 1H), 7.69 (s, 1H), 7.00 (d, 1H), 6.93 (bs, 3H), 4.47 (bs, 1H), 3.92 (m, 2H), 3.71 (m, 2H), 3.68 (m, 3H), 3.57 (m, 4H), 3.21 (m, 1H), 2.25 (m, 2H), 2.03 (m, 5H), 2.61 (bs, 2H), 1.28 (m, 10H), 0.92 (m 2H)

Example 6: (R)—N-(6-(3-(2-ethoxyphenoxy)piperidin-1-yl)pyrazin-2-yl)benzamide

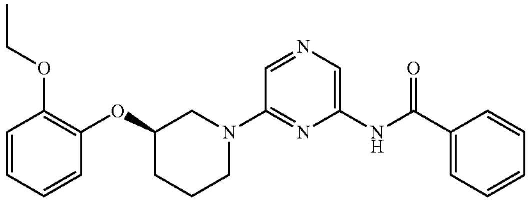 [SMILES: CCOc1ccccc1O[C@@H]1CCCN(c2cncc(NC(=O)c3ccccc3)n2)C1]

(R)-6-(3-(2-ethoxyphenoxy)piperidin-1-yl)pyrazin-2-amine (0.15 g, 0.5 mmol) obtained in Preparation Example 2 and triethylamine (0.35 ml, 2.5 mmol) were dissolved in 10 mL of dichloromethane at 0° C., and benzoyl chloride (0.07 ml, 0.5 mmol) was slowly added dropwise. After stirring at 0° C. for 2 hours, the completion of the reaction was confirmed by TLC, and the resulting product was washed with brine. The organic solvent was dried over magnesium sulfate and removed under reduced pressure. The purification was carried out by by silica gel column (ethyl acetate:hexane=3:1) to obtain the desired product. (Yield: 38%)

$^1$H NMR (300 MHz, CHLOROFORM-D): δ 8.86 (s, 1H), 8.09 (m, 4H), 7.61 (m, 1H), 7.50 (m, 2H), 6.98 (m, 1H), 6.89 (m, 3H), 4.36 (m, 1H), 3.92-4.03 (m, 3H), 3.74 (m, 1H), 3.66 (m, 1H), 3.49 (m, 1H), 2.11 (m, 1H), 2.01 (m, 1H), 1.94 (m, 1H), 1.62 (m, 1H), 1.36 (t, 3H)

Example 7: (R)-4-chloro-N-(6-(3-(2-ethoxyphenoxy)piperidin-1-yl)pyrazin-2-yl)benzamide

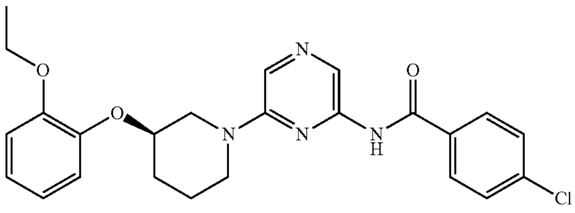 [SMILES: CCOc1ccccc1O[C@@H]1CCCN(c2cncc(NC(=O)c3ccc(Cl)cc3)n2)C1]

(R)-6-(3-(2-ethoxyphenoxy)piperidin-1-yl)pyrazin-2-amine (0.09 g, 0.25 mmol) obtained in Preparation Example 2 and 4-chlorobenzoyl chloride (0.04 g, 0.25 mmol) were used in a similar manner to Example 6 to obtain the desired product. (Yield: 19%)

$^1$H NMR (300 MHz, CHLOROFORM-D): δ 8.83 (s, 1H), 7.95 (s, 1H), 7.82 (m, 3H), 7.45 9 m, 2H), 6.97 (m, 1H), 6.88 (m, 3H), 4.36 (m, 1H), 3.90-4.35 (m, 3H), 3.72 (m, 2H), 3.52 (m, 1H), 2.12 (m, 1H), 2.01 (m, 1H), 1.96 (m, 1H), 1.63 (m, 1H), 1.37 (t, 3H)

Example 8: (R)—N-(6-(3-(2-ethoxyphenoxy)piperidin-1-yl)pyrazin-2-yl)-3-methoxybenzamide

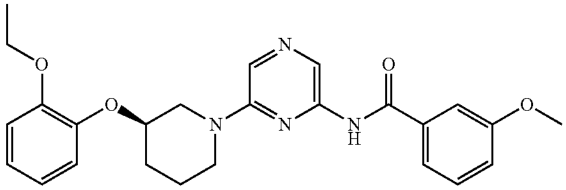 [SMILES: CCOc1ccccc1O[C@@H]1CCCN(c2cncc(NC(=O)c3cccc(OC)c3)n2)C1]

(R)-2-chloro-6-(3-(2-ethoxyphenoxy)piperidin-1-yl) pyrazine (0.05 g, 0.15 mmol) obtained in Preparation Example 1, 3-methoxybenzamide (0.03 g, 0.17 mmol), tris(dibenzylideneacetone)dipalladium(0) (8.2 mg, 0.009 mmol), 4,5-bis(diphenylphosphino)-9,9-dimethylxanthine (7.7 mg, 0.01 mmol) and cesium carbonate (0.12 g, 0.38 mmol) were added to 5 mL of dioxane and stirred under reflux for 4 hours. After completion of the reaction, the resulting product was cooled to room temperature, diluted with ethyl acetate and washed with an aqueous sodium hydrogen carbonate solution and brine. The organic solvent was dried over magnesium sulfate and removed under reduced pressure. The purification was carried out by silica gel column (ethyl acetate:hexane=3:1) to obtain the desired product. (Yield: 52%)

$^1$H-NMR (500 MHz, CHLOROFORM-D): δ 8.85 (s, 1H), 7.92 (s, 1H), 7.90 (s, 1H), 7.47 (m, 1H), 7.41 (m, 2H), 7.12 (m, 1H), 6.99 (m, 1H), 6.92-6.84 (m, 3H), 4.34 (m, 1H), 4.03-3.91 (m, 3H), 3.89 (s, 3H), 3.75 (m, 1H), 3.67 (m, 1H), 3.48 (m, 1H), 2.13 (m, 1H), 2.02 (m, 1H), 1.94 (m, 1H), 1.62 (m, 1H), 1.36 (t, 3H)

Example 9: (R)—N-(6-(3-(2-ethoxyphenoxy)piperidin-1-yl)pyrazin-2-yl)-4-methoxybenzamide

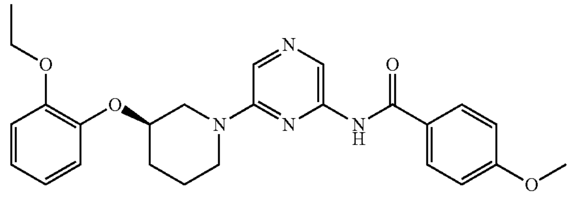 [SMILES: CCOc1ccccc1O[C@@H]1CCCN(c2cncc(NC(=O)c3ccc(OC)cc3)n2)C1]

(R)-2-chloro-6-(3-(2-ethoxyphenoxy)piperidin-1-yl) pyrazine (0.05 g, 0.15 mmol) obtained in Preparation Example 1 and 4-methoxybenzamide (0.03 g, 0.17 mmol) were used in a similar manner to Example 8 to obtain the desired product. (Yield: 54%)

$^1$H-NMR (500 MHz, CHLOROFORM-D): δ 8.84 (s, 1H), 7.91 (s, 1H), 7.84 (m, 3H), 6.99 (m, 3H), 6.92-6.83 (m, 3H), 4.34 (m, 1H), 4.03-3.90 (m, 3H), 3.88 (s, 3H), 3.75 (m, 1H), 3.66 (m, 1H), 3.45 (m, 1H), 2.12 (m, 1H), 2.04 (m, 1H), 1.93 (m, 1H), 1.61 (m, 1H), 1.37 (t, 3H)

Example 10: (R)—N-(6-(3-(2-ethoxyphenoxy)piperidin-1-yl)pyrazin-2-yl)-4-nitrobenzamide

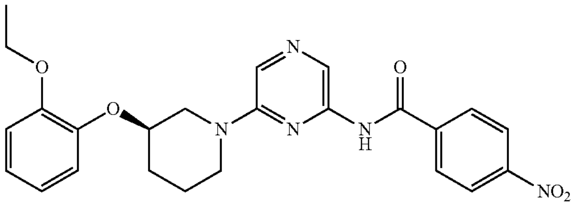 [SMILES: CCOc1ccccc1O[C@@H]1CCCN(c2cncc(NC(=O)c3ccc([N+](=O)[O-])cc3)n2)C1]

(R)-2-chloro-6-(3-(2-ethoxyphenoxy)piperidin-1-yl) pyrazine (0.05 g, 0.15 mmol) obtained in Preparation Example 1 and 4-nitrobenzamide (0.03 g, 0.17 mmol) were used in a similar manner to Example 8 to obtain the desired product. (Yield: 55%)

$^1$H-NMR (500 MHz, CHLOROFORM-D): δ 8.81 (s, 1H), 8.37 (d, 2H), 8.06 (d, 2H), 7.97 (s, 1H), 7.88 (s, 1H), 6.95 (m, 1H), 6.87 (m, 3H), 4.37 (m, 1H), 4.02-3.88 (m, 3H), 3.79 (m, 1H), 3.70 (m, 1H), 3.56 (m, 1H), 2.12 (m, 1H), 2.05 (m, 1H), 1.97 (m, 1H), 1.62 (m, 1H), 1.36 (t, 3H)

Example 11: (R)-2-((6-(3-(2-ethoxyphenoxy)piperidin-1-yl)pyrazin-2-yl)carbamoyl)benzoic acid

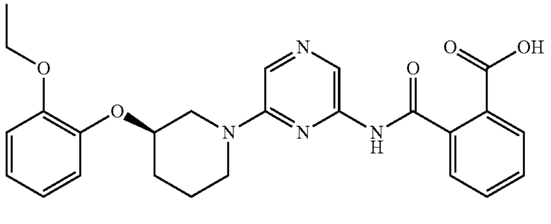 [SMILES: CCOc1ccccc1O[C@@H]1CCCN(c2cncc(NC(=O)c3ccccc3C(=O)O)n2)C1]

(R)-6-(3-(2-ethoxyphenoxy)piperidin-1-yl)pyrazin-2-amine obtained in Preparation Example 2 and phthalic anhydride were used in a similar manner to Example 6 to obtain the desired product.

$^1$H NMR (300 MHz, CHLOROFORM-D): δ 8.71 (s, 1H), 8.03 (s, 1H), 7.92 (m, 2H), 7.56 (m, 3H), 6.95 (m, 1H), 6.84 (s, 3H), 4.31 (bs, 1H), 3.95 (m, 3H), 3.78 (m, 1H), 3.64 (m, 3H), 3.40 (bs, 1H), 1.94-2.25 (m, 4H), 1.50 (m, 1H), 1.27-1.42 (m, 5H), 0.90 (m, 2H)

Example 12: (R)-2-(4-((6-(3-(2-ethoxyphenoxy)piperidin-1-yl)pyrazin-2-yl)carbamoyl)phenyl)acetic acid

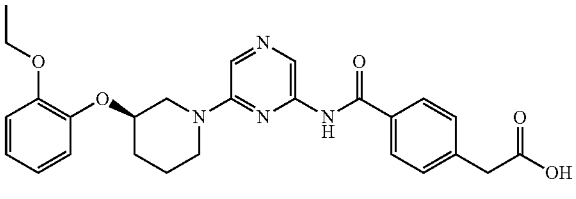 [SMILES: CCOc1ccccc1O[C@@H]1CCCN(c2cncc(NC(=O)c3ccc(CC(=O)O)cc3)n2)C1]

Step 1: Methyl (R)-2-(4-((6-(3-(2-ethoxyphenoxy)piperidin-1-yl)pyrazin-2-yl)carbamoyl)phenyl)acetate (R)-2-chloro-6-(3-(2-ethoxyphenoxy)piperidin-1-yl) pyrazine (0.864 g, 2.59 mmol) obtained in Preparation Example 1 and methyl 2-(4-carbamoylphenyl)acetate (0.6 g, 3.11 mmol) obtained in Preparation Example 3 were used in a similar manner to Example 8 to obtain the desired product. (Yield: 37%)

$^1$H-NMR (400 MHz, CHLOROFORM-D) δ 8.85 (s, 1H), 7.92 (s, 1H), 7.89 (s, 1H), 7.85 (d, 2H), 7.43 (d, 2H), 6.99-6.85 (m, 4H), 4.34 (m, 1H), 4.13-4.10 (m, 3H), 4.01-3.94 (m, 3H), 3.68-3.65 (m, 4H), 3.47 (m, 1H), 2.13 (m, 1H), 1.95 (m, 2H), 1.61 (m, 1H), 1.38-1.35 (t, 3H)

Step 2: (R)-2-(4-((6-(3-(2-ethoxyphenoxy)piperidin-1-yl)pyrazin-2-yl)carbamoyl)phenyl)acetic acid The ester compound obtained in Step 1 was used in a 1 N aqueous lithium hydroxide solution in a similar manner to Step 2 of Example 2 to obtain the desired product. (Yield: 50%)

$^1$H-NMR (400 MHz, CHLOROFORM-D) δ 8.83 (s, 1H), 7.95 (s, 1H), 7.92 (s, 1H), 7.86 (d, 2H), 7.44 (d, 2H), 6.96 (m, 1H), 6.92-6.83 (m, 3H), 4.35-4.34 (m, 1H), 4.02-3.89 (m, 3H), 3.75 (s, 2H), 3.72-3.68 (m, 2H), 3.51-3.46 (m, 1H), 2.1 (m, 1H), 2.02-1.93 (m, 2H), 1.62-1.59 (m, 1H), 1.37-1.33 (t, 3H)

Example 13: (R)-2-(4-((6-(3-(2-ethoxyphenoxy)piperidin-1-yl)pyrazin-2-yl)carbamoyl)phenyl)-2-methylpropanoic acid

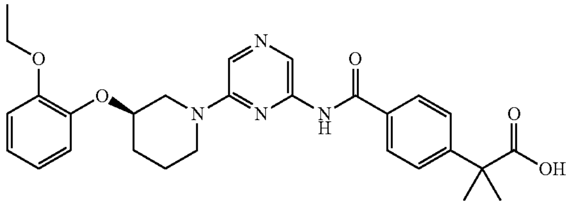 [SMILES: CCOc1ccccc1O[C@@H]1CCCN(c2cncc(NC(=O)c3ccc(C(C)(C)C(=O)O)cc3)n2)C1]

Step 1: Methyl (R)-2-(4-((6-(3-(2-ethoxyphenoxy)piperidin-1-yl)pyrazin-2-yl)carbamoyl)phenyl)-2-Methylpropanoate (R)-2-chloro-6-(3-(2-ethoxyphenoxy)piperidin-1-yl) pyrazine obtained in Preparation Example 1 and methyl 2-(4-carbamoylphenyl)-2-methylpropanate obtained in Preparation Example 4 were used in a similar manner to Example 8 to obtain the desired product. (Yield: 82%)

$^1$H-NMR (400 MHz, CHLOROFORM-D) δ 8.85 (s, 1H), 7.92 (s, 1H), 7.88 (s, 1H), 7.85 (d, J=8 Hz, 2H), 7.47 (d, J=8 Hz, 2H), 6.97-6.87 (m, 4H), 4.38 (m, 1H), 3.98-3.96 (m, 3H), 3.79-3.48 (m, 3H), 3.68 (s, 3H), 2.15-1.95 (m, 3H), 1.63 (s, 6H), 1.63 (m, 1H), 1.37 (t, J=8 Hz, 3H)

Step 2: (R)-2-(4-((6-(3-(2-ethoxyphenoxy)piperidin-1-yl)pyrazin-2-yl)carbamoyl)phenyl)-2-methyl propanoic acid The ester compound obtained in Step 1 was used in a 2 N aqueous sodium hydroxide solution in a similar manner to Step 2 of Example 2 to obtain the desired product. (Yield: 70%)

$^1$H-NMR (400 MHz, CHLOROFORM-D) δ 8.82 (s, 1H), 7.93 (s, 1H), 7.92 (s, 1H), 7.85 (d, J=8 Hz, 2H), 7.54 (d, J=8.4 Hz, 2H), 6.97-6.83 (m, 4H), 4.34 (m, 1H), 3.99-3.90 (m, 3H), 3.70-3.65 (m, 2H), 3.47 (m, 1H), 2.09 (m, 1H), 2.04-1.92 (m, 2H), 1.65 (s, 6H), 1.65 (m, 1H), 1.35 (t, J=6.8 Hz, 3H)

Example 14: (R)-2-(4-((6-(3-(2-ethoxyphenoxy)piperidin-1-yl)pyrazin-2-yl)carbamoyl)phenoxy)-2-methylpropanoic acid

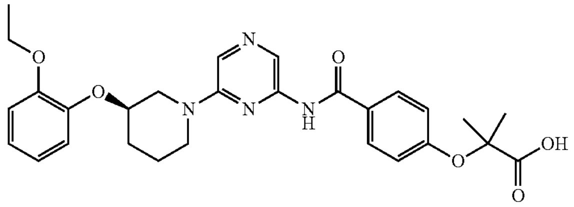 [SMILES: CCOc1ccccc1O[C@@H]1CCCN(c2cncc(NC(=O)c3ccc(OC(C)(C)C(=O)O)cc3)n2)C1]

(R)-2-chloro-6-(3-(2-ethoxyphenoxy)piperidin-1-yl) pyrazine (0.10 g, 0.30 mmol) obtained in Preparation Example 1 and ethyl 2-(4-carbamoylphenoxy)-2-methylpropanoate (0.08 g, 0.30 mmol) obtained in Preparation Example 5 were used in a similar manner to Example 34 to obtain the desired product. (Yield: 43%)

$^1$H-NMR (400 MHz, CHLOROFORM-D): δ 8.72 (s, 1H), 8.04 (s, 1H), 7.86 (s, 1H), 7.76 (d, 2H), 6.93-6.79 (m, 6H), 4.31 (m, 1H), 4.13-3.88 (m, 3H), 3.68 (m, 2H), 3.48 (m, 1H), 2.07 (m, 1H), 1.97 (m, 2H), 1.67 (s, 6H), 1.57 (m, 1H), 1.33 (t, 3H)

Example 15: (R)—N-(6-(3-(2-ethoxyphenoxy)piperidin-1-yl)pyrazin-2-yl)-1-(methylsulfonyl)piperidine)-4-carboxamide

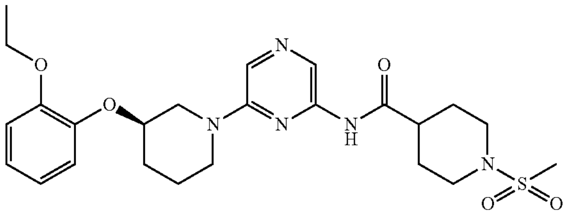 [SMILES: CCOc1ccccc1O[C@@H]1CCCN(c2cncc(NC(=O)C3CCN(S(C)(=O)=O)CC3)n2)C1]

(R)-2-chloro-6-(3-(2-ethoxyphenoxy)piperidin-1-yl) pyrazine (0.05 g, 0.15 mmol) obtained in Preparation Example 1 and 1-(methylsulfonyl)piperidine-4-carboxamide (0.03 g, 0.17 mmol) were used in a similar manner to Example 8 to obtain the desired product. (Yield: 46%)

$^1$H-NMR (500 MHz, CHLOROFORM-D): δ 8.65 (s, 1H), 7.88 (s, 1H), 7.35 (s, 1H), 6.96 (m, 2H), 6.87 (m, 2H), 4.30 (m, 1H), 4.03-3.89 (m, 3H), 3.80 (m, 2H), 3.69 (m, 1H), 3.62 (m, 1H), 3.45 (m, 1H), 2.88 (m, 2H), 2.80 (s, 3H), 2.40 (m, 1H), 2.12 (m, 1H), 2.07-1.87 (m, 6H), 1.59 (m, 1H), 1.35 (t, 3H)

Example 16: (R)-1-acetyl-N-(6-(3-(2-ethoxyphenoxy)piperidin-1-yl)pyrazin-2-yl)piperidine)-4-carboxamide

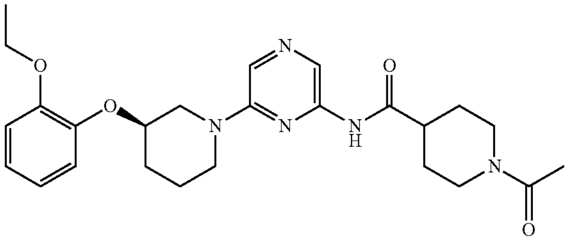 [SMILES: CCOc1ccccc1O[C@@H]1CCCN(c2cncc(NC(=O)C3CCN(C(C)=O)CC3)n2)C1]

(R)-2-chloro-6-(3-(2-ethoxyphenoxy)piperidin-1-yl) pyrazine (0.05 g, 0.15 mmol) obtained in Preparation Example 1 and 1-acetylpiperidine-4-carboxamide (0.03 g, 0.17 mmol) were used in a similar manner to Example 8 to obtain the desired product. (Yield: 43%)

$^1$H-NMR (500 MHz, CHLOROFORM-D): δ 8.66 (s, 1H), 7.88 (s, 1H), 7.33 (s, 1H), 6.94 (m, 2H), 6.88 (m, 2H), 4.65 (m, 1H), 4.31 (m, 1H), 4.03-3.88 (m, 4H), 3.71 (m, 1H), 3.62 (m, 1H), 3.44 (m, 1H), 3.15 (m, 1H), 2.71 (m, 1H), 2.48 (m, 1H), 2.11 (m, 4H), 2.05-1.88 (m, 4H), 1.85-1.65 (m, 2H), 1.60 (m, 1H), 1.36 (t, 3H)

Example 17: (R)—N-(6-(3-(2-ethoxyphenoxy)piperidin-1-yl)pyrazin-2-yl)-1-(isopropylsulfonyl)piperidine-4-carboxamide

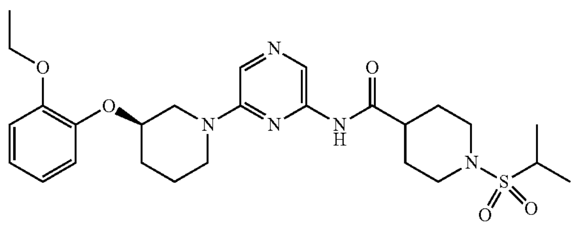 [SMILES: CCOc1ccccc1O[C@@H]1CCCN(c2cncc(NC(=O)C3CCN(S(=O)(=O)C(C)C)CC3)n2)C1]

(R)-2-chloro-6-(3-(2-ethoxyphenoxy)piperidin-1-yl) pyrazine (0.05 g, 0.15 mmol) obtained in Preparation Example 1 and 1-(isopropylsulfonyl)piperidine-4-carboxamide (0.04 g, 0.17 mmol) were used in a similar manner to Example 8 to obtain the desired product. (Yield: 53%)

$^1$H-NMR (500 MHz, CHLOROFORM-D): δ 8.65 (s, 1H), 7.88 (s, 1H), 7.28 (s, 1H), 6.94 (m, 2H), 6.88 (m, 2H), 4.31 (m, 1H), 4.03-3.90 (m, 3H), 3.87 (m, 2H), 3.70 (m, 1H), 3.62 (m, 1H), 3.44 (m, 1H), 3.18 (m, 1H), 3.00 (m, 2H), 2.41 (m, 1H), 2.12 (m, 1H), 2.00 (m, 2H), 1.95-1.82 (m, 3H), 1.60 (m, 2H), 1.35 (m, 9H)

Example 18: (R)—N-(6-(3-(2-ethoxyphenoxy)piperidin-1-yl)pyrazin-2-yl)-1-(5-ethylpyrimidin-2-yl) piperidine-4-carboxamide

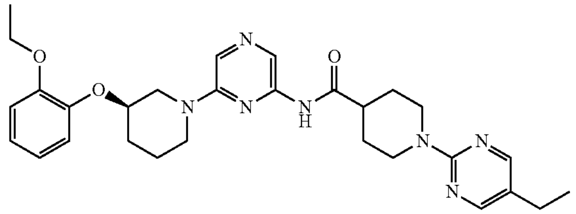 [SMILES: CCOc1ccccc1O[C@@H]1CCCN(c2cncc(NC(=O)C3CCN(c4ncc(CC)cn4)CC3)n2)C1]

(R)-2-chloro-6-(3-(2-ethoxyphenoxy)piperidin-1-yl) pyrazine (0.05 g, 0.15 mmol) obtained in Preparation Example 1 and 1-(5-ethylpyrimidin-2-yl)piperidine-4-carboxamide (0.04 g, 0.17 mmol) obtained in Preparation 35 were used in a similar manner to Example 8 to obtain the desired product. (Yield: 54%)

$^1$H-NMR (500 MHz, CHLOROFORM-D): δ 8.67 (s, 1H), 8.17 (s, 2H), 7.86 (s, 1H), 7.33 (s, 1H), 6.94 (m, 2H), 6.87 (m, 2H), 4.80 (m, 2H), 4.30 (m, 1H), 4.03-3.90 (m, 3H), 3.73 (m, 1H), 3.60 (m, 1H), 3.43 (m, 1H), 2.94 (m, 2H), 2.55-2.42 (m, 3H), 2.13 (m, 1H), 1.99 (m, 3H), 1.93 (m, 1H), 1.80 (m, 2H), 1.59 (m, 1H), 1.35 (t, 3H), 1.20 (t, 3H)

Example 19: (R)-4-((6-(3-(2-ethoxyphenoxy)piperidin-1-yl)pyrazin-2-yl)amino)-4-oxobutanoic acid

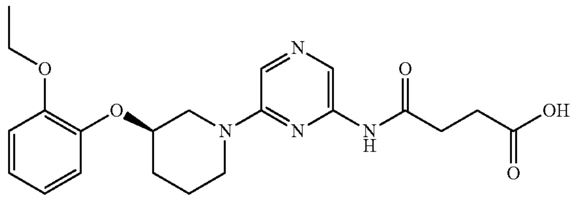 [SMILES: CCOc1ccccc1O[C@@H]1CCCN(c2cncc(NC(=O)CCC(=O)O)n2)C1]

(R)-6-(3-(2-ethoxyphenoxy)piperidin-1-yl)pyrazin-2-amine obtained in Preparation Example 2 and succinic anhydride were used in a similar manner to Example 6 to obtain the desired product.

$^1$H NMR (300 MHz, CHLOROFORM-D): δ 8.63 (s, 1H), 7.88 (s, 1H), 7.51 (s, 1H), 7.30 (s, 1H), 6.88-7.00 (m, 4H), 4.34 (m, 1H), 4.12 (m, 1H), 3.96 (m, 3H), 3.70 (m, 2H), 3.69 (m, 1H), 2.78 (d, 2H), 2.68 (d, 2H), 2.15 (d, 2H), 1.96-2.10 (m, 3H), 1.61 (m, 1H), 1.44 (t, 3H), 0.89 (m, 1H)

Example 20: (1R)-2-((6-((R)-3-(2-ethoxyphenoxy) piperidin-1-yl)pyrazin-2-yl)carbamoyl)cyclopentane-1-carboxylic acid

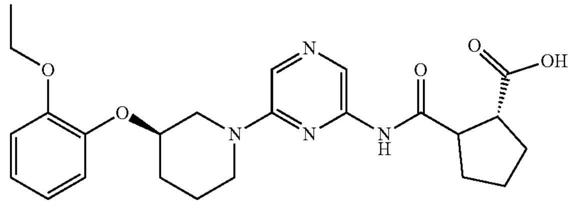 [SMILES: CCOc1ccccc1O[C@@H]1CCCN(c2cncc(NC(=O)C3CCC[C@H]3C(=O)O)n2)C1]

(R)-6-(3-(2-ethoxyphenoxy)piperidin-1-yl)pyrazin-2-amine obtained in Preparation Example 2 was used in a similar manner to Example 6 to obtain the desired product.

$^1$H NMR (300 MHz, Methanol-D): δ 8.26 (s, 1H), 7.69 (s, 1H), 6.89-7.02 (m, 5H), 4.48 (m, 2H), 3.79-3.96 (m, 8H), 3.53-3.65 (m, 6H), 3.22 (q, 2H), 2.30 (m, 2H), 2.09 (m, 10H), 1.61 (bs, 3H), 1.35 (m, 12H), 0.89 (m, 1H)

Example 21: (R)-4-((6-(3-(2-ethoxyphenoxy)piperidin-1-yl)pyrazin-2-yl)carbamoyl)bicyclo[2.2.2]octane-1-carboxylic acid

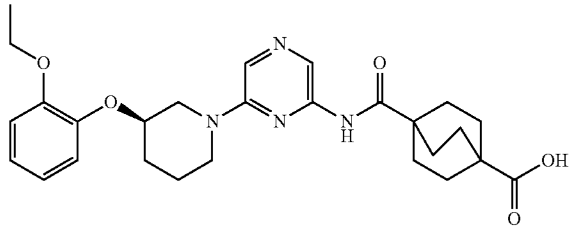 [SMILES: CCOc1ccccc1O[C@@H]1CCCN(c2cncc(NC(=O)C34CCC(C(=O)O)(CC3)CC4)n2)C1]

(R)-2-chloro-6-(3-(2-ethoxyphenoxy)piperidin-1-yl) pyrazine (0.05 g, 0.15 mmol) obtained in Preparation Example 1 and methyl 4-carbamoylbicyclo[2.2.2]octane-1-carboxylate (0.04 g, 0.17 mmol) were used in a similar manner to Example 34 to obtain the desired product. (Yield: 34%)

$^1$H-NMR (500 MHz, CHLOROFORM-D): δ 8.68 (s, 1H), 7.87 (s, 1H), 7.35 (s, 1H), 6.96 (m, 2H), 6.88 (m, 2H), 4.29 (m, 1H), 4.07-3.93 (m, 3H), 3.75 (m, 1H), 3.57 (m, 1H), 3.41 (m, 1H), 2.15 (m, 1H), 2.04-1.86 (m, 14H), 1.59 (m, 1H), 1.37 (t, 3H)

Example 22: (R)-4-((6-(3-(2-ethoxyphenoxy)piperidin-1-yl)pyrazin-2-yl)amino)-2,2-dimethyl-4-oxobutanoic acid

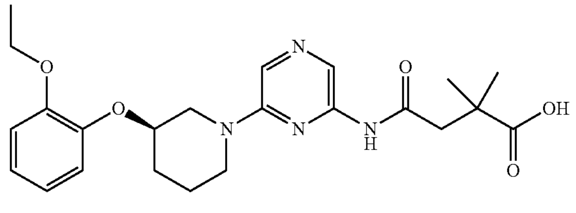 [SMILES: CCOc1ccccc1O[C@@H]1CCCN(c2cncc(NC(=O)CC(C)(C)C(=O)O)n2)C1]

(R)-6-(3-(2-ethoxyphenoxy)piperidin-1-yl)pyrazin-2-amine obtained in Preparation Example 2 and 3,3-dimethylsuccinic anhydride were used in a similar manner to Example 6 to obtain the desired product. (Yield: 51%)

$^1$H NMR (300 MHz, CHLOROFORM-D): δ 8.64 (s, 1H), 7.87 (s, 1H), 7.85 (s, 1H), 6.86-6.98 (m, 4H), 4.3 (m, 1H), 3.94-4.03 (m, 3H), 3.7 (m, 1H), 3.57 (dd, 1H), 3.35 (m, 1H), 2.68 (s, 2H), 2.04 (m, H), 1.93 (m, 2H), 1.5 (m, 1H), 1.33 (m+6H s, 10H)

Example 23: (R)-1-(6-(3-(2-ethoxyphenoxy)piperidin-1-yl)pyrazin-2-yl)-3,3-dimethylpyrrolidine-2,5-dione

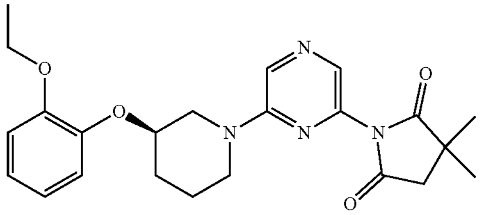 [SMILES: CCOc1ccccc1O[C@@H]1CCCN(c2cncc(N3C(=O)CC(C)(C)C3=O)n2)C1]

A by-product was produced in the course of preparing Example 22, and the desired product was obtained in the course of separation and purification.

$^1$H NMR (300 MHz, CHLOROFORM-D): δ 8.11 (s, 1H), 7.77 (s, 1H), 6.87-7.01 (m, 4H), 4.30 (m, 1H), 4.15 (dd, 1H), 4.03 (q, 2H), 3.85 (m, 1H), 3.50 (m, 2H), 2.10 (m, 1H), 1.97 (m, 2H), 1.60 (m, 1H), 1.45 (s, 6H), 1.38 (t, 3H), 1.27 (m, 2H), 0.90 (m, 1H)

Example 24: (R)-5-((6-(3-(2-ethoxyphenoxy)piperidin-1-yl)pyrazin-2-yl)amino)-2,2-dimethyl-5-oxopentanoic acid

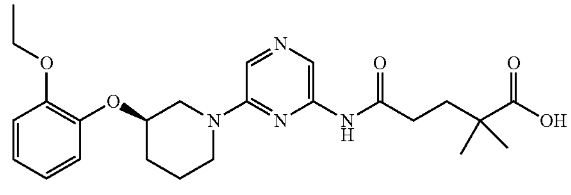 [SMILES: CCOc1ccccc1O[C@@H]1CCCN(c2cncc(NC(=O)CCC(C)(C)C(=O)O)n2)C1]

(R)-6-(3-(2-ethoxyphenoxy)piperidin-1-yl)pyrazin-2-amine obtained in Preparation Example 2 and 3,3-dimethylglutaric anhydride were used in a similar manner to Example 6 to obtain the desired product.

$^1$H NMR (300 MHz, CHLOROFORM-D): δ 8.68 (s, 1H), 7.89 (s, 1H), 7.66 (s, 1H), 6.87-6.98 (m, 4H), 4.20 (m, 1H), 3.95 (m, 3H), 3.70 (m, 1H), 3.58 (dd, 1H), 3.40 (m, 1H), 2.44 (m, 2H), 1.99-2.16 (m, 6H), 1.39 (t, 3H), 0.90 (m, 2H)

Example 25: (R)-5-((6-(3-(2-ethoxyphenoxy)piperidin-1-yl)pyrazin-2-yl)amino)-3,3-dimethyl-5-oxopentanoic acid

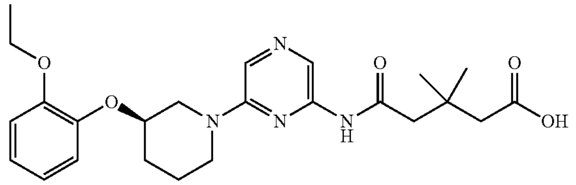 [SMILES: CCOc1ccccc1O[C@@H]1CCCN(c2cncc(NC(=O)CC(C)(C)CC(=O)O)n2)C1]

(R)-6-(3-(2-ethoxyphenoxy)piperidin-1-yl)pyrazin-2-amine obtained in Preparation Example 2 and 4,4-dimethylglutaric anhydride were used in a similar manner to Example 6 to obtain the desired product.

$^1$H NMR (300 MHz, CHLOROFORM-D): δ 8.68 (s, 1H), 8.13 (s, 1H), 7.92 (s, 1H), 6.87-7.00 (m, 4H), 4.31 (m, 1H), 4.00 (m, 3H), 3.72 (m, 1H), 3.62 (dd, 1H), 3.45 (m, 1H), 2.45 (s, 2H), 2.00 (m, 3H), 1.60 (m, 2H), 1.38 (t, 3H), 1.28 (s, 2H), 1.20 (s, 3H), 1.92 (s, 3H), 0.90 (m, 2H)

Example 26: (R)—N-(6-(3-(2-ethoxyphenoxy)piperidin-1-yl)pyrazin-2-yl)-2-(3-trifluoromethyl)phenyl)acetamide

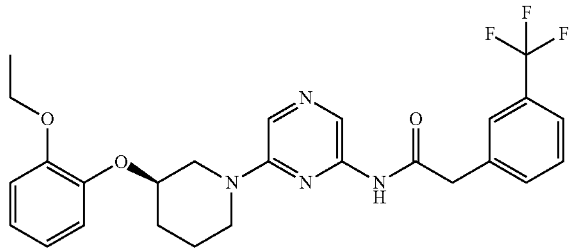 [SMILES: CCOc1ccccc1O[C@@H]1CCCN(c2cncc(NC(=O)Cc3cccc(C(F)(F)F)c3)n2)C1]

(R)-6-(3-(2-ethoxyphenoxy)piperidin-1-yl)pyrazin-2-amine obtained in Preparation Example 2 and 2-(3-trifluoromethyl)phenylacetyl chloride were used in a similar manner to Example 6 to obtain the desired product. (Yield: 54%)

$^1$H NMR (300 MHz, CHLOROFORM-D): δ 8.65 (s, 1H), 7.83 (s, 1H), 7.55 (m, 4H), 7.38 (s, 1H), 6.85-6.96 (m, 4H), 4.28 (m, 1H), 3.94 (m, 3H), 3.77 (s, 2H), 3.65 (m, 2H), 3.42 (m, 1H), 1.93-2.11 (m, 3H), 1.56 (m, 1H), 1.94 (t, 3H)

Example 27: (R)-2-(3,5-bis(trifluoromethyl)phenyl)-N-(6-(3-(2-ethoxyphenoxy)piperidin-1-yl)pyrazin-2-yl)acetamide

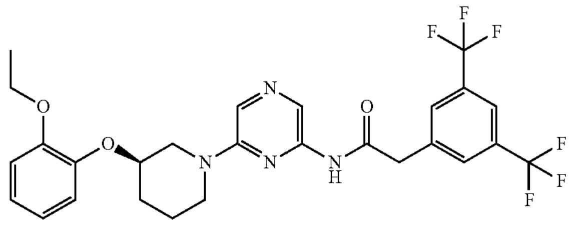 [SMILES: CCOc1ccccc1O[C@@H]1CCCN(c2cncc(NC(=O)Cc3cc(C(F)(F)F)cc(C(F)(F)F)c3)n2)C1]

(R)-6-(3-(2-ethoxyphenoxy)piperidin-1-yl)pyrazin-2-amine obtained in Preparation Example 2 and 3,5-bis(trifluoromethyl)phenylacetyl chloride were used in a similar manner to Example 6 to obtain the desired product. (Yield: 38%)

$^1$H NMR (300 MHz, CHLOROFORM-D): δ 8.64 (s, 1H), 7.92 (s, 1H), 7.84 (s, 1H), 7.82 (s, 2H), 7.50 (s, 1H), 6.68-7.00 (m, 4H), 4.35 (m, 1H), 3.95 (m, 3H), 3.84 (s, 2H), 3.70 (m, 2H), 3.50 (m, 1H), 1.97-2.13 (m, 3H), 1.61 (m, 1H), 1.61 (t, 3H)

Example 28: (R)—N-(6-(3-(2-ethoxyphenoxy)piperidin-1-yl)pyrazin-2-yl)-2-phenylacetamide

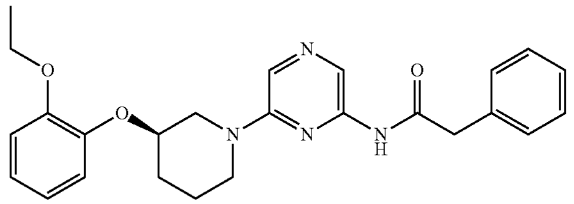 [SMILES: CCOc1ccccc1O[C@@H]1CCCN(c2cncc(NC(=O)Cc3ccccc3)n2)C1]

(R)-6-(3-(2-ethoxyphenoxy)piperidin-1-yl)pyrazin-2-amine (0.17 g, 0.50 mmol) obtained in Preparation Example 2 and phenylacetyl chloride (0.078 g, 0.50 mmol) were used in a similar manner to Example 6 to obtain the desired product. (Yield: 23%)

$^1$H NMR (400 MHz, CHLOROFORM-D): δ 8.69 (s, 1H), 7.78 (s, 1H), 7.29-7.41 (m, 5H), 6.97 (m, 2H), 6.85 (m, 2H), 4.27 (m, 1H), 3.91-4.00 (m, 3H), 3.72 (s, 2H), 3.68 (m, 1H), 3.52 (m, 1H), 3.37 (m, 1H), 2.09 (m, 1H), 1.96 (m, 1H), 1.86 (m, 1H), 1.56 (m, 1H), 1.34 (t, 3H)

Example 29: (R)—N-(6-(3-(2-ethoxyphenoxy)piperidin-1-yl)pyrazin-2-yl)-3-phenylpropanamide

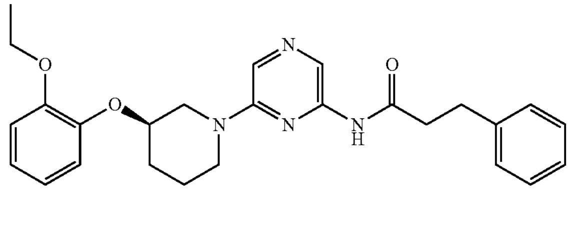 [SMILES: CCOc1ccccc1O[C@@H]1CCCN(c2cncc(NC(=O)CCc3ccccc3)n2)C1]

(R)-6-(3-(2-ethoxyphenoxy)piperidin-1-yl)pyrazin-2-amine (0.17 g, 0.50 mmol) obtained in Preparation Example 2 and 3-phenylpropanoyl chloride (0.08 g, 0.50 mmol) were used in a similar manner to Example 6 to obtain the desired product. (Yield: 46%)

$^1$H-NMR (500 MHz, CHLOROFORM-D): δ 8.67 (s, 1H), 7.86 (s, 1H), 7.30 (t, J=7.6 Hz, 2H), 7.22 (dd, J=17.1, 7.3 Hz, 3H), 7.12 (s, 1H), 6.98-6.90 (m, 2H), 6.88-6.70 (m, 2H), 4.35-4.27 (m, 1H), 4.02-3.85 (m, 3H), 3.72-3.59 (2H), 3.46-3.38 (m, 1H), 3.09-3.01 (m, 2H), 2.66 (t, J=7.6 Hz, 2H), 2.09 (d, J=12.2 Hz, 1H), 2.02-1.87 (m, 2H), 1.57 (q, J=4.3 Hz, 1H), 1.33 (t, J=7.0 Hz, 3H)

Example 30: (R)-2-(3-chlorophenyl)-N-(6-(3-(2-ethoxyphenoxy)piperidin-1-yl)pyrazin-2-yl)acetamide

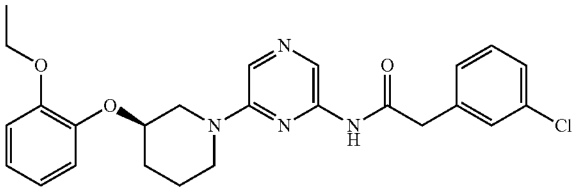 [SMILES: CCOc1ccccc1O[C@@H]1CCCN(c2cncc(NC(=O)Cc3cccc(Cl)c3)n2)C1]

(R)-6-(3-(2-ethoxyphenoxy)piperidin-1-yl)pyrazin-2-amine (0.17 g, 0.50 mmol) obtained in Preparation Example 2 and 3-chlorophenylacetyl chloride (0.08 g, 0.50 mmol) were used in a similar manner to Example 6 to obtain the desired product. (Yield: 30%)

$^1$H NMR (400 MHz, CHLOROFORM-D): δ 8.66 (s, 1H), 7.86 (s, 1H), 7.29-7.33 (m, 3H), 7.21 (m, 1H), 6.97 (m, 2H), 6.86 (m, 2H), 4.29 (m, 1H), 3.90-4.00 (m, 3H), 3.72 (m, 3H), 3.59 (m, 1H), 3.41 (m, 1H), 2.09 (m, 1H), 1.96 (m, 1H), 1.86 (m, 1H), 1.56 (m, 1H), 1.36 (t, 3H)

Example 31: (R)—N-(6-(3-(2-ethoxyphenoxy)piperidin-1-yl)pyrazin-2-yl)-2-methyl-2-phenylpropanamide

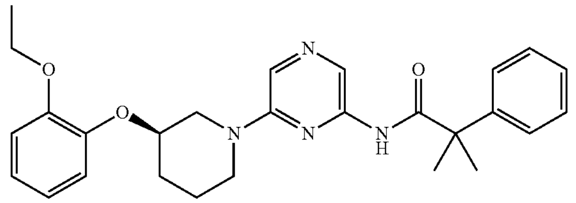 [SMILES: CCOc1ccccc1O[C@@H]1CCCN(c2cncc(NC(=O)C(C)(C)c3ccccc3)n2)C1]

(R)-6-(3-(2-ethoxyphenoxy)piperidin-1-yl)pyrazin-2-amine (0.17 g, 0.50 mmol) obtained in Preparation Example 2 and 2-methyl-2-phenylpropanoyl chloride (0.08 g, 0.50 mmol) were used in a similar manner to Example 6 to obtain the desired product. (Yield: 30%)

$^1$H NMR (400 MHz, CHLOROFORM-D): δ 8.75 (s, 1H), 7.82 (s, 1H), 7.33-7.43 (m, 4H), 7.31 (m, 1H), 7.02 (s, 1H), 6.79-6.93 (m, 4H), 4.23 (m, 1H), 3.91-4.00 (m, 3H), 3.69 (m, 1H), 3.41 (m, 1H), 3.27 (m, 1H), 2.08 (m, 1H), 1.91 (m, 1H), 1.85 (m, 1H), 1.66 (s, 6H), 1.55 (m, 1H), 1.34 (t, 3H)

Example 32: (R)-4-(2-((6-(3-(2-ethoxyphenoxy)piperidin-1-yl)pyrazin-2-yl)amino)-2-oxoethyl)benzoic acid

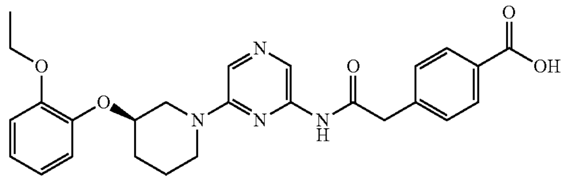 [SMILES: CCOc1ccccc1O[C@@H]1CCCN(c2cncc(NC(=O)Cc3ccc(C(=O)O)cc3)n2)C1]

Step 1: Methyl (R)-4-(2-((6-(3-(2-ethoxyphenoxy)piperidin-1-yl)pyrazin-2-yl)amino)-2-oxoethyl)benzoate (R)-6-(3-(2-ethoxyphenoxy)piperidin-1-yl)pyrazin-2-amine (0.40 g, 1.27 mmol) obtained in Preparation Example 2 and methyl 4-(2-chloro-2-oxoethyl)benzoate (0.74 g, 3.82 mmol) were used in a similar manner to Example 6 to obtain the desired ester compound. (Yield: 51%)

$^1$H-NMR (500 MHz, CHLOROFORM-D): δ 8.65 (s, 1H), 8.05 (d, J=8.6 Hz, 2H), 7.86 (s, 1H), 7.40 (d, J=8.6 Hz, 2H), 7.22 (s, 1H), 6.93 (q, J=7.9 Hz, 2H), 6.83 (q, J=7.1 Hz, 2H), 4.34-4.19 (m, 1H), 4.04-3.85 (m, 6H), 3.76 (s, 2H), 3.71-3.64 (m, 1H), 3.57 (q, J=6.9 Hz, 1H), 3.45-3.33 (m, 1H), 2.09 (td, J=7.9, 4.1 Hz, 1H), 2.03-1.94 (m, 1H), 1.92-1.80 (m, 1H), 1.56 (q, J=4.3 Hz, 1H), 1.33 (t, J=7.0 Hz, 3H)

Step 2: (R)-4-(2-((6-(3-(2-ethoxyphenoxy)piperidin-1-yl)pyrazin-2-yl)amino)-2-oxoethyl)benzoic acid The desired product was obtained by hydrolysis of the ester compound (0.32 g, 0.65 mmol) obtained in Step 1 using 2 N sodium hydroxide. (Yield: 16%)

$^1$H-NMR (500 MHz, CHLOROFORM-D): δ 8.67 (s, 1H), 8.09 (d, J=7.9 Hz, 2H), 7.89 (s, 1H), 7.52 (s, 1H), 7.41 (d, J=7.9 Hz, 2H), 6.92 (q, J=7.7 Hz, 2H), 6.86-6.65 (m, 2H), 4.42-4.13 (m, 1H), 4.11-3.86 (m, 3H), 3.78 (s, 2H), 3.70-3.55 (m, 2H), 3.44-3.36 (m, 1H), 2.33-2.02 (m, 1H), 1.96 (td, J=6.7, 3.7 Hz, 1H), 1.89 (q, J=4.1 Hz, 1H), 1.65-1.48 (m, 1H), 1.31 (t, J=7.0 Hz, 3H)

Example 33: (R)-3-(2-((6-(3-(2-ethoxyphenoxy)piperidin-1-yl)pyrazin-2-yl)amino)-2-oxoethyl)benzoic acid

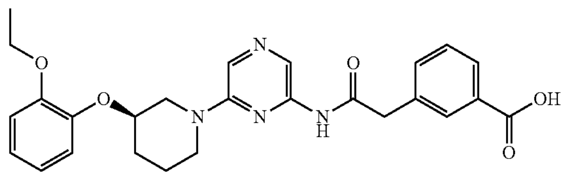 [SMILES: CCOc1ccccc1O[C@@H]1CCCN(c2cncc(NC(=O)Cc3cccc(C(=O)O)c3)n2)C1]

Step 1: Methyl (R)-3-(2-((6-(3-(2-ethoxyphenoxy)piperidin-1-yl)pyrazin-2-yl)amino)-2-oxoethyl)benzoate (R)-6-(3-(2-ethoxyphenoxy)piperidin-1-yl)pyrazin-2-amine (0.40 g, 1.27 mmol) obtained in Preparation Example 2 and methyl 3-(2-chloro-2-oxoethyl)benzoate (0.74 g, 3.82 mmol) were used in a similar manner to Example 6 to obtain the desired ester compound. (Yield: 20%)

$^1$H-NMR (500 MHz, CHLOROFORM-D): δ 8.66 (s, 1H), 8.00 (d, J=6.7 Hz, 2H), 7.86 (s, 1H), 7.55 (d, J=7.3 Hz, 1H), 7.47 (t, J=7.9 Hz, 1H), 7.21 (s, 1H), 6.94 (q, J=7.9 Hz, 2H), 6.87-6.77 (m, 2H), 4.34-4.24 (m, 1H), 4.05-3.84 (m, 6H), 3.76 (s, 2H), 3.73-3.64 (m, 1H), 3.58 (q, J=6.7 Hz, 1H), 3.39 (td, J=8.9, 4.1 Hz, 1H), 2.19-2.05 (m, 1H), 1.98 (q, J=3.3 Hz, 1H), 1.90 (q, J=4.1 Hz, 1H), 1.68-1.58 (1H), 1.33 (t, J=6.7 Hz, 3H)

Step 2: (R)-3-(2-((6-(3-(2-ethoxyphenoxy)piperidin-1-yl)pyrazin-2-yl)amino)-2-oxoethyl)benzoic acid The desired product was obtained through hydrolysis of the ester compound (0.12 g, 0.25 mmol) obtained in Step 1 in a similar manner to Step 2 of Example 32 using 2 N sodium hydroxide. (Yield: 26%)

$^1$H-NMR (500 MHz, CHLOROFORM-D): δ 8.68 (s, 1H), 8.06 (s, 1H), 8.02 (d, J=7.3 Hz, 1H), 7.87 (s, 1H), 7.81 (s, 1H), 7.56 (d, J=7.3 Hz, 1H), 7.47-7.41 (m, 1H), 6.95-6.85 (m, 2H), 6.84-6.71 (m, 2H), 4.35-4.21 (m, 1H), 3.98-3.84 (m, 3H), 3.77 (s, 2H), 3.67-3.54 (m, 2H), 3.43-3.35 (m, 1H), 2.05 (q, J=4.1 Hz, 1H), 1.94 (td, J=6.7, 3.3 Hz, 1H), 1.90-1.80 (m, 1H), 1.64-1.47 (m, 1H), 1.30 (t, J=7.0 Hz, 3H)

Example 34: (R)-2-(4-(2-((6-(3-(2-ethoxyphenoxy)piperidin-1-yl)pyrazin-2-yl)amino)-2-oxoethyl)phenyl)acetic acid

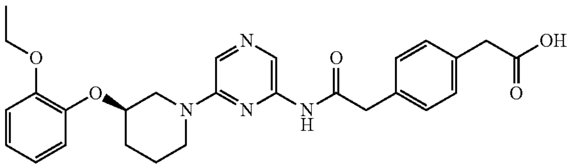 [SMILES: CCOc1ccccc1O[C@@H]1CCCN(c2cncc(NC(=O)Cc3ccc(CC(=O)O)cc3)n2)C1]

Step 1: Methyl (R)-2-(4-(2-((6-(3-(2-ethoxyphenoxy)piperidin-1-yl)pyrazin-2-yl)amino)-2-oxoethyl)phenyl)acetate (R)-2-chloro-6-(3-(2-ethoxyphenoxy)piperidin-1-yl)pyrazine (0.98 g, 2.93 mmol) obtained in Preparation Example 1 and methyl 2-(4-(2-amino-2-oxoethyl)phenyl)acetate (0.61 g, 2.93 mmol) obtained in Preparation Example 6, tris(dibenzylideneacetone)dipalladium(0) (0.16 g, 0.18 mmol), 4,5-bis(diphenylphosphino)-9,9-dimethylxanthine (0.15 g, 0.26 mmol) and cesium carbonate (2.39 g, 7.33 mmol) were added to 50 mL of dioxane and stirred under reflux for 4 hours. After completion of the reaction, the resulting product was cooled to room temperature, diluted with ethyl acetate and washed with an aqueous sodium hydrogen carbonate solution and brine. The organic solvent was dried over magnesium sulfate and removed under reduced pressure. The purification was carried out by silica gel column (ethyl acetate:hexane=3:1) to obtain the desired product. (Yield: 68%)

$^1$H-NMR (500 MHz, CHLOROFORM-D) δ 8.67 (s, 1H), 7.85 (s, 1H), 7.32-7.28 (m, 4H), 7.24 (s, 1H), 6.97-6.89 (m, 2H), 6.88-6.77 (m, 2H), 4.31-4.24 (m, 1H), 4.03-3.89 (m, 3H), 3.69 (m, 3H), 3.67 (d, J=7.9 Hz, 3H), 3.63 (s, 2H), 3.54

(q, J=6.9 Hz, 1H), 3.41-3.33 (m, 1H), 2.08 (q, J=4.1 Hz, 1H), 2.00-1.93 (m, 1H), 1.88 (q, J=4.1 Hz, 1H), 1.55 (t, J=4.6 Hz, 1H), 1.34 (t, J=7.0 Hz, 3H)

Step 2: (R)-2-(4-(2-((6-(3-(2-ethoxyphenoxy)piperidin-1-yl)pyrazin-2-yl)amino)-2-oxo ethyl)phenyl) acetic acid The ester obtained in Step 1 (1.0 g, 1.98 mmol) was dissolved in THF-methanol (40 mL, 3:1), and 2 N sodium hydroxide solution (10 mL, 19.8 mmol) was slowly added dropwise. After stirring at room temperature for 4 hours, the resulting product was diluted with water, neutralized with 2 N hydrochloric acid solution and extracted with ethyl acetate The organic solvent was dried over magnesium sulfate and removed under reduced pressure. The purification was carried out by silica gel column (acetone:dichloromethane=1:1) to obtain the desired product. (Yield: 29%)

$^1$H-NMR (500 MHz, CHLOROFORM-D): δ 8.62 (s, 1H), 7.84 (s, 1H), 7.42 (s, 1H), 7.36-7.17 (m, 4H), 6.95-6.87 (m, 2H), 6.87-6.78 (m, 2H), 4.30-4.21 (m, 1H), 4.00-3.86 (m, 3H), 3.67 (s, 2H), 3.63 (t, J=14.7 Hz, 3H), 3.51 (td, J=14.4, 7.4 Hz, 1H), 3.39-3.29 (m, 1H), 2.06 (q, J=3.5 Hz, 1H), 1.93 (td, J=6.7, 3.1 Hz, 1H), 1.85 (q, J=4.1 Hz, 1H), 1.53 (q, J=4.5 Hz, 1H), 1.31 (t, J=7.0 Hz, 3H)

Example 35: (R)-2-(4-(2-amino-2-oxoethyl)phenyl-N-(6-(3-(2-ethoxyphenoxy)piperidin-1-yl)pyrazin-2-yl)acetamide

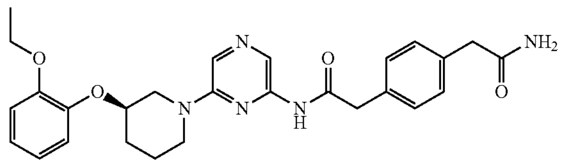 [SMILES: CCOc1ccccc1O[C@@H]1CCCN(c2cncc(NC(=O)Cc3ccc(CC(N)=O)cc3)n2)C1]

(R)-2-(4-(2-((6-(3-(2-ethoxyphenoxy)piperidin-1-yl) pyrazin-2-yl)amino)-2-oxoethyl)phenyl)acetic acid (0.27 g, 0.55 mmol) obtained in Example 34 was dissolved in dichloromethane (10 mL), and thionyl chloride (0.08 mL, 1.1 mmol) was slowly added dropwise at room temperature. After stirring at room temperature for 4 hours, the organic solvent was removed under reduced pressure, and the resulting product was diluted with THF and slowly added dropwise to 25% aqueous ammonia solution at 0° C. The resulting solid was filtered and dried to obtain the desired product. (Yield: 82%)

$^1$H-NMR (500 MHz, CHLOROFORM-D): δ 8.66 (s, 1H), 7.92-7.77 (1H), 7.36-7.27 (m, 5H), 6.99-6.90 (m, 2H), 6.89-6.80 (m, 2H), 5.39 (s, 2H), 4.31-4.24 (m, 1H), 4.03-3.89 (3H), 3.70 (s, 2H), 3.69-3.65 (m, 1H), 3.58 (s, 2H), 3.56-3.50 (1H), 3.41-3.33 (1H), 2.13-2.06 (m, 1H), 1.96 (td, J=6.7, 3.5 Hz, 1H), 1.88 (q, J=4.1 Hz, 1H), 1.59-1.51 (m, 1H), 1.35 (t, J=6.7 Hz, 3H)

Example 36: (R)—N-(6-(3-(2-ethoxyphenoxy)piperidin-1-yl)pyrazin-2-yl)-2-(4-hydroxyphenyl)acetamide

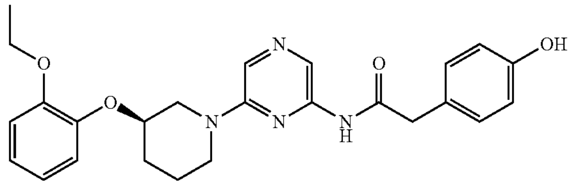 [SMILES: CCOc1ccccc1O[C@@H]1CCCN(c2cncc(NC(=O)Cc3ccc(O)cc3)n2)C1]

(R)-2-chloro-6-(3-(2-ethoxyphenoxy)piperidin-1-yl) pyrazine (0.25 g, 0.75 mmol) obtained in Preparation Example 1 and 2-(4-hydroxyphenyl)acetamide (0.11 g, 0.75 mmol) were used in a similar manner to Example 34 to obtain the desired product. (Yield: 54%)

$^1$H-NMR (500 MHz, CHLOROFORM-D): δ 8.69 (s, 1H), 7.82 (s, 1H), 7.31 (m, 1H), 7.14 (d, 2H), 6.98 (m, 2H), 6.84 (m, 4H), 4.27 (m, 1H), 3.95 (m, 3H), 3.63 (m, 3H), 3.55 (m, 1H), 3.37 (m, 1H), 2.04 (m, 1H), 1.98-1.83 (m, 2H), 1.55 (m, 1H), 1.34 (t, 3H)

Example 37: (R)-4-(4-(2-((6-(3-(2-ethoxyphenoxy)piperidin-1-yl)pyrazin-2-yl)amino)-2-oxoethyl)phenoxy)butanoic acid

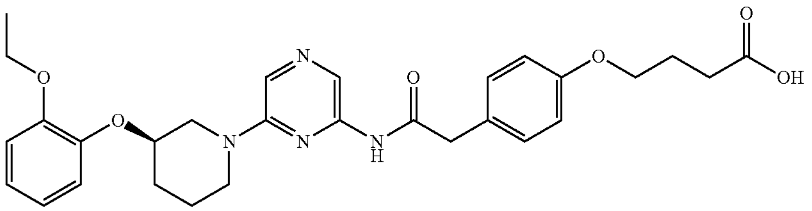 [SMILES: CCOc1ccccc1O[C@@H]1CCCN(c2cncc(NC(=O)Cc3ccc(OCCCC(=O)O)cc3)n2)C1]

(R)-2-chloro-6-(3-(2-ethoxyphenoxy)piperidin-1-yl) pyrazine (0.05 g, 0.15 mmol) obtained in Preparation Example 1 and ethyl 4-(4-(2-amino-2-oxoethyl)phenoxy) butanoate (0.04 g, 0.17 mmol) obtained in Preparation Example 7 were used in a similar manner to Example 34 to obtain the desired product. (Yield: 44%)

$^1$H-NMR (500 MHz, CHLOROFORM-D): δ 8.67 (s, 1H), 7.85 (s, 1H), 7.29 (s, 1H), 7.22 (d, 2H), 6.97-6.80 (m, 6H), 4.26 (m, 1H), 4.02 (t, 2H), 3.94 (m, 3H), 3.67 (m, 3H), 3.52 (m, 1H), 3.37 (m, 1H), 2.57 (t, 2H), 2.13 (m, 3H), 1.98-1.83 (m, 2H), 1.56 (m, 1H), 1.35 (t, 3H)

Example 38: (R)-2-(4-(2-((6-(3-(2-ethoxyphenoxy)piperidin-1-yl)pyrazin-2-yl)amino-2-oxoethyl)phenoxy)-2-methylpropanoic acid

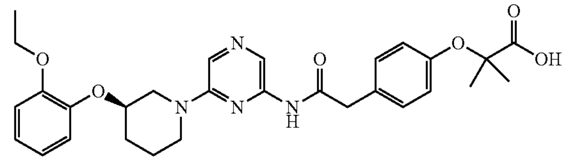 [SMILES: CCOc1ccccc1O[C@@H]1CCCN(c2cncc(NC(=O)Cc3ccc(OC(C)(C)C(=O)O)cc3)n2)C1]

(R)-2-chloro-6-(3-(2-ethoxyphenoxy)piperidin-1-yl)pyrazine (0.30 g, 0.90 mmol) obtained in Preparation Example 1 and ethyl 2-(4-(2-amino-2-oxoethyl)phenoxy)-2-methylpropanoate (0.24 g, 0.90 mmol) obtained in Preparation Example 8 were used in a similar manner to Example 34 to obtain the desired product. (Yield: 52%)

$^1$H-NMR (400 MHz, CHLOROFORM-D): δ 8.62 (s, 1H), 7.85 (s, 1H), 7.50 (s, 1H), 7.17 (d, 2H), 6.96-6.82 (m, 6H), 4.29 (m, 1H), 4.01-3.89 (m, 3H), 3.62 (m, 3H), 3.55 (m, 1H), 3.37 (m, 1H), 2.07 (m, 1H), 1.93 (m, 1H), 1.88 (m, 1H), 1.58 (m, 7H), 1.34 (t, 3H)

Example 39: (R)-2-(4-(1-((6-(3-(2-ethoxyphenoxy)piperidin-1-yl)pyrazin-2-yl)amino)-2-methyl-1-oxopropan-2-yl)phenyl)-2-methylpropanoic acid

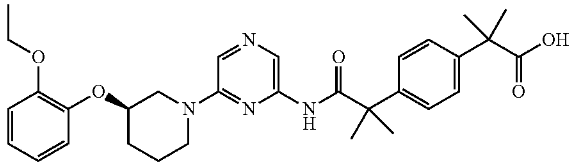 [SMILES: CCOc1ccccc1O[C@@H]1CCCN(c2cncc(NC(=O)C(C)(C)c3ccc(C(C)(C)C(=O)O)cc3)n2)C1]

Step 1: Methyl (R)-2-(4-(1-((6-(3-(2-ethoxyphenoxy)piperidin-1-yl)pyrazin-2-yl)amino)-2-methyl-1-oxopropan-2-yl)phenyl)-2-methylpropanoate (R)-2-chloro-6-(3-(2-ethoxyphenoxy)piperidin-1-yl)pyrazine obtained in Preparation Example 1 and methyl 2-(4-(1-amino-2-methyl-1-oxopropan-2-yl)phenyl)-2-methylpropanoate obtained in Preparation Example 9 were used in a similar manner to Step 1 of Example 34 to obtain the desired product. (Yield 45%)

$^1$H-NMR (500 MHz, CHLOROFORM-D): δ 8.73 (s, 1H), 7.81 (d, J=4.3 Hz, 1H), 7.41-7.27 (m, 4H), 7.06 (s, 1H), 6.98-6.86 (m, 2H), 6.85-6.69 (m, 2H), 4.33-4.16 (m, 1H), 4.04-3.85 (m, 3H), 3.66 (td, J=9.0, 3.7 Hz, 1H), 3.61 (d, J=4.9 Hz, 3H), 3.43 (dd, J=13.1, 7.6 Hz, 1H), 3.37-3.21 (m, 1H), 2.13-2.04 (m, 1H), 1.98-1.78 (m, 2H), 1.62 (s, 6H), 1.58-1.44 (m, 7H), 1.32 (t, J=7.0 Hz, 3H)

Step 2: (R)-2-(4-(1-((6-(3-(2-ethoxyphenoxy)piperidin-1-yl)pyrazin-2-yl)amino)-2-methyl-1-oxopropan-2-yl)phenyl)-2-methylpropanoic acid The ester compound obtained in Step 1 was hydrolyzed in a similar manner to Step 2 of Example 34 to obtain the desired product. (Yield: 48%)

$^1$H-NMR (400 MHz, CHLOROFORM-D): δ 8.69 (s, 1H), 7.83 (s, 1H), 7.44-7.26 (m, 4H), 7.06 (s, 1H), 6.94-6.88 (m, 2H), 6.83-6.77 (m, 2H), 4.23-4.21 (m, 1H), 4.13-3.91 (m, 3H), 3.63 (m, 1H), 3.46 (m, 1H), 3.28 (m, 1H), 2.05 (m, 1H), 1.98-1.78 (m, 2H), 1.64 (s, 3H), 1.59 (s, 3H), 1.58-1.44 (m, 1H), 1.32 (t, J=7.0 Hz, 3H)

Example 40: (R)-4-(3-((6-(3-(2-ethoxyphenoxy)piperidin-1-yl)pyrazin-2-yl)amino)-3-oxopropyl)benzoic acid

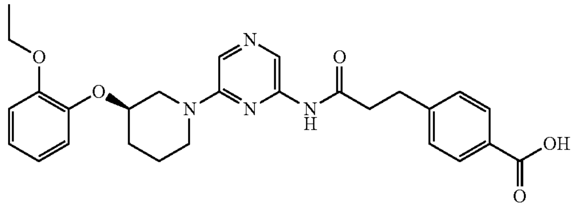 [SMILES: CCOc1ccccc1O[C@@H]1CCCN(c2cncc(NC(=O)CCc3ccc(C(=O)O)cc3)n2)C1]

(R)-2-chloro-6-(3-(2-ethoxyphenoxy)piperidin-1-yl)pyrazine (0.51 g, 1.53 mmol) obtained in Preparation Example 1 and methyl 4-(3-amino-3-oxopropyl)benzoate (0.32 g, 1.53 mmol) obtained in Preparation Example 10 were used in a similar manner to Example 34 to obtain the desired product. (Yield: 62%)

$^1$H-NMR (400 MHz, CHLOROFORM-D): δ 8.67 (s, 1H), 8.02 (d, 2H), 7.89 (s, 1H), 7.33 (m, 3H), 6.93 (m, 2H), 6.84 (m, 2H), 4.31 (m, 1H), 4.00-3.86 (m, 3H), 3.64 (m, 2H), 3.43 (m, 1H), 3.12 (t, 2H), 2.71 (t, 2H), 2.11 (m, 1H), 1.98 (m, 1H), 1.90 (m, 1H), 1.58 (m, 1H), 1.34 (t, 3H)

Example 41: (R,E)-4-(3-((6-(3-(2-ethoxyphenoxy)piperidin-1-yl)pyrazin-2-yl)amino)-3-oxoprop-1-en-1-yl)benzoic acid

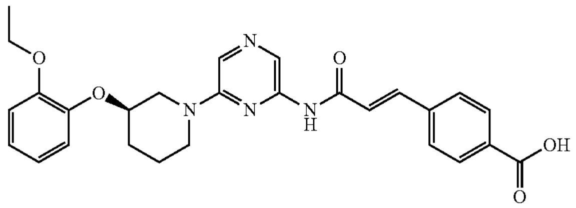 [SMILES: CCOc1ccccc1O[C@@H]1CCCN(c2cncc(NC(=O)/C=C/c3ccc(C(=O)O)cc3)n2)C1]

Step 1: Methyl (R,E)-4-(3-((6-(3-(2-ethoxyphenoxy)piperidin-1-yl)pyrazin-2-yl)amino)-3-oxoprop-1-en-1-yl)benzoate (R)-2-chloro-6-(3-(2-ethoxyphenoxy)piperidin-1-yl)pyrazine (0.09 g, 0.28 mmol) obtained in Preparation Example 1 and methyl (E)-4-(3-amino-3-oxoprop-1-en-1-yl)benzoate (0.07 g, 0.33 mmol) obtained in Preparation Example 11 were used in a similar manner to Step 1 of Example 34 to obtain the desired product. (Yield: 63%)

$^1$H-NMR (500 MHz, CHLOROFORM-D) δ 8.82 (s, 1H), 8.08-7.94 (3H), 7.88 (d, J=4.3 Hz, 1H), 7.81-7.69 (m, 1H), 7.54 (t, J=4.0 Hz, 2H), 7.26 (d, J=4.9 Hz, 0H), 7.01-6.90 (2H), 6.88-6.78 (m, 2H), 6.66 (d, J=15.3 Hz, 1H), 4.36-4.18 (m, 1H), 4.10 (qd, J=7.0, 4.7 Hz, 3H), 4.05-3.94 (m, 3H), 3.93-3.84 (m, 4H), 3.83-3.64 (m, 1H), 3.55 (dt, J=12.8, 3.7 Hz, 1H), 3.37 (td, J=8.9, 3.9 Hz, 1H), 2.19-2.07 (m, 1H), 2.03 (d, J=4.3 Hz, 5H), 1.94 (s, 2H), 1.90-1.78 (m, 1H), 1.63-1.48 (m, 1H), 1.41-1.30 (m, 3H), 1.28-1.10 (m, 6H)

Step 2: (R,E)-4-(3-((6-(3-(2-ethoxyphenoxy)piperidin-1-yl)pyrazin-2-yl)amino)-3-oxoprop-1-en-1-yl)benzoic acid The ester compound (0.07 g, 0.14 mmol) obtained in Step 1 was hydrolyzed in a similar manner to Step 2 of Example 34 to obtain the desired product. (Yield: 64%)

$^1$H-NMR (500 MHz, CHLOROFORM-D) δ 8.80 (s, 1H), 8.12 (d, J=7.9 Hz, 2H), 7.93 (s, 1H), 7.80 (d, J=15.1 Hz, 1H), 7.64 (d, J=7.8 Hz, 2H), 7.48 (d, J=18.3 Hz, 1H), 6.96 (t, J=7.6 Hz, 2H), 6.88 (dd, J=14.2, 8.1 Hz, 2H), 6.62 (d, J=15.9 Hz, 1H), 4.35 (s, 1H), 4.08-3.85 (m, 3H), 3.79-3.62 (m, 2H), 3.49 (s, 1H), 2.15 (d, J=26.9 Hz, 2H), 2.01 (s, 1H), 1.94 (d, J=7.9 Hz, 1H), 1.58 (d, J=38.5 Hz, 2H), 1.44-1.33 (m, 4H), 1.23 (dd, J=38.5, 15.9 Hz, 3H), 0.96-0.75 (m, 2H)

Example 42: (R,E)-4-(3-((6-(3-(2-ethoxyphenoxy)piperidin-1-yl)pyrazin-2-yl)amino)-2-methyl-3-oxoprop-1-en-1-yl)benzoic acid

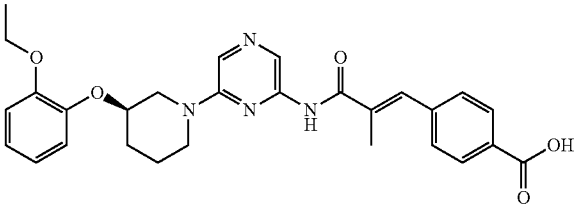 [SMILES: CCOc1ccccc1O[C@@H]1CCCN(c2cncc(NC(=O)/C(C)=C/c3ccc(C(=O)O)cc3)n2)C1]

Step 1: Methyl (R,E)-4-(3-((6-(3-(2-ethoxyphenoxy)piperidin-1-yl)pyrazin-2-yl)amino)-2-methyl-3-oxoprop-1-en-1-yl)benzoate (R)-2-chloro-6-(3-(2-ethoxyphenoxy)piperidin-1-yl)pyrazine (0.66 g, 1.99 mmol) obtained in Preparation Example 1 and methyl (E)-4-(3-amino-2-methyl-3-oxoprop-1-en-1-yl)benzoate (0.52 g, 2.39 mmol) obtained in Preparation Example 12 were used in a similar manner to Step 1 of Example 34 to obtain the desired product. (Yield: 67%)

$^1$H-NMR (500 MHz, CHLOROFORM-D) δ 8.81-8.77 (1H), 8.08 (d, J=7.9 Hz, 2H), 7.92 (d, J=4.3 Hz, 1H), 7.67 (s, 1H), 7.51-7.42 (m, 3H), 7.00-6.95 (m, 1H), 6.95-6.90 (1H), 6.87 (d, J=7.9 Hz, 2H), 4.37-4.29 (m, 1H), 4.06-3.96 (m, 2H), 3.94 (s, 3H), 3.81-3.71 (1H), 3.66 (q, J=6.7 Hz, 1H), 3.52-3.42 (m, 1H), 2.21 (d, J=1.8 Hz, 3H), 2.19-2.08 (m, 1H), 2.03-1.87 (m, 2H), 1.61 (qd, J=8.9, 4.7 Hz, 1H), 1.36 (q, J=6.5 Hz, 3H)

Step 2: (R,E)-4-(3-((6-(3-(2-ethoxyphenoxy)piperidin-1-yl)pyrazin-2-yl)amino)-2-methyl-3-oxoprop-1-en-1-yl)benzoic acid The ester compound (0.69 g, 1.34 mmol) obtained in Step 1 was hydrolyzed in a similar manner to Step 2 of Example 34 to obtain the desired product. (Yield: 41%)

$^1$H-NMR (500 MHz, CHLOROFORM-D) δ 8.79 (s, 1H), 8.13 (s, 2H), 7.93 (s, 1H), 7.69 (s, 1H), 7.48 (s, 3H), 7.02-6.67 (m, 5H), 4.33 (s, 1H), 4.00 (d, J=9.2 Hz, 3H), 3.81-3.59 (2H), 2.21 (s, 3H), 2.13 (s, 1H), 2.03 (s, 1H), 1.96-1.87 (1H), 1.65 (d, J=31.2 Hz, 7H), 1.36 (s, 5H), 1.30-1.16 (1H)

Example 43: 4-(3-((6-((R)-3-(2-ethoxyphenoxy)piperidin-1-yl)pyrazin-2-yl)amino)-2-methyl-3-oxopropyl)benzoic acid

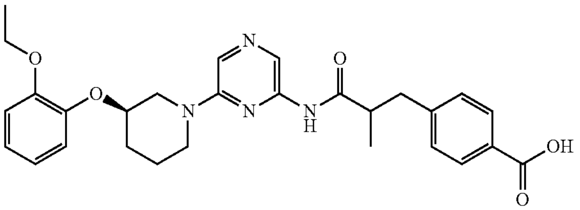 [SMILES: CCOc1ccccc1O[C@@H]1CCCN(c2cncc(NC(=O)C(C)Cc3ccc(C(=O)O)cc3)n2)C1]

Step 1: Methyl 4-(3-((6-((R)-3-(2-ethoxyphenoxy)piperidin-1-yl)pyrazin-2-yl)amino)-2-methyl-3-oxopropyl)benzoate (R)-2-chloro-6-(3-(2-ethoxyphenoxy)piperidin-1-yl)pyrazine (0.95 g, 2.83 mmol) obtained in Preparation Example 1 and methyl 4-(3-amino-2-methyl-3-oxopropyl)benzoate (0.75 g, 3.40 mmol) obtained in Preparation Example 13 were used in a similar manner to Step 1 of Example 34 to obtain the desired product. (Yield: 92%)

$^1$H-NMR (500 MHz, CHLOROFORM-D) δ 8.81-8.77 (1H), 8.08 (d, J=7.9 Hz, 2H), 7.92 (d, J=4.3 Hz, 1H), 7.67 (s, 1H), 7.51-7.42 (m, 3H), 7.00-6.95 (m, 1H), 6.95-6.90 (1H), 6.87 (d, J=7.9 Hz, 2H), 4.37-4.29 (m, 1H), 4.06-3.96 (m, 2H), 3.94 (s, 3H), 3.81-3.71 (1H), 3.66 (q, J=6.7 Hz, 1H), 3.52-3.42 (m, 1H), 2.21 (d, J=1.8 Hz, 3H), 2.19-2.08 (m, 1H), 2.03-1.87 (m, 2H), 1.61 (qd, J=8.9, 4.7 Hz, 1H), 1.36 (q, J=6.5 Hz, 3H)

Step 2: 4-(3-((6-((R)-3-(2-ethoxyphenoxy)piperidin-1-yl)pyrazin-2-yl)amino)-2-methyl-3-oxopropyl)benzoic acid The ester compound (1.35 g, 2.60 mmol) obtained in Step 1 was hydrolyzed in a similar manner to Step 2 of Example 34 to obtain the desired product. (Yield: 39%)

$^1$H-NMR (500 MHz, CHLOROFORM-D) δ 8.67 (d, J=3.4 Hz, 1H), 7.98 (dd, J=12.5, 8.1 Hz, 2H), 7.86 (s, 1H), 7.30 (d, J=10.7 Hz, 2H), 7.18 (s, 0H), 7.04 (s, 0H), 6.98-6.89 (m, 2H), 6.85 (d, J=7.8 Hz, 2H), 6.79 (d, J=8.3 Hz, 0H), 4.29 (s, 1H), 4.05-3.86 (m, 3H), 3.67 (s, 1H), 3.61-3.51 (m, 1H), 3.44-3.29 (m, 1H), 3.21-3.08 (m, 1H), 2.88-2.75 (m, 1H), 2.64 (t, J=6.3 Hz, 1H), 2.13 (d, J=35.2 Hz, 1H), 1.96 (s, 1H), 1.91-1.76 (m, 1H), 1.64-1.49 (m, 1H), 1.34 (q, J=6.3 Hz, 3H), 1.29 (d, J=6.8 Hz, 3H)

Example 44: (R)-4-(3-((6-(3-(2-ethoxyphenoxy)piperidin-1-yl)pyrazin-2-yl)amino)-3-oxopropyl)-2-fluorobenzoic acid

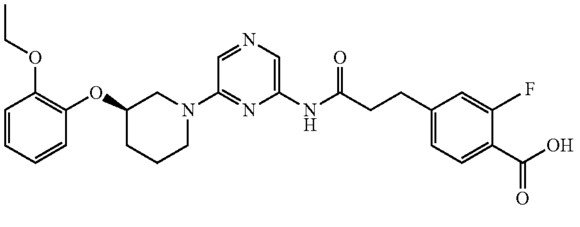 [SMILES: CCOc1ccccc1O[C@@H]1CCCN(c2cncc(NC(=O)CCc3ccc(C(=O)O)c(F)c3)n2)C1]

Step 1: Methyl (R)-4-(3-((6-(3-(2-ethoxyphenoxy)piperidin-1-yl)pyrazin-2-yl)amino)-3-oxopropyl)-2-fluorobenzoate (R)-2-chloro-6-(3-(2-ethoxyphenoxy)piperidin-1-yl)pyrazine (0.39 g, 1.15 mmol) obtained in Preparation Example 1 and methyl 4-(3-amino-3-oxopropyl)-2-fluorobenzoate (0.26 g, 1.15 mmol) obtained in Preparation Example 14 were used in a similar manner to Step 1 of Example 34 to obtain the desired product. (Yield: 68%)

$^1$H-NMR (500 MHz, CHLOROFORM-D): δ 8.65 (s, 1H), 7.87 (t, J=7.6 Hz, 2H), 7.24-7.15 (1H), 7.08 (d, J=7.9 Hz, 1H), 7.02 (d, J=12.2 Hz, 1H), 6.93 (t, J=7.3 Hz, 2H), 6.84 (q, J=7.9 Hz, 2H), 4.40-4.24 (m, 1H), 3.96 (dd, J=15.0, 8.3 Hz, 2H), 3.91 (s, 3H), 3.88 (d, J=2.4 Hz, 1H), 3.67 (t, J=3.1 Hz, 1H), 3.62 (t, J=6.4 Hz, 1H), 3.44 (t, J=4.6 Hz, 1H), 3.08 (t, J=7.6 Hz, 2H), 2.68 (t, J=7.3 Hz, 2H), 2.15-2.06 (m, 1H), 1.97 (t, J=3.4 Hz, 1H), 1.91 (q, J=4.1 Hz, 1H), 1.57 (q, J=4.3 Hz, 1H), 1.33 (t, J=7.0 Hz, 3H)

Step 2: (R)-4-(3-((6-(3-(2-ethoxyphenoxy)piperidin-1-yl)pyrazin-2-yl)amino)-3-oxopropyl)-2-fluorobenzoic acid The ester compound (0.41 g, 0.79 mmol) obtained in Step 1 was hydrolyzed in a similar manner to Step 2 of Example 34 to obtain the desired product. (Yield: 50%)

$^1$H-NMR (500 MHz, CHLOROFORM-D): δ 8.65 (s, 1H), 7.93 (d, J=7.3 Hz, 1H), 7.89 (s, 1H), 7.44-7.30 (1H), 7.09 (d, J=7.9 Hz, 1H), 7.03 (d, J=11.9 Hz, 1H), 6.92 (t, J=7.3 Hz, 2H), 6.84 (q, J=7.1 Hz, 2H), 4.31 (d, J=3.1 Hz, 1H), 4.05-3.82 (m, 3H), 3.71-3.57 (m, 2H), 3.55-3.37 (m, 1H), 3.09 (t, J=7.4 Hz, 2H), 2.77-2.53 (2H), 2.09 (d, J=4.3 Hz, 1H), 1.98 (s, 1H), 1.90 (d, J=8.6 Hz, 1H), 1.57 (q, J=4.3 Hz, 1H), 1.33 (t, J=7.0 Hz, 3H)

Example 45: (R)-4-(3-((6-(3-(2-ethoxyphenoxy)piperidin-1-yl)pyrazin-2-yl)amino)-3-oxopropyl)-2-methylbenzoic acid

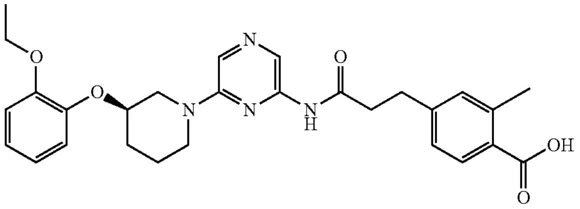 [SMILES: CCOc1ccccc1O[C@@H]1CCCN(c2cncc(NC(=O)CCc3ccc(C(=O)O)c(C)c3)n2)C1]

Step 1: Methyl (R)-4-(3-((6-(3-(2-ethoxyphenoxy)piperidin-1-yl)pyrazin-2-yl)amino)-3-oxopropyl)-2-methylbenzoate (R)-2-chloro-6-(3-(2-ethoxyphenoxy)piperidin-1-yl)pyrazine (0.35 g, 1.05 mmol) obtained in Preparation Example 1 and methyl 4-(3-amino-3-oxopropyl)-2-methylbenzoate (0.23 g, 1.05 mmol) obtained in Preparation Example 15 were used in a similar manner to Step 1 of Example 34 to obtain the desired product. (Yield: 63%)

$^1$H-NMR (500 MHz, CHLOROFORM-D): δ 8.66 (s, 1H), 7.85 (d, J=7.3 Hz, 2H), 7.23 (s, 1H), 7.10 (d, J=6.1 Hz, 2H), 7.03-6.90 (m, 2H), 6.89-6.73 (m, 2H), 4.45-4.24 (m, 1H), 4.09-3.80 (m, 6H), 3.80-3.57 (2H), 3.42 (dd, J=8.9, 3.4 Hz, 1H), 3.03 (t, J=7.9 Hz, 2H), 2.66 (t, J=7.6 Hz, 2H), 2.57 (s, 3H), 2.09 (d, J=4.9 Hz, 1H), 1.97 (td, J=6.7, 3.7 Hz, 1H), 1.91 (q, J=4.1 Hz, 1H), 1.57 (t, J=4.3 Hz, 1H), 1.44-1.29 (m, 3H)

Step 2: (R)-4-(3-((6-(3-(2-ethoxyphenoxy)piperidin-1-yl)pyrazin-2-yl)amino)-3-oxopropyl)-2-methylbenzoic acid The ester compound (0.33 g, 0.64 mmol) obtained in Step 1 was hydrolyzed in a similar manner to Step 2 of Example 34 to obtain the desired product. (Yield: 22%)

$^1$H-NMR (400 MHz, CHLOROFORM-D): δ 8.66 (s, 1H), 7.98 (d, J=8.8 Hz, 1H), 7.87 (s, 1H), 7.14 (s, 3H), 6.95-6.91 (m, 2H), 6.88-6.83 (m, 2H), 4.31 (m, 1H), 3.98-3.92 (m, 3H), 3.65 (2H), 3.45 (m, 1H), 3.06 (m, 2H), 2.68 (m, 2H), 2.61 (s, 3H), 2.09 (m, 1H), 1.97 (m, 1H), 1.91 (m, 1H), 1.57 (m, 1H), 1.35 (t, 3H)

Example 46: (R)-4-(3-((6-(3-(2-ethoxyphenoxy)piperidin-1-yl)pyrazin-2-yl)amino)-3-oxopropyl)-2-methoxybenzoic acid

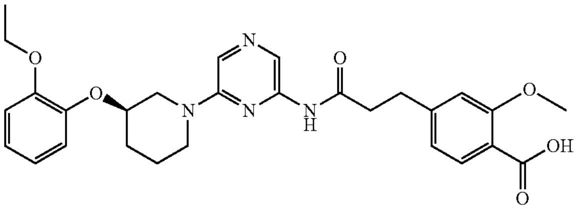 [SMILES: CCOc1ccccc1O[C@@H]1CCCN(c2cncc(NC(=O)CCc3ccc(C(=O)O)c(OC)c3)n2)C1]

(R)-2-chloro-6-(3-(2-ethoxyphenoxy)piperidin-1-yl)pyrazine (0.10 g, 0.30 mmol) obtained in Preparation Example 1 and methyl 4-(3-amino-3-oxopropyl)-2-methoxybenzoate (0.07 g, 0.30 mmol) obtained in Preparation Example 16 were used in a similar manner to Example 34 to obtain the desired product. (Yield: 38%)

$^1$H-NMR (400 MHz, CHLOROFORM-D): δ 8.65 (s, 1H), 8.09 (d, 1H), 7.88 (s, 1H), 7.38 (s, 1H), 7.02-6.83 (m, 6H), 4.31 (m, 1H), 4.05-3.89 (m, 6H), 3.63 (m, 2H), 3.44 (m, 1H), 3.12 (t, 2H), 2.73 (t, 2H), 2.08 (m, 1H), 1.94 (m, 2H), 1.58 (m, 1H), 1.35 (t, 3H)

Example 47: (R)-2-chloro-4-(3-((6-(3-(2-ethoxyphenoxy)piperidin-1-yl)pyrazin-2-yl)amino)-3-oxopropyl)benzoic acid

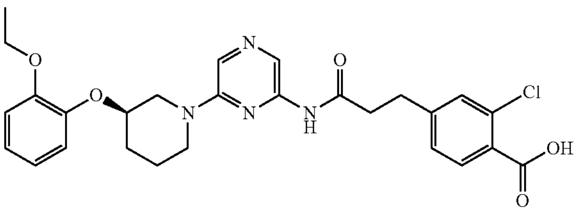 [SMILES: CCOc1ccccc1O[C@@H]1CCCN(c2cncc(NC(=O)CCc3ccc(C(=O)O)c(Cl)c3)n2)C1]

Step 1: Methyl (R)-2-chloro-4-(3-((6-(3-(2-ethoxyphenoxy)piperidin-1-yl)pyrazin-2-yl)amino)-3-oxopropyl)benzoate (R)-2-chloro-6-(3-(2-ethoxyphenoxy)piperidin-1-yl)pyrazine obtained in Preparation Example 1 and methyl 4-(3-amino)-3-oxopropyl)-2-chlorobenzoate obtained in Preparation Example 17 were used in a similar manner to Step 1 of Example 34 to obtain the desired product. (Yield: 42%)

$^1$H-NMR (400 MHz, CHLOROFORM-D) δ 8.65 (s, 1H), 7.87 (s, 1H), 7.78 (d, J=8 Hz, 1H), 7.36-7.33 (m, 2H), 7.18 (d, J=8 Hz, 1H), 7.36-7.33 (m, 2H), 7.18 (d, J=8 Hz, 1H), 6.95-6.91 (m, 2H), 6.87-6.82 (m, 2H), 4.31-4.30 (m, 1H), 3.99-3.92 (m, 3H), 3.91 (s, 3H), 3.66-3.61 (m, 2H), 3.42 (m, 1H), 3.05 (t, J=7.4 Hz, 2H), 2.67 (t, J=7.4 Hz, 2H), 2.09-2.07 (m, 1H), 1.96-1.89 (m, 2H), 1.58 (m, 1H), 1.33 (t, J=7 Hz, 3H)

Step 2: (R)-2-chloro-4-(3-((6-(3-(2-ethoxyphenoxy)piperidin-1-yl)pyrazin-2-yl)amino)-3-oxopropyl)benzoic acid The ester compound obtained in Step 1 was hydrolyzed in a similar manner to Step 2 of Example 34 to obtain the desired product. (Yield: 18%)

$^1$H-NMR (400 MHz, CHLOROFORM-D) δ 8.64 (s, 1H), 7.88 (s, 1H), 7.79 (m, 1H), 7.64 (m, 1H), 7.11 (m, 1H), 6.91-6.89 (m, 2H), 6.85-6.81 (m, 2H), 4.29 (m, 1H), 3.98-3.88 (m, 3H), 3.62 (m, 2H), 3.40 (m, 1H), 3.00 (m, 2H), 2.66 (m, 2H), 2.04 (m, 1H), 1.94 (m, 1H), 1.88 (m, 1H), 1.56 (m, 1H), 1.31 (t, J=6 Hz, 3H)

Example 48: (R)-3-(3-((6-(3-(2-ethoxyphenoxy)piperidin-1-yl)pyrazin-2-yl)amino)-3-oxopropyl)benzoic acid

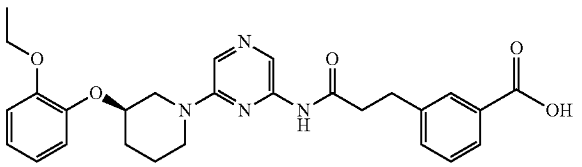 [SMILES: CCOc1ccccc1O[C@@H]1CCCN(c2cncc(NC(=O)CCc3cccc(C(=O)O)c3)n2)C1]

(R)-2-chloro-6-(3-(2-ethoxyphenoxy)piperidin-1-yl)pyrazine (0.10 g, 0.30 mmol) obtained in Preparation Example 1 and methyl 3-(3-amino-3-oxopropyl)benzoate (0.06 g, 0.30 mmol) obtained in Preparation Example 18 were used in a similar manner to Example 34 to obtain the desired product. (Yield: 35%)

$^1$H-NMR (400 MHz, CHLOROFORM-D): δ 8.69 (s, 1H), 8.01 (s, 1H), 7.98 (d, 1H), 7.90 (s, 1H), 7.60 (s, 1H), 7.49 (d, 1H), 7.45 (t, 1H), 7.02-6.80 (m, 4H), 4.32 (m, 1H), 4.02-3.85 (m, 3H), 3.67 (m, 2H), 3.46 (m, 1H), 3.14 (t, 2H), 2.74 (t, 2H), 2.12-1.92 (m, 3H), 1.60 (m, 1H), 1.37 (t, 3H)

Example 49: (R)-2-(4-(3-((6-(3-(2-ethoxyphenoxy)piperidin-1-yl)pyrazin-2-yl)amino)-3-oxopropyl)phenyl)acetic acid

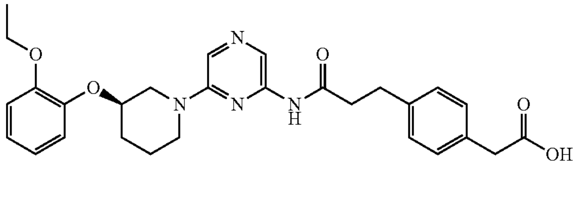 [SMILES: CCOc1ccccc1O[C@@H]1CCCN(c2cncc(NC(=O)CCc3ccc(CC(=O)O)cc3)n2)C1]

Step 1: Methyl (R)-2-(4-(3-((6-(3-(2-ethoxyphenoxy)piperidin-1-yl)pyrazin-2-yl)amino)-3-oxopropyl)phenyl)acetate (R)-2-chloro-6-(3-(2-ethoxyphenoxy)piperidin-1-yl)pyrazine (1.00 g, 3.00 mmol) obtained in Preparation Example 1 and methyl 2-(4-(3-amino-3-oxopropyl)phenyl)acetate (0.66 g, 3.00 mmol) obtained in Preparation Example 19 were used in a similar manner to Step 1 of Example 34 to obtain the desired product. (Yield: 80%)

$^1$H-NMR (500 MHz, CHLOROFORM-D): δ 8.67 (s, 1H), 7.90-7.81 (1H), 7.35 (d, J=7.3 Hz, 1H), 7.18 (td, J=8.9, 2.6 Hz, 4H), 6.96-6.88 (m, 2H), 6.86-6.75 (m, 2H), 4.37-4.24 (m, 1H), 4.00-3.86 (m, 3H), 3.69 (t, J=2.4 Hz, 1H), 3.66 (s, 3H), 3.61 (t, J=6.7 Hz, 1H), 3.58 (s, 2H), 3.40 (td, J=8.7, 3.9 Hz, 1H), 3.09-2.94 (m, 2H), 2.64 (t, J=7.6 Hz, 2H), 2.08 (q, J=4.1 Hz, 1H), 1.96 (td, J=6.7, 3.1 Hz, 1H), 1.92-1.83 (m, 1H), 1.56 (q, J=4.5 Hz, 1H), 1.32 (t, J=6.7 Hz, 3H)

Step 2: (R)-2-(4-(3-((6-(3-(2-ethoxyphenoxy)piperidin-1-yl)pyrazin-2-yl)amino)-3-oxo propyl)phenyl)acetic acid The ester compound (1.24 g, 2.39 mmol) obtained in Step 1 was hydrolyzed in a similar manner to Step 2 of Example 34 to obtain the desired product. (Yield: 57%)

$^1$H-NMR (500 MHz, CHLOROFORM-D): δ 8.64 (s, 1H), 7.94-7.77 (1H), 7.40 (s, 1H), 7.19 (dd, J=19.9, 8.3 Hz, 4H), 6.95-6.88 (m, 2H), 6.87-6.73 (2H), 4.35-4.26 (m, 1H), 4.04-3.84 (m, 3H), 3.69-3.60 (m, 2H), 3.59 (s, 2H), 3.41 (t, J=4.6 Hz, 1H), 3.00 (t, J=7.3 Hz, 2H), 2.63 (t, J=7.6 Hz, 2H), 2.07 (q, J=4.1 Hz, 1H), 1.96 (q, J=3.3 Hz, 1H), 1.89 (q, J=4.1 Hz, 1H), 1.55 (q, J=4.3 Hz, 1H), 1.31 (t, J=6.7 Hz, 3H)

Example 50: (R)-3-(4-(2-amino-2-oxoethyl)phenyl-N-(6-(3-(2-ethoxyphenoxy)piperidin-1-yl)pyrazin-2-yl)propanamide

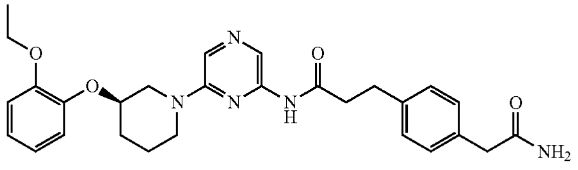 [SMILES: CCOc1ccccc1O[C@@H]1CCCN(c2cncc(NC(=O)CCc3ccc(CC(N)=O)cc3)n2)C1]

(R)-2-(4-(3-((6-(3-(2-ethoxyphenoxy)piperidin-1-yl)pyrazin-2-yl)amino)-3-oxopropyl)phenyl)acetic acid (0.21 g, 0.42 mmol) obtained in Example 49 was used in a similar manner to Example 35 to obtain the desired product. (Yield: 62%)

$^1$H-NMR (500 MHz, CHLOROFORM-D): δ 8.66 (s, 1H), 7.86 (s, 1H), 7.21 (q, J=7.5 Hz, 5H), 6.98-6.90 (m, 2H), 6.89-6.80 (m, 2H), 5.38 (s, 2H), 4.35-4.25 (m, 1H), 4.02-3.87 (m, 3H), 3.68 (qd, J=6.5, 4.0 Hz, 1H), 3.61 (q, J=6.9 Hz, 1H), 3.54 (s, 2H), 3.46-3.37 (1H), 3.03 (t, J=7.6 Hz, 2H), 2.66 (t, J=7.6 Hz, 2H), 2.15-2.05 (m, 1H), 2.04-1.94 (m, 1H), 1.94-1.83 (m, 1H), 1.57 (q, J=4.5 Hz, 1H), 1.34 (t, J=7.0 Hz, 3H)

Example 51: (R)-2-(4-(3-((6-(3-(2-ethoxyphenoxy)piperidin-1-yl)pyrazin-2-yl)amino)-3-oxopropyl)phenyl)-2-methylpropanoic acid

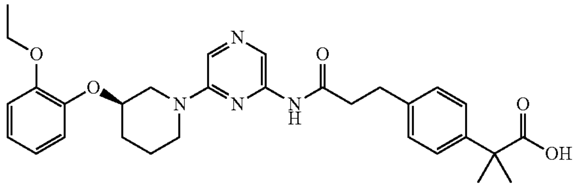 [SMILES: CCOc1ccccc1O[C@@H]1CCCN(c2cncc(NC(=O)CCc3ccc(C(C)(C)C(=O)O)cc3)n2)C1]

Step 1: Methyl (R)-2-(4-(3-((6-(3-(2-ethoxyphenoxy)piperidin-1-yl)pyrazin-2-yl)amino)-3-oxopropyl)phenyl)-2-methylpropanoate (R)-2-chloro-6-(3-(2-ethoxyphenoxy)piperidin-1-yl)pyrazine (0.48 g, 1.44 mmol) prepared in Preparation Example 1 and methyl 2-(4-(3-amino-3-oxopropyl)phenyl)-2-methylpropanoate 0.36 g, 1.44 mmol) obtained in Preparation Example 20 were used in a similar manner to Step 1 of Example 34 to obtain the desired product. (Yield: 91%)

$^1$H-NMR (500 MHz, CHLOROFORM-D): δ 8.68 (s, 1H), 7.86 (s, 1H), 7.27 (d, J=7.9 Hz, 2H), 7.20 (d, J=8.6 Hz, 2H), 7.16 (s, 1H), 6.93 (qd, J=7.3, 1.5 Hz, 2H), 6.85 (td, J=7.6, 1.4 Hz, 1H), 6.80 (d, J=7.9 Hz, 1H), 4.45-4.24 (m, 1H), 4.06-3.80 (m, 3H), 3.78-3.65 (m, 2H), 3.64-3.57 (3H), 3.45 (q, J=3.9 Hz, 1H), 3.15-2.93 (2H), 2.65 (t, J=7.6 Hz, 2H), 2.21-2.07 (1H), 1.99 (td, J=6.7, 3.1 Hz, 1H), 1.92 (q, J=4.1 Hz, 1H), 1.59 (t, J=4.0 Hz, 1H), 1.55 (s, 6H), 1.33 (t, J=7.0 Hz, 3H)

Step 2: (R)-2-(4-(3-((6-(3-(2-ethoxyphenoxy)piperidin-1-yl)pyrazin-2-yl)amino)-3-oxopropyl)phenyl)-2-methylpropanoic acid The ester compound (0.72 g, 1.32 mmol) obtained in Step 1 was hydrolyzed in a similar manner to Step 2 of Example 34 to obtain the desired product. (Yield: 14%)

$^1$H-NMR (500 MHz, CHLOROFORM-D): δ 8.66 (s, 1H), 7.86 (s, 1H), 7.33 (d, J=8.6 Hz, 2H), 7.19 (d, J=7.9 Hz, 3H), 6.98-6.89 (m, 2H), 6.88-6.76 (m, 2H), 4.29 (q, J=3.7 Hz, 1H), 4.08-3.81 (m, 3H), 3.65 (d, J=2.4 Hz, 1H), 3.60 (q, J=6.7 Hz, 1H), 3.40 (s, 1H), 3.01 (t, J=7.3 Hz, 2H), 2.65 (t, J=4.0 Hz, 2H), 2.08 (q, J=4.1 Hz, 1H), 1.96 (q, J=3.5 Hz, 1H), 1.89 (q, J=4.3 Hz, 1H), 1.57 (s, 7H), 1.32 (t, J=7.0 Hz, 3H)

Example 52: (R)-1-(4-(3-((6-(3-(2-ethoxyphenoxy)piperidin-1-yl)pyrazin-2-yl)amino)-3-oxopropyl)phenyl)cyclopropane-1-carboxylic acid

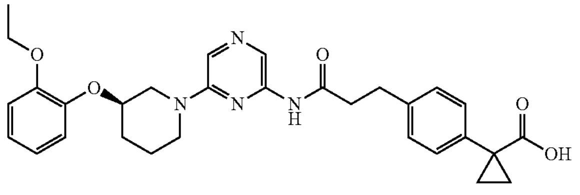 [SMILES: CCOc1ccccc1O[C@@H]1CCCN(c2cncc(NC(=O)CCc3ccc(C4(C(=O)O)CC4)cc3)n2)C1]

Step 1: Methyl (R)-1-(4-(3-((6-(3-(2-ethoxyphenoxy)piperidin-1-yl)pyrazin-2-yl)amino)-3-oxopropyl)phenyl)cyclopropane-1-carboxylate (R)-2-chloro-6-(3-(2-ethoxyphenoxy)piperidin-1-yl)pyrazine (0.48 g, 1.44 mmol) obtained in Preparation Example 1 and methyl 1-(4-(3-amino-3-oxopropyl)phenyl)cyclopropane-1-carboxylate (0.36 g, 1.44 mmol) obtained in Preparation Example 21 were used in a similar manner to Step 1 of Example 34 to obtain the desired product. (Yield: 76%)

$^1$H-NMR (500 MHz, CHLOROFORM-D): δ 8.68 (s, 1H), 7.86 (s, 1H), 7.35-7.24 (m, 2H), 7.21-7.10 (m, 3H), 6.98-6.89 (m, 2H), 6.86 (dd, J=7.6, 1.5 Hz, 1H), 6.81 (dd, J=7.6, 1.5 Hz, 1H), 4.37-4.26 (m, 1H), 4.06-3.83 (m, 3H), 3.72-3.62 (m, 2H), 3.60 (s, 3H), 3.48-3.38 (m, 1H), 3.03 (td, J=7.6, 3.3 Hz, 2H), 2.66 (t, J=7.3 Hz, 2H), 2.15-2.06 (m, 1H), 2.02-1.95 (m, 1H), 1.92 (q, J=4.1 Hz, 1H), 1.60-1.51 (m, 3H), 1.33 (t, J=7.0 Hz, 3H), 1.15 (q, J=3.5 Hz, 2H)

Step 2: (R)-1-(4-(3-((6-(3-(2-ethoxyphenoxy)piperidin-1-yl)pyrazin-2-yl)amino)-3-oxopropyl)phenyl)cyclopropane-1-carboxylic acid The ester compound (0.6 g, 1.10 mmol) obtained in Step 1 was hydrolyzed in a similar manner to Step 2 of Example 34 to obtain the desired product. (Yield: 34%)

$^1$H-NMR (500 MHz, CHLOROFORM-D): δ 8.66 (s, 1H), 7.86 (s, 1H), 7.36-7.27 (3H), 7.17 (d, J=7.9 Hz, 2H), 6.92 (t, J=7.0 Hz, 2H), 6.84 (q, J=7.9 Hz, 2H), 4.30 (q, J=3.5 Hz, 1H), 4.07-3.82 (m, 3H), 3.76-3.55 (m, 2H), 3.42 (t, J=4.6 Hz, 1H), 3.01 (t, J=7.6 Hz, 2H), 2.64 (t, J=7.6 Hz, 2H), 2.08 (q, J=4.1 Hz, 1H), 2.04-1.94 (m, 1H), 1.90 (q, J=4.1 Hz, 1H), 1.63 (q, J=3.3 Hz, 2H), 1.56 (q, J=4.3 Hz, 1H), 1.33 (t, J=7.0 Hz, 3H), 1.21 (q, J=3.3 Hz, 2H)

Example 53: (R)-4-(3-((6-(3-(2-ethoxyphenoxy)piperidin-1-yl)pyrazin-2-yl)amino)-3-oxopropyl)-2,6-difluorobenzoic acid

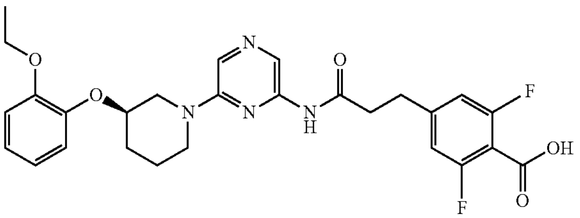 [SMILES: CCOc1ccccc1O[C@@H]1CCCN(c2cncc(NC(=O)CCc3cc(F)c(C(=O)O)c(F)c3)n2)C1]

(R)-2-chloro-6-(3-(2-ethoxyphenoxy)piperidin-1-yl)pyrazine (0.10 g, 0.30 mmol) obtained in Preparation Example 1 and methyl 4-(3-amino-3-oxopropyl)phenyl)-2,6-difluorobenzoate (0.07 g, 0.30 mmol) obtained in Preparation Example 22 were used in a similar manner to Example 34 to obtain the desired product. (Yield: 34%)

$^1$H-NMR (400 MHz, CHLOROFORM-D): δ 8.61 (s, 1H), 7.90 (s, 1H), 7.44 (s, 1H), 7.05-6.80 (m, 6H), 4.33 (m, 1H), 4.06-3.85 (m, 3H), 3.68 (m, 2H), 3.47 (m, 1H), 3.04 (t, 2H), 2.67 (t, 2H), 2.15-1.84 (m, 3H), 1.60 (m, 1H), 1.34 (t, 3H)

Example 54: (R)-2,6-dichloro-4-(3-((6-(3-(2-ethoxyphenoxy)piperidin-1-yl)pyrazin-2-yl)amino)-3-oxopropyl)benzoic acid

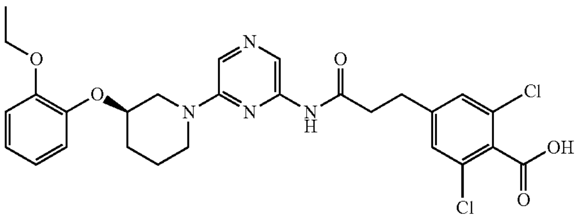 [SMILES: CCOc1ccccc1O[C@@H]1CCCN(c2cncc(NC(=O)CCc3cc(Cl)c(C(=O)O)c(Cl)c3)n2)C1]

Step 1: 2-(Trimethylsilyl)ethyl (R)-2,6-dichloro-4-(3-((6-(3-(2-ethoxyphenoxy)piperidin-1-yl)pyrazine-2-yl)amino)-3-oxopropyl)benzoate (R)-2-chloro-6-(3-(2-ethoxyphenoxy)piperidin-1-yl) pyrazine obtained in Preparation Example 1 and 2-(trimethylsilyl)ethyl 4-(3-amino-3-oxopropyl)2,6-dichlorobenzoate obtained in Preparation Example 23 were used in a similar manner to Example 8 to obtain the desired product. (Yield: 76%)

$^1$H NMR (300 MHz, CHLOROFORM-D): δ 8.65 (s, 1H), 7.89 (s, 1H), 7.32 (s, 1H), 7.22 (s, 2H), 6.97-6.84 (m, 4H), 4.50-4.44 (m, 2H), 4.41-4.33 (m, 1H), 3.98-3.89 (m, 1H), 3.98-3.89 (m, 2H), 3.73-3.66 (m, 2H), 3.51-3.38 (m, 1H), 3.04-2.66 (m, 4H), 2.13-2.06 (m, 4H), 1.34 (t, J=7.2 Hz, 3H), 1.19-1.13 (m, 2H), 0.09 (s, 9H)

Step 2: (R)-2,6-dichloro-4-(3-((6-(3-(2-ethoxyphenoxy)piperidin-1-yl)pyrazin-2-yl)amino)-3-oxopropyl)benzoic acid The ester compound obtained in Step 1 was dissolved in 1 mL of THF in the presence of nitrogen, and 1.0 M tetrabutylammonium fluoride (0.063 mL, 0.063 mmol) was added at 0° C., followed by stirring at room temperature for 12 hours. After confirming that the starting materials disappeared by TLC, THF was concentrated under reduced pressure, adjusted to pH 2 with 1 N hydrochloric acid solution together with 3 mL of water. The resulting solid was filtered to obtain the title compound.

$^1$H NMR (300 MHz, CHLOROFORM-D): δ 8.58 (s, 1H), 7.88 (s, 1H), 7.47 (s, 1H), 7.18 (s, 2H), 6.96-6.86 (m, 4H), 4.41-4.35 (m, 1H), 4.00-3.88 (m, 1H), 4.00-3.88 (m, 2H), 3.73-3.69 (m, 2H), 3.67-3.54 (m, 1H), 3.01-2.66 (m, 4H), 2.14-1.42 (m, 4H), 1.00 (t, J=7.2 Hz, 3H)

Example 55: (R)-4-(3-((6-(3-(2-ethoxyphenoxy)piperidin-1-yl)pyrazin-2-yl)amino)-3-oxopropyl)-2,6-dimethylbenzoic acid

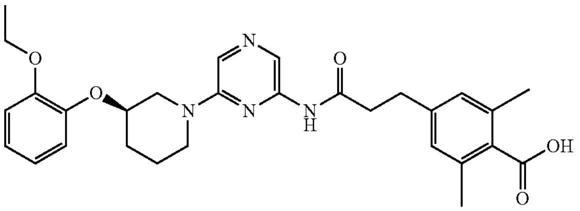 [SMILES: CCOc1ccccc1O[C@@H]1CCCN(c2cncc(NC(=O)CCc3cc(C)c(C(=O)O)c(C)c3)n2)C1]

Step 1: 2-(Trimethylsilyl)ethyl (R)-4-(3-((6-(3-(2-ethoxyphenoxy)piperidin-1-yl)pyrazin-2-yl)amino)-3-oxopropyl)-2,6-dimethylbenzoate (R)-2-chloro-6-(3-(2-ethoxyphenoxy)piperidin-1-yl) pyrazine (0.35 g, 1.05 mmol) obtained in Preparation Example 1 and 2-(trimethylsilyl)ethyl 4-(3-amino-3-oxopropyl)-2,6-dimethylbenzoate (0.34 g, 1.05 mmol) obtained in Preparation Example 24 were used in a similar manner to Example 8 to obtain the desired product. (Yield: 45%)

$^1$H NMR (400 MHz, CHLOROFORM-D): δ 8.67 (s, 1H), 7.87 (s, 1H), 7.13 (s, 1H), 6.81-6.96 (m, 6H), 4.37-4.41 (m, 2H), 4.31 (m, 1H), 3.94 (m, 2H), 3.66-3.75 (m, 2H), 3.45 (m, 1H), 2.99 (m, 2H), 2.63 (m, 2H), 2.30 (s, 6H), 2.15 (m, 1H), 2.02 (m, 1H), 1.85 (m, 1H), 1.34 (t, 3H), 1.12 (m, 2H)

Step 2: (R)-4-(3-((6-(3-(2-ethoxyphenoxy)piperidin-1-yl)pyrazin-2-yl)amino)-3-oxopropyl)-2,6-dimethylbenzoic acid The ester compound obtained in Step 1 (0.29 g, 0.47 mmol) was used in a similar manner to Step 2 of Example 54 to obtain the desired product. (Yield: 48%).

$^1$H NMR (400 MHz, CHLOROFORM-D): δ 8.63 (s, 1H), 7.86 (s, 1H), 7.19 (s, 1H), 6.82-6.95 (m, 6H), 4.31 (m, 1H), 3.91-3.78 (m, 3H), 3.65 (m, 2H), 3.43 (m, 1H), 2.97 (m, 2H), 2.64 (m, 2H), 2.38 (s, 6H), 2.08 (m, 1H), 1.92 (m, 1H), 1.89 (m, 1H), 1.59 (m, 1H), 1.34 (t, 3H)

Example 56: (R)-1-(4-(3-((6-(3-(2-ethoxyphenoxy)piperidin-1-yl)pyrazin-2-yl)amino)-3-oxopropyl)phenyl)piperidine-4-carboxylic acid

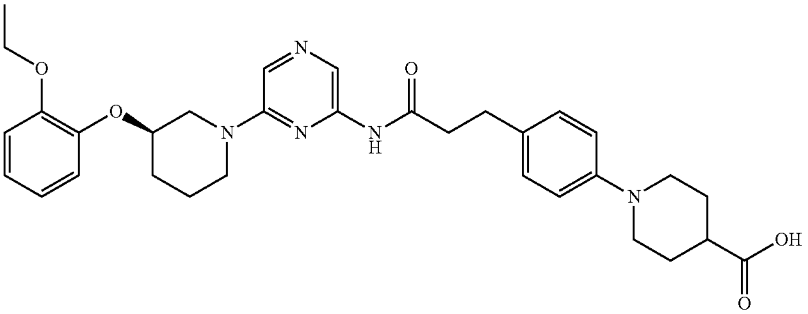 [SMILES: CCOc1ccccc1O[C@@H]1CCCN(c2cncc(NC(=O)CCc3ccc(N4CCC(C(=O)O)CC4)cc3)n2)C1]

(R)-2-chloro-6-(3-(2-ethoxyphenoxy)piperidin-1-yl) pyrazine (0.10 g, 0.30 mmol) obtained in Preparation Example 1 and ethyl 1-(4-(3-amino-3-oxopropyl)phenyl) piperidine-4-carboxylate (0.09 g, 0.30 mmol) obtained in Preparation Example 25 were used in a similar manner to Example 34 to obtain the desired product. (Yield: 44%)

$^1$H-NMR (400 MHz, CHLOROFORM-D): δ 8.67 (s, 1H), 7.87 (s, 1H), 7.14 (s, 1H), 7.14 (d, 2H), 6.95-6.82 (m, 6H), 4.31 (m, 1H), 4.15-3.89 (m, 3H), 3.70-3.58 (m, 4H), 3.46 (m, 1H), 2.98 (t, 2H), 2.76 (t, 2H), 2.65 (t, 2H), 2.47 (m, 1H), 2.17-1.91 (m, 7H), 1.59 (m, 1H), 1.36 (t, 3H)

Example 57: (R)-1-(4-((6-(3-(2-ethoxyphenoxy) piperidin-1-yl)pyrazin-2-yl)carbamoyl-2,6-difluoro-phenyl)piperidine-4-carboxylic acid

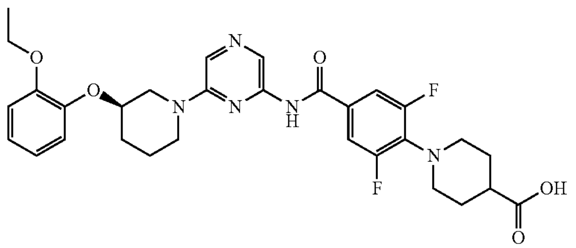 [SMILES: CCOc1ccccc1O[C@@H]1CCCN(c2cncc(NC(=O)c3cc(F)c(N4CCC(C(=O)O)CC4)c(F)c3)n2)C1]

(R)-2-chloro-6-(3-(2-ethoxyphenoxy)piperidin-1-yl) pyrazine (0.10 g, 0.30 mmol) obtained in Preparation Example 1 and ethyl 1-(4-carbamoyl-2,6-difluorophenyl) piperidine-4-carboxylate (0.09 g, 0.30 mmol) obtained in Preparation Example 26 were used in a similar manner to Example 34 to obtain the desired product. (Yield: 38%)

$^1$H-NMR (400 MHz, CHLOROFORM-D): δ 8.77 (s, 1H), 7.94 (s, 1H), 7.80 (s, 1H), 7.39 (d, 2H), 6.98-6.84 (m, 4H), 4.36 (m, 1H), 4.04-3.91 (m, 3H), 3.80-3.68 (m, 2H), 3.53 (m, 1H), 3.49 (m, 2H), 3.21 (t, 2H), 2.57 (m, 1H), 2.11-1.88 (m, 7H), 1.63 (m, 1H), 1.36 (t, 3H)

Example 58: (R)-2-(1-(4-((6-(3-(2-ethoxyphenoxy) piperidin-1-yl)pyrazin-2-yl)carbamoyl-2,6-difluoro-phenyl)piperidin-4-yl)acetic acid

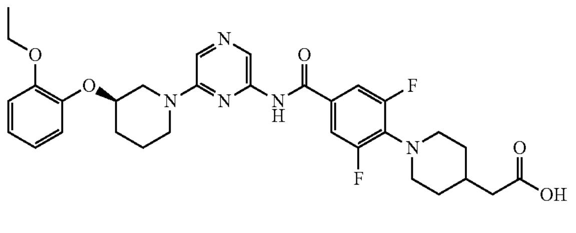 [SMILES: CCOc1ccccc1O[C@@H]1CCCN(c2cncc(NC(=O)c3cc(F)c(N4CCC(CC(=O)O)CC4)c(F)c3)n2)C1]

(R)-2-chloro-6-(3-(2-ethoxyphenoxy)piperidin-1-yl) pyrazine (0.10 g, 0.30 mmol) obtained in Preparation Example 1 and ethyl 2-(1-(4-carbamoyl-2,6-difluorophenyl) piperidin-4-yl)acetate (0.10 g, 0.30 mmol) obtained in Preparation Example 27 were used in a similar manner to Example 34 to obtain the desired product. (Yield: 36%)

$^1$H-NMR (400 MHz, CHLOROFORM-D): δ 8.77 (s, 1H), 7.93 (s, 1H), 7.81 (s, 1H), 7.40 (d, 2H), 6.98-6.83 (m, 4H), 4.36 (m, 1H), 4.04-3.90 (m, 3H), 3.78-3.68 (m, 2H), 3.52 (m, 1H), 3.49 (m, 2H), 3.17 (t, 2H), 2.36 (m, 2H), 2.21 (m, 1H), 1.99 (m, 3H), 1.85 (m, 2H), 1.62 (m, 1H), 1.45 (m, 2H), 1.36 (t, 3H)

Example 59: (R)-4-(4-((6-(3-(2-ethoxyphenoxy) piperidin-1-yl)pyrazin-2-yl)carbamoyl)piperidin-1-yl)benzoic acid

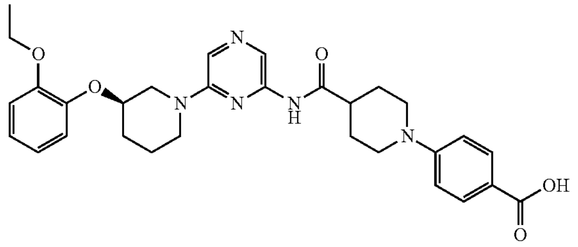 [SMILES: CCOc1ccccc1O[C@@H]1CCCN(c2cncc(NC(=O)C3CCN(c4ccc(C(=O)O)cc4)CC3)n2)C1]

(R)-2-chloro-6-(3-(2-ethoxyphenoxy)piperidin-1-yl) pyrazine (0.10 g, 0.30 mmol) obtained in Preparation Example 1 and ethyl 4-(4-carbamoylpiperidin-1-yl)benzoate (0.08 g, 0.30 mmol) obtained in Preparation Example 34 were used in a similar manner to Example 34 to obtain the desired product. (Yield: 34%)

$^1$H-NMR (400 MHz, CHLOROFORM-D): δ 8.69 (s, 1H), 7.98-7.90 (m, 3H), 7.54 (s, 1H), 7.02-6.86 (m, 6H), 4.32 (m, 1H), 4.13-3.87 (m, 5H), 3.69 (m, 1H), 3.63 (m, 1H), 3.43 (m, 1H), 2.94 (m, 2H), 2.50 (m, 1H), 2.09-1.92 (m, 7H), 1.60 (m, 1H), 1.39 (t, 3H)

Example 60: (R)-2-(4-(3-((6-(3-(2-ethoxyphenoxy) piperidin-1-yl)pyrazin-2-yl)amino)-3-oxopropyl) phenoxy)-2-methylpropanoic acid

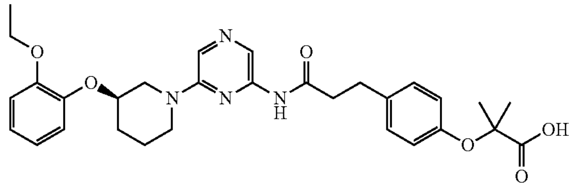 [SMILES: CCOc1ccccc1O[C@@H]1CCCN(c2cncc(NC(=O)CCc3ccc(OC(C)(C)C(=O)O)cc3)n2)C1]

(R)-2-chloro-6-(3-(2-ethoxyphenoxy)piperidin-1-yl) pyrazine (0.10 g, 0.30 mmol) obtained in Preparation Example 1 and ethyl 2-(4-(3-amino-3-oxopropyl)phenoxy)-2-methylpropanoate (0.08 g, 0.30 mmol) obtained in Preparation Example 28 were used in a similar manner to Example 34 to obtain the desired product. (Yield: 32%)

$^1$H-NMR (400 MHz, CHLOROFORM-D): δ 8.62 (s, 1H), 7.85 (s, 1H), 7.36 (s, 1H), 7.09 (d, 2H), 6.95-6.80 (m, 6H), 4.30 (m, 1H), 4.00-3.87 (m, 3H), 3.63 (m, 2H), 3.42 (m, 1H), 2.98 (t, 2H), 2.2.64 (t, 2H), 2.08 (m, 1H), 1.96 (m, 1H), 1.90 (m, 1H), 1.56 (m, 7H), 1.33 (t, 3H)

Example 61: (R)-3-(4-(3-((6-(3-(2-ethoxyphenoxy) piperidin-1-yl)pyrazin-2-yl)amino)-3-oxopropyl) phenyl)propanoic acid

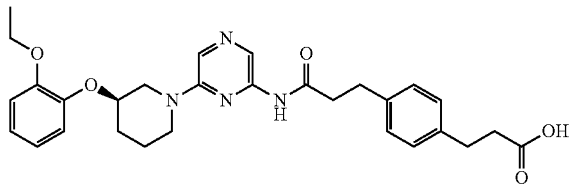 [SMILES: CCOc1ccccc1O[C@@H]1CCCN(c2cncc(NC(=O)CCc3ccc(CCC(=O)O)cc3)n2)C1]

(R)-2-chloro-6-(3-(2-ethoxyphenoxy)piperidin-1-yl)pyrazine (0.10 g, 0.30 mmol) obtained in Preparation Example 1 and ethyl 3-(4-(3-amino-3-oxopropyl)phenyl)propanoate (0.08 g, 0.30 mmol) obtained in Preparation Example 29 were used in a similar manner to Example 34 to obtain the desired product. (Yield: 34%)

$^1$H-NMR (400 MHz, CHLOROFORM-D): δ 8.65 (s, 1H), 7.85 (s, 1H), 7.43 (s, 1H), 7.15 (m, 4H), 6.93 (m, 2H), 6.82 (m, 2H), 4.30 (m, 1H), 3.94 (m, 3H), 3.64 (m, 2H), 3.43 (m, 1H), 2.99 (t, 2H), 2.92 (t, 2H), 2.64 (m, 4H), 2.08 (m, 1H), 1.96 (m, 1H), 1.90 (m, 1H), 1.57 (m, 1H), 1.33 (t, 3H)

Example 62: (R)-4-(4-((6-(3-(2-ethoxyphenoxy)piperidin-1-yl)pyrazin-2-yl)carbamoyl)phenoxy)benzoic acid

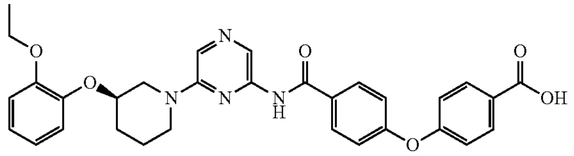 [SMILES: CCOc1ccccc1O[C@@H]1CCCN(c2cncc(NC(=O)c3ccc(Oc4ccc(C(=O)O)cc4)cc3)n2)C1]

(R)-2-chloro-6-(3-(2-ethoxyphenoxy)piperidin-1-yl)pyrazine (0.10 g, 0.30 mmol) obtained in Preparation Example 1 and ethyl 4-(4-carbamoylphenoxy)benzoate (0.09 g, 0.30 mmol) obtained in Preparation Example 30 were used in a similar manner to Example 34 to obtain the desired product. (Yield: 40%)

$^1$H-NMR (400 MHz, CHLOROFORM-D): δ 8.84 (s, 1H), 8.14 (d, 2H), 7.93 (m, 4H), 7.16 (d, 2H), 7.10 (d, 2H), 6.97 (m, 1H), 6.88 (m, 3H), 4.36 (m, 1H), 4.00 (m, 3H), 3.73 (m, 2H), 3.52 (m, 1H), 2.12 (m, 1H), 2.04 (m, 1H), 1.95 (m, 1H), 1.62 (m, 1H), 1.45 (t, 3H)

Example 63: (R)-3-(4-(3-((6-(R)-3-(2-ethoxyphenoxy)piperidin-1-yl)pyrazin-2-yl)amino)-2-oxoethyl)phenyl)-2-methylpropanoic acid

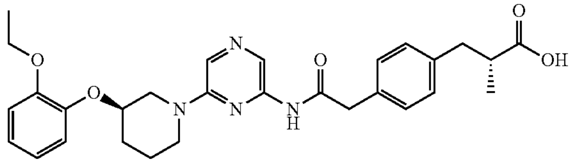 [SMILES: CCOc1ccccc1O[C@@H]1CCCN(c2cncc(NC(=O)Cc3ccc(C[C@@H](C)C(=O)O)cc3)n2)C1]

(R)-2-chloro-6-(3-(2-ethoxyphenoxy)piperidin-1-yl)pyrazine (0.10 g, 0.30 mmol) obtained in Preparation Example 1 and methyl (R)-3-(4-(2-amino-2-oxoethyl)phenyl)-2-methylpropenoate (0.07 g, 0.30 mmol) obtained in Preparation Example 31 were used in a similar manner to Example 34 to obtain the desired product. (Yield: 56%)

$^1$H-NMR (400 MHz, CHLOROFORM-D): δ 8.64 (s, 1H), 7.83 (s, 1H), 7.49 (s, 1H), 7.21 (m, 4H), 6.89 (m, 2H), 6.83 (m, 2H), 4.25 (m, 1H), 3.95 (m, 3H), 3.66 (m, 3H), 3.50 (m, 1H), 3.33 (m, 1H), 3.02 (m, 1H), 2.74 (m, 2H), 2.04 (m, 1H), 1.92 (m, 1H), 1.85 (m, 1H), 1.54 (m, 1H), 1.32 (t, 3H), 1.17 (d, 3H)

Example 64: (S)-3-(4-(3-((6-(R)-3-(2-ethoxyphenoxy)piperidin-1-yl)pyrazin-2-yl)amino)-2-oxoethyl)phenyl)-2-methylpropanoic acid

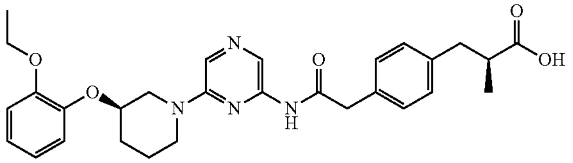 [SMILES: CCOc1ccccc1O[C@@H]1CCCN(c2cncc(NC(=O)Cc3ccc(C[C@H](C)C(=O)O)cc3)n2)C1]

(R)-2-chloro-6-(3-(2-ethoxyphenoxy)piperidin-1-yl)pyrazine (0.10 g, 0.30 mmol) obtained in Preparation Example 1 and methyl (S)-3-(4-(2-amino-2-oxoethyl)phenyl)-2-methylpropenoate (0.07 g, 0.30 mmol) obtained in Preparation Example 32 were used in a similar manner to Example 34 to obtain the desired product. (Yield: 48%)

$^1$H-NMR (400 MHz, CHLOROFORM-D): δ 8.64 (s, 1H), 7.83 (s, 1H), 7.52 (s, 1H), 7.22 (m, 4H), 6.89 (m, 2H), 6.83 (m, 2H), 4.25 (m, 1H), 3.94 (m, 3H), 3.66 (m, 3H), 3.53 (m, 1H), 3.35 (m, 1H), 3.04 (m, 1H), 2.73 (m, 2H), 2.06 (m, 1H), 1.92 (m, 1H), 1.86 (m, 1H), 1.53 (m, 1H), 1.32 (t, 3H), 1.16 (d, 3H)

Example 65: (R)-3-(4-(2-((6-(3-(2-ethoxyphenoxy)piperidin-1-yl)pyrazin-2-yl)amino)-2-oxoethyl)phenyl)-2,2-dimethylpropanoic acid

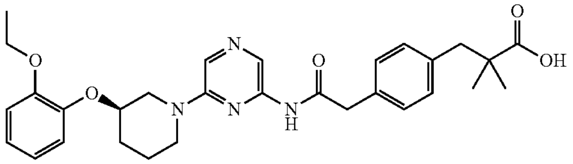 [SMILES: CCOc1ccccc1O[C@@H]1CCCN(c2cncc(NC(=O)Cc3ccc(CC(C)(C)C(=O)O)cc3)n2)C1]

(R)-2-chloro-6-(3-(2-ethoxyphenoxy)piperidin-1-yl)pyrazine (0.10 g, 0.30 mmol) obtained in Preparation Example 1 and methyl 3-(4-(2-amino-2-oxoethyl)phenyl)-2,2-dimethylpropanoate (0.08 g, 0.30 mmol) obtained in Preparation Example 33 were used in a similar manner to Example 34 to obtain the desired product. (Yield: 47%)

$^1$H-NMR (400 MHz, CHLOROFORM-D): δ 8.62 (s, 1H), 7.85 (s, 1H), 7.36 (s, 1H), 7.09 (d, 2H), 6.91 (m, 2H), 6.85 (m, 4H), 4.30 (m, 1H), 3.92 (m, 3H), 3.63 (m, 2H), 3.42 (m, 1H), 2.98 (t, 2H), 2.64 (t, 2H), 2.08 (m, 1H), 1.96 (m, 1H), 1.90 (m, 1H), 1.56 (m, 7H), 1.33 (t, 3H)

Example 66: (R)-2-(4-(2-((6-(3-(2-ethoxyphenoxy)piperidin-1-yl)pyridin-2-yl)amino)-2-oxoethyl)phenyl)acetic acid

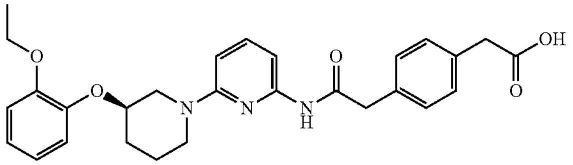 [SMILES: CCOc1ccccc1O[C@@H]1CCCN(c2cccc(NC(=O)Cc3ccc(CC(=O)O)cc3)n2)C1]

Step 1: Methyl (R)-2-(4-(2-((6-(3-(2-ethoxyphenoxy)piperidin-1-yl)pyridin-2-yl)amino)-2-oxoethyl)phenyl)acetate (R)-2-chloro-6-(3-(2-ethoxyphenoxy)piperidin-1-yl)pyridine obtained in Preparation Example 71 and methyl 2-(4-(2-amino-2-oxoethyl)phenyl)acetate obtained in Preparation Example 6 were used in a similar manner to Example 8 to obtain the desired product. (Yield: 74.2%)

$^1$H-NMR (400 MHz, CHLOROFORM-D) δ 7.78 (d, J=27.0 Hz, 1H), 7.52-7.36 (m, 2H), 7.30-7.19 (4H), 6.99-6.90 (m, 2H), 6.89-6.78 (m, 2H), 6.40-6.28 (m, 1H), 4.28-4.18 (m, 1H), 4.18-4.07 (1H), 4.05-3.91 (m, 2H), 3.86-3.74 (m, 1H), 3.65 (d, J=8.2 Hz, 3H), 3.64-3.60 (m, 2H), 3.59 (s, 2H), 3.31-3.19 (1H), 3.15-3.02 (m, 1H), 2.20-2.05 (m, 1H), 1.86 (qd, J=8.6, 4.5 Hz, 1H), 1.81-1.69 (m, 1H), 1.60-1.46 (m, 1H), 1.41-1.31 (m, 3H)

Step 2: (R)-2-(4-(2-((6-(3-(2-ethoxyphenoxy)piperidin-1-yl)pyridin-2-yl)amino)-2-oxo ethyl)phenyl)acetic acid The desired product was obtained through hydrolysis of the ester compound obtained in Step 1 using 5 N aqueous sodium hydroxide solution. (Yield: 61.7%)

$^1$H-NMR (400 MHz, CHLOROFORM-D) δ 7.64 (s, 1H), 7.47-7.37 (m, 2H), 7.27 (s, 4H), 7.00-6.91 (m, 2H), 6.91-6.78 (m, 2H), 6.34 (t, J=4.6 Hz, 1H), 4.30-4.12 (m, 2H), 4.08-3.95 (m, 2H), 3.83-3.72 (1H), 3.66 (s, 2H), 3.63-3.56 (2H), 3.15 (dd, J=12.8, 8.2 Hz, 1H), 3.10-2.97 (m, 1H), 2.22-2.08 (m, 1H), 1.86 (q, J=4.4 Hz, 1H), 1.79-1.65 (m, 1H), 1.61-1.48 (m, 1H), 1.42-1.31 (m, 3H)

Example 67: (R)-2-(4-(3-(6-(3-(2-ethoxyphenoxy)piperidin-1-yl)pyrazin-2-yl)ureido)phenyl)acetic acid

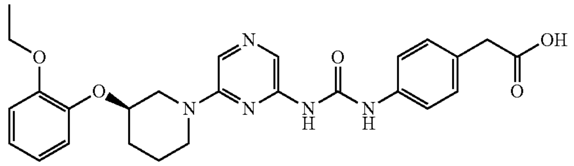 [SMILES: CCOc1ccccc1O[C@@H]1CCCN(c2cncc(NC(=O)Nc3ccc(CC(=O)O)cc3)n2)C1]

Step 1: Methyl (R)-2-(4-(3-(6-(3-(2-ethoxyphenoxy)piperidin-1-yl)pyrazin-2-yl)ureido)phenyl)acetate Methyl 2-(4-aminophenyl)acetate (0.2 g, 1.211 mmol) was dissolved in DCM (18 mL), and triphosgene (0.119 g, 0.400 mmol) and TEA (0.338 ml, 2.421 mmol) were added at 0° C. After stirring for 3 hours, the solvent was removed under reduced pressure. The obtained compound and (R)-6-(3-(2-ethoxyphenoxy)piperidin-1-yl)pyrazin-2-amine (190 mg, 0.606 mmol) obtained in Preparation Example 2 were mixed with THF (20 mL), and DIPEA (0.317 mL, 1.817 mmol) was added thereto. The reaction was terminated by addition of water and extracted with ethyl acetate. The organic solvent was dried over magnesium sulfate and removed under reduced pressure. The purification was carried out by silica gel column to obtain the desired product. (Yield: 29.2%).

$^1$H-NMR (400 MHz, CHLOROFORM-D) δ 10.86 (s, 1H), 9.15-9.09 (1H), 7.74 (d, J=12.3 Hz, 1H), 7.61 (s, 1H), 7.51-7.41 (m, 2H), 7.15 (t, J=9.1 Hz, 2H), 7.03-6.72 (m, 4H), 4.44-4.36 (m, 1H), 4.06-3.85 (m, 3H), 3.73 (q, J=6.7 Hz, 1H), 3.68 (s, 3H), 3.67-3.63 (m, 1H), 3.56 (s, 2H), 3.54 (s, 1H), 2.16-2.01 (m, 2H), 2.01-1.86 (m, 1H), 1.74-1.60 (m, 1H), 1.31 (q, J=7.3 Hz, 3H)

Step 2: (R)-2-(4-(3-(6-(3-(2-ethoxyphenoxy)piperidin-1-yl)pyrazin-2-yl)ureido)phenyl)acetic acid Methyl (R)-2-(4-(3-(6-(3-(2-ethoxyphenoxy)piperidin-1-yl)pyrazin-2-yl)ureido)phenyl)acetate (11 mg, 0.022 mmol) obtained in Step 1 was used in a similar manner to Step 2 of Preparation Example 34 to obtain the desired product. (Yield: 15.9%)

$^1$H-NMR (400 MHz, METHANOL-D4) δ 7.83 (s, 1H), 7.70 (s, 1H), 7.68-7.64 (1H), 7.35 (d, J=8.7 Hz, 2H), 7.15 (d, J=8.7 Hz, 2H), 6.90-6.78 (m, 2H), 6.75-6.68 (m, 1H), 4.51 (d, J=2.7 Hz, 1H), 4.00-3.90 (1H), 3.90-3.72 (m, 4H), 3.60-3.53 (1H), 3.51 (s, 2H), 2.11-2.00 (m, 2H), 1.95 (s, 1H), 1.25-1.14 (m, 3H), 0.79-0.68 (m, 1H)

Example 68: (R)-2-(4-(2-((6-(3-(2-ethoxyphenoxy)piperidin-1-yl)pyridin-2-yl)amino)-2-oxoethyl)phenyl)-2-methylpropanoic acid

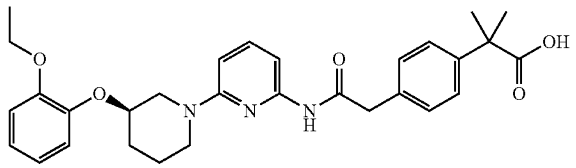 [SMILES: CCOc1ccccc1O[C@@H]1CCCN(c2cccc(NC(=O)Cc3ccc(C(C)(C)C(=O)O)cc3)n2)C1]

(R)-2-chloro-6-(3-(2-ethoxyphenoxy)piperidin-1-yl)pyridine (0.120 g, 0.361 mmol) obtained in Preparation Example 71 and methyl 2-(4-(2-amino-2-oxoethyl)phenyl)2-methylpropanoate (0.102 g, 0.433 mmol) obtained in Preparation Example 36 were used in a similar manner to Example 34 to obtain the desired product. (2 steps yield: 37.2%)

$^1$H-NMR (400 MHz, CHLOROFORM-D) δ 8.23 (s, 1H), 7.54-7.39 (m, 2H), 7.36 (d, J=7.8 Hz, 2H), 7.31-7.25 (m, 2H), 7.02-6.90 (m, 2H), 6.90-6.76 (m, 2H), 6.40-6.26 (m, 1H), 4.31-4.16 (m, 1H), 4.10-4.04 (m, 1H), 4.04-3.90 (m, 2H), 3.83-3.70 (m, 1H), 3.66 (d, J=11.9 Hz, 2H), 3.19 (dd, J=12.6, 8.5 Hz, 1H), 3.11-2.98 (m, 1H), 2.20-2.06 (m, 1H), 1.85 (q, J=4.4 Hz, 1H), 1.79-1.65 (m, 1H), 1.63-1.54 (m, 6H), 1.54-1.44 (m, 1H), 1.42-1.30 (m, 3H)

Example 69: (R)-2-(4-(2-((6-(3-(2-ethoxyphenoxy)piperidin-1-yl)pyrazin-2-yl)amino)-2-oxoethyl)phenyl)-2-methylpropanoic acid

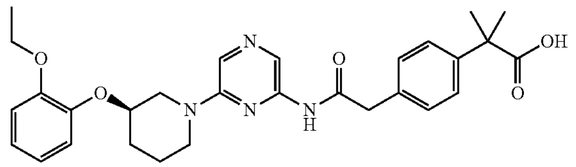 [SMILES: CCOc1ccccc1O[C@@H]1CCCN(c2cncc(NC(=O)Cc3ccc(C(C)(C)C(=O)O)cc3)n2)C1]

(R)-2-chloro-6-(3-(2-ethoxyphenoxy)piperidin-1-yl)pyrazine (0.118 g, 0.354 mmol) obtained in Preparation Example 1 and methyl 2-(4-(2-amino-2-oxoethyl)phenyl)2-methylpropanoate (0.1 g, 0.425 mmol) obtained in Preparation Example 36 were used in a similar manner to Example 34 to obtain the desired product. (2 steps yield: 20.1%)

$^{1}$H-NMR (400 MHz, CHLOROFORM-D) δ 8.62 (s, 1H), 7.82 (d, J=16.0 Hz, 1H), 7.55-7.43 (1H), 7.43-7.33 (m, 2H), 7.26 (dd, J=23.8, 15.1 Hz, 2H), 6.91 (ddd, J=14.8, 6.5, 1.7 Hz, 2H), 6.86-6.75 (m, 2H), 4.31-4.20 (m, 1H), 4.02-3.84 (m, 3H), 3.68 (d, J=14.2 Hz, 2H), 3.62 (q, J=4.3 Hz, 1H), 3.52 (q, J=6.9 Hz, 1H), 3.41-3.28 (m, 1H), 2.11-2.04 (m, 1H), 1.99-1.78 (m, 2H), 1.61 (t, J=15.3 Hz, 6H), 1.56-1.46 (m, 1H), 1.31 (q, J=7.2 Hz, 3H)

Example 70: (R)-2-(4-(3-((6-(3-(2-ethoxyphenoxy)piperidin-1-yl)pyridin-2-yl)amino)-3-oxopropyl)phenyl)-2-methylpropanoic acid

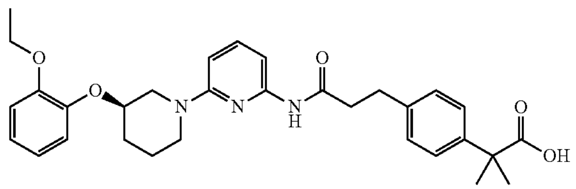 [SMILES: CCOc1ccccc1O[C@@H]1CCCN(c2cccc(NC(=O)CCc3ccc(C(C)(C)C(=O)O)cc3)n2)C1]

(R)-2-chloro-6-(3-(2-ethoxyphenoxy)piperidin-1-yl)pyridine (0.50 g, 1.50 mmol) obtained in Preparation Example 71 and methyl 2-(4-(3-amino-3-oxopropyl)phenyl-2-methylpropanoate (0.38 g, 1.50 mmol) obtained in Preparation Example 20 were used in a similar manner to Example 34 to obtain the desired product. (Yield: 26%)

$^{1}$H-NMR (400 MHz, CHLOROFORM-D): δ 7.84 (s, 1H), 7.46 (d, J=4.6 Hz, 2H), 7.32 (d, J=8.2 Hz, 2H), 7.17 (d, J=8.2 Hz, 2H), 6.83-6.99 (m, 4H), 6.36 (t, J=4.3 Hz, 1H), 4.25 (td, J=8.2, 4.0 Hz, 1H), 4.08-4.13 (m, 1H), 3.96-4.04 (m, 2H), 3.79 (td, J=8.7, 4.1 Hz, 1H), 3.28 (dd, J=12.8, 8.2 Hz, 1H), 3.10-3.16 (m, 1H), 2.99 (t, J=7.8 Hz, 2H), 2.61 (t, J=7.5 Hz, 2H), 2.15 (dd, J=12.6, 4.3 Hz, 1H), 1.89 (q, J=4.4 Hz, 1H), 1.74-1.83 (m, 1H), 1.53-1.61 (m, 7H), 1.37 (t, J=7.1 Hz, 3H)

Example 71: (R)-3-(4-(2-((6-(3-(2-ethoxyphenoxy)piperidin-1-yl)pyridin-2-yl)amino-2-oxoethyl)phenyl)-2,2-dimethylpropanoic acid

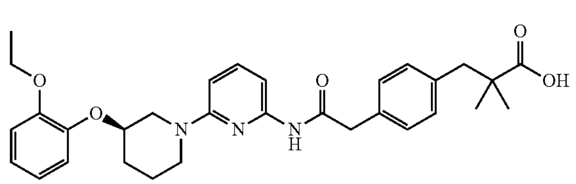 [SMILES: CCOc1ccccc1O[C@@H]1CCCN(c2cccc(NC(=O)Cc3ccc(CC(C)(C)C(=O)O)cc3)n2)C1]

(R)-2-chloro-6-(3-(2-ethoxyphenoxy)piperidin-1-yl)pyridine (0.15 g, 0.45 mmol) obtained in Preparation Example 71 and methyl 3-(4-(2-amino-2-oxoethyl)phenyl)-2,2-dimethylpropenoate (0.11 g, 0.45 mmol) obtained in Preparation Example 33 were used in a similar manner to Example 34 to obtain the desired product. (Yield: 50%)

$^{1}$H-NMR (400 MHz, CHLOROFORM-D): δ 7.87 (s, 1H), 7.51-7.38 (m, 2H), 7.18 (dd, J=22.9, 8.2 Hz, 4H), 7.02-6.78 (m, 4H), 6.34 (d, J=8.7 Hz, 1H), 4.27-4.17 (m, 1H), 4.16-4.04 (m, 1H), 4.04-3.92 (m, 2H), 3.79 (td, J=8.7, 4.3 Hz, 1H), 3.65 (s, 2H), 3.21 (dd, J=12.8, 8.7 Hz, 1H), 3.12-3.02 (m, 1H), 2.87 (s, 2H), 2.18-2.07 (m, 1H), 1.92-1.69 (m, 2H), 1.61-1.46 (m, 1H), 1.37 (t, J=6.9 Hz, 3H), 1.19 (s, 6H)

Example 72: (R)-3-(4-(2-((4-(3-(2-ethoxyphenoxy)piperidin-1-yl)-6-(trifluoromethyl)pyrimidin-2-yl)amino-2-oxoethyl)phenyl)-2,2-dimethylpropanoic acid

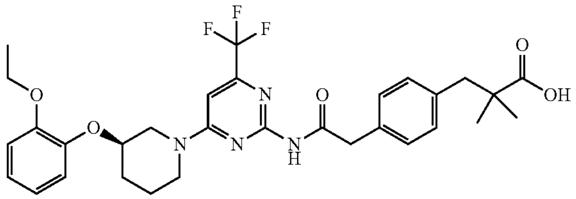 [SMILES: CCOc1ccccc1O[C@@H]1CCCN(c2cc(C(F)(F)F)nc(NC(=O)Cc3ccc(CC(C)(C)C(=O)O)cc3)n2)C1]

To tert-butyl (R)-3-(4-(2-((4-(3-(2-ethoxyphenoxy)piperidin-1-yl)-6-(trifluoromethyl) pyrimidin-2-yl)amino)-2-oxoethyl)phenyl)-2,2-dimethylpropanoate obtained by using (R)-2-chloro-4-(3-(2-ethoxyphenoxy)piperidin-1-yl)-6-(trifluoromethyl)pyrimidine (0.18 g, 0.45 mmol) obtained in Preparation Example 72 and tert-butyl 3-(4-(2-amino-2-oxoethyl)phenyl)-2,2-dimethylpropanoate (0.13 g, 0.45 mmol) obtained in Preparation Example 63 in a similar manner to Example 8, DCM (0.30 mL) and TFA (0.45 mL) were slowly added and stirred at room temperature for 1 hour. The reaction mixture was neutralized by adding 1N HCl, extracted with ethyl acetate and washed with water and brine. The mixed solution was dried over magnesium sulfate, and the solvent was removed under reduced pressure. The purification was carried out by column chromatography to obtain the title compound. (Yield: 59%)

$^{1}$H-NMR (400 MHz, METHANOL-D4): δ 7.24-7.04 (m, 4H), 6.97-6.07 (m, 5H), 4.46 (s, 1H), 4.12-3.49 (m, 5H), 3.49-3.31 (m, 1H), 3.28 (s, 2H), 2.81 (d, J=9.6 Hz, 2H), 1.96 (d, J=2.3 Hz, 3H), 1.54 (s, 1H), 1.17 (t, J=7.1 Hz, 3H), 1.09 (d, J=15.1 Hz, 6H)

Example 73: (R)-3-(4-(1-((6-(3-(2-ethoxyphenoxy)piperidin-1-yl)pyrazin-2-yl)amino)-2-methyl-1-oxopropan-2-yl)phenyl)propanoic acid

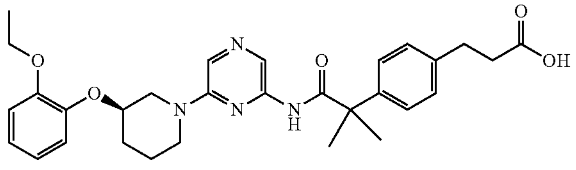 [SMILES: CCOc1ccccc1O[C@@H]1CCCN(c2cncc(NC(=O)C(C)(C)c3ccc(CCC(=O)O)cc3)n2)C1]

(R)-2-chloro-6-(3-(2-ethoxyphenoxy)piperidin-1-yl)pyrazine (0.15 g, 0.45 mmol) obtained in Preparation Example 1 and methyl 3-(4-(1-amino-2-methyl-1-oxopropan-2-yl)phenyl)propanoate (0.11 g, 0.45 mmol) obtained in Preparation Example 37 were used in a similar manner to Example 34 to obtain the desired product. (Yield: 63%)

$^{1}$H-NMR (400 MHz, CHLOROFORM-D): δ 8.71 (s, 1H), 7.83 (s, 1H), 7.33 (d, J=8.2 Hz, 2H), 7.24 (d, J=8.2 Hz, 2H), 7.07 (s, 1H), 6.96-6.73 (m, 4H), 4.27-4.17 (m, 1H), 4.03-3.86 (m, 3H), 3.73-3.59 (m, 1H), 3.42 (dd, J=13.0, 7.5 Hz, 1H), 3.36-3.23 (m, 1H), 2.97 (t, J=7.8 Hz, 2H), 2.66 (t, J=7.8 Hz, 2H), 2.08 (m, 1H), 1.97-1.74 (m, 2H), 1.63 (s, 6H), 1.54 (m, 1H), 1.33 (t, J=6.9 Hz, 3H)

Example 74: (R)-3-(4-((2-((6-(3-(2-ethoxyphenoxy)piperidin-1-yl)pyrazin-2-yl)carbamoyl)allyl)amino)phenyl)propanoic acid

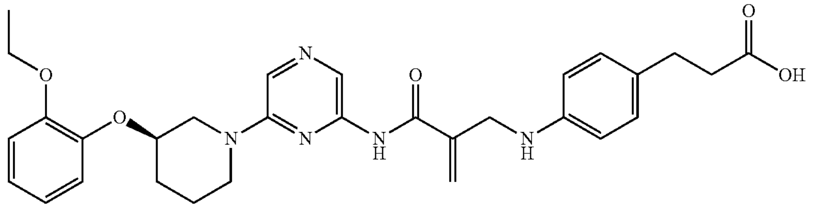 [SMILES: C=C(CNc1ccc(CCC(=O)O)cc1)C(=O)Nc1cncc(N2CCC[C@@H](Oc3ccccc3OCC)C2)n1]

Step 1: Ethyl (R)-3-(4-((2-((6-(3-(2-ethoxyphenoxy)piperidin-1-yl)pyrazin-2-yl)carbamoyl)allyl)amino)phenyl)propanoate (R)-2-chloro-6-(3-(2-ethoxyphenoxy)piperidin-1-yl)pyrazine (20.13 mg, 0.060 mmol) obtained in Preparation Example 1 and ethyl-3-(4-(3-carbamoylazetidin-1-yl)phenyl)propanoate (20 mg, 0.072 mmol) obtained in Preparation Example 38 were used in a similar manner to Example 8 to obtain the desired product. (Yield: 37%).

$^1$H-NMR (400 MHz, CHLOROFORM-D) δ 8.78-8.63 (m, 1H), 8.42 (s, 1H), 7.94-7.78 (m, 1H), 7.01 (dd, J=8.7, 2.7 Hz, 2H), 6.91 (td, J=7.8, 2.4 Hz, 2H), 6.86-6.72 (m, 2H), 6.62 (dd, J=8.2, 2.7 Hz, 2H), 6.01 (d, J=2.7 Hz, 1H), 5.72 (s, 1H), 4.28 (q, J=3.5 Hz, 1H), 4.11 (td, J=7.1, 2.9 Hz, 5H), 4.03-3.81 (m, 4H), 3.81-3.63 (m, 1H), 3.63-3.48 (m, 1H), 3.50-3.29 (m, 1H), 2.92-2.72 (m, 2H), 2.54 (td, J=7.8, 2.7 Hz, 2H), 2.19-2.02 (m, 1H), 2.02-1.78 (m, 2H), 1.47-1.29 (m, 3H), 1.29-1.09 (m, 3H)

Step 2: (R)-3-(4-((2-((6-(3-(2-ethoxyphenoxy)piperidin-1-yl)pyrazin-2-yl)carbamoyl)allyl)amino)phenyl)propanoic acid The ester compound obtained in Step 1 was hydrolyzed using 1 N aqueous lithium hydroxide solution to obtain the title compound. (Yield: 51%)

$^1$H-NMR (400 MHz, CHLOROFORM-D) δ 8.70 (s, 1H), 8.42 (s, 1H), 7.86 (s, 1H), 7.02 (d, J=8.2 Hz, 2H), 6.91 (t, J=7.5 Hz, 2H), 6.83 (d, J=6.4 Hz, 2H), 6.62 (d, J=8.2 Hz, 2H), 6.01 (s, 1H), 5.72 (s, 1H), 4.28 (d, J=3.7 Hz, 1H), 4.10 (d, J=12.3 Hz, 2H), 4.02-3.80 (m, 4H), 3.77-3.63 (m, 1H), 3.58 (q, J=6.9 Hz, 1H), 3.52-3.29 (m, 1H), 3.00-2.74 (m, 2H), 2.60 (t, J=7.5 Hz, 2H), 2.18-2.02 (m, 1H), 2.01-1.77 (m, 2H), 1.57 (td, J=8.6, 4.1 Hz, 2H), 1.33 (t, J=7.1 Hz, 2H), 0.84 (q, J=6.6 Hz, 3H)

Example 75: (R)-2-(4-((6-(3-(2-ethoxyphenoxy)piperidin-1-yl)pyrazin-2-yl)carbamoyl)piperidin-1-yl)pyrimidine-5-carboxylic acid

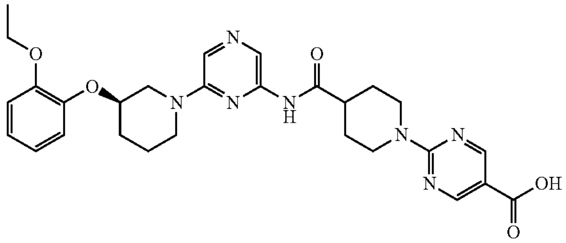 [SMILES: CCOc1ccccc1O[C@@H]1CCCN(c2cncc(NC(=O)C3CCN(c4ncc(C(=O)O)cn4)CC3)n2)C1]

Step 1: Methyl (R)-2-(4-((6-(3-(2-ethoxyphenoxy)piperidin-1-yl)pyrazin-2-yl)carbamoyl)piperidin-1-yl)pyrimidine-5-carboxylate (R)-2-chloro-6-(3-(2-ethoxyphenoxy)piperidin-1-yl)pyrazine (20.13 mg, 0.060 mmol) obtained in Preparation Example 1 and methyl 2-(4-carbamoylpiperidin-1-yl)pyrimidine-5-carboxylate (95 mg, 0.359 mmol) obtained in Preparation Example 39 were used in a similar manner to Example 8 to obtain the desired product. (Yield: 61%)

$^1$H-NMR (400 MHz, CHLOROFORM-D) δ 8.84 (d, J=9.1 Hz, 2H), 8.66 (s, 1H), 7.87 (s, 1H), 7.03-6.78 (m, 5H), 4.94 (d, J=14.2 Hz, 2H), 4.39-4.22 (1H), 4.04-3.89 (m, 4H), 3.87 (s, 3H), 3.77-3.66 (m, 1H), 3.60 (q, J=6.9 Hz, 1H), 3.51-3.33 (m, 1H), 3.19-2.98 (m, 2H), 2.64-2.47 (m, 1H), 2.15-2.07 (m, 1H), 2.02-1.88 (m, 2H), 1.83 (t, J=12.3 Hz, 2H), 1.67-1.56 (m, 1H), 1.35 (t, J=6.9 Hz, 3H)

Step 2: (R)-2-(4-((6-(3-(2-ethoxyphenoxy)piperidin-1-yl)pyrazin-2-yl)carbamoyl)piperidin-1-yl)pyrimidine-5-carboxylic acid The ester compound obtained in Step 1 was hydrolyzed in a similar manner to Step 2 of Example 2 to obtain the title compound. (Yield: 69%)

$^1$H-NMR (400 MHz, CHLOROFORM-D) δ 8.84 (d, J=9.1 Hz, 2H), 8.66 (s, 1H), 7.87 (s, 1H), 7.03-6.78 (m, 5H), 4.94 (d, J=14.2 Hz, 2H), 4.39-4.22 (1H), 4.04-3.89 (m, 4H), 3.87 (s, 3H), 3.77-3.66 (m, 1H), 3.60 (q, J=6.9 Hz, 1H), 3.51-3.33 (m, 1H), 3.19-2.98 (m, 2H), 2.64-2.47 (m, 1H), 2.15-2.07 (m, 1H), 2.02-1.88 (m, 2H), 1.83 (t, J=12.3 Hz, 2H), 1.67-1.56 (m, 1H), 1.35 (t, J=6.9 Hz, 3H)

Example 76: 3-(3-((R)-3-((6-((R)-3-((3-ethoxypyridin-2-yl)oxy)piperidin-1-yl)pyrazin-2-yl)carbamoyl)piperidin-1-yl)phenyl-2,2-dimethylpropanoic acid

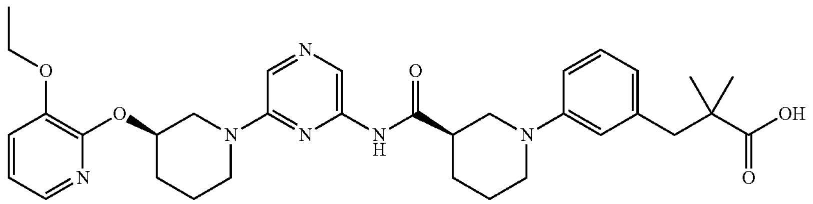 [SMILES: CCOc1cccnc1O[C@@H]1CCCN(c2cncc(NC(=O)[C@@H]3CCCN(c4cccc(CC(C)(C)C(=O)O)c4)C3)n2)C1]

(R)-2-chloro-6-(3-((3-ethoxypyridin-2-yl)oxy)piperidin-1-yl)pyrazine (0.10 g, 0.30 mmol) obtained in Preparation Example 70 and tert-butyl (R)-3-(3-(3-carbamoylpiperidin-1-yl)phenyl)-2,2-dimethylpropanoate (0.11 g, 0.30 mmol) obtained in Preparation Example 64 were used in a similar manner to Example 72 to obtain the desired product. (Yield: 28%)

$^1$H-NMR (400 MHz, METHANOL-D4): δ 8.44 (s, 1H), 7.75 (d, J=4.1 Hz, 1H), 7.66-7.58 (m, 1H), 7.18-7.05 (m, 2H), 6.94-6.75 (m, 3H), 6.70 (d, J=7.3 Hz, 1H), 5.16 (q, J=2.7 Hz, 1H), 4.14-3.93 (m, 1H), 3.94-3.70 (m, 4H), 3.65-3.50 (m, 2H), 3.49-3.40 (m, 1H), 3.05-2.94 (m, 1H), 2.90-2.69 (m, 4H), 2.18-1.90 (m, 4H), 1.90-1.65 (m, 3H), 1.60 (d, J=9.1 Hz, 1H), 1.24-1.16 (m, 3H), 1.12 (d, J=2.3 Hz, 6H)

Example 77: (R)-3-(4-(1-((4-(3-(2-ethoxyphenoxy)piperidin-1-yl)pyrimidin-2-yl)amino)-2-methyl-1-oxopropan-2-yl)phenyl)-2,2-dimethylpropanoic acid

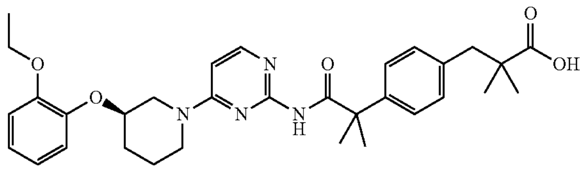 [SMILES: CCOc1ccccc1O[C@@H]1CCCN(c2ccnc(NC(=O)C(C)(C)c3ccc(CC(C)(C)C(=O)O)cc3)n2)C1]

(R)-2-chloro-4-(3-(2-ethoxyphenoxy)piperidin-1-yl)pyrimidine (0.10 g, 0.30 mmol) obtained in Preparation Example 69 and tert-butyl 3-(4-(1-amino-2-methyl-1-oxopropan-2-yl)phenyl)-2,2-dimethylpropanoate (0.096 g, 0.30 mmol) obtained in Preparation Example 59 were used in a similar manner to Example 72 to obtain the desired product. (Yield: 66%)

$^1$H-NMR (400 MHz, CHLOROFORM-D): δ 11.51 (s, 1H), 8.34 (s, 1H), 7.89-7.76 (m, 1H), 7.29 (d, J=7.3 Hz, 2H), 7.10 (d, J=7.3 Hz, 2H), 7.01-6.87 (m, 2H), 6.87-6.74 (m, 2H), 6.07 (d, J=5.9 Hz, 1H), 4.24 (s, 1H), 4.02-3.42 (m, 6H), 2.75 (s, 2H), 2.12-1.80 (m, 3H), 1.67-1.45 (m, 7H), 1.32 (td, J=6.9, 1.4 Hz, 3H), 1.10 (s, 6H)

Example 78: (R)-3-(4-(1-((4-(3-((3-ethoxypyridin-2-yl)oxy)piperidin-1-yl)pyrimidin-2-yl)amino)-2-methyl-1-oxopropan-2-yl)phenyl)-2,2-dimethylpropanoic acid

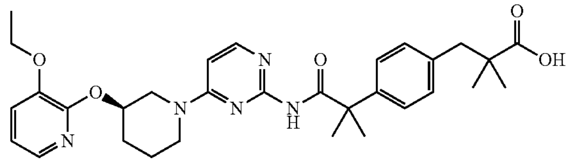 [SMILES: CCOc1cccnc1O[C@@H]1CCCN(c2ccnc(NC(=O)C(C)(C)c3ccc(CC(C)(C)C(=O)O)cc3)n2)C1]

(R)-2-chloro-4-(3-((3-ethoxypyridin-2-yl)oxy)piperidin-1-yl)pyrimidine (0.10 g, 0.30 mmol) obtained in Preparation Example 66 and tert-butyl 3-(4-(1-amino-2-methyl-1-oxopropan-2-yl)phenyl)-2,2-dimethylpropanoate (0.095 g, 0.30 mmol) obtained in Preparation Example 59 were used in a similar manner to Example 72 to obtain the desired product. (Yield: 71%)

$^1$H-NMR (400 MHz, CHLOROFORM-D): δ 11.71-10.30 (bs, 1H), 7.80 (d, J=5.5 Hz, 1H), 7.73-7.61 (m, 1H), 7.28 (d, J=7.8 Hz, 2H), 7.11 (d, J=8.2 Hz, 2H), 6.96 (d, J=7.8 Hz, 1H), 6.82-6.69 (m, 1H), 6.10 (d, J=6.4 Hz, 1H), 5.13-5.03 (m, 1H), 4.01-3.48 (m, 6H), 2.76 (dd, J=17.2, 13.5 Hz, 2H), 2.14-2.02 (m, 1H), 1.99-1.86 (m, 2H), 1.59 (s, 7H), 1.33-1.17 (m, 3H), 1.11 (s, 6H)

Example 79: (R)-2-(4-(4-((6-(3-(2-ethoxyphenoxy)piperidin-1-yl)pyrazin-2-yl)carbamoyl)piperidin-1-yl)phenyl)acetic acid

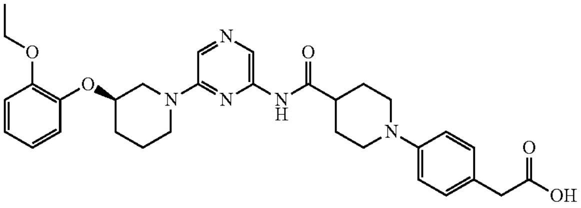 [SMILES: CCOc1ccccc1O[C@@H]1CCCN(c2cncc(NC(=O)C3CCN(c4ccc(CC(=O)O)cc4)CC3)n2)C1]

(R)-2-chloro-6-(3-(2-ethoxyphenoxy)piperidin-1-yl)pyrazine (0.032 g, 0.097 mmol) obtained in Preparation Example 1 and tert-butyl 2-(4-(4-carbamoylpiperidin-1-yl)phenyl)acetate (0.031 g, 0.097 mmol) obtained in Preparation Example 40 were used in a similar manner to Example 72 to obtain the desired product. (2 steps yield: 9.0%)

$^1$H-NMR (400 MHz, CHLOROFORM-D) δ 8.68 (s, 1H), 7.87 (s, 1H), 7.46 (s, 1H), 7.17 (d, J=8.7 Hz, 2H), 6.99-6.81 (m, 6H), 4.35-4.25 (m, 1H), 4.03-3.88 (m, 3H), 3.78-3.67 (m, 3H), 3.60 (q, J=6.6 Hz, 1H), 3.55 (s, 2H), 3.46-3.37 (1H), 2.82-2.66 (2H), 2.43-2.29 (m, 1H), 2.19-2.06 (1H), 2.02-1.82 (m, 6H), 1.58 (td, J=8.8, 4.4 Hz, 1H), 1.35 (t, J=7.1 Hz, 3H)

Example 80: (R)-2-(4-(4-((6-(3-(2-ethoxyphenoxy)piperidin-1-yl)pyrazin-2-yl)carbamoyl)piperidin-1-yl)phenyl)-2-methylpropanoic acid

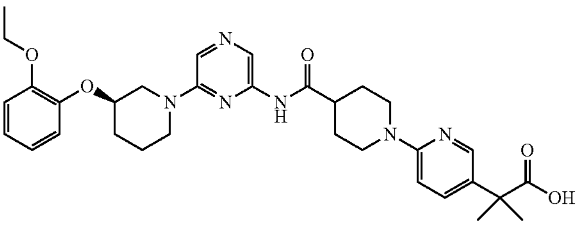 [SMILES: CCOc1ccccc1O[C@@H]1CCCN(c2cncc(NC(=O)C3CCN(c4ccc(C(C)(C)C(=O)O)cn4)CC3)n2)C1]

(R)-2-chloro-6-(3-(2-ethoxyphenoxy)piperidin-1-yl)pyrazine (0.12 g, 0.36 mmol) obtained in Preparation Example 1 and methyl 2-(4-(4-carbamoylpiperidin-1-yl)phenyl)-2-methylpropanoate (0.11 g, 0.36 mmol) obtained in Preparation Example 41 were used in a similar manner to Example 34 to obtain the desired product. (Yield: 26%)

$^1$H-NMR (400 MHz, CHLOROFORM-D): δ 8.68 (s, 1H), 7.87 (s, 1H), 7.40 (s, 1H), 7.32-7.26 (m, 2H), 6.99-6.81 (m, 6H), 4.35-4.25 (m, 1H), 4.04-3.88 (m, 3H), 3.79-3.66 (m, 3H), 3.59 (q, J=6.9 Hz, 1H), 3.47-3.36 (m, 1H), 2.75 (t, J=11.4 Hz, 2H), 2.37 (t, J=11.2 Hz, 1H), 2.18-2.06 (m, 1H), 2.02-1.83 (m, 6H), 1.65-1.48 (m, 7H), 1.35 (t, J=7.1 Hz, 3H)

Example 81: (R)-2-(6-(4-((6-(3-(2-ethoxyphenoxy)piperidin-1-yl)pyrazin-2-yl)carbamoyl)piperidin-1-yl)pyridin-3-yl)-2-methylpropanoic acid

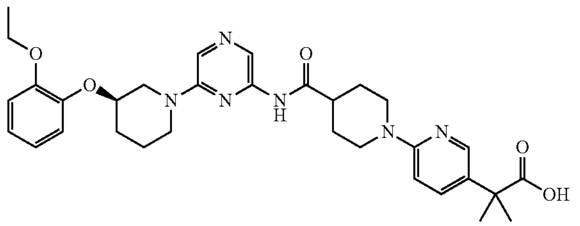 [SMILES: CCOc1ccccc1O[C@@H]1CCCN(c2cncc(NC(=O)C3CCN(c4ccc(C(C)(C)C(=O)O)cn4)CC3)n2)C1]

(R)-2-chloro-6-(3-(2-ethoxyphenoxy)piperidin-1-yl)pyrazine (0.080 g, 0.24 mmol) obtained in Preparation Example 1 and methyl 2-(6-(4-carbamoylpiperidin-1-yl)pyridin-3-yl)-2-methylpropanoate (0.073 g, 0.24 mmol) obtained in Preparation Example 42 were used in a similar manner to Example 34 to obtain the desired product. (Yield: 34%)

$^1$H-NMR (400 MHz, CHLOROFORM-D): δ 8.65 (s, 1H), 8.23 (d, J=2.3 Hz, 1H), 7.86 (s, 1H), 7.57-7.41 (m, 2H), 6.98-6.89 (m, 2H), 6.89-6.78 (m, 2H), 6.65 (d, J=9.1 Hz, 1H), 4.31 (d, J=11.9 Hz, 3H), 4.03-3.87 (m, 3H), 3.69 (d, J=13.7 Hz, 1H), 3.59 (q, J=6.9 Hz, 1H), 3.41 (t, J=9.6 Hz, 1H), 2.88 (t, J=12.6 Hz, 2H), 2.46 (t, J=10.7 Hz, 1H), 2.16-2.04 (1H), 2.02-1.73 (m, 6H), 1.64-1.48 (7H), 1.34 (dd, J=7.5, 6.6 Hz, 3H)

Example 82: (R)-2-(5-(4-((6-(3-(2-ethoxyphenoxy)piperidin-1-yl)pyrazin-2-yl)carbamoyl)piperidin-1-yl)-2H-tetrazol-2-yl)acetic acid

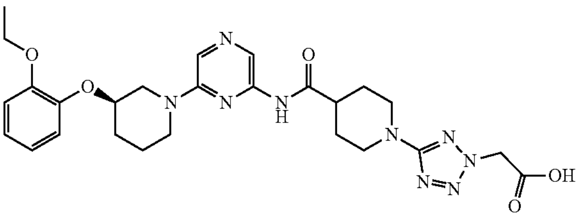 [SMILES: CCOc1ccccc1O[C@@H]1CCCN(c2cncc(NC(=O)C3CCN(c4nnn(CC(=O)O)n4)CC3)n2)C1]

Step 1: Ethyl (R)-2-(5-(4-((6-(3-(2-ethoxyphenoxy)piperidin-1-yl)pyrazin-2-yl)carbamoyl)piperidin-1-yl)-2H-tetrazol-2-yl)acetate (R)-2-chloro-6-(3-(2-ethoxyphenoxy)piperidin-1-yl)pyrazine (167 mg, 0.499 mmol) obtained in Preparation Example 1 and ethyl 2-(5-(4-carbamoylpiperidin-1-yl)-2H-tetrazol-2-yl)acetate (141 mg, 0.499 mmol) obtained in Preparation Example 43 were used in a similar manner to Example 8 to obtain the desired product. (Yield: 17%)

$^{1}$H-NMR (400 MHz, CHLOROFORM-D) δ 8.66 (s, 1H), 7.87 (s, 1H), 7.35-7.27 (1H), 7.05-6.90 (m, 2H), 6.90-6.77 (2H), 5.19 (s, 2H), 4.31 (t, J=3.7 Hz, 1H), 4.29-4.23 (2H), 4.19 (d, J=14.2 Hz, 2H), 4.11 (q, J=7.0 Hz, 2H), 4.06-3.84 (4H), 3.81-3.66 (m, 1H), 3.60 (dd, J=13.5, 7.5 Hz, 1H), 3.42 (t, J=9.6 Hz, 1H), 3.02 (t, J=11.9 Hz, 2H), 2.43 (d, J=11.0 Hz, 1H), 2.20-2.05 (m, 2H), 2.02-1.79 (m, 7H), 1.60 (q, J=4.6 Hz, 1H), 1.36 (q, J=6.9 Hz, 5H), 1.28 (t, J=7.1 Hz, 3H), 1.23 (d, J=7.3 Hz, 3H)

Step 2: (R)-2-(5-(4-((6-(3-(2-ethoxyphenoxy)piperidin-1-yl)pyrazin-2-yl)carbamoyl)piperidin-1-yl)-2H-tetrazol-2-yl)acetic acid The ester compound obtained in Step 1 was hydrolyzed in a similar manner to Step 2 of Example 2 to obtain the title compound. (Yield: 33%)

$^{1}$H-NMR (400 MHz, METHANOL-D4) δ 8.45 (s, 1H), 7.73 (s, 1H), 7.04-6.76 (m, 4H), 4.99 (s, 2H), 4.42 (s, 1H), 4.07 (q, J=7.2 Hz, 3H), 4.00-3.86 (m, 1H), 3.86-3.80 (m, 3H), 3.80-3.68 (m, 1H), 3.62-3.50 (m, 1H), 3.32 (s, 1H), 3.08-2.86 (m, 2H), 2.62 (t, J=11.4 Hz, 1H), 2.13-2.00 (m, 2H), 1.97-1.68 (m, 6H), 1.57 (s, 1H), 1.25 (t, J=6.4 Hz, 3H)

Example 83: (R)-4-(4-((6-(3-(2-ethoxyphenoxy)piperidin-1-yl)pyrazin-2-yl)carbamoyl)piperidin-1-yl)-4-oxobutanoic acid

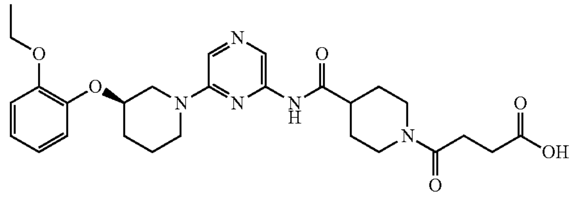 [SMILES: CCOc1ccccc1O[C@@H]1CCCN(c2cncc(NC(=O)C3CCN(C(=O)CCC(=O)O)CC3)n2)C1]

Step 1: (R)—N-(6-(3-(2-ethoxyphenoxy)piperidin-1-yl)pyrazin-2-yl)piperidine-4-carboxamide (R)-2-chloro-6-(3-(2-ethoxyphenoxy)piperidin-1-yl)pyrazine (0.50 g, 1.50 mmol) obtained in Preparation Example 1 and tert-butyl 4-carbamoylpiperidine-1-carboxylate (0.41 g, 1.80 mmol) were used in a similar manner to Example 72 to obtain the desired product. (Yield: 45%)

Step 2: (R)-4-(4-((6-(3-(2-ethoxyphenoxy)piperidin-1-yl)pyrazin-2-yl)carbamoyl)piperidin-1-yl)-4-oxobutanoic acid To (R)—N-(6-(3-(2-ethoxyphenoxy)piperidin-1-yl)pyrazin-2-yl)piperidine-4-carboxamide (0.095 g, 0.22 mmol) obtained in Step 1 in DCM (2 mL), DIPEA (0.078 mL, 0.45 mmol) and succinic anhydride (0.034 g, 0.34 mmol) were slowly added and stirred at room temperature for 30 minutes. The reaction mixture was washed with 2 N HCl and brine, and dried over magnesium sulfate. The solvent was removed under reduced pressure, and the purification was carried out by column chromatography to obtain the title compound. (Yield: 55%)

$^{1}$H-NMR (400 MHz, CHLOROFORM-D): δ 8.65 (s, 1H), 7.89 (s, 1H), 7.53 (s, 1H), 7.01-6.80 (m, 4H), 4.58 (d, J=11.4 Hz, 1H), 4.31 (q, J=3.5 Hz, 1H), 4.07-3.87 (m, 4H), 3.71 (d, J=13.7 Hz, 1H), 3.60 (q, J=6.7 Hz, 1H), 3.43 (t, J=9.6 Hz, 1H), 3.23-3.07 (1H), 2.88-2.61 (m, 5H), 2.51 (d, J=10.5 Hz, 1H), 2.20-2.05 (m, 1H), 2.05-1.66 (m, 6H), 1.66-1.48 (m, 1H), 1.36 (t, J=6.9 Hz, 3H)

Example 84: (R)-2-(4-((6-(3-(2-ethoxyphenoxy)piperidin-1-yl)pyrazin-2-yl)carbamoyl)piperidin-1-yl)acetic acid

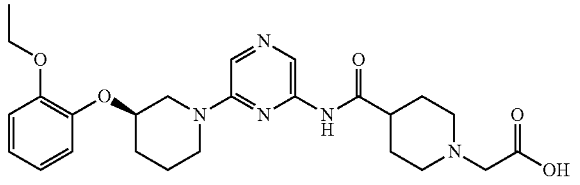 [SMILES: CCOc1ccccc1O[C@@H]1CCCN(c2cncc(NC(=O)C3CCN(CC(=O)O)CC3)n2)C1]

Step 1: Ethyl (R)-2-(4-((6-(3-(2-ethoxyphenoxy)piperidin-1-yl)pyrazin-2-yl)carbamoyl)piperidin-1-yl) acetate (R)-2-chloro-6-(3-(2-ethoxyphenoxy)piperidin-1-yl)pyrazine (232 mg, 0.696 mmol) obtained in Preparation Example 1 and ethyl 2-(4-carbamoylpiperidin-1-yl)acetate (179 mg, 0.835 mmol) obtained in Preparation Example 44 were used in a similar manner to Example 8 to obtain the desired product. (Yield: 91%)

$^{1}$H-NMR (CHLOROFORM-D) δ 8.70 (s, 1H), 7.89 (s, 1H), 7.33 (s, 1H), 7.04-6.92 (m, 2H), 6.92-6.83 (m, 2H), 4.39-4.27 (m, 1H), 4.21 (q, J=7.2 Hz, 2H), 4.09-3.90 (m, 4H), 3.79-3.69 (m, 1H), 3.61 (dd, J=13.4, 7.3 Hz, 1H), 3.49-3.36 (m, 1H), 3.27 (s, 2H), 3.04 (dd, J=10.4, 2.7 Hz, 2H), 2.42-2.30 (m, 2H), 2.30-2.21 (m, 1H), 2.21-2.10 (m, 1H), 2.05-1.85 (m, 7H), 1.68-1.55 (m, 1H), 1.36-1.21 (m, 6H)

Step 2: (R)-2-(4-((6-(3-(2-ethoxyphenoxy)piperidin-1-yl)pyrazin-2-yl)carbamoyl)piperidin-1-yl)acetic acid The ester compound obtained in Step 1 was hydrolyzed in a similar manner to Step 2 of Example 2 to obtain the title compound. (Yield: 41%)

$^1$H-NMR (MeOD) δ 8.50 (s, 1H), 7.85 (s, 1H), 7.02-6.82 (m, 5H), 4.52 (s, 1H), 4.12 (s, 2H), 4.08-3.92 (m, 3H), 3.92-3.84 (m, 1H), 3.81 (dd, J=13.7, 2.4 Hz, 1H), 3.79-3.70 (1H), 3.56 (s, 1H), 2.17 (s, 3H), 2.10-1.93 (m, 2H), 1.62 (d, J=3.1 Hz, 1H), 1.28 (t, J=7.0 Hz, 3H)

Example 85: 3-(3-((R)-3-((6-((R)-3-(2-ethoxyphenoxy)piperidin-1-yl)pyrazin-2-yl) carbamoyl)piperidin-1-yl)phenyl)-2,2-dimethylpropanoic acid

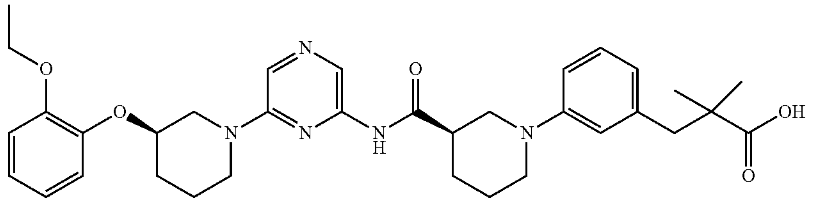 [SMILES: CCOc1ccccc1O[C@@H]1CCCN(c2cncc(NC(=O)[C@@H]3CCCN(c4cccc(CC(C)(C)C(=O)O)c4)C3)n2)C1]

(R)-2-chloro-6-(3-(2-ethoxyphenoxy)piperidin-1-yl) pyrazine (0.10 g, 0.30 mmol) obtained in Preparation Example 1 and tert-butyl (R)-3-(3-(3-carbamoylpiperidin-1-yl)phenyl)-2,2-dimethylpropanoate (0.11 g, 0.30 mmol) obtained in Preparation Example 64 were used in a similar manner to Example 72 to obtain the desired product. (Yield: 61%)

$^1$H-NMR (400 MHz, CHLOROFORM-D): δ 9.33 (s, 1H), 8.67 (s, 1H), 7.91-7.79 (m, 1H), 7.15 (t, J=7.8 Hz, 1H), 7.00-6.75 (m, 6H), 6.65 (d, J=7.3 Hz, 1H), 4.34-4.21 (m, 1H), 4.04-3.86 (m, 3H), 3.78-3.57 (m, 2H), 3.51 (dd, J=12.8, 7.3 Hz, 2H), 3.42-3.29 (m, 1H), 3.22 (dd, J=13.3, 8.7 Hz, 1H), 3.17-3.03 (m, 1H), 3.03-2.91 (m, 1H), 2.68 (d, J=13.3 Hz, 2H), 2.16-2.04 (m, 1H), 2.01-1.80 (m, 4H), 1.78-1.65 (m, 2H), 1.65-1.49 (m, 1H), 1.35 (td, J=7.0, 3.5 Hz, 3H), 1.25 (s, 3H), 1.09 (s, 3H)

Example 86: (R)-1-(4-(1-((6-(3-(2-ethoxyphenoxy)piperidin-1-yl)pyrazin-2-yl)amino)-2-methyl-1-oxopropan-2-yl)phenyl)piperidine-4-carboxylic acid

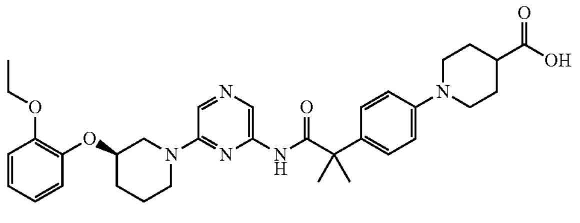 [SMILES: CCOc1ccccc1O[C@@H]1CCCN(c2cncc(NC(=O)C(C)(C)c3ccc(N4CCC(C(=O)O)CC4)cc3)n2)C1]

(R)-2-chloro-6-(3-(2-ethoxyphenoxy)piperidin-1-yl) pyrazine (0.12 g, 0.36 mmol) obtained in Preparation Example 1 and ethyl 1-(4-(1-amino-2-methyl-1-oxopropan-2-yl)phenyl)piperidine-4-carboxylate (0.11 g, 0.36 mmol) obtained in Preparation Example 45 were used in a similar manner to Example 34 to obtain the desired product. (Yield: 38%)

$^1$H-NMR (400 MHz, CHLOROFORM-D): δ 8.72 (s, 1H), 7.81 (s, 1H), 7.27 (d, J=8.7 Hz, 2H), 7.09 (s, 1H), 6.97-6.73 (m, 6H), 4.26-4.15 (m, 1H), 4.03-3.87 (m, 3H), 3.72-3.59 (m, 3H), 3.39 (dd, J=13.3, 7.8 Hz, 1H), 3.33-3.19 (m, 1H), 2.87-2.73 (m, 2H), 2.53-2.41 (m, 1H), 2.07 (d, J=3.7 Hz, 3H), 1.97-1.74 (m, 4H), 1.66-1.46 (m, 7H), 1.33 (t, J=7.1 Hz, 3H)

Example 87: 6-(3-((6-((R)-3-(2-ethoxyphenoxy)piperidin-1-yl)pyrazin-2-yl)carbamoyl)pyrrolidin-1-yl)nicotinic acid

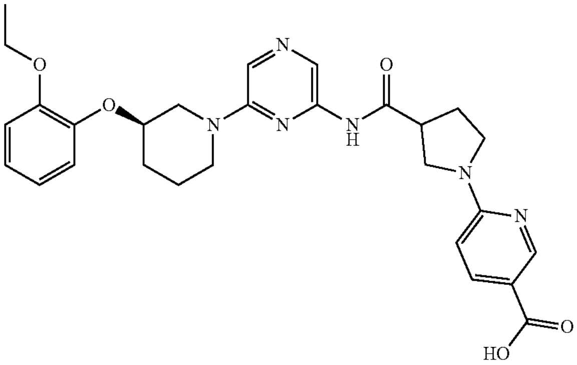 [SMILES: CCOc1ccccc1O[C@@H]1CCCN(c2cncc(NC(=O)C3CCN(c4ccc(C(=O)O)cn4)C3)n2)C1]

Step 1: Methyl 6-(3-((6-((R)-3-(2-ethoxyphenoxy)piperidin-1-yl)pyrazin-2-yl)carbamoyl)pyrrolidin-1-yl)nicotinate (R)-2-chloro-6-(3-(2-ethoxyphenoxy)piperidin-1-yl) pyrazine (34.8 mg, 0.104 mmol) obtained in Preparation Example 1 and methyl 6-(3-carbamoylpyrrolidin-1-yl)nicotinate (26 mg, 0.104 mmol) obtained in Preparation Example 46 were used in a similar manner to Example 8 to obtain the desired product. (Yield: 31%)

$^1$H-NMR (CHLOROFORM-D) δ 8.83 (d, J=2.4 Hz, 1H), 8.68 (s, 1H), 8.05 (d, J=8.8 Hz, 1H), 7.92 (s, 1H), 7.40 (d, J=3.7 Hz, 1H), 6.94 (dd, J=39.5, 8.7 Hz, 5H), 6.39 (dd, J=8.8, 3.1 Hz, 1H), 4.35 (q, J=3.6 Hz, 1H), 4.02 (q, J=7.2 Hz, 1H), 3.99-3.91 (m, 3H), 3.89 (s, 4H), 3.88-3.77 (m, 2H), 3.71 (s, 2H), 3.60 (d, J=8.8 Hz, 1H), 3.49 (s, 1H), 3.29-3.13

(1H), 2.49-2.35 (m, 2H), 2.13 (s, 1H), 2.06-1.89 (2H), 1.61 (s, 11H), 1.38 (t, J=7.0 Hz, 3H)

Step 2: 6-(3-((6-((R)-3-(2-ethoxyphenoxy)piperidin-1-yl)pyrazin-2-yl)carbamoyl)pyrrolidin-1-yl)nicotinic acid The ester compound obtained in Step 1 was hydrolyzed in a similar manner to Step 2 of Example 2 to obtain the title compound. (Yield: 59%)

$^1$H-NMR (MeOD) δ 8.71 (s, 1H), 8.51 (s, 1H), 8.06 (d, J=9.2 Hz, 1H), 8.00 (s, 1H), 7.85-7.74 (1H), 7.00 (d, J=7.6 Hz, 1H), 6.98-6.83 (m, 3H), 6.57 (d, J=8.8 Hz, 1H), 4.48 (s, 1H), 4.03-3.90 (m, 1H), 3.90-3.86 (m, 3H), 3.84 (d, J=14.3 Hz, 2H), 3.80-3.68 (m, 2H), 3.68-3.52 (m, 2H), 3.48-3.35 (1H), 2.45-2.28 (2H), 2.13-2.02 (2H), 1.96 (d, J=9.2 Hz, 1H), 1.63 (s, 1H), 1.29 (td, J=7.0, 1.5 Hz, 3H)

Example 88: N-(6-((R)-3-(2-ethoxyphenoxy)piperidin-1-yl)pyrazin-2-yl)-3-methylpyrrolidine-3-carboxamide

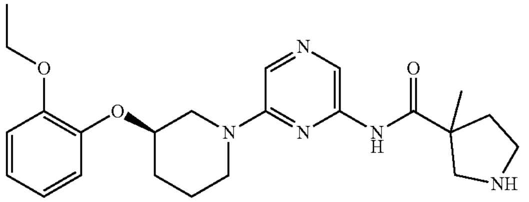 [SMILES: CCOc1ccccc1O[C@@H]1CCCN(c2cncc(NC(=O)C3(C)CCNC3)n2)C1]

Step 1: Tert-butyl 3-((6-((R)-3-(2-ethoxyphenoxy)piperidin-1-yl)pyrazin-2-yl)carbamoyl)-3-methylpyrrolidine-1-carboxylate (R)-2-chloro-6-(3-(2-ethoxyphenoxy)piperidin-1-yl)pyrazine (59.5 mg, 0.178 mmol) obtained in Preparation Example 1 and tert-butyl 3-carbamoyl-3-methylpyrrolidine-1-carboxylate (26 mg, 0.104 mmol) obtained in Preparation Example 47 were used in a similar manner to Example 8 to obtain the desired product. (Yield: 99%)

$^1$H-NMR (CHLOROFORM-D) δ 8.71 (s, 1H), 7.91 (s, 1H), 7.41 (s, 1H), 7.04-6.83 (m, 4H), 4.33 (q, J=3.7 Hz, 1H), 4.10-3.91 (m, 3H), 3.87-3.70 (m, 2H), 3.69-3.24 (m, 5H), 2.52-2.24 (1H), 2.13 (d, J=8.2 Hz, 1H), 2.02 (s, 1H), 1.99-1.81 (m, 2H), 1.62 (qd, J=8.8, 4.3 Hz, 4H), 1.49 (s, 10H), 1.46 (s, 3H), 1.39 (t, J=7.0 Hz, 3H)

Step 2: N-(6-((R)-3-(2-ethoxyphenoxy)piperidin-1-yl)pyrazin-2-yl)-3-methylpyrrolidine-3-carboxamide The ester compound obtained in Step 1 was dissolved in DCM, and trifluoroacetic acid (0.31 mL, 4.04 mmol) was added thereto, followed by stirring at room temperature for 2 hours. After completion of the reaction, the resulting product was distilled under reduced pressure to remove excess organic solvent, and then neutralized with 1 N sodium hydroxide aqueous solution. After extraction with an organic solvent, the resulting product was dried over magnesium sulfate and purified by column chromatography (hexane:ethyl acetate) to obtain the desired compound. (Yield: 99%)

$^1$H-NMR (400 MHz, METHANOL-D4) δ 8.45 (s, 1H), 7.78 (s, 1H), 7.03-6.76 (m, 4H), 4.51-4.34 (m, 1H), 3.97-3.71 (m, 6H), 3.64-3.50 (m, 1H), 3.50-3.37 (m, 1H), 3.03 (dd, J=11.9, 1.4 Hz, 1H), 2.62-2.43 (m, 1H), 2.17-1.99 (m, 3H), 1.99-1.83 (m, 2H), 1.66-1.55 (m, 1H), 1.53 (s, 3H), 1.33-1.22 (m, 4H)

Example 89: 6-(3-((6-((R)-3-(2-ethoxyphenoxy)piperidin-1-yl)pyrazin-2-yl)carbamoyl)-3-methylpyrrolidin-1-yl)nicotinic acid

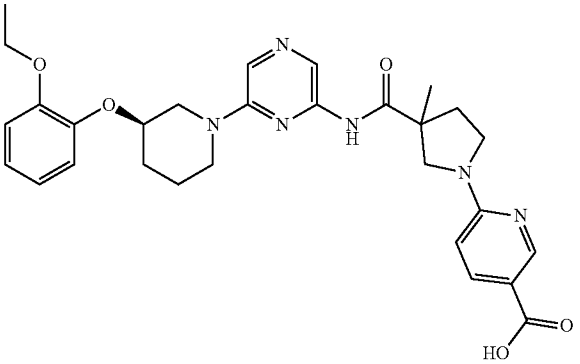 [SMILES: CCOc1ccccc1O[C@@H]1CCCN(c2cncc(NC(=O)C3(C)CCN(c4ccc(C(=O)O)cn4)C3)n2)C1]

Step 1: Methyl 6-(3-((6-((R)-3-(2-ethoxyphenoxy)piperidin-1-yl)pyrazin-2-yl)carbamoyl)-3-methylpyrrolidin-1-yl)nicotinate (R)-2-chloro-6-(3-(2-ethoxyphenoxy)piperidin-1-yl)pyrazine (138 mg, 0.414 mmol) obtained in Preparation Example 1 and methyl 6-(3-carbamoyl-3-methylpyrrolidin-1-yl)nicotinate (99 mg, 0.376 mmol) obtained in Preparation Example 48 were used in a similar manner to Example 8 to obtain the desired product. (Yield: 33%)

$^1$H-NMR (400 MHz, METHANOL-D4) a 8.64 (d, J=2.3 Hz, 1H), 8.42 (s, 1H), 8.06-7.91 (1H), 7.78-7.67 (1H), 7.02-6.75 (m, 5H), 6.50 (d, J=9.1 Hz, 1H), 4.42 (s, 1H), 4.01-3.84 (m, 3H), 3.82 (s, 4H), 3.81-3.71 (m, 3H), 3.70-3.37 (m, 5H), 2.55 (t, J=6.4 Hz, 1H), 2.17-1.99 (m, 3H), 1.98-1.83 (m, 2H), 1.64-1.51 (m, 1H), 1.51-1.41 (3H), 1.25-1.21 (3H)

Step 2: 6-(3-((6-((R)-3-(2-ethoxyphenoxy)piperidin-1-yl)pyrazin-2-yl)carbamoyl)-3-methylpyrrolidin-1-yl)nicotinic acid The ester compound obtained in Step 1 was hydrolyzed in a similar manner to Step 2 of Example 2 to obtain the title compound. (Yield: 14%)

$^1$H-NMR (400 MHz, METHANOL-D4) a 8.66 (d, J=2.3 Hz, 1H), 8.42 (s, 1H), 8.01 (dd, J=9.1, 2.3 Hz, 1H), 7.74 (d, J=3.2 Hz, 1H), 6.95 (d, J=7.3 Hz, 1H), 6.92-6.77 (m, 3H), 6.51 (d, J=9.1 Hz, 1H), 4.43 (s, 1H), 4.16-3.97 (m, 2H), 3.97-3.86 (m, 2H), 3.86-3.70 (m, 3H), 3.70-3.49 (m, 3H), 3.46 (d, J=11.0 Hz, 1H), 2.56 (t, J=6.4 Hz, 1H), 2.18-2.04 (1H), 2.04-1.87 (m, 6H), 1.54 (d, J=23.3 Hz, 1H), 1.49 (s, 3H), 1.34-1.24 (m, 2H), 1.21 (dd, J=7.3, 6.4 Hz, 3H)

Example 90: (R)-2-(4-(2-((6-(3-(2-isopropoxyphenoxy)piperidin-1-yl)pyrazin-2-yl)amino)-2-oxoethyl)phenyl)acetic acid

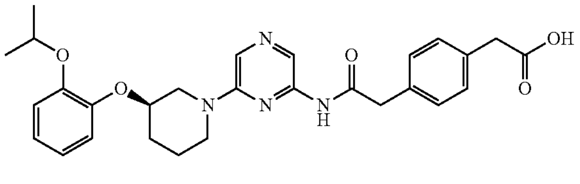 [SMILES: CC(C)Oc1ccccc1O[C@@H]1CCCN(c2cncc(NC(=O)Cc3ccc(CC(=O)O)cc3)n2)C1]

Step 1: Methyl (R)-2-(4-(2-((6-(3-(2-isopropoxyphenoxy)piperidin-1-yl)pyrazin-2-yl)amino)-2-oxoethyl)phenyl)acetate (R)-2-chloro-6-(3-(2-isopropoxyphenoxy)piperidin-1-yl)pyrazine (70 mg, 0.201 mmol) obtained in Preparation Example 73 and methyl 2-(4-(2-amino-2-oxoethyl)phenyl)acetate (50 mg, 0.241 mmol) obtained in Preparation Example 6 were used in a similar manner to Example 8 to obtain the desired product. (Yield: 77%)

m/z $(M+H)^+$ calculated for $C_{29}H_{34}N_4O_5$: 518.6, found 519.3

Step 2: (R)-2-(4-(2-((6-(3-(2-isopropoxyphenoxy)piperidin-1-yl)pyrazin-2-yl)amino)-2-oxoethyl)phenyl)acetic acid The ester compound obtained in Step 1 was hydrolyzed using 5 N aqueous sodium hydroxide solution in a similar manner to Step 2 of Example 2 to obtain the desired product. (Yield: 64%)

$^1$H NMR (500 MHz, CHLOROFORM-D) δ 8.67 (s, 1H), 7.93 (s, 1H), 7.74 (s, 1H), 7.33-7.21 (m, 3H), 7.01-6.85 (m, 4H), 4.4 (td, 1H), 4.25 (m, 1H), 4.02 (dd, 1H), 3.71 (qd, 3H), 3.65 (m, 2H), 3.39 (m, 1H), 3.31 (m, 1H), 2.12-2.05 (m, 1H), 2.03-1.85 (m, 2H), 1.61 (qd, J=8.7, 4.3 Hz, 1H), 1.32-1.18 (m, 6H)

Example 91: (R)-2-(4-(3-((6-(3-(2-methoxyphenoxy)piperidin-1-yl)pyrazin-2-yl)amino)-3-oxopropyl)phenyl)-2-methylpropanoic acid

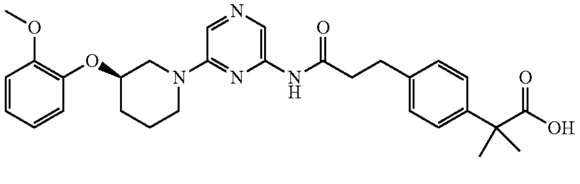 [SMILES: COc1ccccc1O[C@@H]1CCCN(c2cncc(NC(=O)CCc3ccc(C(C)(C)C(=O)O)cc3)n2)C1]

(R)-2-chloro-6-(3-(2-methoxyphenoxy)piperidin-1-yl)pyrazine (0.13 g, 0.40 mmol) obtained in Preparation Example 74 and methyl 2-(4-(3-amino-3-oxopropyl)phenyl-2-methylpropanoate (0.10 g, 0.40 mmol) obtained in Preparation Example 20 were used in a similar manner to Example 34 to obtain the desired product. (2 steps yield: 12%)

$^1$H-NMR (400 MHz, CHLOROFORM-D) δ 8.68 (s, 1H), 7.88 (s, 1H), 7.32 (t, J=8.7 Hz, 2H), 7.26-7.09 (m, 3H), 7.01-6.76 (m, 4H), 4.40-4.21 (m, 1H), 4.05 (d, J=13.3 Hz, 1H), 3.89-3.58 (m, 4H), 3.57-3.39 (m, 1H), 3.39-3.21 (m, 1H), 3.02 (t, J=7.3 Hz, 2H), 2.77-2.56 (2H), 2.16-2.06 (m, 1H), 2.03-1.78 (m, 2H), 1.72-1.46 (m, 7H)

Example 92: (R)-2-methyl-2-(4-(3-oxo-3-((6-(3-(2-(trifluoromethoxy)phenoxy)piperidin-1-yl)pyrazin-2-yl)amino)propyl)phenyl)propanoic acid

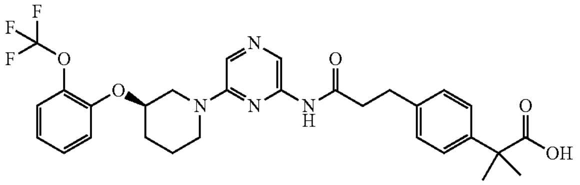 [SMILES: CC(C)(C(=O)O)c1ccc(CCC(=O)Nc2cncc(N3CCC[C@@H](Oc4ccccc4OC(F)(F)F)C3)n2)cc1]

(R)-2-chloro-6-(3-(2-(trifluoromethoxy)phenoxy)piperidin-1-yl)pyrazine (0.15 g, 0.40 mmol) obtained in Preparation Example 75 and methyl 2-(4-(3-amino-3-oxopropyl)phenyl-2-methylpropanoate (0.10 g, 0.40 mmol) obtained in Preparation Example 20 were used in a similar manner to Example 34 to obtain the desired product. (2 steps yield: 10%)

$^1$H-NMR (400 MHz, CHLOROFORM-D) δ 8.68 (s, 1H), 7.88 (s, 1H), 7.43 (s, 1H), 7.33 (d, J=8.2 Hz, 2H), 7.25-7.10 (m, 4H), 7.10-6.86 (m, 2H), 4.44-4.26 (m, 1H), 4.07 (dd, J=13.3, 2.7 Hz, 1H), 3.83-3.58 (m, 1H), 3.48 (dd, J=13.3, 7.8 Hz, 1H), 3.41-3.25 (m, 1H), 2.97 (dt, J=32.6, 7.9 Hz, 2H), 2.66 (t, J=7.5 Hz, 2H), 2.23-2.05 (m, 1H), 2.02-1.76 (m, 2H), 1.76-1.37 (m, 7H)

Example 93: (R)-2-(4-(3-((6-(3-(2-(2-fluoroethoxy)phenoxy)piperidin-1-yl)pyrazin-2-yl)amino)-3-oxopropyl)phenyl)-2-methylpropanoic acid

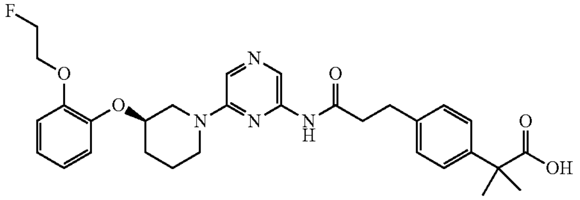 [SMILES: CC(C)(C(=O)O)c1ccc(CCC(=O)Nc2cncc(N3CCC[C@@H](Oc4ccccc4OCCF)C3)n2)cc1]

(R)-2-chloro-6-(3-(2-(2-fluoroethoxy)phenoxy)piperidin-1-yl)pyrazine (0.14 g, 0.40 mmol) obtained in Preparation Example 76 and methyl 2-(4-(3-amino-3-oxopropyl)phenyl-2-methylpropanoate (0.10 g, 0.40 mmol) obtained in Preparation Example 20 were used in a similar manner to Example 34 to obtain the desired product. (2 steps yield: 12%)

$^1$H-NMR (400 MHz, CHLOROFORM-D) δ 8.66 (s, 1H), 7.86 (s, 1H), 7.33 (d, J=8.2 Hz, 3H), 7.18 (dd, J=14.6, 8.2 Hz, 2H), 7.04-6.77 (m, 4H), 4.64 (dt, J=47.6, 4.1 Hz, 2H), 4.38-4.23 (m, 1H), 4.23-4.00 (m, 2H), 3.96 (dd, J=13.3, 2.7 Hz, 1H), 3.68-3.53 (m, 2H), 3.53-3.34 (m, 1H), 3.02 (t, J=7.5 Hz, 2H), 2.65 (t, J=7.5 Hz, 2H), 2.13-2.05 (m, 1H), 2.04-1.79 (m, 2H), 1.68-1.46 (m, 7H)

Example 94: (R)-3-(4-(2-((6-(3-(2-(2-fluoroethoxy) phenoxy)piperidin-1-yl)pyrazin-2-yl)amino)-2-oxo-ethyl)phenyl)-2,2-dimethylpropanoic acid

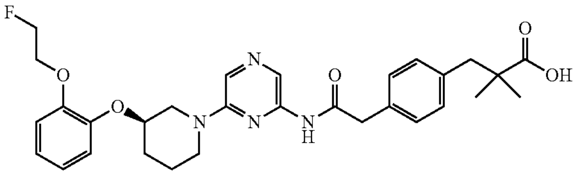 [SMILES: CC(C)(Cc1ccc(CC(=O)Nc2cncc(N3CCC[C@@H](Oc4ccccc4OCCF)C3)n2)cc1)C(=O)O]

(R)-2-chloro-6-(3-(2-(2-fluoroethoxy)phenoxy)piperidin-1-yl)pyrazine (0.080 g, 0.23 mmol) obtained in Preparation Example 76 and methyl 3-(4-(2-amino-2-oxoethyl)phenyl)-2,2-dimethylpropanoate (0.057 g, 0.23 mmol) obtained in Preparation Example 33 were used in a similar manner to Example 34 to obtain the desired product. (Yield: 39%)

$^1$H-NMR (400 MHz, CHLOROFORM-D): δ 8.65 (s, 1H), 7.83 (s, 1H), 7.56 (s, 1H), 7.23-7.08 (m, 4H), 6.99-6.82 (m, 4H), 4.69 (t, J=4.1 Hz, 1H), 4.58 (t, J=4.1 Hz, 1H), 4.30-4.21 (m, 1H), 4.20-3.99 (m, 2H), 3.94 (dd, J=13.0, 3.0 Hz, 1H), 3.66 (s, 2H), 3.64-3.57 (m, 1H), 3.52 (q, J=6.9 Hz, 1H), 3.42-3.30 (m, 1H), 2.91-2.81 (m, 2H), 2.12-2.05 (m, 1H), 1.99-1.78 (m, 2H), 1.53 (qd, J=8.6, 4.5 Hz, 1H), 1.22-1.13 (s, 6H)

Example 95: (R)-3-(4-(2-((6-(3-(2-cyclopropoxy-phenoxy)piperidin-1-yl)pyrazin-2-yl)amino)-2-oxo-ethyl)phenyl)-2,2-dimethylpropanoic acid

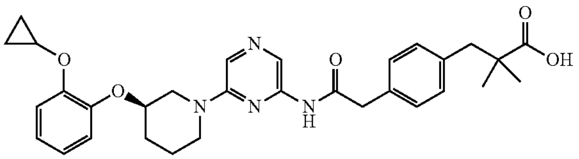 [SMILES: CC(C)(Cc1ccc(CC(=O)Nc2cncc(N3CCC[C@@H](Oc4ccccc4OC4CC4)C3)n2)cc1)C(=O)O]

(R)-2-chloro-6-(3-(2-cyclopropoxyphenoxy)piperidin-1-yl)pyrazine (0.14 g, 0.41 mmol) obtained in Preparation Example 77 and tert-butyl 3-(4-(2-amino-2-oxoethyl)phenyl)-2,2-dimethylpropanoate (0.12 g, 0.41 mmol) obtained in Preparation Example 63 were used in a similar manner to Example 72 to obtain the desired product. (Yield: 34%)

$^1$H-NMR (400 MHz, CHLOROFORM-D): δ 8.66 (s, 1H), 7.87-7.79 (m, 1H), 7.60 (s, 1H), 7.24-7.10 (m, 5H), 7.01-6.78 (m, 3H), 4.23-4.14 (m, 1H), 4.01-3.92 (m, 1H), 3.73-3.60 (m, 4H), 3.45-3.34 (m, 1H), 3.32-3.20 (m, 1H), 2.87 (t, J=14.0 Hz, 2H), 2.11-1.99 (m, 1H), 1.96-1.72 (m, 2H), 1.61-1.44 (m, 1H), 1.21-1.12 (m, 6H), 0.75-0.63 (m, 4H)

Example 96: (R)-3-(4-(2-((6-(3-(2-cyclobutoxyphenoxy)piperidin-1-yl)pyrazin-2-yl)amino)-2-oxoethyl) phenyl)-2,2-dimethylpropanoic acid

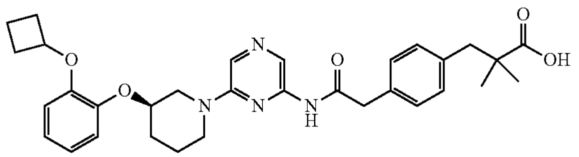 [SMILES: CC(C)(Cc1ccc(CC(=O)Nc2cncc(N3CCC[C@@H](Oc4ccccc4OC4CCC4)C3)n2)cc1)C(=O)O]

(R)-2-chloro-6-(3-(2-cyclobutoxyphenoxy)piperidin-1-yl)pyrazine (0.14 g, 0.39 mmol) obtained in Preparation Example 57 and tert-butyl 3-(4-(2-amino-2-oxoethyl)phenyl)-2,2-dimethylpropanoate (0.11 g, 0.39 mmol) obtained in Preparation Example 63 were used in a similar manner to Example 72 to obtain the desired product. (Yield: 59%)

$^1$H-NMR (400 MHz, CHLOROFORM-D): δ 8.66 (s, 1H), 7.86 (d, J=20.1 Hz, 1H), 7.65-7.47 (m, 1H), 7.18 (q, J=8.1 Hz, 4H), 6.97-6.84 (m, 2H), 6.84-6.74 (m, 1H), 6.71 (d, J=7.8 Hz, 1H), 4.53 (td, J=14.6, 7.6 Hz, 1H), 4.29-4.18 (m, 1H), 3.93 (dd, J=13.3, 3.2 Hz, 1H), 3.73-3.58 (m, 3H), 3.48 (dd, J=13.0, 7.5 Hz, 1H), 3.39-3.27 (m, 1H), 2.87 (t, J=14.2 Hz, 2H), 2.42-2.27 (m, 2H), 2.17-2.04 (m, 3H), 1.98-1.70 (m, 3H), 1.68-1.44 (m, 2H), 1.21-1.11 (m, 6H)

Example 97: (R)-2-(4-(3-((6-(3-(2-cyclopropoxy-phenoxy)piperidin-1-yl)pyrazin-2-yl)amino)-3-oxo-propyl)phenyl)-2-methylpropanoic acid

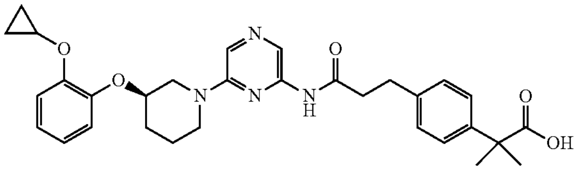 [SMILES: CC(C)(C(=O)O)c1ccc(CCC(=O)Nc2cncc(N3CCC[C@@H](Oc4ccccc4OC4CC4)C3)n2)cc1]

To benzyl (R,E)-2-(4-(3-((6-(3-(2-cyclopropoxyphenoxy) piperidin-1-yl)pyrazin-2-yl) amino)-3-oxoprop-1-en-1-yl) phenyl)-2-methylpropanoate obtained by using (R)-2-chloro-6-(3-(2-cyclopropoxyphenoxy)piperidin-1-yl) pyrazine (0.14 g, 0.41 mmol) obtained in Preparation Example 77 and benzyl (E)-2-(4-(3-amino-3-oxoprop-1-en-1-yl)phenyl)-2-methylpropanoate (0.13 g, 0.41 mmol) obtained in Preparation Example 65 in a similar manner to Example 8, methanol (1.82 mL) and palladium/carbon (12 mg) were added and stirred at room temperature for 4 hours while filling with hydrogen gas. The reaction mixture was filtered using a Celite, and the solvent was removed under reduced pressure. The purification was carried out by column chromatography to obtain the title compound. (Yield: 59%)

$^1$H-NMR (400 MHz, CHLOROFORM-D): δ 8.64 (s, 1H), 7.88-7.81 (m, 1H), 7.56-7.39 (m, 1H), 7.32 (d, J=8.2 Hz, 2H), 7.22-7.12 (m, 3H), 7.00-6.79 (m, 3H), 4.22 (s, 1H), 4.00-3.90 (m, 1H), 3.73-3.60 (m, 2H), 3.49 (ddd, J=13.0, 7.5, 2.7 Hz, 1H), 3.40-3.27 (m, 1H), 3.00 (t, J=7.3 Hz, 2H), 2.65 (t, J=7.5 Hz, 2H), 2.12-2.04 (m, 1H), 1.98-1.76 (m, 2H), 1.63-1.46 (m, 7H), 0.75-0.62 (m, 4H)

Example 98: (R)-2-(4-(3-((6-(3-(2-cyclobutoxyphenoxy)piperidin-1-yl)pyrazin-2-yl)amino)-3-oxopropyl)phenyl)-2-methylpropanoic acid

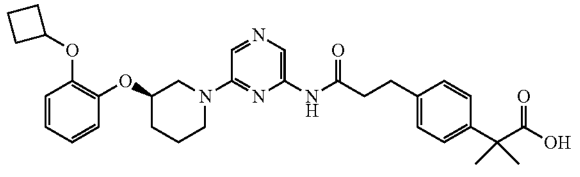 [SMILES: CC(C)(C(=O)O)c1ccc(CCC(=O)Nc2cncc(N3CCC[C@@H](Oc4ccccc4OC4CCC4)C3)n2)cc1]

(R)-2-chloro-6-(3-(2-cyclobutoxyphenoxy)piperidin-1-yl)pyrazine (0.14 g, 0.39 mmol) obtained in Preparation Example 57 and benzyl (E)-2-(4-(3-amino-3-oxoprop-1-en-1-yl)phenyl)-2-methylpropanoate (0.13 g, 0.39 mmol) obtained in Preparation Example 65 were used in a similar manner to Example 97 to obtain the desired product (Yield 53%)

$^1$H-NMR (400 MHz, CHLOROFORM-D): δ 8.64 (s, 1H), 7.88-7.81 (m, 1H), 7.46 (d, J=32.5 Hz, 1H), 7.32 (d, J=8.2 Hz, 2H), 7.20-7.12 (m, 2H), 6.94-6.78 (m, 3H), 6.69 (dd, J=7.8, 1.4 Hz, 1H), 4.55-4.45 (m, 1H), 4.32-4.22 (m, 1H), 3.92 (dd, J=13.3, 3.2 Hz, 1H), 3.71-3.52 (m, 2H), 3.45-3.33 (m, 1H), 3.05-2.94 (m, 2H), 2.70-2.58 (m, 2H), 2.44-2.27 (m, 2H), 2.17-2.04 (m, 3H), 2.01-1.70 (m, 3H), 1.69-1.47 (m, 8H)

Example 99: (R)-2-(4-(2-((6-(3-(2-ethoxyphenoxy)piperidin-1-yl)pyrazin-2-yl)amino-2-oxoethyl)phenoxy)acetic acid

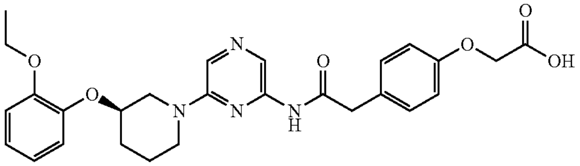 [SMILES: CCOc1ccccc1O[C@@H]1CCCN(c2cncc(NC(=O)Cc3ccc(OCC(=O)O)cc3)n2)C1]

(R)-2-chloro-6-(3-(2-ethoxyphenoxy)piperidin-1-yl)pyrazine (0.10 g, 0.30 mmol) obtained in Preparation Example 1 and tert-butyl 2-(4-(2-amino-2-oxoethyl)phenoxy)acetate (0.079 g, 0.30 mmol) obtained in Preparation Example 49 were used in a similar manner to Example 72 to obtain the desired product. (Yield: 72%)

$^1$H-NMR (400 MHz, METHANOL-D4): δ 8.42 (s, 1H), 7.71 (s, 1H), 7.23 (d, J=8.2 Hz, 2H), 6.97-6.78 (m, 6H), 4.58 (s, 2H), 4.40 (s, 1H), 4.00-3.66 (m, 4H), 3.62 (d, J=7.8 Hz, 3H), 3.58-3.46 (m, 1H), 2.08-1.78 (m, 3H), 1.63-1.48 (m, 1H), 1.21 (t, J=7.1 Hz, 3H)

Example 100: (R)-2-(4-(2-((6-(3-(2-ethoxyphenoxy)piperidin-1-yl)pyrazin-2-yl)amino)-2-oxoethoxy)phenyl)acetic acid

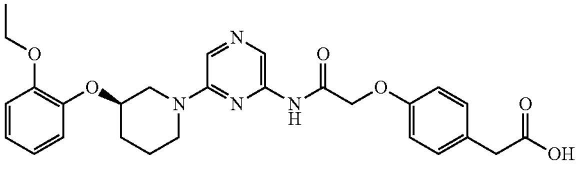

(R)-2-chloro-6-(3-(2-ethoxyphenoxy)piperidin-1-yl)pyrazine (0.15 g, 0.45 mmol) obtained in Preparation Example 1 and methyl 2-(4-(2-amino-2-oxoethoxy)phenyl)acetate (0.10 g, 0.45 mmol) obtained in Preparation Example 50 were used in a similar manner to Example 34 to obtain the desired product. (Yield: 35%)

$^1$H-NMR (400 MHz, CHLOROFORM-D): δ 8.71 (s, 1H), 8.37 (s, 1H), 7.93 (s, 1H), 7.28 (m, 2H), 7.04-6.88 (4H), 6.88-6.78 (m, 2H), 4.59 (s, 2H), 4.35-4.25 (m, 1H), 4.08-3.85 (m, 3H), 3.73 (m, 1H), 3.65-3.54 (m, 3H), 3.49-3.39 (m, 1H), 2.17-2.06 (m, 1H), 2.03-1.85 (m, 2H), 1.59 (m, 1H), 1.34 (q, J=7.3 Hz, 3H)

Example 101: 2-(4-(2-((6-((R)-3-(2-ethoxyphenoxy)piperidin-1-yl)pyrazin-2-yl)amino)-2-oxoethoxy)phenyl)propanoic acid

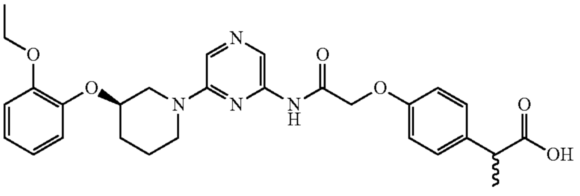 [SMILES: CCOc1ccccc1O[C@@H]1CCCN(c2cncc(NC(=O)COc3ccc(C(C)C(=O)O)cc3)n2)C1]

(R)-2-chloro-6-(3-(2-ethoxyphenoxy)piperidin-1-yl)pyrazine (0.70 g, 2.1 mmol) obtained in Preparation Example 1 and methyl 2-(4-(2-amino-2-oxoethoxy)phenyl)propanoate (0.50 g, 2.1 mmol) obtained in Preparation Example 51 were used in a similar manner to Example 34 to obtain the desired product. (Yield: 26%)

$^1$H-NMR (400 MHz, CHLOROFORM-D): δ 8.69 (s, 1H), 8.36 (s, 1H), 7.91 (s, 1H), 7.42-7.26 (m, 2H), 7.04-6.75 (m, 6H), 4.57 (s, 2H), 4.36-4.22 (m, 1H), 4.09-3.83 (m, 3H), 3.71 (q, J=7.2 Hz, 2H), 3.66-3.53 (m, 1H), 3.52-3.35 (m, 1H), 2.29-1.76 (m, 3H), 1.67-1.52 (m, 1H), 1.49 (d, J=6.9 Hz, 3H), 1.39-1.26 (m, 3H)

Example 102: (R)-3-(4-(2-((6-(3-(2-ethoxyphenoxy)piperidin-1-yl)pyrazin-2-yl)amino)-2-oxoethyl)phenoxy-2,2-dimethylpropanoic acid

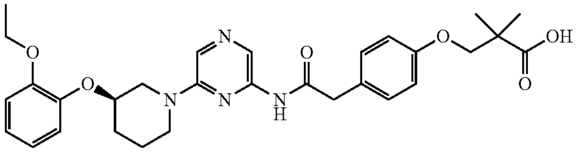 [SMILES: CCOc1ccccc1O[C@@H]1CCCN(c2cncc(NC(=O)Cc3ccc(OCC(C)(C)C(=O)O)cc3)n2)C1]

(R)-2-chloro-6-(3-(2-ethoxyphenoxy)piperidin-1-yl)pyrazine (0.12 g, 0.36 mmol) prepared in Preparation Example 1 and methyl 3-(4-(2-amino-2-oxoethyl)phenoxy)-2,2-dimethylpropanoate (0.095 g, 0.36 mmol) obtained in Preparation Example 52 were used in a similar manner to Example 34 to obtain the desired product. (Yield: 38%)

$^1$H-NMR (400 MHz, CHLOROFORM-D): δ 8.65 (s, 1H), 7.84 (s, 1H), 7.38-7.27 (1H), 7.19 (d, J=8.7 Hz, 2H), 6.99-6.76 (m, 6H), 4.29-4.20 (m, 1H), 4.01-3.86 (m, 5H), 3.71-3.59 (m, 3H), 3.51 (dd, J=13.0, 7.5 Hz, 1H), 3.40-3.28 (m, 1H), 2.13-2.04 (m, 1H), 2.00-1.80 (m, 2H), 1.61-1.47 (m, 1H), 1.32 (t, J=6.6 Hz, 9H)

Example 103: (R)-2-(4-(2-((6-((R)-3-(2-ethoxyphenoxy)piperidin-1-yl)pyrazin-2-yl)amino)-2-oxoethyl)phenoxy)propanoic acid

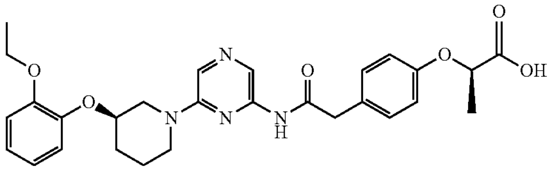 [SMILES: CCOc1ccccc1O[C@@H]1CCCN(c2cncc(NC(=O)Cc3ccc(O[C@H](C)C(=O)O)cc3)n2)C1]

(R)-2-chloro-6-(3-(2-ethoxyphenoxy)piperidin-1-yl) pyrazine (0.18 g, 0.54 mmol) obtained in Preparation Example 1 and ethyl (R)-2-(4-(2-amino-2-oxoethyl)phenoxy)propanoate (0.14 g, 0.54 mmol) obtained in Preparation Example 53 were used in a similar manner to Example 34 to obtain the desired product. (Yield: 24%)

$^1$H-NMR (400 MHz, METHANOL-D4): δ 8.42 (s, 1H), 7.71 (s, 1H), 7.21 (d, J=8.7 Hz, 2H), 6.99-6.77 (m, 6H), 4.69 (q, J=6.7 Hz, 1H), 4.39 (dd, J=8.5, 3.4 Hz, 1H), 3.95-3.70 (m, 5H), 3.60 (s, 2H), 3.56-3.45 (m, 1H), 2.07-1.82 (m, 3H), 1.53 (d, J=6.9 Hz, 4H), 1.21 (t, J=7.1 Hz, 3H)

Example 104: (S)-2-(4-(2-((6-((R)-3-(2-ethoxyphenoxy)piperidin-1-yl)pyrazin-2-yl)amino)-2-oxoethyl) phenoxy)propanoic acid

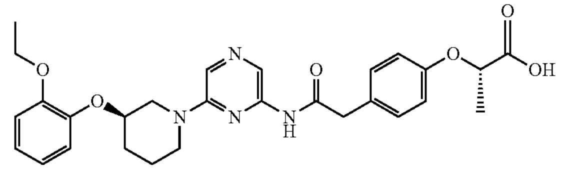 [SMILES: CCOc1ccccc1O[C@@H]1CCCN(c2cncc(NC(=O)Cc3ccc(O[C@@H](C)C(=O)O)cc3)n2)C1]

(R)-2-chloro-6-(3-(2-ethoxyphenoxy)piperidin-1-yl) pyrazine (0.354 g, 1.061 mmol) obtained in Preparation Example 1 and methyl (S)-2-(4-(2-amino-2-oxoethyl)phenoxy)propanoate (0.277 g, 1.168 mmol) obtained in Preparation Example 54 were used in a similar manner to Example 34 to obtain the desired product. (2 steps yield: 3.7%)

1H-NMR (CHLOROFORM-D) δ 8.61 (s, 1H), 7.85 (s, 1H), 7.42 (d, J=8.2 Hz, 1H), 7.25-7.15 (2H), 7.01-6.88 (m, 4H), 6.88-6.77 (m, 2H), 4.78 (q, J=6.8 Hz, 1H), 4.28 (td, J=7.2, 3.8 Hz, 1H), 4.01-3.82 (m, 3H), 3.72-3.49 (m, 4H), 3.46-3.31 (m, 1H), 2.09-2.05 (m, 1H), 1.96 (td, J=6.7, 3.4 Hz, 1H), 1.91-1.80 (m, 1H), 1.68 (d, J=6.7 Hz, 3H), 1.61-1.47 (1H), 1.37-1.29 (3H)

Example 105: (R)-2-(4-(2-((6-(3-((3-ethoxypyridin-2-yl)oxy)piperidin-1-yl)pyrazin-2-yl)amino)-2-oxoethyl)phenoxy)-2-methylpropanoic acid

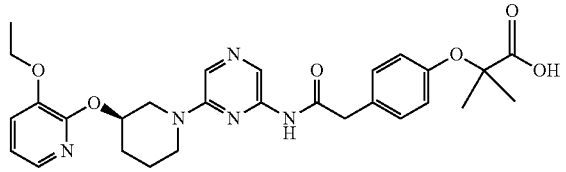 [SMILES: CCOc1cccnc1O[C@@H]1CCCN(c2cncc(NC(=O)Cc3ccc(OC(C)(C)C(=O)O)cc3)n2)C1]

(R)-2-chloro-6-(3-((3-ethoxypyridin-2-yl)oxy)piperidin-1-yl)pyrazine (0.060 g, 0.18 mmol) obtained in Preparation Example 70 and ethyl 2-(4-(2-amino-2-oxoethyl)phenoxy)-2-methylpropanoate (0.048 g, 0.18 mmol) obtained in Preparation Example 55 were used in a similar manner to Example 34 to obtain the desired product. (Yield: 29%)

$^1$H-NMR (400 MHz, CHLOROFORM-D): δ 8.56 (s, 1H), 7.85 (s, 1H), 7.70-7.66 (m, 1H), 7.35 (d, J=13.3 Hz, 1H), 7.21-7.11 (m, 2H), 6.98-6.87 (m, 3H), 6.79-6.75 (m, 1H), 5.15-5.05 (m, 1H), 3.93-3.71 (m, 4H), 3.61 (d, J=11.0 Hz, 3H), 3.50-3.39 (m, 1H), 2.14-2.04 (m, 1H), 1.92 (t, J=5.0 Hz, 2H), 1.60 (s, 7H), 1.25 (t, J=7.0 Hz, 3H)

Example 106: (R)-2-(4-(2-((2-(3-(2-ethoxyphenoxy) piperidin-1-yl)pyrimidin-4-yl)amino)-2-oxoethyl) phenoxy)-2-methylpropanoic acid

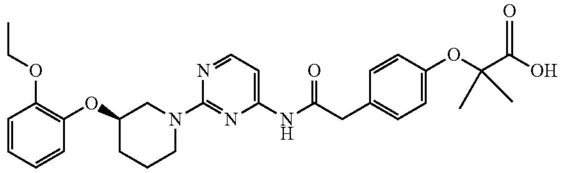 [SMILES: CCOc1ccccc1O[C@@H]1CCCN(c2nccc(NC(=O)Cc3ccc(OC(C)(C)C(=O)O)cc3)n2)C1]

(R)-4-chloro-2-(3-(2-ethoxyphenoxy)piperidin-1-yl)pyrimidine (0.060 g, 0.18 mmol) obtained in Preparation Example 68 and ethyl 2-(4-(2-amino-2-oxoethyl)phenoxy)-2-methylpropanoate (0.048 g, 0.18 mmol) obtained in Preparation Example 55 were used in a similar manner to Example 34 to obtain the desired product. (Yield: 29%)

$^1$H-NMR (400 MHz, CHLOROFORM-D): δ 8.18 (d, J=5.5 Hz, 1H), 7.68 (s, 1H), 7.34-7.21 (m, 1H), 7.11 (d, J=6.4 Hz, 2H), 7.04-6.77 (m, 6H), 4.41-4.13 (m, 2H), 4.09-3.85 (m, 3H), 3.58 (s, 2H), 3.55-3.44 (m, 1H), 3.44-3.30 (m, 1H), 2.12-1.99 (m, 1H), 1.95-1.74 (m, 2H), 1.67-1.40 (m, 7H), 1.35 (t, J=7.2 Hz, 3H)

Example 107: (R)-2-(4-((4-(2-((6-(3-(2-ethoxyphenoxy)piperidin-1-yl)pyrazin-2-yl)amino)-2-oxoethyl) phenoxy)methyl)phenyl)-2-methylpropanoic acid

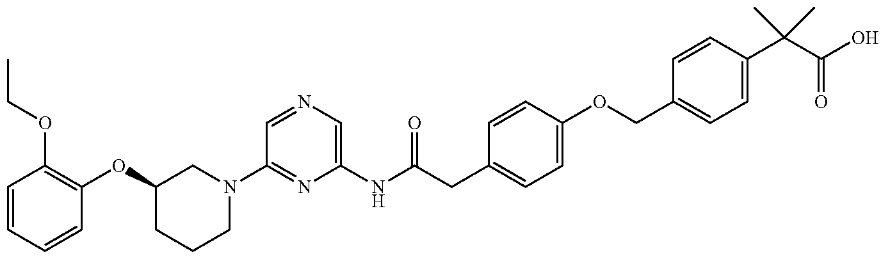 [SMILES: CCOc1ccccc1O[C@@H]1CCCN(c2cncc(NC(=O)Cc3ccc(OCc4ccc(C(C)(C)C(=O)O)cc4)cc3)n2)C1]

(R)-2-chloro-6-(3-(2-ethoxyphenoxy)piperidin-1-yl) pyrazine (0.18 g, 0.54 mmol) obtained in Preparation Example 1 and methyl 2-(4-((4-(2-amino-2-oxoethyl)phenoxy)methyl)phenyl)-2-methylpropanoate (0.18 g, 0.54 mmol) obtained in Preparation Example 56 were used in a similar manner to Example 34 to obtain the desired product. (Yield: 39%)

$^1$H-NMR (400 MHz, METHANOL-D4): δ 8.42 (s, 1H), 7.71 (s, 1H), 7.41-7.30 (m, 4H), 7.21 (d, J=8.7 Hz, 2H), 7.18-7.11 (m, 1H), 6.95-6.76 (m, 5H), 5.01 (s, 2H), 4.43-4.34 (m, 1H), 4.01-3.68 (m, 5H), 3.60 (s, 2H), 3.55-3.49 (m, 1H), 2.08-1.80 (m, 3H), 1.58-1.45 (m, 7H), 1.24-1.15 (m, 3H)

Example 108: (R)-2-(4-(3-((6-(3-((3-ethoxypyridin-2-yl)oxy)piperidin-1-yl)pyrazin-2-yl)amino)-3-oxopropyl)phenoxy)-2-methylpropanoic acid

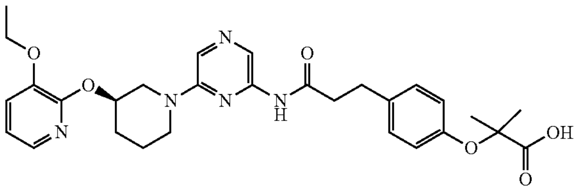 [SMILES: CCOc1cccnc1O[C@@H]1CCCN(c2cncc(NC(=O)CCc3ccc(OC(C)(C)C(=O)O)cc3)n2)C1]

(R)-2-chloro-6-(3-((3-ethoxypyridin-2-yl)oxy)piperidin-1-yl)pyrazine (0.050 g, 0.15 mmol) obtained in Preparation Example 70 and ethyl 2-(4-(3-amino-3-oxopropyl)phenoxy)-2-methylpropanoate (0.042 g, 0.15 mmol) obtained in Preparation Example 28 were used in a similar manner to Example 34 to obtain the desired product. (Yield: 34%)

$^1$H-NMR (400 MHz, CHLOROFORM-D): δ 8.57 (s, 1H), 7.85 (s, 1H), 7.69 (dd, J=5.0, 1.4 Hz, 1H), 7.18 (d, J=5.5 Hz, 1H), 7.08 (d, J=8.2 Hz, 2H), 6.86 (t, J=8.5 Hz, 3H), 6.74 (dd, J=7.8, 5.0 Hz, 1H), 5.19-5.08 (m, 1H), 3.91-3.71 (m, 4H), 3.66-3.44 (m, 2H), 3.04-2.86 (m, 2H), 2.58 (dd, J=7.3, 5.5 Hz, 2H), 2.08 (dd, J=9.6, 3.7 Hz, 1H), 2.02-1.87 (m, 2H), 1.68-1.47 (m, 7H), 1.24 (t, J=7.1, 3H)

Example 109: (R)-2-(4-(3-((2-(3-(2-ethoxyphenoxy)piperidin-1-yl)pyrimidin-4-yl)amino)-3-oxopropyl)phenoxy)-2-methylpropanoic acid

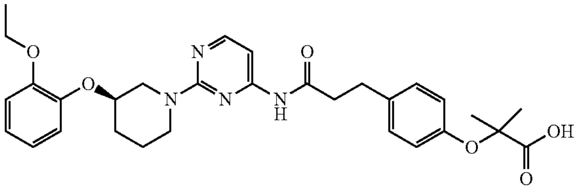 [SMILES: CCOc1ccccc1O[C@@H]1CCCN(c2nccc(NC(=O)CCc3ccc(OC(C)(C)C(=O)O)cc3)n2)C1]

(R)-4-chloro-2-(3-(2-ethoxyphenoxy)piperidin-1-yl)pyrimidine (0.050 g, 0.15 mmol) obtained in Preparation Example 68 and ethyl 2-(4-(3-amino-3-oxopropyl)phenoxy)-2-methylpropanoate (0.042 g, 0.15 mmol) obtained in Preparation Example 28 were used in a similar manner to Example 34 to obtain the desired product. (Yield: 34%)

$^1$H-NMR (400 MHz, CHLOROFORM-D): δ 8.19 (d, J=5.9 Hz, 1H), 7.61-7.48 (m, 1H), 7.30-7.20 (m, 1H), 7.11-6.74 (m, 8H), 4.32-4.09 (m, 2H), 4.07-3.86 (m, 3H), 3.68-3.52 (m, 1H), 3.53-3.19 (m, 1H), 2.92 (t, J=7.3 Hz, 2H), 2.59 (t, J=7.3 Hz, 2H), 2.18-2.04 (m, 1H), 1.98-1.75 (m, 2H), 1.52 (s, 7H), 1.35 (t, J=7.1, 3H)

Example 110: (R)-3-(4-(1-((6-(3-(2-ethoxyphenoxy)piperidin-1-yl)pyrazin-2-yl)amino)-2-methyl-1-oxopropan-2-yl)phenyl)-2,2-dimethylpropanoic acid

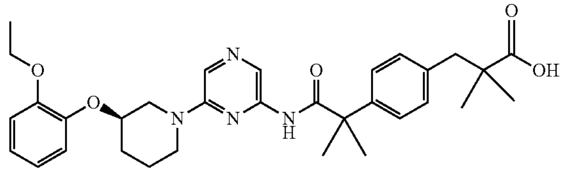 [SMILES: CCOc1ccccc1O[C@@H]1CCCN(c2cncc(NC(=O)C(C)(C)c3ccc(CC(C)(C)C(=O)O)cc3)n2)C1]

(R)-2-chloro-6-(3-(2-ethoxyphenoxy)piperidin-1-yl) pyrazine (0.50 g, 1.50 mmol) obtained in Preparation Example 1 and tert-butyl 3-(4-(1-amino-2-methyl-1-oxopropan-2-yl)phenyl)-2,2-dimethylpropanoate (0.48 g, 1.50 mmol) obtained in Preparation Example 59 were used in a similar manner to Example 72 to obtain the desired product. (Yield: 49%)

$^1$H-NMR (400 MHz, CHLOROFORM-D): δ 8.68 (d, J=10.5 Hz, 1H), 7.80 (s, 1H), 7.29 (d, J=8.2 Hz, 2H), 7.18 (d, J=8.2 Hz, 2H), 7.04 (s, 1H), 6.95-6.72 (m, 4H), 4.21 (t, J=3.0 Hz, 1H), 4.01-3.77 (m, 3H), 3.58 (td, J=9.7, 3.7 Hz, 1H), 3.47 (dd, J=13.0, 7.5 Hz, 1H), 3.38-3.26 (m, 1H), 2.87 (s, 2H), 2.08-1.96 (m, 1H), 1.96-1.74 (m, 2H), 1.63 (t, J=6.4 Hz, 6H), 1.56-1.41 (m, 1H), 1.30 (t, J=7.1 Hz, 3H), 1.16 (s, 6H)

Example 111: (R)-2-(4-(3-((6-(3-(2-ethoxyphenoxy)piperidin-1-yl)pyrazin-2-yl)amino)-2,2-dimethyl-3-oxopropyl)phenyl)-2-methylpropanoic acid

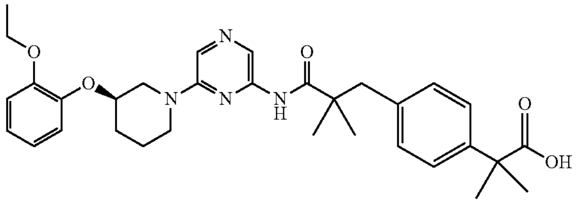 [SMILES: CCOc1ccccc1O[C@@H]1CCCN(c2cncc(NC(=O)C(C)(C)Cc3ccc(C(C)(C)C(=O)O)cc3)n2)C1]

(R)-2-chloro-6-(3-(2-ethoxyphenoxy)piperidin-1-yl) pyrazine (0.50 g, 1.50 mmol) obtained in Preparation Example 1 and methyl 2-(4-(3-amino-2,2-dimethyl-3-oxopropyl)phenyl)-2-methylpropanoate (0.48 g, 1.50 mmol) obtained in Preparation Example 58 were used in a similar manner to Example 34 to obtain the desired product. (Yield: 54%)

$^1$H-NMR (400 MHz, CHLOROFORM-D): δ 8.70 (s, 1H), 7.86 (s, 1H), 7.36-7.22 (m, 3H), 7.09 (d, J=8.7 Hz, 2H), 6.97-6.71 (m, 4H), 4.33-4.23 (m, 1H), 4.00-3.82 (m, 3H), 3.70-3.55 (m, 2H), 3.43 (t, J=9.1 Hz, 1H), 2.88 (dd, J=24.2, 13.3 Hz, 2H), 2.12-1.80 (m, 3H), 1.59-1.47 (m, 7H), 1.35-1.21 (m, 9H)

Example 112: (R)-3-(4-(2-((2-(3-(2-ethoxyphenoxy)piperidin-1-yl)pyrimidin-4-yl)amino)-2-oxoethyl)phenyl)-2,2-dimethylpropanoic acid

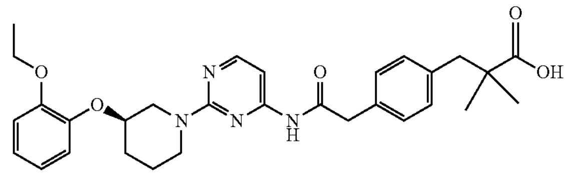 [SMILES: CCOc1ccccc1O[C@@H]1CCCN(c2nccc(NC(=O)Cc3ccc(CC(C)(C)C(=O)O)cc3)n2)C1]

(R)-4-chloro-2-(3-(2-ethoxyphenoxy)piperidin-1-yl)pyrimidine (1.35 g, 4.04 mmol) obtained in Preparation Example 68 and tert-butyl 3-(4-(2-amino-2-oxoethyl)phenyl)-2,2-dimethylpropanoate (1.07 g, 3.67 mmol) obtained in Preparation Example 63 were used in a similar manner to Example 72 to obtain the desired product. (Yield: 67%)

$^1$H-NMR (400 MHz, METHANOL-D4): δ 8.09 (d, J=5.5 Hz, 1H), 7.29-7.16 (m, 3H), 7.13 (d, J=8.2 Hz, 2H), 7.04-6.74 (m, 4H), 4.39-4.22 (m, 1H), 4.12 (dd, J=13.5, 3.4 Hz, 1H), 4.00-3.81 (m, 3H), 3.75 (q, J=6.7 Hz, 1H), 3.69-3.55 (m, 3H), 2.82 (s, 2H), 2.11-2.00 (m, 1H), 1.96-1.76 (m, 2H), 1.61-1.42 (m, 1H), 1.32-1.23 (m, 3H), 1.12 (s, 6H)

Example 113: (R)-3-(4-(2-((4-(3-(2-ethoxyphenoxy)piperidin-1-yl)pyrimidin-2-yl)amino)-2-oxoethyl)phenyl)-2,2-dimethylpropanoic acid

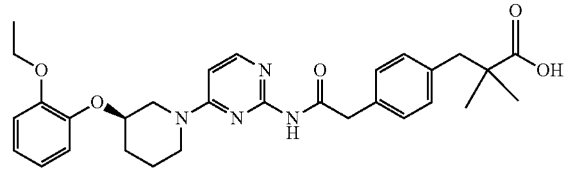 [SMILES: CCOc1ccccc1O[C@@H]1CCCN(c2ccnc(NC(=O)Cc3ccc(CC(C)(C)C(=O)O)cc3)n2)C1]

(R)-2-chloro-4-(3-(2-ethoxyphenoxy)piperidin-1-yl)pyrimidine (0.18 g, 0.54 mmol) obtained in Preparation Example 69 and tert-butyl 3-(4-(2-amino-2-oxoethyl)phenyl)-2,2-dimethylpropanoate (0.16 g, 0.54 mmol) obtained in Preparation Example 63 were used in a similar manner to Example 72 to obtain the desired product. (Yield: 59%)

$^1$H-NMR (400 MHz, METHANOL-D4): δ 7.77 (d, J=64.5 Hz, 1H), 7.22 (d, J=7.3 Hz, 2H), 7.15 (d, J=7.8 Hz, 2H), 6.99-6.44 (m, 5H), 4.64 (s, 1H), 4.33-3.31 (m, 8H), 2.83 (s, 2H), 2.10-1.85 (m, 3H), 1.65 (s, 1H), 1.30-1.14 (m, 3H), 1.12 (s, 6H)

Example 114: (R)-3-(4-(2-((4-(3-((3-ethoxypyridin-2-yl)oxy)piperidin-1-yl)pyrimidin-2-yl)amino)-2-oxoethyl)phenyl)-2,2-dimethylpropanoic acid

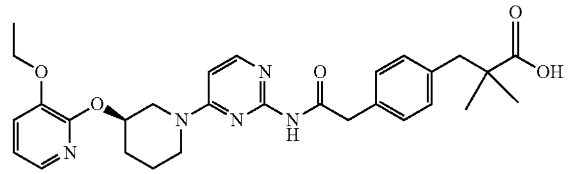 [SMILES: CCOc1cccnc1O[C@@H]1CCCN(c2ccnc(NC(=O)Cc3ccc(CC(C)(C)C(=O)O)cc3)n2)C1]

(R)-2-chloro-4-(3-((3-ethoxypyridin-2-yl)oxy)piperidin-1-yl)pyrimidine (0.18 g, 0.54 mmol) obtained in Preparation Example 66 and tert-butyl 3-(4-(2-amino-2-oxoethyl)phenyl)-2,2-dimethylpropanoate (0.16 g, 0.54 mmol) obtained in Preparation Example 63 were used in a similar manner to Example 72 to obtain the desired product. (Yield: 42%)

$^1$H-NMR (400 MHz, METHANOL-D4): δ 8.06-7.51 (m, 2H), 7.29-7.07 (m, 5H), 7.02-6.46 (m, 2H), 5.35 (d, J=44.8 Hz, 1H), 4.65-3.49 (m, 8H), 2.83 (s, 2H), 2.06 (s, 3H), 1.71 (s, 1H), 1.14 (t, J=6.6 Hz, 9H)

Example 115: (R)-3-(4-(2-((2-(3-((3-ethoxypyridin-2-yl)oxy)piperidin-1-yl)pyrimidin-4-yl)amino)-2-oxoethyl)phenyl)-2,2-dimethylpropanoic acid

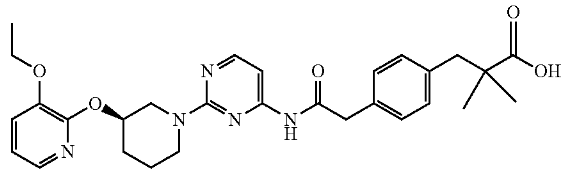 [SMILES: CCOc1cccnc1O[C@@H]1CCCN(c2nccc(NC(=O)Cc3ccc(CC(C)(C)C(=O)O)cc3)n2)C1]

Using (R)-3-ethoxy-2-(piperidin-3-yloxy)pyridine hydrochloride (0.40 g, 1.55 mmol) obtained in Step 3 of Preparation Example 70 and tert-butyl 3-(4-(2-((2-chloropyrimidin-4-yl)amino)-2-oxoethyl)phenyl)-2,2-dimethylpropanoate (0.62 g, 1.55 mmol) obtained in Preparation Example 67, the methods of Step 3 of Preparation Example 1 and Step 2 of Example 88 were sequentially preformed to obtain the desired product. (Yield: 63%)

$^1$H-NMR (400 MHz, CHLOROFORM-D): δ 8.15 (d, J=5.5 Hz, 1H), 7.74 (dd, J=5.0, 1.4 Hz, 1H), 7.49 (s, 1H), 7.28-7.00 (m, 5H), 6.96 (dd, J=7.5, 1.6 Hz, 1H), 6.82-6.69 (m, 1H), 5.09 (s, 1H), 4.01-3.47 (m, 8H), 2.99-2.70 (m, 2H), 2.12-1.83 (m, 3H), 1.64-1.56 (m, 1H), 1.33-1.09 (m, 9H)

Example 116: (R)-3-(4-(2-((6-(3-((3-ethoxypyridin-2-yl)oxy)piperidin-1-yl)pyrazin-2-yl)amino)-2-oxoethyl)phenyl)-2,2-dimethylpropanoic acid

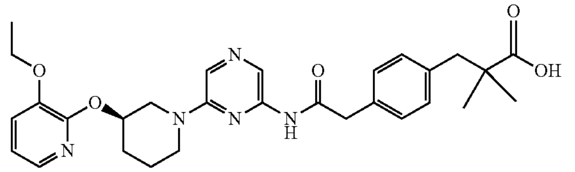 [SMILES: CCOc1cccnc1O[C@@H]1CCCN(c2cncc(NC(=O)Cc3ccc(CC(C)(C)C(=O)O)cc3)n2)C1]

(R)-2-chloro-6-(3-((3-ethoxypyridin-2-yl)oxy)piperidin-1-yl)pyrazine (1.50 g, 4.48 mmol) obtained in Preparation Example 70 and tert-butyl 3-(4-(2-amino-2-oxoethyl)phenyl)-2,2-dimethylpropanoate (1.31 g, 4.48 mmol) obtained in Preparation Example 63 were used in a similar manner to Example 72 to obtain the desired product. (Yield: 52%)

$^1$H-NMR (400 MHz, CHLOROFORM-D): δ 8.60 (s, 1H), 7.86 (s, 1H), 7.77-7.70 (m, 1H), 7.30 (s, 1H), 7.18 (s, 4H), 6.96 (dd, J=7.8, 1.4 Hz, 1H), 6.78 (dd, J=7.5, 5.3 Hz, 1H), 5.11 (td, J=6.4, 3.2 Hz, 1H), 3.97-3.77 (m, 3H), 3.72 (d, J=12.3 Hz, 1H), 3.64 (s, 2H), 3.61-3.42 (m, 2H), 2.99-2.89 (m, 1H), 2.82 (d, J=13.3 Hz, 1H), 2.13-1.87 (m, 3H), 1.69-1.53 (m, 1H), 1.27 (t, J=7.1 Hz, 3H), 1.20 (d, J=12.8 Hz, 6H)

Example 117: (R)-4-(3-((6-(3-(2-ethoxyphenoxy)piperidin-1-yl)pyrazin-2-yl)amino)-3-oxopropyl)bicyclo[2.2.2]octane-1-carboxylic acid

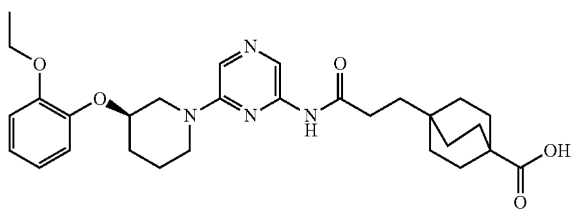 [SMILES: CCOc1ccccc1O[C@@H]1CCCN(c2cncc(NC(=O)CCC34CCC(C(=O)O)(CC3)CC4)n2)C1]

(R)-2-chloro-6-(3-(2-ethoxyphenoxy)piperidin-1-yl)pyrazine (0.20 g, 0.60 mmol) obtained in Preparation Example 1 and benzyl (E)-4-(3-amino-3-oxoprop-1-en-1-yl)bicyclo[2.2.2]octane-1-carboxylate (0.19 g, 0.60 mmol) obtained in Preparation Example 60 were used in a similar manner to Example 97 to obtain the desired product. (Yield: 45%)

$^1$H-NMR (400 MHz, CHLOROFORM-D): δ 8.64 (s, 1H), 7.86 (s, 1H), 7.28 (s, 1H), 6.99-6.82 (m, 4H), 4.36-4.24 (m, 1H), 4.05-3.87 (m, 3H), 3.77-3.65 (m, 1H), 3.60 (q, J=6.9 Hz, 1H), 3.47-3.35 (m, 1H), 2.27 (t, J=8.5 Hz, 2H), 2.17-2.05 (m, 1H), 2.01-1.85 (m, 2H), 1.81 (t, J=7.8 Hz, 6H), 1.68-1.50 (m, 3H), 1.42 (t, J=7.8 Hz, 6H), 1.36 (t, J=7.0, 3H)

Example 118: (R)-4-(2-((6-(3-(2-ethoxyphenoxy)piperidin-1-yl)pyrazin-2-yl)amino)-2-oxoethyl)bicyclo[2.2.2]octane-1-carboxylic acid

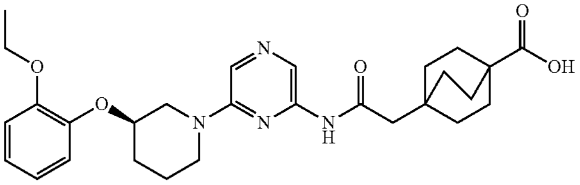 [SMILES: CCOc1ccccc1O[C@@H]1CCCN(c2cncc(NC(=O)CC34CCC(C(=O)O)(CC3)CC4)n2)C1]

(R)-2-chloro-6-(3-(2-ethoxyphenoxy)piperidin-1-yl)pyrazine (0.50 g, 1.50 mmol) obtained in Preparation Example 1 and methyl 4-(2-amino-2-oxoethyl)bicyclo[2.2.2]octane-1-carboxylate (0.48 g, 1.50 mmol) obtained in Preparation Example 61 were used in a similar manner to Example 34 to obtain the desired product. (Yield: 47%)

$^1$H-NMR (400 MHz, CHLOROFORM-D): δ 8.67 (d, J=7.3 Hz, 1H), 7.86 (s, 1H), 7.14 (s, 1H), 7.00-6.92 (m, 2H), 6.89-6.83 (m, 2H), 4.33-4.24 (m, 1H), 4.05-3.91 (m, 3H), 3.79-3.68 (m, 1H), 3.63 (s, 2H), 3.55 (dd, J=13.3, 7.8 Hz, 1H), 3.44-3.34 (m, 1H), 2.16-2.07 (m, 1H), 2.02-1.92 (m, 1H), 1.92-1.85 (m, 1H), 1.85-1.75 (m, 6H), 1.67-1.56 (m, 7H), 1.36 (td, J=6.9, 2.7 Hz, 3H)

Example 119: (R)-4-(3-((2-(3-(2-ethoxyphenoxy)piperidin-1-yl)pyrimidin-4-yl)amino)-3-oxopropyl)bicyclo[2.2.2]octane-1-carboxylic acid

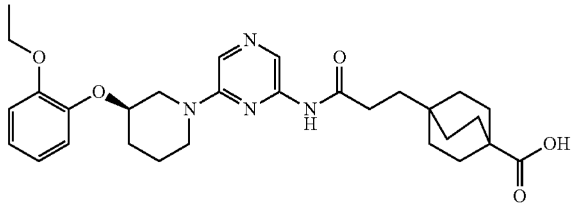 [SMILES: CCOc1ccccc1O[C@@H]1CCCN(c2cncc(NC(=O)CCC34CCC(C(=O)O)(CC3)CC4)n2)C1]

(R)-4-chloro-2-(3-(2-ethoxyphenoxy)piperidin-1-yl)pyrimidine (0.20 g, 0.60 mmol) obtained in Preparation Example 68 and benzyl (E)-4-(3-amino-3-oxoprop-1-en-1-yl)bicyclo[2.2.2]octane-1-carboxylate (0.19 g, 0.60 mmol) obtained in Preparation Example 60 were used in a similar manner to Example 97 to obtain the desired product. (Yield: 24%)

$^1$H-NMR (400 MHz, CHLOROFORM-D): δ 8.20 (d, J=5.5 Hz, 1H), 7.66 (s, 1H), 7.26 (s, 1H), 7.01-6.81 (m, 4H), 4.36-4.20 (m, 2H), 4.06-3.88 (m, 3H), 3.58 (dd, J=12.8, 7.8 Hz, 1H), 3.50-3.39 (m, 1H), 2.29-2.17 (m, 2H), 2.11 (q, J=4.9 Hz, 1H), 1.97-1.82 (m, 2H), 1.82-1.72 (m, 6H), 1.60-1.47 (m, 3H), 1.46-1.30 (m, 9H)

Example 120: (R)-4-(3-((6-(3-((3-ethoxypyridin-2-yl)oxy)piperidin-1-yl)pyrazin-2-yl)amino)-3-oxopropyl)bicyclo[2.2.2]octane-1-carboxylic acid

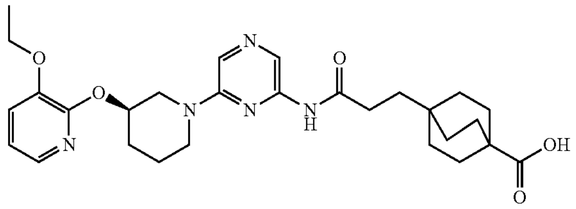 [SMILES: CCOc1cccnc1O[C@@H]1CCCN(c2cncc(NC(=O)CCC34CCC(C(=O)O)(CC3)CC4)n2)C1]

(R)-2-chloro-6-(3-((3-ethoxypyridin-2-yl)oxy)piperidin-1-yl)pyrazine (0.20 g, 0.60 mmol) obtained in Preparation Example 70 and benzyl (E)-4-(3-amino-3-oxoprop-1-en-1-yl)bicyclo[2.2.2]octane-1-carboxylate (0.19 g, 0.60 mmol) obtained in Preparation Example 60 were used in a similar manner to Example 97 to obtain the desired product. (Yield: 41%)

$^1$H-NMR (400 MHz, CHLOROFORM-D): δ 8.60 (s, 1H), 7.88 (s, 1H), 7.71 (q, J=2.3 Hz, 1H), 7.21 (s, 1H), 7.03-6.94 (m, 1H), 6.79 (dd, J=7.5, 4.8 Hz, 1H), 5.23-5.12 (m, 1H), 4.00-3.76 (m, 4H), 3.75-3.69 (m, 1H), 3.56-3.44 (m, 1H), 2.24 (t, J=8.2 Hz, 2H), 2.15 (qd, J=9.2, 4.5 Hz, 1H), 2.02-1.90 (m, 2H), 1.87-1.73 (m, 6H), 1.70-1.59 (m, 1H), 1.58-1.49 (m, 2H), 1.45-1.39 (m, 6H), 1.31 (t, J=6.8 Hz, 3H)

Example 121: (R,E)-4-(3-((6-(3-(2-ethoxyphenoxy)piperidin-1-yl)pyrazin-2-yl)amino)-3-oxoprop-1-en-1-yl)bicyclo[2.2.2]octane-1-carboxylic acid

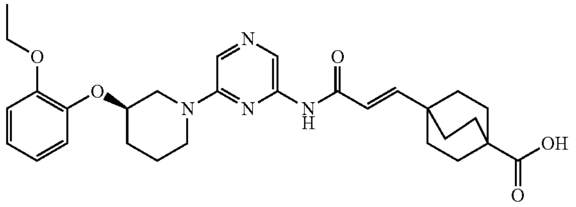 [SMILES: CCOc1ccccc1O[C@@H]1CCCN(c2cncc(NC(=O)/C=C/C34CCC(C(=O)O)(CC3)CC4)n2)C1]

The title compound was obtained as a by-product in the course of the preparation of Example 117.

$^{1}$H-NMR (400 MHz, CHLOROFORM-D): 8.72 (s, 1H), 7.88 (d, J=7.8 Hz, 1H), 6.99-6.90 (m, 3H), 6.90-6.81 (m, 3H), 5.74 (d, J=15.6 Hz, 1H), 4.37-4.27 (m, 1H), 4.03-3.86 (m, 3H), 3.75-3.67 (m, 1H), 3.63 (q, J=6.9 Hz, 1H), 3.49-3.38 (m, 1H), 2.16-2.05 (m, 1H), 2.02-1.77 (m, 7H), 1.70-1.53 (m, 8H), 1.34 (t, J=7.0, 3H)

Example 122: (R)-2-(4-(3-((2-(3-(2-ethoxyphenoxy)piperidin-1-yl)pyrimidin-4-yl)amino)-3-oxopropyl)phenyl)-2-methylpropanoic acid

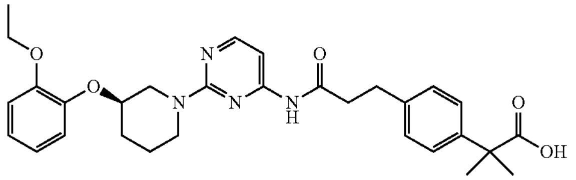 [SMILES: CCOc1ccccc1O[C@@H]1CCCN(c2nccc(NC(=O)CCc3ccc(C(C)(C)C(=O)O)cc3)n2)C1]

(R)-4-chloro-2-(3-(2-ethoxyphenoxy)piperidin-1-yl)pyrimidine (0.20 g, 0.60 mmol) obtained in Preparation Example 68 and benzyl (E)-2-(4-(3-amino-3-oxoprop-1-en-1-yl)phenyl)-2-methylpropanoate (0.19 g, 0.60 mmol) obtained in Preparation Example 65 were used in a similar manner to Example 97 to obtain the desired product. (Yield: 28%)

$^{1}$H-NMR (400 MHz, CHLOROFORM-D): δ 8.23-8.17 (m, 1H), 7.69 (d, J=11.4 Hz, 1H), 7.35-7.26 (m, 3H), 7.15 (d, J=8.2 Hz, 2H), 6.99-6.77 (m, 4H), 4.30-4.18 (m, 2H), 4.03-3.85 (m, 3H), 3.59 (dd, J=13.7, 8.2 Hz, 1H), 3.52-3.41 (m, 1H), 2.96 (t, J=7.5 Hz, 2H), 2.61 (t, J=7.8 Hz, 2H), 2.14-2.04 (m, 1H), 1.95-1.79 (m, 2H), 1.60-1.44 (m, 7H), 1.32 (t, J=6.9 Hz, 3H)

Example 123: (R)-2-(4-(3-((6-(3-((3-ethoxypyridin-2-yl)oxy)piperidin-1-yl)pyrazin-2-yl)amino)-3-oxopropyl)phenyl)-2-methylpropanoic acid

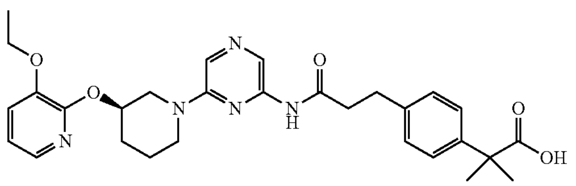 [SMILES: CCOc1cccnc1O[C@@H]1CCCN(c2cncc(NC(=O)CCc3ccc(C(C)(C)C(=O)O)cc3)n2)C1]

(R)-2-chloro-6-(3-((3-ethoxypyridin-2-yl)oxy)piperidin-1-yl)pyrazine (0.20 g, 0.60 mmol) obtained in Preparation Example 70 and benzyl (E)-2-(4-(3-amino-3-oxoprop-1-en-1-yl)phenyl)-2-methylpropanoate (0.19 g, 0.60 mmol) obtained in Preparation Example 65 were used in a similar manner to Example 97 to obtain the desired product. (Yield: 47%)

$^{1}$H-NMR (400 MHz, CHLOROFORM-D): δ 8.60 (s, 1H), 7.86 (s, 1H), 7.69 (dd, J=5.0, 1.4 Hz, 1H), 7.32 (d, J=8.2 Hz, 2H), 7.24-7.13 (m, 3H), 6.84 (dd, J=8.0, 1.6 Hz, 1H), 6.73 (dd, J=7.8, 5.0 Hz, 1H), 5.19-5.08 (m, 1H), 3.95-3.70 (m, 4H), 3.66-3.55 (m, 1H), 3.55-3.44 (m, 1H), 3.07-2.89 (m, 2H), 2.60 (dt, J=20.4, 7.3 Hz, 2H), 2.15-2.04 (m, 1H), 2.01-1.87 (m, 2H), 1.68-1.50 (m, 7H), 1.24 (t, J=7.1 Hz, 3H)

Example 124: (R)-3-(4-(1-((2-(3-(2-ethoxyphenoxy)piperidin-1-yl)pyrimidin-4-yl)amino)-2-methyl-1-oxopropan-2-yl)phenyl)-2,2-dimethylpropanoic acid

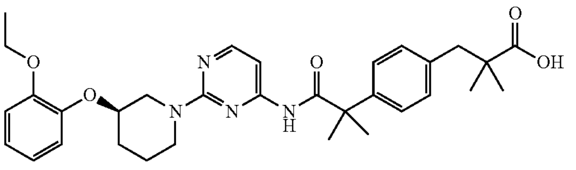 [SMILES: CCOc1ccccc1O[C@@H]1CCCN(c2nccc(NC(=O)C(C)(C)c3ccc(CC(C)(C)C(=O)O)cc3)n2)C1]

(R)-4-chloro-2-(3-(2-ethoxyphenoxy)piperidin-1-yl)pyrimidine (0.10 g, 0.30 mmol) obtained in Preparation Example 68 and tert-butyl 3-(4-(1-amino-2-methyl-1-oxopropan-2-yl)phenyl)-2,2-dimethylpropanoate (0.096 g, 0.30 mmol) obtained in Preparation Example 59 were used in a similar manner to Example 72 to obtain the desired product. (Yield: 60%)

$^{1}$H-NMR (400 MHz, CHLOROFORM-D): δ 8.18 (d, J=5.9 Hz, 1H), 7.36-7.26 (m, 3H), 7.22-7.07 (m, 3H), 6.97-6.75 (m, 4H), 4.29 (d, J=12.8 Hz, 1H), 4.21-4.11 (m, 1H), 4.06-3.88 (m, 3H), 3.40 (d, J=5.0 Hz, 2H), 2.87 (dd, J=22.4, 13.3 Hz, 2H), 2.12-2.04 (m, 1H), 1.91-1.72 (m, 2H), 1.61 (s, 6H), 1.47 (dd, J=9.4, 3.9 Hz, 1H), 1.32 (t, J=6.9 Hz, 3H), 1.18 (d, J=3.7 Hz, 6H)

Example 125: (R)-3-(4-(1-((6-(3-((3-ethoxypyridin-2-yl)oxy)piperidin-1-yl)pyrazin-2-yl)amino)-2-methyl-1-oxopropan-2-yl)phenyl)-2,2-dimethylpropanoic acid

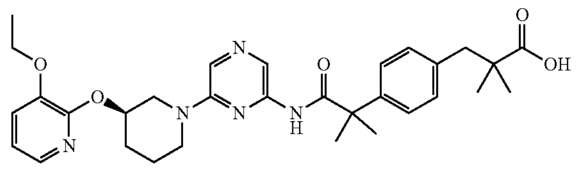 [SMILES: CCOc1cccnc1O[C@@H]1CCCN(c2cncc(NC(=O)C(C)(C)c3ccc(CC(C)(C)C(=O)O)cc3)n2)C1]

(R)-2-chloro-6-(3-((3-ethoxypyridin-2-yl)oxy)piperidin-1-yl)pyrazine (0.10 g, 0.30 mmol) obtained in Preparation Example 70 and tert-butyl 3-(4-(1-amino-2-methyl-1-oxopropan-2-yl)phenyl)-2,2-dimethylpropanoate (0.095 g, 0.30 mmol) obtained in Preparation Example 59 were used in a similar manner to Example 72 to obtain the desired product. (Yield: 77%)

$^{1}$H-NMR (400 MHz, CHLOROFORM-D): δ 8.61 (s, 1H), 7.82 (s, 1H), 7.75-7.67 (m, 1H), 7.28 (d, J=8.7 Hz, 2H), 7.23-7.11 (m, 2H), 6.95 (dd, J=8.0, 1.1 Hz, 1H), 6.87 (s, 1H), 6.78 (dd, J=7.8, 5.0 Hz, 1H), 5.14-5.02 (m, 1H), 3.95-3.65 (m, 4H), 3.59-3.37 (m, 2H), 3.00-2.75 (m, 2H), 2.05 (t, J=4.1 Hz, 1H), 2.00-1.84 (m, 2H), 1.59 (dd, J=18.3, 2.7 Hz, 7H), 1.34-1.25 (m, 3H), 1.23-1.12 (m, 6H)

Example 126: (R)-3-(4-(1-((6-(3-(2-cyclobutoxyphenoxy)piperidin-1-yl)pyrazin-2-yl)amino)-2-methyl-1-oxopropan-2-yl)phenyl)-2,2-dimethylpropanoic acid

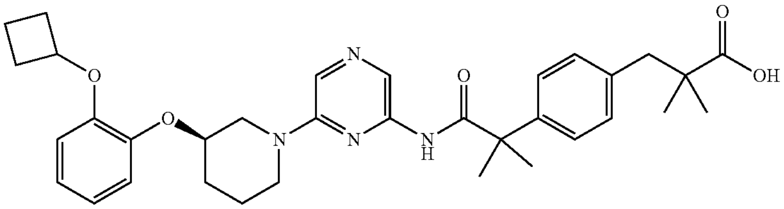 [SMILES: CC(C)(Cc1ccc(C(C)(C)C(=O)Nc2cncc(N3CCC[C@@H](Oc4ccccc4OC4CCC4)C3)n2)cc1)C(=O)O]

(R)-2-chloro-6-(3-(2-cyclobutoxyphenoxy)piperidin-1-yl)pyrazine (0.080 g, 0.22 mmol) obtained in Preparation Example 57 and tert-butyl 3-(4-(1-amino-2-methyl-1-oxopropan-2-yl)phenyl)-2,2-dimethylpropanoate (0.071 g, 0.22 mmol) obtained in Preparation Example 59 were used in a similar manner to Example 72 to obtain the desired product. (Yield: 62%)

$^1$H-NMR (400 MHz, CHLOROFORM-D): δ 8.69 (s, 1H), 7.80 (s, 1H), 7.29 (d, J=8.2 Hz, 2H), 7.18 (d, J=8.2 Hz, 2H), 7.04 (s, 1H), 6.91-6.81 (m, 2H), 6.81-6.72 (m, 1H), 6.72-6.63 (m, 1H), 4.58-4.43 (m, 1H), 4.25-4.14 (m, 1H), 3.90 (dd, J=13.3, 2.7 Hz, 1H), 3.67-3.54 (m, 1H), 3.43 (dd, J=13.0, 7.5 Hz, 1H), 3.36-3.20 (m, 1H), 2.87 (dd, J=15.1, 13.3 Hz, 2H), 2.42-2.26 (m, 2H), 2.16-2.03 (m, 3H), 1.97-1.68 (m, 3H), 1.67-1.40 (m, 8H), 1.20-1.09 (m, 6H)

Example 127: (R)-3-(3-(3-((6-(3-(2-ethoxyphenoxy)piperidin-1-yl)pyrazin-2-yl)amino)-3-oxopropyl)phenyl)-2,2-dimethylpropanoic acid

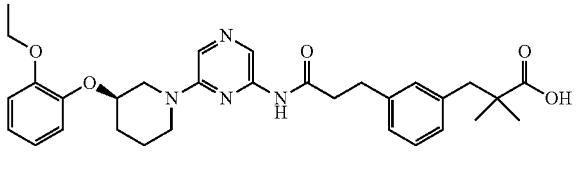 [SMILES: CCOc1ccccc1O[C@@H]1CCCN(c2cncc(NC(=O)CCc3cccc(CC(C)(C)C(=O)O)c3)n2)C1]

(R)-2-chloro-6-(3-(2-ethoxyphenoxy)piperidin-1-yl)pyrazine (0.10 g, 0.30 mmol) obtained in Preparation Example 1 and tert-butyl 3-(3-(3-amino-3-oxopropyl)phenyl)-2,2-dimethylpropanoate (0.091 g, 0.30 mmol) obtained in Preparation Example 62 were used in a similar manner to Example 72 to obtain the desired product. (Yield: 61%)

$^1$H-NMR (400 MHz, CHLOROFORM-D): δ 8.64 (s, 1H), 7.84 (s, 1H), 7.66 (s, 1H), 7.15 (t, J=8.0 Hz, 1H), 7.03 (d, J=6.9 Hz, 2H), 6.98 (d, J=7.3 Hz, 1H), 6.94-6.87 (m, 2H), 6.87-6.76 (m, 2H), 4.27 (td, J=7.2, 3.5 Hz, 1H), 4.00-3.83 (m, 3H), 3.69-3.51 (m, 2H), 3.45-3.32 (m, 1H), 2.95 (t, J=7.5 Hz, 2H), 2.83 (s, 2H), 2.59 (t, J=7.8 Hz, 2H), 2.10-2.00 (m, 1H), 2.00-1.80 (m, 2H), 1.53 (td, J=8.5, 4.3 Hz, 1H), 1.31 (t, J=7.1 Hz, 3H), 1.16 (s, 6H)

Example 128: (R)-3-(3-(3-((6-(3-((3-ethoxypyridin-2-yl)oxy)piperidin-1-yl)pyrazin-2-yl)amino)-3-oxopropyl)phenyl)-2,2-dimethylpropanoic acid

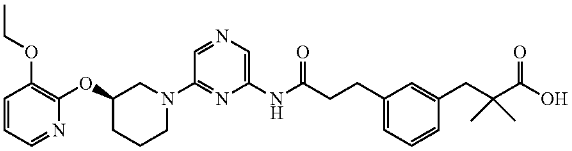 [SMILES: CCOc1cccnc1O[C@@H]1CCCN(c2cncc(NC(=O)CCc3cccc(CC(C)(C)C(=O)O)c3)n2)C1]

(R)-2-chloro-6-(3-((3-ethoxypyridin-2-yl)oxy)piperidin-1-yl)pyrazine (0.10 g, 0.30 mmol) obtained in Preparation Example 70 and tert-butyl 3-(3-(3-amino-3-oxopropyl)phenyl)-2,2-dimethylpropanoate (0.091 g, 0.30 mmol) obtained in Preparation Example 62 were used in a similar manner to Example 72 to obtain the desired product. (Yield: 58%)

$^1$H-NMR (400 MHz, CHLOROFORM-D): δ 8.58 (s, 1H), 7.86 (s, 1H), 7.73 (dd, J=5.0, 1.4 Hz, 2H), 7.15 (t, J=7.5 Hz, 1H), 7.04 (d, J=9.1 Hz, 2H), 7.00-6.90 (m, 2H), 6.80 (dd, J=7.8, 5.0 Hz, 1H), 5.20-5.11 (m, 1H), 3.97-3.72 (m, 4H), 3.71-3.60 (m, 1H), 3.56-3.42 (m, 1H), 2.96 (t, J=7.1 Hz, 2H), 2.82 (dd, J=19.2, 13.3 Hz, 2H), 2.62 (t, J=7.3 Hz, 2H), 2.19-2.07 (m, 1H), 2.02-1.90 (m, 2H), 1.71-1.55 (m, 1H), 1.28 (t, J=7.1 Hz, 3H), 1.17 (s, 3H), 1.14 (s, 3H)

Example 129: (R)-3-(3'-((6-(3-(2-ethoxyphenoxy)piperidin-1-yl)pyrazin-2-yl)carbamoyl)-[1,1'-biphenyl]-3-yl)-2,2-dimethylpropanoic acid

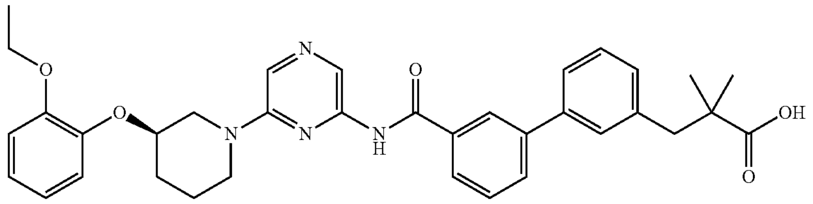 [SMILES: CCOc1ccccc1O[C@@H]1CCCN(c2cncc(NC(=O)c3cccc(-c4cccc(CC(C)(C)C(=O)O)c4)c3)n2)C1]

(R)-2-chloro-6-(3-(2-ethoxyphenoxy)piperidin-1-yl)pyrazine (0.029 g, 0.086 mmol) obtained in Preparation Example 1 and tert-butyl 3-(3'-(chlorocarbonyl)-[1,1'-biphenyl]-3-yl)-2,2-dimethylpropanoate (0.034 g, 0.095 mmol) obtained in Preparation Example 79 were used in a similar manner to Example 72 to obtain the desired product. (Yield: 55%)

$^1$H-NMR (400 MHz, CHLOROFORM-D): δ 8.80 (s, 1H), 8.09-7.93 (m, 2H), 7.86 (s, 1H), 7.77 (dd, J=30.2, 8.2 Hz, 2H), 7.59-7.41 (m, 3H), 7.35 (t, J=7.5 Hz, 1H), 7.22-7.11 (1H), 7.01-6.87 (m, 1H), 6.87-6.70 (m, 3H), 4.31 (td, J=7.1, 3.5 Hz, 1H), 4.03-3.79 (m, 3H), 3.77-3.56 (m, 2H), 3.52-3.32 (m, 1H), 2.96 (s, 2H), 2.17-2.04 (m, 1H), 2.01-1.79 (m, 2H), 1.56 (qd, J=8.5, 4.2 Hz, 1H), 1.32 (t, J=7.1 Hz, 3H), 1.24-1.06 (m, 6H)

Example 130: (R)-3-(3'-((6-(3-(2-ethoxyphenoxy)piperidin-1-yl)pyrazin-2-yl)carbamoyl)-[1,1'-biphenyl]-4-yl)-2,2-dimethylpropanoic acid

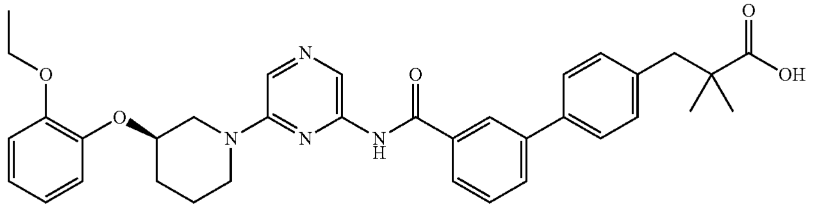 [SMILES: CCOc1ccccc1O[C@@H]1CCCN(c2cncc(NC(=O)c3cccc(-c4ccc(CC(C)(C)C(=O)O)cc4)c3)n2)C1]

(R)-2-chloro-6-(3-(2-ethoxyphenoxy)piperidin-1-yl)pyrazine (0.052 g, 0.154 mmol) obtained in Preparation Example 1 and tert-butyl 3-(3'-(chlorocarbonyl)-[1,1'-biphenyl]-4-yl)-2,2-dimethylpropanoate (0.060 g, 0.170 mmol) obtained in Preparation Example 80 were used in a similar manner to Example 72 to obtain the desired product. (Yield: 69%)

$^1$H-NMR (400 MHz, CHLOROFORM-D): δ 8.86 (s, 1H), 8.08 (d, J=12.3 Hz, 2H), 7.93 (s, 1H), 7.78 (dd, J=22.0, 7.8 Hz, 2H), 7.62-7.43 (m, 3H), 7.29 (d, J=8.2 Hz, 2H), 7.03-6.89 (m, 1H), 6.88-6.72 (3H), 4.41-4.23 (m, 1H), 4.04-3.80 (m, 3H), 3.69 (q, J=6.7 Hz, 2H), 3.57-3.37 (m, 1H), 2.97 (d, J=8.7 Hz, 2H), 2.18-2.05 (m, 1H), 2.03-1.81 (m, 2H), 1.58 (qd, J=8.4, 4.5 Hz, 1H), 1.33 (t, J=7.1 Hz, 3H), 1.26 (s, 6H)

Experimental Example: Measurement of Inhibitory Effect Against DGAT2 Enzyme Activity The inhibitory effect against the DGAT2 enzyme activity was investigated by performing the following experiment on the compounds of Formula (1) according to the present invention.

1. Preparation of DGAT2 Expression Vector

In order to prepare the pBacPAK9-DGAT2, which is DGAT2 expression vector, the human DGAT2 gene amplified by polymerase chain reaction (PCR) was cloned into the EcoR1 and Xho1 sites of the pBacPAK9 (clonctech) vector. The nucleotide sequence of the primers used in PCR was the forward primer 5' CTATAAATACGGATCCCGGGAATT-CATGGACTACAAGGACGACGATGACAAGCTTA AGACCCTCATAGCCGCC and the reverse primer 5' TAAGCGGCCGCCCTGCAGGCCTCGAGTCAGTT-CACCTCCAGGAC. The composition of the reaction solution was to contain 50 ng of cDNA clone (OriGene), 200 μM of dATP, dCTP, dTTP, dGTP, 200 nM of each primer, 1 unit of Tag DNA Polymerase (Toyobo), 1×PCR buffer, and the final volume was adjusted to 20 μl. The reaction conditions were denatured at 95° C. for 5 minutes, followed by 30 times of 94° C. for 20 seconds, 60° C. for 20 seconds, and 72° C. for 90 seconds, followed by further reaction at 72° C. for 7 minutes.

2. DGAT2 Expression and Preparation of Membrane Protein

Recombinant human DGAT2 protein was expressed in Sf-21 cells, which are insect cells, by using the BacPack baculovirus expression system (Clontech). The brief manufacturing process is as follows. First, the pBacPAK9-DGAT2 expression vector was transfected with BacPAK6 virus DNA (Bsu36I digest) into sf21 cells using Bacfectin to prepare a recombinant DGAT2 expressing baculovirus. The thus prepared baculovirus was infected with Sf-21 cells at 10 MOI (multiplicity of infection), and after 72 hours, infected insect cells were collected and membrane proteins were isolated. For membrane protein separation, the cell pellet was dissolved in a sucrose solution containing 250 mM sucrose, 10 mM Tris (pH 7.4), and 1 mM ethylenediaminetetraacetic acid (EDTA), and then homogenized by using a dounce homogenizer, and the supernatant was taken by centrifuging at 600×g for 15 minutes, and centrifuged at 100,000×g for 1 hour to discard the supernatant, and the remaining pellet was resuspended in 20 mM HEPES buffer (pH 7.4). The prepared DGAT2 overexpressing membrane protein was dispensed in 100 μl and stored at −80° C. until use. Protein concentration was quantified by using the BCA Protein Assay Kit (Thermo Scientific).

3. Measurement of Inhibitory Effect Against DGAT2 Enzyme Activity

In vitro DGAT2 analysis was performed using a Phospholipid Flash Plate (PerkinElmer) based on the principle of SPA (Scintillation Proximity Assay). First, DGAT2 inhibition compounds serially diluted 5 times from 3 nM to 10 μM (final concentration, 1% DMSO) were mixed in a buffer solution containing 2 μg DGAT2-membrane protein and 20 mM HEPES, 20 mM $MgCl_2$, 1 mg/mL BSA, 50 μM 1,2 sn-oleoyl glycerol (Sigma), put in a 96-well flash plate (FlashPlate) and reacted at 37° C. for 20 minutes, and then 1 μM [14C] ole oil CoA (PerkinElmer, NEC651050UC) was added to be a final volume of 100 μL and further reacted at 37° C. for 15 minutes. After the enzymatic reaction was completed, 100 μL of isopropanol was added, the plate was sealed with a film, and the plate was shaken slowly in a plate shaker. The next day, the amplified scintillation signal (cpm) in Topcounter (Packard) was measured to measure the degree of production of [14C]-labeled triacyl glycerol (TG) as a reaction product. The measured value when the compound was not treated was used as a positive control, and the measured value of the compound treated group was calculated as a relative % to measure the inhibition effect of the compound on TG production. The $IC_{50}$ value, which is the concentration of the compound that inhibits TG production by 50%, was determined by treating the response value according to the compound concentration with a nonlinear regression curve using PRISM (Graphpad Inc.).

As a result of measuring the inhibition effect on the DGAT2 enzyme action for the compound of formula (1), specific $IC_{50}$ values of the individual Example compounds were as shown in Table 1 below.

TABLE 1

| Example | $IC_{50}$ (μM) |
|---|---|
| 1 | 0.045 |
| 2 | 16 |
| 3 | 2.3 |
| 4 | 1.6 |
| 5 | 51 |
| 6 | 0.053 |
| 7 | 0.045 |
| 8 | 0.23 |
| 9 | 0.09 |
| 10 | 0.019 |
| 11 | 16 |
| 12 | 4 |

TABLE 1-continued

| Example | $IC_{50}$ (μM) |
|---|---|
| 13 | 9.1 |
| 14 | 12 |
| 15 | 0.025 |
| 16 | 0.39 |
| 17 | 0.01 |
| 18 | 0.008 |
| 19 | ~15 |
| 20 | 4 |
| 21 | 4.8 |
| 22 | 1.3 |
| 23 | 7.4 |
| 24 | 0.3 |
| 25 | 1.8 |
| 26 | 0.054 |
| 27 | 0.049 |
| 28 | 0.032 |
| 29 | 0.018 |
| 30 | 0.029 |
| 31 | 0.18 |
| 32 | 6.9 |
| 33 | 4.5 |
| 34 | 1.10 |
| 35 | 0.03 |
| 36 | 0.012 |
| 37 | 0.46 |
| 38 | 0.2 |
| 39 | 0.77 |
| 40 | 0.16 |
| 41 | 3.1 |
| 42 | 1.3 |
| 43 | 0.33 |
| 44 | 0.17 |
| 45 | 0.15 |
| 46 | 0.51 |
| 47 | 0.31 |
| 48 | 0.71 |
| 49 | 0.10 |
| 50 | 0.0096 |
| 51 | 0.033 |
| 52 | 0.066 |
| 53 | 0.39 |
| 54 | 0.088 |
| 55 | 0.28 |
| 56 | 0.82 |
| 57 | 5.3 |
| 58 | 7.5 |
| 59 | 1 |
| 60 | 0.42 |
| 61 | 0.15 |
| 62 | 2.1 |
| 63 | 0.14 |
| 64 | 0.12 |
| 65 | 0.035 |
| 66 | 2.7 |
| 67 | 6.1 |
| 68 | 0.63 |
| 69 | 0.97 |
| 70 | 0.35 |
| 71 | 0.25 |
| 72 | 1.8 |
| 73 | 0.31 |
| 74 | 1.3 |
| 75 | 1.2 |
| 76 | 0.13 |
| 77 | 0.41 |
| 78 | 2.5 |
| 79 | 0.93 |
| 80 | 1.3 |
| 81 | 0.74 |
| 82 | 6.8 |
| 83 | >10 |
| 84 | >10 |
| 85 | 0.042 |
| 86 | >10 |
| 87 | 0.16 |
| 88 | 6.2 |
| 89 | 0.59 |
| 90 | >10 |

TABLE 1-continued

| Example | $IC_{50}$ (μM) |
|---|---|
| 91 | 0.37 |
| 92 | >10 |
| 93 | 0.19 |
| 94 | 0.11 |
| 95 | 0.15 |
| 96 | 0.2 |
| 97 | 0.059 |
| 98 | 0.081 |
| 99 | 2.9 |
| 100 | 0.59 |
| 101 | 0.32 |
| 102 | 0.45 |
| 103 | 0.62 |
| 104 | 0.66 |
| 105 | 0.09 |
| 106 | 0.73 |
| 107 | 0.07 |
| 108 | 0.078 |
| 109 | 1.1 |
| 110 | 0.076 |
| 111 | 0.69 |
| 112 | 0.06 |
| 113 | 0.15 |
| 114 | 0.14 |
| 115 | 0.14 |
| 116 | 0.038 |
| 117 | 0.14 |
| 118 | 0.17 |
| 119 | 1.2 |
| 120 | 0.25 |
| 121 | 0.098 |
| 122 | 0.06 |
| 123 | 0.035 |
| 124 | 0.33 |
| 125 | 0.035 |
| 126 | 3.8 |
| 127 | 0.083 |
| 128 | 0.1 |
| 129 | 0.54 |
| 130 | 0.38 |

The invention claimed is:

1. A compound of the following Formula (1), or a pharmaceutically acceptable salt or stereoisomer thereof:

[Formula (1)]

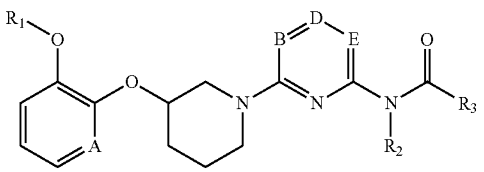

wherein

A, B and E are each independently CH or N;

D is N, CH or C-haloalkyl;

$R_1$ is alkyl, cycloalkyl or haloalkyl;

$R_2$ is hydrogen or alkyl;

$R_3$ is -G-J-L;

wherein G is —NH— or a direct bond;

J is alkylene, alkenylene, alkylene-arylene, alkylene-amino-arylene, alkylene-aryloxylene-alkylene, alkylene-cycloalkyl, alkenylene-cycloalkyl, alkoxylene-arylene, arylene, cycloalkyl, aryl, aryl-alkyl, heterocycloalkylene, heterocycloalkylene-arylene, heterocycloalkylene-heteroarylene or heterocycloalkyl; and L is hydrogen, halo, amino, nitro, carboxy (—COOH), aminocarbonylalkyl, carboxyalkyl, carboxyalkoxy, carboxyalkyl-aryl, cycloalkyl, aryl, aryloxy, heterocycloalkyl or heteroaryl; or $R_2$ and $R_3$ together with nitrogen atom to which they are attached may form heterocycloalkyl; and wherein the alkyl, alkylene, alkylene-arylene, alkenyl, alkenylene, cycloalkyl, carboxyalkyl, carboxyalkoxy, alkoxyalkyl, aminocarbonyl, aryl, aryl-alkyl, arylene, aryloxy, heterocycloalkyl or heteroaryl is optionally substituted with one or more substituents selected from hydroxy, halo, oxo, nitro, —COOH, —$CH_2$COOH, alkyl, alkenyl, alkoxy, haloalkyl, alkylsulfonyl, alkylcarbonyl, alkoxycarbonyl and heteroaryl-alkyl; and the heterocycloalkylene, heterocycloalkyl, heteroarylene or heteroaryl includes one or more heteroatoms selected from N, O and S.

2. The compound, or a pharmaceutically acceptable salt or stereoisomer thereof according to claim 1, wherein A, B and E are each independently CH or N;

D is N, CH or C-halo-$C_1$-$C_7$ alkyl;

$R_1$ is $C_1$-$C_7$ alkyl, $C_3$-$C_{10}$ cycloalkyl or halo-$C_1$-$C_7$ alkyl;

$R_2$ is hydrogen or $C_1$-$C_7$ alkyl;

$R_3$ is -G-J-L;

wherein G is —NH— or a direct bond;

J is $C_1$-$C_7$ alkylene, $C_2$-$C_7$ alkenylene, $C_1$-$C_7$ alkylene-$C_6$-$C_{10}$ arylene, $C_1$-$C_7$ alkylene-amino-$C_6$-$C_{10}$ arylene, $C_1$-$C_7$ alkylene-$C_6$-$C_{10}$ aryloxylene-$C_1$-$C_7$ alkylene, $C_1$-$C_7$ alkylene-$C_3$-$C_{10}$ cycloalkyl, $C_2$-$C_7$ alkenylene-$C_3$-$C_{10}$ cycloalkyl, $C_1$-$C_7$ alkoxylene-$C_6$-$C_{10}$ arylene, $C_6$-$C_{10}$ arylene, $C_3$-$C_{10}$ cycloalkyl, $C_6$-$C_{10}$ aryl, $C_6$-$C_{10}$ aryl-$C_1$-$C_7$ alkyl, 5- to 12-membered heterocycloalkylene, 5- to 12-membered heterocycloalkylene-$C_6$-$C_{10}$ arylene, 5- to 12-membered heterocycloalkylene-5- to 12-membered heteroarylene or 5- to 12-membered heterocycloalkyl;

L is hydrogen, halo, amino, nitro, carboxy (—COOH), aminocarbonyl-$C_1$-$C_7$ alkyl, carboxy-$C_1$-$C_7$ alkyl, carboxy-$C_1$-$C_7$ alkoxy, carboxy-$C_1$-$C_7$ alkyl-$C_6$-$C_{10}$ aryl, $C_3$-$C_{10}$ cycloalkyl, $C_6$-$C_{10}$ aryl, $C_6$-$C_{10}$ aryloxy, 5- to 12-membered heterocycloalkyl or 5- to 12-membered heteroaryl; or $R_2$ and $R_3$ together with nitrogen atom to which they are attached may form 5- to 12-membered heterocycloalkyl; and wherein the alkyl, alkylene, alkylene-arylene, alkenyl, alkenylene, cycloalkyl, carboxyalkyl, carboxyalkoxy, alkoxyalkyl, aminocarbonyl, aryl, aryl-alkyl, arylene, aryloxy, heterocycloalkyl or heteroaryl is optionally substituted with 1 to 4 substituents selected from hydroxy, halo, oxo, nitro, —COOH, —$CH_2$COOH, $C_1$-$C_7$ alkyl, $C_2$-$C_7$ alkenyl, $C_1$-$C_7$ alkoxy, halo-$C_1$-$C_7$ alkyl, $C_1$-$C_7$ alkylsulfonyl, $C_1$-$C_7$ alkylcarbonyl, $C_1$-$C_7$ alkoxycarbonyl and 5- to 12-membered heteroaryl-$C_1$-$C_7$ alkyl; and the heterocycloalkylene, heterocycloalkyl, heteroarylene or heteroaryl includes 1 to 5 heteroatoms selected from N, O and S.

3. The compound, or a pharmaceutically acceptable salt or stereoisomer thereof according to claim 1, wherein the compound is selected from the following group:

(R)-1-(3,5-bis(trifluoromethyl)phenyl)-3-(6-(3-(2-ethoxyphenoxy)piperidin-1-yl)pyrazin-2-yl)urea;

((6-((R)-3-(2-ethoxyphenoxy)piperidin-1-yl)pyrazin-2-yl)carbamoyl)-L-phenylalanine;

(R)—N-(6-(3-(2-ethoxyphenoxy)piperidin-1-yl)pyrazin-2-yl)morpholine-4-carboxamide;

(R)—N-(6-(3-(2-ethoxyphenoxy)piperidin-1-yl)pyrazin-2-yl)pyrrolidine-1-carboxamide;

1-((6-((R)-3-(2-ethoxyphenoxy)piperidin-1-yl)pyrazin-2-yl)carbamoyl)pyrrolidine-3-carboxylic acid;

(R)—N-(6-(3-(2-ethoxyphenoxy)piperidin-1-yl)pyrazin-2-yl)benzamide;
(R)-4-chloro-N-(6-(3-(2-ethoxyphenoxy)piperidin-1-yl)pyrazin-2-yl)benzamide;
(R)—N-(6-(3-(2-ethoxyphenoxy)piperidin-1-yl)pyrazin-2-yl)-3-methoxybenzamide;
(R)—N-(6-(3-(2-ethoxyphenoxy)piperidin-1-yl)pyrazin-2-yl)-4-methoxybenzamide;
(R)—N-(6-(3-(2-ethoxyphenoxy)piperidin-1-yl)pyrazin-2-yl)-4-nitrobenzamide;
(R)-2-((6-(3-(2-ethoxyphenoxy)piperidin-1-yl)pyrazin-2-yl)carbamoyl)benzoic acid;
(R)-2-(4-((6-(3-(2-ethoxyphenoxy)piperidin-1-yl)pyrazin-2-yl)carbamoyl)phenyl)acetic acid;
(R)-2-(4-((6-(3-(2-ethoxyphenoxy)piperidin-1-yl)pyrazin-2-yl)carbamoyl)phenyl)-2-methylpropanoic acid;
(R)-2-(4-((6-(3-(2-ethoxyphenoxy)piperidin-1-yl)pyrazin-2-yl)carbamoyl)phenoxy)-2-methylpropanoic acid;
(R)—N-(6-(3-(2-ethoxyphenoxy)piperidin-1-yl)pyrazin-2-yl)-1-(methylsulfonyl)piperidine)-4-carboxamide;
(R)-1-acetyl-N-(6-(3-(2-ethoxyphenoxy)piperidin-1-yl)pyrazin-2-yl)piperidine)-4-carboxamide;
(R)—N-(6-(3-(2-ethoxyphenoxy)piperidin-1-yl)pyrazin-2-yl)-1-(isopropylsulfonyl)piperidine-4-carboxamide;
(R)—N-(6-(3-(2-ethoxyphenoxy)piperidin-1-yl)pyrazin-2-yl)-1-(5-ethylpyrimidin-2-yl)piperidine-4-carboxamide;
(R)-4-((6-(3-(2-ethoxyphenoxy)piperidin-1-yl)pyrazin-2-yl)amino)-4-oxobutanoic acid;
(1R)-2-((6-((R)-3-(2-ethoxyphenoxy)piperidin-1-yl)pyrazin-2-yl)carbamoyl)cyclopentane-1-carboxylic acid;
(R)-4-((6-(3-(2-ethoxyphenoxy)piperidin-1-yl)pyrazin-2-yl)carbamoyl)bicyclo[2.2.2]octane-1-carboxylic acid;
(R)-4-((6-(3-(2-ethoxyphenoxy)piperidin-1-yl)pyrazin-2-yl)amino)-2,2-dimethyl-4-oxobutanoic acid;
(R)-1-(6-(3-(2-ethoxyphenoxy)piperidin-1-yl)pyrazin-2-yl)-3,3-dimethylpyrrolidine-2,5-dione;
(R)-5-((6-(3-(2-ethoxyphenoxy)piperidin-1-yl)pyrazin-2-yl)amino)-2,2-dimethyl-5-oxopentanoic acid;
(R)-5-((6-(3-(2-ethoxyphenoxy)piperidin-1-yl)pyrazin-2-yl)amino)-3,3-dimethyl-5-oxopentanoic acid;
(R)—N-(6-(3-(2-ethoxyphenoxy)piperidin-1-yl)pyrazin-2-yl)-2-(3-trifluoromethyl)phenyl)acetamide;
(R)-2-(3,5-bis(trifluoromethyl)phenyl)-N-(6-(3-(2-ethoxyphenoxy)piperidin-1-yl)pyrazin-2-yl)acetamide;
(R)—N-(6-(3-(2-ethoxyphenoxy)piperidin-1-yl)pyrazin-2-yl)-2-phenylacetamide;
(R)—N-(6-(3-(2-ethoxyphenoxy)piperidin-1-yl)pyrazin-2-yl)-3-phenylpropanamide;
(R)-2-(3-chlorophenyl)-N-(6-(3-(2-ethoxyphenoxy)piperidin-1-yl)pyrazin-2-yl)acetamide;
(R)—N-(6-(3-(2-ethoxyphenoxy)piperidin-1-yl)pyrazin-2-yl)-2-methyl-2-phenylpropanamide;
(R)-4-(2-((6-(3-(2-ethoxyphenoxy)piperidin-1-yl)pyrazin-2-yl)amino)-2-oxoethyl)benzoic acid;
(R)-3-(2-((6-(3-(2-ethoxyphenoxy)piperidin-1-yl)pyrazin-2-yl)amino)-2-oxoethyl)benzoic acid;
(R)-2-(4-(2-((6-(3-(2-ethoxyphenoxy)piperidin-1-yl)pyrazin-2-yl)amino)-2-oxoethyl)phenyl)acetic acid;
(R)-2-(4-(2-amino-2-oxoethyl)phenyl-N-(6-(3-(2-ethoxyphenoxy)piperidin-1-yl)pyrazin-2-yl)acetamide;
(R)—N-(6-(3-(2-ethoxyphenoxy)piperidin-1-yl)pyrazin-2-yl)-2-(4-hydroxyphenyl)acetamide;
(R)-4-(4-(2-((6-(3-(2-ethoxyphenoxy)piperidin-1-yl)pyrazin-2-yl)amino)-2-oxoethyl)phenoxy)butanoic acid;
(R)-2-(4-(2-((6-(3-(2-ethoxyphenoxy)piperidin-1-yl)pyrazin-2-yl)amino-2-oxoethyl)phenoxy)-2-methylpropanoic acid;
(R)-2-(4-(1-((6-(3-(2-ethoxyphenoxy)piperidin-1-yl)pyrazin-2-yl)amino)-2-methyl-1-oxopropan-2-yl)phenyl)-2-methylpropanoic acid;
(R)-4-(3-((6-(3-(2-ethoxyphenoxy)piperidin-1-yl)pyrazin-2-yl)amino)-3-oxopropyl)benzoic acid;
(R,E)-4-(3-((6-(3-(2-ethoxyphenoxy)piperidin-1-yl)pyrazin-2-yl)amino)-3-oxoprop-1-en-1-yl)benzoic acid;
(R,E)-4-(3-((6-(3-(2-ethoxyphenoxy)piperidin-1-yl)pyrazin-2-yl)amino)-2-methyl-3-oxoprop-1-en-1-yl)benzoic acid;
4-(3-((6-((R)-3-(2-ethoxyphenoxy)piperidin-1-yl)pyrazin-2-yl)amino)-2-methyl-3-oxopropyl)benzoic acid;
(R)-4-(3-((6-(3-(2-ethoxyphenoxy)piperidin-1-yl)pyrazin-2-yl)amino)-3-oxopropyl)-2-fluorobenzoic acid;
(R)-4-(3-((6-(3-(2-ethoxyphenoxy)piperidin-1-yl)pyrazin-2-yl)amino)-3-oxopropyl)-2-methylbenzoic acid;
(R)-4-(3-((6-(3-(2-ethoxyphenoxy)piperidin-1-yl)pyrazin-2-yl)amino)-3-oxopropyl)-2-methoxybenzoic acid;
(R)-2-chloro-4-(3-((6-(3-(2-ethoxyphenoxy)piperidin-1-yl)pyrazin-2-yl)amino)-3-oxopropyl)benzoic acid;
(R)-3-(3-((6-(3-(2-ethoxyphenoxy)piperidin-1-yl)pyrazin-2-yl)amino)-3-oxopropyl)benzoic acid;
(R)-2-(4-(3-((6-(3-(2-ethoxyphenoxy)piperidin-1-yl)pyrazin-2-yl)amino)-3-oxopropyl)phenyl)acetic acid;
(R)-3-(4-(2-amino-2-oxoethyl)phenyl-N-(6-(3-(2-ethoxyphenoxy)piperidin-1-yl)pyrazin-2-yl)propanamide;
(R)-2-(4-(3-((6-(3-(2-ethoxyphenoxy)piperidin-1-yl)pyrazin-2-yl)amino)-3-oxopropyl)phenyl)-2-methylpropanoic acid;
(R)-1-(4-(3-((6-(3-(2-ethoxyphenoxy)piperidin-1-yl)pyrazin-2-yl)amino)-3-oxopropyl)phenyl)cyclopropane-1-carboxylic acid;
(R)-4-(3-((6-(3-(2-ethoxyphenoxy)piperidin-1-yl)pyrazin-2-yl)amino)-3-oxopropyl)-2,6-difluorobenzoic acid;
(R)-2,6-dichloro-4-(3-((6-(3-(2-ethoxyphenoxy)piperidin-1-yl)pyrazin-2-yl)amino)-3-oxopropyl)benzoic acid;
(R)-4-(3-((6-(3-(2-ethoxyphenoxy)piperidin-1-yl)pyrazin-2-yl)amino)-3-oxopropyl)-2,6-dimethylbenzoic acid;
(R)-1-(4-(3-((6-(3-(2-ethoxyphenoxy)piperidin-1-yl)pyrazin-2-yl)amino)-3-oxopropyl)phenyl)piperidine-4-carboxylic acid;
(R)-1-(4-((6-(3-(2-ethoxyphenoxy)piperidin-1-yl)pyrazin-2-yl)carbamoyl-2,6-difluorophenyl)piperidine-4-carboxylic acid;
(R)-2-(1-(4-((6-(3-(2-ethoxyphenoxy)piperidin-1-yl)pyrazin-2-yl)carbamoyl-2,6-difluorophenyl)piperidin-4-yl)acetic acid;
(R)-4-(4-((6-(3-(2-ethoxyphenoxy)piperidin-1-yl)pyrazin-2-yl)carbamoyl)piperidin-1-yl)benzoic acid;
(R)-2-(4-(3-((6-(3-(2-ethoxyphenoxy)piperidin-1-yl)pyrazin-2-yl)amino)-3-oxopropyl)phenoxy)-2-methylpropanoic acid;

(R)-3-(4-(3-((6-(3-(2-ethoxyphenoxy)piperidin-1-yl) pyrazin-2-yl)amino)-3-oxopropyl)phenyl)propanoic acid;

(R)-4-(4-((6-(3-(2-ethoxyphenoxy)piperidin-1-yl) pyrazin-2-yl)carbamoyl)phenoxy)benzoic acid;

(R)-3-(4-(3-((6-(R)-3-(2-ethoxyphenoxy)piperidin-1-yl) pyrazin-2-yl)amino)-2-oxoethyl)phenyl)-2-methylpropanoic acid;

(S)-3-(4-(3-((6-(R)-3-(2-ethoxyphenoxy)piperidin-1-yl) pyrazin-2-yl)amino)-2-oxoethyl)phenyl)-2-methylpropanoic acid;

(R)-3-(4-(2-((6-(3-(2-ethoxyphenoxy)piperidin-1-yl) pyrazin-2-yl)amino)-2-oxoethyl)phenyl)-2,2-dimethylpropanoic acid;

(R)-2-(4-(2-((6-(3-(2-ethoxyphenoxy)piperidin-1-yl)pyridin-2-yl)amino)-2-oxoethyl)phenyl)acetic acid;

(R)-2-(4-(3-(6-(3-(2-ethoxyphenoxy)piperidin-1-yl) pyrazin-2-yl)ureido)phenyl)acetic acid;

(R)-2-(4-(2-((6-(3-(2-ethoxyphenoxy)piperidin-1-yl)pyridin-2-yl)amino)-2-oxoethyl)phenyl)-2-methylpropanoic acid;

(R)-2-(4-(2-((6-(3-(2-ethoxyphenoxy)piperidin-1-yl) pyrazin-2-yl)amino)-2-oxoethyl)phenyl)-2-methylpropanoic acid;

(R)-2-(4-(3-((6-(3-(2-ethoxyphenoxy)piperidin-1-yl)pyridin-2-yl)amino)-3-oxopropyl)phenyl)-2-methylpropanoic acid;

(R)-3-(4-(2-((6-(3-(2-ethoxyphenoxy)piperidin-1-yl)pyridin-2-yl)amino-2-oxoethyl)phenyl)-2,2-dimethylpropanoic acid;

(R)-3-(4-(2-((4-(3-(2-ethoxyphenoxy)piperidin-1-yl)-6-(trifluoromethyl)pyrimidin-2-yl)amino-2-oxoethyl) phenyl)-2,2-dimethylpropanoic acid;

(R)-3-(4-(1-((6-(3-(2-ethoxyphenoxy)piperidin-1-yl) pyrazin-2-yl)amino)-2-methyl-1-oxopropan-2-yl)phenyl)propanoic acid;

(R)-3-(4-((2-((6-(3-(2-ethoxyphenoxy)piperidin-1-yl) pyrazin-2-yl)carbamoyl) allyl)amino)phenyl)propanoic acid;

(R)-2-(4-((6-(3-(2-ethoxyphenoxy)piperidin-1-yl) pyrazin-2-yl)carbamoyl)piperidin-1-yl)pyrimidine-5-carboxylic acid;

3-(3-((R)-3-((6-((R)-3-((3-ethoxypyridin-2-yl)oxy)piperidin-1-yl)pyrazin-2-yl) carbamoyl)piperidin-1-yl) phenyl-2,2-dimethylpropanoic acid;

(R)-3-(4-(1-((4-(3-(2-ethoxyphenoxy)piperidin-1-yl)pyrimidin-2-yl)amino)-2-methyl-1-oxopropan-2-yl)phenyl)-2,2-dimethylpropanoic acid;

(R)-3-(4-(1-((4-(3-((3-ethoxypyridin-2-yl)oxy)piperidin-1-yl)pyrimidin-2-yl)amino)-2-methyl-1-oxopropan-2-yl)phenyl)-2,2-dimethylpropanoic acid;

(R)-2-(4-(4-((6-(3-(2-ethoxyphenoxy)piperidin-1-yl) pyrazin-2-yl)carbamoyl)piperidin-1-yl)phenyl)acetic acid;

(R)-2-(4-(4-((6-(3-(2-ethoxyphenoxy)piperidin-1-yl) pyrazin-2-yl)carbamoyl)piperidin-1-yl)phenyl)-2-methylpropanoic acid;

(R)-2-(6-(4-((6-(3-(2-ethoxyphenoxy)piperidin-1-yl) pyrazin-2-yl)carbamoyl)piperidin-1-yl)pyridin-3-yl)-2-methylpropanoic acid;

(R)-2-(5-(4-((6-(3-(2-ethoxyphenoxy)piperidin-1-yl) pyrazin-2-yl)carbamoyl)piperidin-1-yl)-2H-tetrazol-2-yl)acetic acid;

(R)-4-(4-((6-(3-(2-ethoxyphenoxy)piperidin-1-yl) pyrazin-2-yl)carbamoyl)piperidin-1-yl)-4-oxobutanoic acid;

(R)-2-(4-((6-(3-(2-ethoxyphenoxy)piperidin-1-yl) pyrazin-2-yl)carbamoyl)piperidin-1-yl)acetic acid;

3-(3-((R)-3-((6-((R)-3-(2-ethoxyphenoxy)piperidin-1-yl) pyrazin-2-yl) carbamoyl)piperidin-1-yl)phenyl)-2,2-dimethylpropanoic acid;

(R)-1-(4-(1-((6-(3-(2-ethoxyphenoxy)piperidin-1-yl) pyrazin-2-yl)amino)-2-methyl-1-oxopropan-2-yl)phenyl)piperidine-4-carboxylic acid;

6-(3-((6-((R)-3-(2-ethoxyphenoxy)piperidin-1-yl) pyrazin-2-yl)carbamoyl) pyrrolidin-1-yl)nicotinic acid;

N-(6-((R)-3-(2-ethoxyphenoxy)piperidin-1-yl)pyrazin-2-yl)-3-methylpyrrolidine-3-carboxamide;

6-(3-((6-((R)-3-(2-ethoxyphenoxy)piperidin-1-yl) pyrazin-2-yl)carbamoyl)-3-methylpyrrolidin-1-yl) nicotinic acid;

(R)-2-(4-(2-((6-(3-(2-isopropoxyphenoxy)piperidin-1-yl) pyrazin-2-yl)amino)-2-oxoethyl)phenyl)acetic acid;

(R)-2-(4-(3-((6-(3-(2-methoxyphenoxy)piperidin-1-yl) pyrazin-2-yl)amino)-3-oxopropyl)phenyl)-2-methylpropanoic acid;

(R)-2-methyl-2-(4-(3-oxo-3-((6-(3-(2-(trifluoromethoxy) phenoxy)piperidin-1-yl)pyrazin-2-yl)amino)propyl) phenyl)propanoic acid;

(R)-2-(4-(3-((6-(3-(2-(2-fluoroethoxy)phenoxy)piperidin-1-yl)pyrazin-2-yl)amino)-3-oxopropyl)phenyl)-2-methylpropanoic acid;

(R)-3-(4-(2-((6-(3-(2-(2-fluoroethoxy)phenoxy)piperidin-1-yl)pyrazin-2-yl)amino)-2-oxoethyl)phenyl)-2,2-dimethylpropanoic acid;

(R)-3-(4-(2-((6-(3-(2-cyclopropoxyphenoxy)piperidin-1-yl)pyrazin-2-yl)amino)-2-oxoethyl)phenyl)-2,2-dimethylpropanoic acid;

(R)-3-(4-(2-((6-(3-(2-cyclobutoxyphenoxy)piperidin-1-yl)pyrazin-2-yl)amino)-2-oxoethyl)phenyl)-2,2-dimethylpropanoic acid;

(R)-2-(4-(3-((6-(3-(2-cyclopropoxyphenoxy)piperidin-1-yl)pyrazin-2-yl)amino)-3-oxopropyl)phenyl)-2-methylpropanoic acid;

(R)-2-(4-(3-((6-(3-(2-cyclobutoxyphenoxy)piperidin-1-yl)pyrazin-2-yl)amino)-3-oxopropyl)phenyl)-2-methylpropanoic acid;

(R)-2-(4-(2-((6-(3-(2-ethoxyphenoxy)piperidin-1-yl) pyrazin-2-yl)amino-2-oxoethyl)phenoxy)acetic acid;

(R)-2-(4-(2-((6-(3-(2-ethoxyphenoxy)piperidin-1-yl) pyrazin-2-yl)amino)-2-oxoethoxy)phenyl)acetic acid;

2-(4-(2-((6-((R)-3-(2-ethoxyphenoxy)piperidin-1-yl) pyrazin-2-yl)amino)-2-oxoethoxy)phenyl)propanoic acid;

(R)-3-(4-(2-((6-(3-(2-ethoxyphenoxy)piperidin-1-yl) pyrazin-2-yl)amino)-2-oxoethyl)phenoxy-2,2-dimethylpropanoic acid;

(R)-2-(4-(2-((6-((R)-3-(2-ethoxyphenoxy)piperidin-1-yl) pyrazin-2-yl)amino)-2-oxoethyl)phenoxy)propanoic acid;

(S)-2-(4-(2-((6-((R)-3-(2-ethoxyphenoxy)piperidin-1-yl) pyrazin-2-yl)amino)-2-oxoethyl)phenoxy)propanoic acid;

(R)-2-(4-(2-((6-(3-((3-ethoxypyridin-2-yl)oxy)piperidin-1-yl)pyrazin-2-yl)amino)-2-oxoethyl)phenoxy)-2-methylpropanoic acid;

(R)-2-(4-(2-((2-(3-(2-ethoxyphenoxy)piperidin-1-yl)pyrimidin-4-yl)amino)-2-oxoethyl)phenoxy)-2-methylpropanoic acid;

(R)-2-(4-((4-(2-((6-(3-(2-ethoxyphenoxy)piperidin-1-yl) pyrazin-2-yl)amino)-2-oxoethyl)phenoxy)methyl)phenyl)-2-methylpropanoic acid;

(R)-2-(4-(3-((6-(3-((3-ethoxypyridin-2-yl)oxy)piperidin-1-yl)pyrazin-2-yl)amino)-3-oxopropyl)phenoxy)-2-methylpropanoic acid;

(R)-2-(4-(3-((2-(3-(2-ethoxyphenoxy)piperidin-1-yl)pyrimidin-4-yl)amino)-3-oxopropyl)phenoxy)-2-methylpropanoic acid;

(R)-3-(4-(1-((6-(3-(2-ethoxyphenoxy)piperidin-1-yl)pyrazin-2-yl)amino)-2-methyl-1-oxopropan-2-yl)phenyl)-2,2-dimethylpropanoic acid;

(R)-2-(4-(3-((6-(3-(2-ethoxyphenoxy)piperidin-1-yl)pyrazin-2-yl)amino)-2,2-dimethyl-3-oxopropyl)phenyl)-2-methylpropanoic acid;

(R)-3-(4-(2-((2-(3-(2-ethoxyphenoxy)piperidin-1-yl)pyrimidin-4-yl)amino)-2-oxoethyl)phenyl)-2,2-dimethylpropanoic acid;

(R)-3-(4-(2-((4-(3-(2-ethoxyphenoxy)piperidin-1-yl)pyrimidin-2-yl)amino)-2-oxoethyl)phenyl)-2,2-dimethylpropanoic acid;

(R)-3-(4-(2-((4-(3-((3-ethoxypyridin-2-yl)oxy)piperidin-1-yl)pyrimidin-2-yl)amino)-2-oxoethyl)phenyl)-2,2-dimethylpropanoic acid;

(R)-3-(4-(2-((2-(3-((3-ethoxypyridin-2-yl)oxy)piperidin-1-yl)pyrimidin-4-yl)amino)-2-oxoethyl)phenyl)-2,2-dimethylpropanoic acid;

(R)-3-(4-(2-((6-(3-((3-ethoxypyridin-2-yl)oxy)piperidin-1-yl)pyrazin-2-yl)amino)-2-oxoethyl)phenyl)-2,2-dimethylpropanoic acid;

(R)-4-(3-((6-(3-(2-ethoxyphenoxy)piperidin-1-yl)pyrazin-2-yl)amino)-3-oxopropyl)bicyclo[2.2.2]octane-1-carboxylic acid;

(R)-4-(2-((6-(3-(2-ethoxyphenoxy)piperidin-1-yl)pyrazin-2-yl)amino)-2-oxoethyl)bicyclo[2.2.2]octane-1-carboxylic acid;

(R)-4-(3-((2-(3-(2-ethoxyphenoxy)piperidin-1-yl)pyrimidin-4-yl)amino)-3-oxopropyl)bicyclo[2.2.2]octane-1-carboxylic acid;

(R)-4-(3-((6-(3-((3-ethoxypyridin-2-yl)oxy)piperidin-1-yl)pyrazin-2-yl)amino)-3-oxopropyl)bicyclo[2.2.2]octane-1-carboxylic acid;

(R,E)-4-(3-((6-(3-(2-ethoxyphenoxy)piperidin-1-yl)pyrazin-2-yl)amino)-3-oxoprop-1-en-1-yl)bicyclo[2.2.2]octane-1-carboxylic acid;

(R)-2-(4-(3-((2-(3-(2-ethoxyphenoxy)piperidin-1-yl)pyrimidin-4-yl)amino)-3-oxopropyl)phenyl)-2-methylpropanoic acid (R)-2-(4-(3-((6-(3-((3-ethoxypyridin-2-yl)oxy)piperidin-1-yl)pyrazin-2-yl)amino)-3-oxopropyl)phenyl)-2-methylpropanoic acid;

(R)-3-(4-(1-((2-(3-(2-ethoxyphenoxy)piperidin-1-yl)pyrimidin-4-yl)amino)-2-methyl-1-oxopropan-2-yl)phenyl)-2,2-dimethylpropanoic acid;

(R)-3-(4-(1-((6-(3-((3-ethoxypyridin-2-yl)oxy)piperidin-1-yl)pyrazin-2-yl)amino)-2-methyl-1-oxopropan-2-yl)phenyl)-2,2-dimethylpropanoic acid;

(R)-3-(4-(1-((6-(3-(2-cyclobutoxyphenoxy)piperidin-1-yl)pyrazin-2-yl)amino)-2-methyl-1-oxopropan-2-yl)phenyl)-2,2-dimethylpropanoic acid;

(R)-3-(3-(3-((6-(3-(2-ethoxyphenoxy)piperidin-1-yl)pyrazin-2-yl)amino)-3-oxopropyl)phenyl)-2,2-dimethylpropanoic acid;

(R)-3-(3-(3-((6-(3-((3-ethoxypyridin-2-yl)oxy)piperidin-1-yl)pyrazin-2-yl)amino)-3-oxopropyl)phenyl)-2,2-dimethylpropanoic acid;

(R)-3-(3'-((6-(3-(2-ethoxyphenoxy)piperidin-1-yl)pyrazin-2-yl)carbamoyl)-[1,1'-biphenyl]-3-yl)-2,2-dimethylpropanoic acid; and (R)-3-(3'-((6-(3-(2-ethoxyphenoxy)piperidin-1-yl)pyrazin-2-yl)carbamoyl)-[1,1'-biphenyl]-4-yl)-2,2-dimethylpropanoic acid.

4. A pharmaceutical composition comprising the compound of Formula (1), or a pharmaceutically acceptable salt or stereoisomer thereof as defined in claim 1 as an active ingredient, together with a pharmaceutically acceptable carrier.

5. A method for treating diseases associated with diacylglycerol acyltransferase 2 (DGAT2) by administering the compound of Formula (1), or a pharmaceutically acceptable salt or stereoisomer thereof as defined in claim 1 as an active ingredient.

6. The method according to claim 5, wherein the disease associated with DGAT2 is selected from the group consisting of fatty liver, nonalcoholic steatohepatitis (NASH), nonalcoholic fatty liver disease (NAFLD), diabetes, obesity, hyperlipidemia, atherosclerosis and hypercholesterolemia.

* * * * *